(12) United States Patent
Campbell et al.

(10) Patent No.: US 12,336,816 B2
(45) Date of Patent: Jun. 24, 2025

(54) METHOD FOR IMPROVED SENSOR SENSITIVITY OF A MICRONEEDLE-BASED CONTINUOUS ANALYTE MONITORING SYSTEM

(71) Applicant: Biolinq Incorporated, San Diego, CA (US)

(72) Inventors: Alan Steven Campbell, La Mesa, CA (US); Robert McKinlay, San Marcos, CA (US); Shuai Xu, San Diego, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 18/431,808

(22) Filed: Feb. 2, 2024

(65) Prior Publication Data

US 2024/0315614 A1    Sep. 26, 2024

Related U.S. Application Data

(60) Provisional application No. 63/613,566, filed on Dec. 21, 2023, provisional application No. 63/443,010, (Continued)

(51) Int. Cl.
*A61B 5/145* (2006.01)
*A61B 5/00* (2006.01)

(52) U.S. Cl.
CPC .......... *A61B 5/14546* (2013.01); *A61B 5/685* (2013.01); *A61B 2562/125* (2013.01)

(58) Field of Classification Search
CPC .......... A61B 2562/125; A61B 5/14514; A61B 5/14532; A61B 5/14546; A61B 5/1486;
(Continued)

(56) References Cited

U.S. PATENT DOCUMENTS 3,964,482 A   6/1976 Gerstel et al.
4,305,401 A   12/1981 Reissmueller et al.
(Continued)

FOREIGN PATENT DOCUMENTS

CN   101068591 A   11/2007
CN   112617822 A   4/2021
(Continued)

OTHER PUBLICATIONS

American Diabetes Association, "Diabetes and Emotional Health: A Practical Guide for Health Professionals Supporting Adults with Type 1 and Type 2 Diabetes" U.S. Edition (2021), 214 pages.
(Continued)

*Primary Examiner* — Eric J Messersmith
(74) *Attorney, Agent, or Firm* — Cooley LLP

(57) ABSTRACT

Described herein are variations of an analyte monitoring system, including an analyte monitoring device. For example, an analyte monitoring device may include an implantable microneedle array for use in measuring one or more analytes (e.g., glucose), such as in a continuous manner. Each microneedle of the microneedle array may include a microneedle body, an electrode material on the microneedle body, a biorecognition layer on the electrode material, a diffusion-limiting layer on the biorecognition layer, an interferent blocking agent, and/or an attachment enhancer between the biorecognition layer and the diffusion-limiting layer, where the interferent blocking agent and the attachment enhancer are configured to improve sensor sensitivity variability.

15 Claims, 60 Drawing Sheets

Specification includes a Sequence Listing.

Related U.S. Application Data filed on Feb. 2, 2023, provisional application No. 63/443,024, filed on Feb. 2, 2023.

(58) Field of Classification Search
CPC .......... A61B 5/14865; A61B 5/150022; A61B 5/685; A61B 5/150984
See application file for complete search history.

(56) References Cited

U.S. PATENT DOCUMENTS

| | | |
|---|---|---|
| 4,323,996 A | 4/1982 | Ganter |
| 4,407,295 A | 10/1983 | Steuer et al. |
| 4,450,842 A | 5/1984 | Zick et al. |
| 4,908,117 A | 3/1990 | Kinlen et al. |
| 4,969,468 A | 11/1990 | Byers et al. |
| 5,035,711 A | 7/1991 | Aoki et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 5,832,410 A | 11/1998 | Lin et al. |
| 5,869,078 A | 2/1999 | Baudino |
| 5,953,306 A | 9/1999 | Yi |
| 6,036,055 A | 3/2000 | Mogadam et al. |
| 6,091,975 A | 7/2000 | Daddona et al. |
| 6,132,449 A | 10/2000 | Lum et al. |
| 6,132,499 A | 10/2000 | Wong et al. |
| 6,132,755 A | 10/2000 | Eicher et al. |
| 6,139,718 A | 10/2000 | Kurnik et al. |
| 6,175,752 B1 | 1/2001 | Say et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,465,091 B1 | 10/2002 | Ou-Yang |
| 6,471,903 B2 | 10/2002 | Sherman et al. |
| 6,527,762 B1 | 3/2003 | Santini, Jr. et al. |
| 6,551,849 B1 | 4/2003 | Kenney |
| 6,587,705 B1 | 7/2003 | Kim et al. |
| 6,599,408 B1 | 7/2003 | Chan et al. |
| 6,603,987 B2 | 8/2003 | Whitson |
| 6,611,707 B1 | 8/2003 | Prausnitz et al. |
| 6,793,789 B2 | 9/2004 | Choi et al. |
| 6,801,041 B2 | 10/2004 | Karinka et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,081,195 B2 | 7/2006 | Simpson et al. |
| 7,097,776 B2 | 8/2006 | Govinda Raju |
| 7,132,054 B1 | 11/2006 | Kravitz et al. |
| 7,183,068 B2 | 2/2007 | Burson et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,366,556 B2 | 4/2008 | Brister et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,471,972 B2 | 12/2008 | Rhodes et al. |
| 7,473,244 B2 | 1/2009 | Frazier et al. |
| 7,493,232 B1 | 2/2009 | Surina |
| 7,534,330 B2 | 5/2009 | Yu et al. |
| 7,583,990 B2 | 9/2009 | Goode, Jr. et al. |
| 7,599,726 B2 | 10/2009 | Goode, Jr. et al. |
| 7,613,491 B2 | 11/2009 | Boock et al. |
| 7,645,263 B2 | 1/2010 | Angel et al. |
| 7,715,893 B2 | 5/2010 | Kamath et al. |
| 7,725,148 B2 | 5/2010 | Shah et al. |
| 7,768,408 B2 | 8/2010 | Reggiardo et al. |
| 7,778,680 B2 | 8/2010 | Goode, Jr. et al. |
| 7,797,028 B2 | 9/2010 | Goode, Jr. et al. |
| 7,811,231 B2 | 10/2010 | Jin et al. |
| 7,837,654 B2 | 11/2010 | Shumate et al. |
| 7,885,697 B2 | 2/2011 | Brister et al. |
| 7,905,833 B2 | 3/2011 | Brister et al. |
| 7,917,186 B2 | 3/2011 | Kamath et al. |
| 7,949,382 B2 | 5/2011 | Jina |
| 7,959,569 B2 | 6/2011 | Goode et al. |
| 8,005,526 B2 | 8/2011 | Martin et al. |
| 8,010,174 B2 | 8/2011 | Goode, Jr. et al. |
| 8,022,292 B2 | 9/2011 | Arianpour et al. |
| 8,064,977 B2 | 11/2011 | Boock et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,110,079 B2 | 2/2012 | Gooding et al. |
| 8,125,331 B2 | 2/2012 | Allen et al. |
| 8,130,095 B2 | 3/2012 | Allen et al. |
| 8,160,665 B2 | 4/2012 | Mischler et al. |
| 8,160,671 B2 | 4/2012 | Kamath et al. |
| 8,160,834 B2 | 4/2012 | Liang et al. |
| 8,162,901 B2 | 4/2012 | Gonnelli et al. |
| RE43,399 E | 5/2012 | Simpson et al. |
| 8,216,138 B1 | 7/2012 | McGarraugh |
| 8,236,368 B2 | 8/2012 | Jung et al. |
| 8,249,684 B2 | 8/2012 | Kamath et al. |
| 8,257,324 B2 | 9/2012 | Prausnitz et al. |
| 8,280,475 B2 | 10/2012 | Brister et al. |
| 8,280,476 B2 | 10/2012 | Jina |
| 8,284,046 B2 | 10/2012 | Allen et al. |
| 8,287,453 B2 | 10/2012 | Li et al. |
| 8,308,960 B2 | 11/2012 | Kalvesten et al. |
| 8,346,335 B2 | 1/2013 | Harper et al. |
| 8,376,945 B2 | 2/2013 | Hayter et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,452,369 B2 | 5/2013 | Huys et al. |
| 8,463,350 B2 | 6/2013 | Kamath et al. |
| 8,483,793 B2 | 7/2013 | Simpson et al. |
| 8,506,529 B1 | 8/2013 | Yang |
| 8,548,553 B2 | 10/2013 | Kamath et al. |
| 8,565,848 B2 | 10/2013 | Brister et al. |
| 8,574,165 B2 | 11/2013 | Marsh |
| 8,617,069 B2 | 12/2013 | Bernstein et al. |
| RE44,695 E | 1/2014 | Simpson et al. |
| 8,626,257 B2 | 1/2014 | Li et al. |
| 8,637,351 B2 | 1/2014 | Kalvesten et al. |
| 8,660,628 B2 | 2/2014 | Wang et al. |
| 8,700,114 B2 | 4/2014 | Gottlieb et al. |
| 8,708,966 B2 | 4/2014 | Allen et al. |
| 8,798,799 B2 | 8/2014 | Deo et al. |
| 8,815,070 B2 | 8/2014 | Wang et al. |
| 8,870,763 B2 | 10/2014 | Yang et al. |
| 8,882,665 B2 | 11/2014 | Yang et al. |
| 9,008,743 B2 | 4/2015 | Hayter et al. |
| 9,008,745 B2 | 4/2015 | Pushpala et al. |
| 9,055,901 B2 | 6/2015 | Brister et al. |
| 9,125,625 B2 | 9/2015 | Wang et al. |
| 9,182,368 B2 | 11/2015 | Pushpala et al. |
| 9,234,872 B2 | 1/2016 | Homyk et al. |
| 9,248,273 B2 | 2/2016 | Guvanasen et al. |
| 9,332,934 B2 | 5/2016 | Hayter et al. |
| 9,336,423 B2 | 5/2016 | Goodnow et al. |
| 9,357,951 B2 | 6/2016 | Simpson et al. |
| 9,386,954 B2 | 7/2016 | Saini et al. |
| 9,387,000 B2 | 7/2016 | Corrie et al. |
| 9,414,778 B2 | 8/2016 | Mao et al. |
| 9,420,965 B2 | 8/2016 | Brauker et al. |
| 9,532,741 B2 | 1/2017 | Brauker et al. |
| 9,551,698 B2 | 1/2017 | Huys et al. |
| 9,662,056 B2 | 5/2017 | Budiman et al. |
| 9,737,247 B2 | 8/2017 | Wang et al. |
| 9,743,870 B2 | 8/2017 | Wang et al. |
| 9,743,871 B2 | 8/2017 | Simpson et al. |
| 9,757,061 B2 | 9/2017 | Shults et al. |
| 9,770,211 B2 | 9/2017 | Hayter et al. |
| 9,804,114 B2 | 10/2017 | Rhodes et al. |
| 9,933,387 B1 | 4/2018 | McCanna et al. |
| 9,958,409 B2 | 5/2018 | Gerber et al. |
| 10,022,076 B2 | 7/2018 | Hoss et al. |
| 10,039,480 B2 | 8/2018 | Brauker et al. |

(56) References Cited

U.S. PATENT DOCUMENTS

| | | |
|---|---|---|
| 10,046,114 B1 | 8/2018 | Biederman et al. |
| 10,052,055 B2 | 8/2018 | Li et al. |
| 10,092,207 B1 | 10/2018 | Windmiller |
| 10,136,846 B2 | 11/2018 | Wang et al. |
| 10,173,042 B2 | 1/2019 | Pushpala et al. |
| 10,182,748 B2 | 1/2019 | Catt et al. |
| 10,188,333 B2 | 1/2019 | Kamath et al. |
| 10,228,341 B2 | 3/2019 | Katsuki et al. |
| 10,299,712 B2 | 5/2019 | Brister et al. |
| 10,327,678 B2 | 6/2019 | Gottlieb et al. |
| 10,492,708 B1 | 12/2019 | Windmiller |
| D875,254 S | 2/2020 | Cooke et al. |
| 10,549,080 B2 | 2/2020 | Pushpala et al. |
| 10,610,103 B2 | 4/2020 | Brister et al. |
| 10,709,332 B2 | 7/2020 | Brister et al. |
| 10,743,800 B2 | 8/2020 | Larvenz et al. |
| 10,780,222 B2 | 9/2020 | Ward et al. |
| 10,820,860 B2 | 11/2020 | Pushpala et al. |
| 10,881,334 B2 | 1/2021 | Facchinetti et al. |
| 10,932,700 B2 | 3/2021 | Simpson et al. |
| 10,983,083 B2 | 4/2021 | Harding et al. |
| 11,020,026 B2 | 6/2021 | Boock et al. |
| 11,035,872 B2 | 6/2021 | Boutelle et al. |
| 11,045,142 B1 | 6/2021 | Windmiller et al. |
| 11,051,724 B2 | 7/2021 | Pace et al. |
| 11,123,532 B2 | 9/2021 | Pushpala et al. |
| 11,179,068 B2 | 11/2021 | Pace et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,331,022 B2 | 5/2022 | Halac et al. |
| 11,359,300 B1 | 6/2022 | Beer et al. |
| 11,406,818 B2 | 8/2022 | Windmiller |
| 11,478,194 B2 | 10/2022 | Windmiller et al. |
| 11,596,332 B2 | 3/2023 | Shults et al. |
| 11,654,270 B2 | 5/2023 | Mansfield, III et al. |
| D988,160 S | 6/2023 | Morelock |
| 11,672,965 B2 | 6/2023 | Mansfield, III et al. |
| 11,697,007 B2 | 7/2023 | Gu et al. |
| D996,999 S | 8/2023 | Morelock |
| 11,819,650 B2 | 11/2023 | Pushpala et al. |
| D1,012,744 S | 1/2024 | Morelock |
| 11,857,344 B2 | 1/2024 | Windmiller et al. |
| 11,865,289 B2 | 1/2024 | Pushpala et al. |
| 11,872,055 B2 | 1/2024 | Tangney et al. |
| D1,013,544 S | 2/2024 | Morelock |
| 11,896,792 B2 | 2/2024 | Pushpala et al. |
| 11,896,793 B2 | 2/2024 | Pushpala et al. |
| 11,903,738 B2 | 2/2024 | Pushpala et al. |
| 11,904,127 B2 | 2/2024 | Mansfield et al. |
| 11,963,796 B1 | 4/2024 | Windmiller et al. |
| 11,986,614 B2 | 5/2024 | Mansfield et al. |
| 11,992,314 B2 | 5/2024 | Hahn et al. |
| 12,011,294 B2 | 6/2024 | Campbell et al. |
| D1,033,641 S | 7/2024 | Morelock |
| D1,035,004 S | 7/2024 | Morelock |
| 12,048,558 B2 | 7/2024 | Kendall et al. |
| D1,038,794 S | 8/2024 | Morelock |
| 12,070,307 B2 | 8/2024 | Ebejer et al. |
| 12,070,313 B2 | 8/2024 | Fuchs et al. |
| 12,109,032 B1 | 10/2024 | Windmiller et al. |
| D1,051,745 S | 11/2024 | Morelock |
| D1,057,153 S | 1/2025 | Morelock |
| 2002/0004640 A1 | 1/2002 | Conn et al. |
| 2002/0020688 A1 | 2/2002 | Sherman et al. |
| 2002/0055704 A1 | 5/2002 | Scott et al. |
| 2002/0072784 A1 | 6/2002 | Sheppard, Jr. et al. |
| 2002/0105080 A1 | 8/2002 | Speakman |
| 2002/0120186 A1 | 8/2002 | Keimel |
| 2002/0187556 A1 | 12/2002 | Shartle et al. |
| 2003/0068666 A1 | 4/2003 | Zweig |
| 2003/0088166 A1 | 5/2003 | Say et al. |
| 2003/0095582 A1 | 5/2003 | Ackley |
| 2003/0100040 A1 | 5/2003 | Bonnecaze et al. |
| 2003/0104119 A1* | 6/2003 | Wilson ................ C12Q 1/005 427/430.1 |
| 2003/0135158 A1 | 7/2003 | Gonnelli |
| 2003/0199788 A1 | 10/2003 | Erickson et al. |
| 2003/0208167 A1 | 11/2003 | Prausnitz et al. |
| 2003/0225360 A1 | 12/2003 | Eppstein et al. |
| 2003/0235817 A1 | 12/2003 | Bartkowiak et al. |
| 2004/0065158 A1 | 4/2004 | Schrepfer et al. |
| 2004/0082875 A1 | 4/2004 | Donoghue et al. |
| 2004/0138543 A1 | 7/2004 | Russell et al. |
| 2004/0189311 A1 | 9/2004 | Glezer et al. |
| 2004/0220625 A1 | 11/2004 | Silvestri et al. |
| 2005/0036020 A1 | 2/2005 | Li et al. |
| 2005/0101841 A9 | 5/2005 | Kaylor et al. |
| 2005/0137536 A1 | 6/2005 | Gonnelli |
| 2005/0209565 A1 | 9/2005 | Yuzhakov et al. |
| 2005/0267440 A1 | 12/2005 | Herman et al. |
| 2005/0272989 A1 | 12/2005 | Shah et al. |
| 2006/0015061 A1 | 1/2006 | Kuo et al. |
| 2006/0016700 A1 | 1/2006 | Brister et al. |
| 2006/0173259 A1 | 8/2006 | Flaherty et al. |
| 2006/0264716 A1 | 11/2006 | Zander |
| 2006/0281121 A1 | 12/2006 | Unger et al. |
| 2007/0060815 A1 | 3/2007 | Martin et al. |
| 2007/0078445 A1 | 4/2007 | Malloy |
| 2007/0169533 A1 | 7/2007 | Shah et al. |
| 2007/0170054 A2 | 7/2007 | Wilsey |
| 2007/0191733 A1 | 8/2007 | Gianchandani et al. |
| 2007/0213044 A1 | 9/2007 | Steingart et al. |
| 2007/0282246 A1 | 12/2007 | Henley |
| 2008/0009800 A1 | 1/2008 | Nickel |
| 2008/0009801 A1 | 1/2008 | Nickel |
| 2008/0027369 A1 | 1/2008 | Carter et al. |
| 2008/0033269 A1 | 2/2008 | Zhang |
| 2008/0097280 A1 | 4/2008 | Martin et al. |
| 2008/0097352 A1 | 4/2008 | Beck et al. |
| 2008/0119707 A1 | 5/2008 | Stafford |
| 2008/0154107 A1 | 6/2008 | Jina |
| 2008/0156661 A1 | 7/2008 | Cooper et al. |
| 2008/0213461 A1 | 9/2008 | Gill et al. |
| 2008/0221408 A1 | 9/2008 | Hoarau et al. |
| 2008/0234562 A1 | 9/2008 | Jina |
| 2008/0255434 A1 | 10/2008 | Hayter et al. |
| 2008/0275327 A1 | 11/2008 | Faarbaek et al. |
| 2008/0319298 A1 | 12/2008 | Huys et al. |
| 2009/0043250 A1 | 2/2009 | Gonnelli |
| 2009/0057148 A1 | 3/2009 | Wieder et al. |
| 2009/0062752 A1 | 3/2009 | Gonnelli |
| 2009/0066348 A1 | 3/2009 | Shin et al. |
| 2009/0069651 A1 | 3/2009 | Zimmermann et al. |
| 2009/0069697 A1 | 3/2009 | Frazier et al. |
| 2009/0084678 A1 | 4/2009 | Joshi et al. |
| 2009/0088652 A1 | 4/2009 | Tremblay |
| 2009/0090623 A1 | 4/2009 | Chuang et al. |
| 2009/0099427 A1 | 4/2009 | Jina et al. |
| 2009/0101498 A1 | 4/2009 | Papadimitrakopoulo et al. |
| 2009/0118672 A1 | 5/2009 | Gonnelli et al. |
| 2009/0131778 A1 | 5/2009 | Jina et al. |
| 2009/0143761 A1 | 6/2009 | Cantor et al. |
| 2009/0152598 A1 | 6/2009 | Baek et al. |
| 2009/0191616 A1 | 7/2009 | Lu et al. |
| 2009/0198118 A1 | 8/2009 | Hayter et al. |
| 2009/0218239 A1 | 9/2009 | Gooding et al. |
| 2009/0259118 A1 | 10/2009 | Feldman et al. |
| 2009/0294306 A1 | 12/2009 | Feldman et al. |
| 2010/0006451 A1 | 1/2010 | Gordon et al. |
| 2010/0021637 A1 | 1/2010 | Revol Cavalier et al. |
| 2010/0022416 A1 | 1/2010 | Flemming et al. |
| 2010/0025238 A1 | 2/2010 | Gottlieb et al. |
| 2010/0030045 A1 | 2/2010 | Gottlieb et al. |
| 2010/0049021 A1 | 2/2010 | Jina et al. |
| 2010/0052892 A1 | 3/2010 | Allen et al. |
| 2010/0052897 A1 | 3/2010 | Allen et al. |
| 2010/0052898 A1 | 3/2010 | Allen et al. |
| 2010/0052915 A1 | 3/2010 | Allen et al. |
| 2010/0056873 A1 | 3/2010 | Allen et al. |
| 2010/0108509 A1 | 5/2010 | Curry et al. |
| 2010/0137779 A1 | 6/2010 | Seitz |
| 2010/0160756 A1 | 6/2010 | Petisce et al. |

(56) References Cited

U.S. PATENT DOCUMENTS

| | | |
|---|---|---|
| 2010/0200538 A1 | 8/2010 | Petisce et al. |
| 2010/0279377 A1 | 11/2010 | Shah et al. |
| 2010/0286803 A1 | 11/2010 | Tillotson et al. |
| 2011/0027127 A1 | 2/2011 | Simpson et al. |
| 2011/0042241 A1 | 2/2011 | Kotsis et al. |
| 2011/0077490 A1 | 3/2011 | Simpson et al. |
| 2011/0105871 A1 | 5/2011 | Zimmermann et al. |
| 2011/0140703 A1 | 6/2011 | Chiao et al. |
| 2011/0196216 A1 | 8/2011 | Quarder et al. |
| 2011/0210017 A1 | 9/2011 | Lai et al. |
| 2011/0224515 A1 | 9/2011 | Mir et al. |
| 2011/0230736 A1 | 9/2011 | Tepper et al. |
| 2011/0237925 A1 | 9/2011 | Yue et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0067734 A1 | 3/2012 | Wang et al. |
| 2012/0078071 A1 | 3/2012 | Bohm et al. |
| 2012/0123232 A1 | 5/2012 | Najarian et al. |
| 2012/0172692 A1 | 7/2012 | Tamada et al. |
| 2012/0209244 A1 | 8/2012 | Gray |
| 2012/0277629 A1 | 11/2012 | Bernstein et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0135158 A1 | 5/2013 | Faraone et al. |
| 2013/0144131 A1 | 6/2013 | Wang et al. |
| 2013/0158376 A1 | 6/2013 | Hayter et al. |
| 2013/0225956 A1 | 8/2013 | Huang et al. |
| 2013/0281808 A1 | 10/2013 | Shieh |
| 2013/0324820 A1 | 12/2013 | Petillo et al. |
| 2013/0338632 A1 | 12/2013 | Kaplan et al. |
| 2013/0338746 A1 | 12/2013 | Guvanasen et al. |
| 2013/0345597 A1 | 12/2013 | Hagino et al. |
| 2014/0135679 A1 | 5/2014 | Mann et al. |
| 2014/0259652 A1 | 9/2014 | Pushpala et al. |
| 2014/0275897 A1 | 9/2014 | Pushpala et al. |
| 2014/0275899 A1 | 9/2014 | Gottlieb et al. |
| 2014/0275907 A1 | 9/2014 | Feldman et al. |
| 2014/0303471 A1 | 10/2014 | Rajaraman et al. |
| 2014/0336487 A1 | 11/2014 | Wang et al. |
| 2014/0378804 A1 | 12/2014 | Kalvesten et al. |
| 2015/0073238 A1 | 3/2015 | Matsumoto et al. |
| 2015/0126834 A1 | 5/2015 | Wang et al. |
| 2015/0208970 A1 | 7/2015 | Huang |
| 2015/0243851 A1 | 8/2015 | Lee et al. |
| 2015/0276758 A1 | 10/2015 | Addisu |
| 2015/0313527 A1 | 11/2015 | Renlund |
| 2016/0022187 A1 | 1/2016 | Pushpala et al. |
| 2016/0029937 A1 | 2/2016 | Sia et al. |
| 2016/0058342 A1 | 3/2016 | Maiz-Aguinaga et al. |
| 2016/0095541 A1 | 4/2016 | Wang et al. |
| 2016/0095547 A1 | 4/2016 | Wang et al. |
| 2016/0139069 A1 | 5/2016 | Wang |
| 2016/0157764 A1 | 6/2016 | Di Palma et al. |
| 2016/0158514 A1 | 6/2016 | Stoeber et al. |
| 2016/0166184 A1 | 6/2016 | Teng et al. |
| 2016/0213908 A1 | 7/2016 | McAllister et al. |
| 2016/0258945 A1 | 9/2016 | Malima et al. |
| 2016/0270704 A1 | 9/2016 | DeTURK |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0003766 A1 | 1/2017 | Budiman |
| 2017/0007813 A1 | 1/2017 | Negi et al. |
| 2017/0035331 A1 | 2/2017 | Paranjape et al. |
| 2017/0055835 A1 | 3/2017 | Scherer et al. |
| 2017/0086713 A1 | 3/2017 | Pushpala et al. |
| 2017/0108459 A1 | 4/2017 | Katsuki et al. |
| 2017/0127989 A1 | 5/2017 | Feldman et al. |
| 2017/0128009 A1 | 5/2017 | Pushpala et al. |
| 2017/0164881 A1 | 6/2017 | Fujita et al. |
| 2017/0251958 A1 | 9/2017 | Pushpala et al. |
| 2017/0251959 A1 | 9/2017 | Feldman et al. |
| 2017/0251960 A1 | 9/2017 | Crouther et al. |
| 2017/0347925 A1 | 12/2017 | Wang et al. |
| 2018/0116572 A1 | 5/2018 | Simpson et al. |
| 2018/0140235 A1 | 5/2018 | Pushpala et al. |
| 2018/0279929 A1 | 10/2018 | Huang et al. |
| 2018/0317820 A1 | 11/2018 | Pace et al. |
| 2018/0338712 A1 | 11/2018 | Cass et al. |
| 2018/0340203 A1 | 11/2018 | Holmes et al. |
| 2019/0008425 A1 | 1/2019 | Srinivasan et al. |
| 2019/0022365 A1 | 1/2019 | Chowdhury et al. |
| 2019/0029577 A1 | 1/2019 | Koelker et al. |
| 2019/0076075 A1 | 3/2019 | Miller et al. |
| 2019/0090811 A1 | 3/2019 | Reitz et al. |
| 2019/0091455 A1 | 3/2019 | Reitz et al. |
| 2019/0094169 A1 | 3/2019 | Shah et al. |
| 2019/0101551 A1 | 4/2019 | Plaxco et al. |
| 2019/0110724 A1 | 4/2019 | Kamath et al. |
| 2019/0125223 A1 | 5/2019 | Wang et al. |
| 2019/0167167 A1 | 6/2019 | Mitchell et al. |
| 2019/0170739 A1 | 6/2019 | Garner et al. |
| 2019/0201675 A1 | 7/2019 | Miller et al. |
| 2019/0209095 A1 | 7/2019 | Kamath et al. |
| 2019/0223795 A1 | 7/2019 | Patolsky et al. |
| 2019/0224712 A1 | 7/2019 | Petisce et al. |
| 2019/0231263 A1 | 8/2019 | Ribet et al. |
| 2019/0241926 A1 | 8/2019 | Mckinlay et al. |
| 2019/0261907 A1 | 8/2019 | Brister et al. |
| 2019/0274599 A1 | 9/2019 | Polsky et al. |
| 2019/0274600 A1 | 9/2019 | Pesantez et al. |
| 2019/0298210 A1 | 10/2019 | Bennet et al. |
| 2019/0307379 A1 | 10/2019 | Boock et al. |
| 2019/0309433 A1 | 10/2019 | Sattayasamitsathit et al. |
| 2019/0310219 A1 | 10/2019 | Boock |
| 2019/0357827 A1 | 11/2019 | Li et al. |
| 2020/0000387 A1 | 1/2020 | Gerhardt et al. |
| 2020/0029876 A1 | 1/2020 | Brister et al. |
| 2020/0037938 A1 | 2/2020 | Rong et al. |
| 2020/0101286 A1 | 4/2020 | Windmiller et al. |
| 2020/0121902 A1 | 4/2020 | Pushpala et al. |
| 2020/0178853 A1 | 6/2020 | Pushpala et al. |
| 2020/0187778 A1 | 6/2020 | Brister et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0305771 A1 | 10/2020 | Feldman et al. |
| 2020/0330007 A1 | 10/2020 | Garai et al. |
| 2020/0359949 A1 | 11/2020 | Brauker et al. |
| 2020/0390395 A1 | 12/2020 | Pushpala et al. |
| 2020/0405234 A1 | 12/2020 | Pushpala et al. |
| 2021/0045663 A1 | 2/2021 | Simpson et al. |
| 2021/0045665 A1 | 2/2021 | Simpson et al. |
| 2021/0045666 A1 | 2/2021 | Simpson et al. |
| 2021/0100452 A1 | 4/2021 | Brister et al. |
| 2021/0100504 A1 | 4/2021 | Pushpala et al. |
| 2021/0100505 A1* | 4/2021 | Pushpala .............. A61B 5/4839 |
| 2021/0183508 A1 | 6/2021 | Parker et al. |
| 2021/0187286 A1 | 6/2021 | Windmiller et al. |
| 2021/0190719 A1 | 6/2021 | LaTour et al. |
| 2021/0236057 A1 | 8/2021 | Pushpala et al. |
| 2021/0321942 A1 | 10/2021 | Pushpala et al. |
| 2021/0345916 A1 | 11/2021 | Boock et al. |
| 2021/0353229 A1 | 11/2021 | Pierart et al. |
| 2021/0379370 A1 | 12/2021 | Windmiller et al. |
| 2021/0386338 A1 | 12/2021 | Zhang et al. |
| 2021/0393201 A1 | 12/2021 | Morelock et al. |
| 2022/0031244 A1 | 2/2022 | Windmiller et al. |
| 2022/0047190 A1 | 2/2022 | Taylor et al. |
| 2022/0054813 A1 | 2/2022 | Pushpala et al. |
| 2022/0054814 A1 | 2/2022 | Pushpala et al. |
| 2022/0104773 A1 | 4/2022 | Lee et al. |
| 2022/0151516 A1 | 5/2022 | Wang et al. |
| 2022/0151518 A1 | 5/2022 | Pushpala et al. |
| 2022/0151519 A1 | 5/2022 | Pushpala et al. |
| 2022/0151558 A1 | 5/2022 | Pushpala et al. |
| 2022/0175278 A1 | 6/2022 | Campbell et al. |
| 2022/0175279 A1 | 6/2022 | Pushpala et al. |
| 2022/0175282 A1 | 6/2022 | Hoss et al. |

(56) References Cited

U.S. PATENT DOCUMENTS

| | | |
|---|---|---|
| 2022/0214300 A1 | 7/2022 | Wang et al. |
| 2022/0225901 A1 | 7/2022 | Chapman et al. |
| 2022/0233107 A1 | 7/2022 | Pushpala et al. |
| 2022/0249189 A1 | 8/2022 | Choi et al. |
| 2022/0257181 A1 | 8/2022 | Wang et al. |
| 2022/0298291 A1 | 9/2022 | Shin et al. |
| 2022/0322975 A1 | 10/2022 | Baker et al. |
| 2022/0322977 A1 | 10/2022 | Simpson et al. |
| 2022/0361776 A1 | 11/2022 | Wang et al. |
| 2022/0370011 A1 | 11/2022 | Windmiller et al. |
| 2023/0003725 A1 | 1/2023 | Wang et al. |
| 2023/0012662 A1 | 1/2023 | Tehrani et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |
| 2023/0256220 A1 | 8/2023 | Mansfield et al. |
| 2023/0301552 A1 | 9/2023 | Mallires et al. |
| 2023/0310823 A1 | 10/2023 | Mansfield et al. |
| 2023/0414102 A1 | 12/2023 | Allen et al. |
| 2024/0008777 A1 | 1/2024 | Fuchs et al. |
| 2024/0081740 A1 | 3/2024 | Windmiller et al. |
| 2024/0164719 A1 | 5/2024 | Campbell et al. |
| 2024/0252115 A1 | 8/2024 | Tangney et al. |
| 2024/0341636 A1 | 10/2024 | Yang et al. |
| 2024/0366125 A1 | 11/2024 | Alonso-Soski et al. |
| 2024/0366149 A1 | 11/2024 | Kendall et al. |
| 2024/0382157 A1 | 11/2024 | Windmiller et al. |
| 2024/0408366 A1 | 12/2024 | Mansfield et al. |
| 2024/0423526 A1 | 12/2024 | Windmiller et al. |
| 2025/0000395 A1 | 1/2025 | Brister et al. |

FOREIGN PATENT DOCUMENTS

| | | |
|---|---|---|
| CN | 113717955 A | 11/2021 |
| DE | 102015209669 A1 | 12/2016 |
| EP | 1006868 B1 | 6/2004 |
| EP | 1372602 B1 | 4/2007 |
| EP | 1792565 B1 | 10/2008 |
| EP | 1187653 B1 | 3/2010 |
| EP | 2898821 B1 | 12/2017 |
| EP | 3364183 A1 | 8/2018 |
| EP | 3381370 A1 | 10/2018 |
| EP | 3829418 B1 | 11/2024 |
| EP | 3829437 B1 | 11/2024 |
| EP | 4009865 B1 | 11/2024 |
| EP | 4482372 A1 | 1/2025 |
| JP | H0222552 A | 1/1990 |
| JP | H0231741 A | 2/1990 |
| JP | H067324 A | 1/1994 |
| JP | H07275227 A | 10/1995 |
| JP | 2003038464 A | 2/2003 |
| JP | 2003038465 A | 2/2003 |
| JP | 2003111742 A | 4/2003 |
| JP | 2004180773 A | 7/2004 |
| JP | 2005087613 A | 4/2005 |
| JP | 2005525141 A | 8/2005 |
| JP | 2005322591 A | 11/2005 |
| JP | 2006510467 A | 3/2006 |
| JP | 2008512162 A | 4/2008 |
| JP | 2008540013 A | 11/2008 |
| JP | 2008544763 A | 12/2008 |
| JP | 2010523167 A | 7/2010 |
| JP | 2013506847 A | 2/2013 |
| JP | 2013521942 A | 6/2013 |
| JP | 2014533523 A | 12/2014 |
| JP | 2017108763 A | 6/2017 |
| JP | 2019107040 A | 7/2019 |
| JP | 2019526332 A | 9/2019 |
| JP | 2019205852 A | 12/2019 |
| JP | 2020170011 A | 10/2020 |
| JP | 2022501100 A | 1/2022 |
| JP | 2022508575 A | 1/2022 |
| KR | 20160108111 A | 9/2016 |
| WO | WO-0074763 A2 | 12/2000 |
| WO | WO-2006060106 A1 | 6/2006 |
| WO | WO-2006093422 A1 | 9/2006 |
| WO | WO-2006116242 A2 | 11/2006 |
| WO | WO-2007040938 A1 | 4/2007 |
| WO | WO-2009034313 A2 | 3/2009 |
| WO | WO-2009064164 A2 | 5/2009 |
| WO | WO-2009124095 A1 | 10/2009 |
| WO | WO-2010014959 A2 | 2/2010 |
| WO | WO-2010022252 A2 | 2/2010 |
| WO | WO-2010045247 A1 | 4/2010 |
| WO | WO-2010059276 A1 | 5/2010 |
| WO | WO-2010120364 A2 | 10/2010 |
| WO | WO-2011056095 A1 | 5/2011 |
| WO | WO-2012020332 A2 | 2/2012 |
| WO | WO-2012142625 A2 | 10/2012 |
| WO | WO-2013058879 A2 | 4/2013 |
| WO | WO-2014120114 A1 | 8/2014 |
| WO | WO-2015073459 A1 | 5/2015 |
| WO | WO-2016189301 A1 | 12/2016 |
| WO | WO-2017129980 A1 | 8/2017 |
| WO | WO-2017189707 A1 | 11/2017 |
| WO | WO-2018017196 A1 | 1/2018 |
| WO | WO-2018071265 A1 | 4/2018 |
| WO | WO-2018164886 A1 | 9/2018 |
| WO | WO-2018170363 A1 | 9/2018 |
| WO | WO-2019046333 A1 | 3/2019 |
| WO | WO-2019156934 A1 | 8/2019 |
| WO | WO-2019222615 A1 | 11/2019 |
| WO | WO-2019239258 A1 | 12/2019 |
| WO | WO-2020023804 A1 | 1/2020 |
| WO | WO-2020069565 A1 | 4/2020 |
| WO | WO-2020069567 A1 | 4/2020 |
| WO | WO-2020069570 A1 | 4/2020 |
| WO | WO-2020117918 A1 | 6/2020 |
| WO | WO-2021015389 A1 | 1/2021 |
| WO | WO-2021025260 A1 | 2/2021 |
| WO | WO-2021062475 A1 | 4/2021 |
| WO | WO-2021086690 A1 | 5/2021 |
| WO | WO-2021118124 A1 | 6/2021 |
| WO | WO-2021118431 A1 | 6/2021 |
| WO | WO-2021216186 A2 | 10/2021 |
| WO | WO-2021216186 A9 | 12/2021 |
| WO | WO-2022026764 A1 | 2/2022 |
| WO | WO-2022066985 A1 | 3/2022 |
| WO | WO-2022066992 A1 | 3/2022 |
| WO | WO-2022090741 A1 | 5/2022 |
| WO | WO-2022136785 A1 | 6/2022 |
| WO | WO-2022240700 A1 | 11/2022 |
| WO | WO-2023055755 A1 | 4/2023 |
| WO | WO-2023064877 A1 | 4/2023 |
| WO | WO-2023133468 A1 | 7/2023 |
| WO | WO-2023229662 A2 | 11/2023 |
| WO | WO-2024000015 A1 | 1/2024 |
| WO | WO-2024010827 A1 | 1/2024 |
| WO | WO-2024163950 A2 | 8/2024 |
| WO | WO-2024238798 A1 | 11/2024 |

OTHER PUBLICATIONS

American Diabetes Association Professional Practice Committee, "6. Glycemic Goals and Hypoglycemia: Standards of Care in Diabetes-2024" Diabetes Care Jan. 1, 2024; 47(Suppl 1):S111-S125.

American Diabetes Association Professional Practice Committee, "7. Diabetes Technology: Standards of Medical Care in Diabetes-2022" Diabetes Care Jan. 1, 2022; 45(Suppl 1):S97-S112.

Centers for Disease Control, "National Diabetes Statistics Report" May 2024, 16 pages.

Diabetes Control and Complications Trial Research Group, "The effect of intensive treatment of diabetes on the development and progression of long-term complications in insulin-dependent diabetes mellitus" N Engl J Med Sep. 30, 1993; 329(14):977-986.

Elsayed et al., "2. Classification and Diagnosis of Diabetes: Standards of Care in Diabetes-2023" Diabetes Care Jan. 1, 2023; 46(Suppl 1):S19-S40.

Extended European Search Report for European Application No. 21901579.9 mailed Oct. 4, 2024, 10 pages.

(56) References Cited

OTHER PUBLICATIONS

Extended European Search Report for European Application No. 23218205.5 dated Jun. 11, 2024, 7 pages.
Extended European Search Report for European Application No. EP21837561.6 dated Jun. 21, 2024, 7 pages.
Final Office Action for U.S. Appl. No. 18/527,128 mailed Sep. 6, 2024, 19 pages.
Final Office Action for U.S. Appl. No. 18/630,936 mailed Sep. 20, 2024, 16 pages.
Final Office Action mailed on Jul. 15, 2022, for U.S. Appl. No. 17/650,056, filed Feb. 4, 2022, 25 pages.
Final Office Action mailed on Mar. 15, 2024, for U.S. Appl. No. 17/367,274, filed Jul. 2, 2021, 33 pages.
Final Office Action mailed on Sep. 7, 2023, for U.S. Appl. No. 17/650,056, filed Feb. 4, 2022, 29 pages.
International Search Report and Written Opinion for PCT Application No. PCT/US2024/014324 mailed Sep. 20, 2024, 22 pages.
International Search Report and Written Opinion mailed on Feb. 6, 2024, for International Application No. PCT/US2022/078819, filed on Oct. 27, 2022, 13 pages.
Invitation to pay additional fees for International Application No. PCT/US2024/014324, dated Jul. 30, 2024, 16 pages.
Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.
Miller et al., "Hypoglycemia in patients with type 2 diabetes mellitus" Arch Intern Med Jul. 9, 2001; 161(13):1653-1659.
Newton et al., "Diabetic ketoacidosis in type 1 and type 2 diabetes mellitus: clinical and biochemical differences" Arch Intern Med Sep. 27, 2004; 164(17):1925-1931.
Non-Final Office Action for U.S. Appl. No. 17/073,331 mailed Aug. 28, 2024, 13 pages.
Non-Final Office Action for U.S. Appl. No. 18/630,936 mailed Jun. 13, 2024, 19 pages.
Non-Final Office Action mailed on Jul. 30, 2024, for U.S. Appl. No. 17/650,056, filed Feb. 4, 2022, 32 pages.
Non-Final Office Action mailed on Mar. 29, 2023, for U.S. Appl. No. 17/650,056, filed Feb. 4, 2022, 27 pages.
Non-Final Office Action mailed on May 24, 2024, for U.S. Appl. No. 18/527,128, filed Dec. 1, 2023, 17 pages.
Notice of Allowance (Corrected) mailed on Apr. 19, 2024, for U.S. Appl. No. 18/086,543, filed Dec. 21, 2022, 4 pages.
Notice of Allowance (Corrected) mailed on Mar. 18, 2024, for U.S. Appl. No. 17/349,234, filed Jun. 16, 2021, 9 pages.
Notice of Allowance for U.S. Appl. No. 17/389,156 mailed Sep. 25, 2024, 12 pages.
Notice of Allowance mailed on Apr. 10, 2024, for U.S. Appl. No. 18/086,543, filed Dec. 21, 2022, 10 pages.
Notice of Allowance mailed on Jun. 11, 2024, for U.S. Appl. No. 15/913,709, filed Mar. 6, 2018, 9 pages.
Notice of Allowance mailed on Mar. 21, 2024, for U.S. Appl. No. 18/086,543, filed Dec. 21, 2022, 6 pages.
Notice of Allowance mailed on Mar. 4, 2024, for U.S. Appl. No. 18/086,543, filed Dec. 21, 2022, 10 pages.
Segel et al., "Hypoglycemia—associated autonomic failure in advanced type 2 diabetes" Diabetes Mar. 2022; 51(3):724-733.
Shivers et al., "Turn it off!: diabetes device alarm fatigue considerations for the present and the future" J Diabetes Sci Technol May 1, 2013; 7(3):789-794.
Tanenbaum et al., "Diabetes Device Use in Adults With Type 1 Diabetes: Barriers to Uptake and Potential Intervention Targets" Diabetes Care Feb. 2017; 40(2):181-187.
UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.

Ward et al., "A Wired-Based Dual-Analyte Sensor for Glucose and Lactate: In Vitro and In Vivo Evaluation" Diabetes Technology and Therapeutics Jun. 2004; 6(3):389-401.
Abbot Press Release (2020). "New late-breaking data show use of Abbott's Freestyle® Libre System significantly reduces HBA1C levels in people with type 2 diabetes using insulin or not," 3 pages.
Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. 8 pages.
Allen et al., "Continuous glucose monitoring counseling improves physical activity behaviors of individuals with type 2 diabetes: A randomized clinical trial" Diabetes Res Clin Pract. Jun. 2008; 80(3): 371-379. doi:10.1016/j.diabres.2008.01.006.
American Diabetes Association® Press Release (2020). "American Diabetes Association® Applauds policymakers' Focus on Addressing High Costs of Insulin for Seven Million Americans," 4 pages.
Bantle, J.P. et al. (1997). "Glucose measurement in patients with diabetes mellitus with dermal interstitial fluid," J. Lab. Clin. Med. 130:436-441.
Barrett et al., "Risk for Newly Diagnosed Diabetes 30 Days After SARS-CoV-2 Infection Among Persons Aged 18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.
Beckles, G.L. et al. (2016). "Disparities in the prevalence of diagnosed diabetes—United States, 1999-2002 and 2011-2014," MMWR 65:1265-1269.
Brown, "Design of Electronics for Wearable Electrochemical Sensors" University of California, San Diego, Master's Thesis (2019) 48 pages.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Centers for Disease Control, "National Diabetes Statistics Report 2020 Estimates of Diabetes and Its Burden in the United States" (2020) 32 pages.
Chang, H. et al. (2017). "A swellable microneedle patch to rapidly extract skin interstitial fluid for timely metabolic analysis," Adv. Mater. 29:1702243. 8 pages.
Chen et al., "Electrochemically Mediated Electrodeposition/Electropolymerization to Yield a Glucose Microbiosensor with Improved Characteristics" Anal. Chem. (2002) 74:368-372.
DEXCOM (2020). Analyst Day Presentation, 19 total pages.
DEXCOM (2020). Analyst Day Presentation, 27 total pages.
Diabetes Care (2021). "7. Diabetes Technology: Standards of Medical Care in Diabetes—2021," Diabetes Care 44(Supplement 1):S85-S99.
Donnelly, R.F. et al. (2007). "Microstructured Devices for Transdermal Drug Delivery and Minimally-Invasive Patient Monitoring," Recent Patents on Drug Delivery & Formulation 1:195-200.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al., "Behavior Modification in Prediabetes and Diabetes: Potential Use of Real-Time Continuous Glucose Monitoring " Journal of Diabetes Science and Technology Mar. 2019; 13(2):271-275.
Ehrhardt et al., "Continuous Glucose Monitoring as a Behavior Modification Tool" Clin Diabetes. Apr. 2020; 38(2):126-131. doi: 10.2337/cd19-0037.
Ehrhardt et al., "The Effect of Real-Time Continuous Glucose Monitoring on Glycemic Control in Patients with Type 2 Diabetes Mellitus" Journal of Diabetes Science and Technology May 2011; 5(3):668-675.
Extended European Search Report mailed on Mar. 30, 2023, for European Application No. EP20881425.1, 8 pages.
Extended European Search Report mailed on May 8, 2015, for EP Application No. 12 842 020.5, filed on Aug. 31, 2012, 7 pages.

(56) References Cited

OTHER PUBLICATIONS

Extended European Search Report mailed on Oct. 27, 2022, for EP Application No. 21 850 331.6, filed on Jul. 29, 2021, 8 pages.
Fang, M. et al. (2021). "Trends in Diabetes Treatment and Control in U.S. Adults, 1999-2018," N. Engl. Med. 384:2219-2228.
Final Office Action mailed on Aug. 15, 2022, for U.S. Appl. No. 16/051,398, filed Jul. 31, 2018, 15 pages.
Final Office Action mailed on Aug. 19, 2016, for U.S. Appl. No. 14/965,755, filed Dec. 10, 2015, 17 pages.
Final Office Action mailed on Aug. 29, 2023, for U.S. Appl. No. 18/086,543, filed Dec. 21, 2022, 17 pages.
Final Office Action mailed on Dec. 7, 2020, for U.S. Appl. No. 15/961,793, filed Apr. 24, 2018, 13 pages.
Final Office Action mailed on Feb. 1, 2024, for U.S. Appl. No. 17/073,331, filed Oct. 17, 2020, 12 pages.
Final Office Action mailed on Feb. 8, 2024, for U.S. Appl. No. 16/051,398, filed Jul. 31, 2018, 15 pages.
Final Office Action mailed on Jun. 9, 2021, for U.S. Appl. No. 16/169,939, filed Oct. 24, 2018, 24 pages.
Final Office Action mailed on May 18, 2018, for U.S. Appl. No. 15/687,145, filed Aug. 25, 2017, 23 pages.
Final Office Action mailed on May 21, 2021, for U.S. Appl. No. 16/051,398, filed Jul. 31, 2018, 11 pages.
Final Office Action mailed on May 9, 2022, for U.S. Appl. No. 17/389,153, filed Jul. 29, 2021, 17 pages.
Final Office Action mailed on Nov. 27, 2023, for U.S. Appl. No. 17/389,156, filed Jul. 29, 2021, 29 pages.
Final Office Action mailed on Nov. 28, 2016, for U.S. Appl. No. 14/342,536, filed Jul. 30, 2014, 34 pages.
Final Office Action mailed on Oct. 27, 2022, for U.S. Appl. No. 15/913,709, filed Mar. 6, 2018, 21 pages.
Final Office Action mailed on Sep. 23, 2021, for U.S. Appl. No. 15/913,709, filed Mar. 6, 2018, 17 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gittard, S.D. et al. (2009). "Fabrication of Polymer Microneedles Using a Two-Photon Polymerization and Micromolding Process," J. Diabetes Sci. Technol. 3:304-311.
Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24. 11 pages.
Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
International Search Report mailed on Aug. 29, 2022, for PCT Application No. PCT/US2022/028196, filed on May 6, 2022, 2 pages.
International Search Report mailed on Dec. 30, 2021, for PCT Application No. PCT/US2021/043786, filed on Jul. 29, 2021, 7 pages.
International Search Report mailed on Feb. 4, 2021, for PCT Application No. PCT/US2020/056517, filed on Oct. 20, 2020, 2 pages.
International Search Report mailed on Jun. 27, 2013, for PCT Application No. PCT/US2012/053544, filed on Aug. 31, 2012, 4 pages.
International Search Report mailed on Sep. 10, 2020, for PCT Application No. PCT/US2020/037379, filed on Jun. 12, 2020, 2 pages.
International Search Report mailed on Sep. 30, 2021, for PCT Application No. PCT/US2021/040385, filed on Jul. 2, 2021, 2 pages.
Jeon, G. et al. (2011). "Electrically Actuatable Smart Nanoporous Membrane for Pulsatile Drug Release," Nano Lett. 11:1284-1288.
Jina, A et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring With Glycemic Control and Acute Metabolic Events Among Patients With Insulin-Treated Diabetes," JAMA 325:2273-2284.
Lhernould, M.S. et al. (2015). "Review of Patents for Microneedle Application Devices Allowing Fluid Injections Through the Skin," Recent Patents on Drug Delivery & Formulation 9:146-157.
Malitesta et al. (1990). "Glucose fast-response amperometric sensor based on glucose oxidase immobilized in an electropolymerized poly(o-phenylenediamine) film," Anal. Chem. 62:2735-2740.
Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.
McClatchey, P.M. et al. (2019). "Fibrotic Encapsulation is the Dominant Source of Continuous Glucose Monitor Delays," Diabetes 68:1892-1901.
Miller, P.R. et al. (2011). "Integrated carbon fiber electrodes within hollow polymer microneedles for transdermal electrochemical sensing," BioMicrofluidics 5(1):013415. 14 pages.
Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Non-Final Office Action mailed on Apr. 13, 2020, for U.S. Appl. No. 15/961,793, filed Apr. 24, 2018, 13 pages.
Non-Final Office Action mailed on Apr. 6, 2017, for U.S. Appl. No. 14/342,536, filed Jul. 30, 2014, 32 pages.
Non-Final Office Action mailed on Apr. 8, 2022, for U.S. Appl. No. 17/650,056, filed Feb. 4, 2022, 14 pages.
Non-Final Office Action mailed on Dec. 13, 2023, for U.S. Appl. No. 18/086,543, filed Dec. 21, 2022, 16 pages.
Non-Final Office Action mailed on Dec. 21, 2022, for U.S. Appl. No. 16/051,398, filed Jul. 31, 2018, 12 pages.
Non-Final Office Action mailed on Feb. 16, 2023 for U.S. Appl. No. 17/738,990, 9 pages.
Non-Final Office Action mailed on Jan. 19, 2018, for U.S. Appl. No. 14/843,926, filed Sep. 2, 2015, 11 pages.
Non-Final Office Action mailed on Jan. 26, 2024, for U.S. Appl. No. 15/913,709, filed Mar. 6, 2018, 20 pages.
Non-Final Office Action mailed on Jan. 27, 2023, for U.S. Appl. No. 17/971,415, filed Oct. 21, 2022, 15 pages.
Non-Final Office Action mailed on Jun. 2, 2023, for U.S. Appl. No. 17/367,274, filed Jul. 2, 2021, 27 pages.
Non-Final Office Action mailed on Jun. 20, 2023, for U.S. Appl. No. 17/073,331, filed Oct. 17, 2020, 10 pages.
Non-Final Office Action mailed on Mar. 10, 2016, for U.S. Appl. No. 14/965,755, filed Dec. 10, 2015, 15 pages.
Non-Final Office Action mailed on Mar. 30, 2016, for U.S. Appl. No. 14/342,536, filed Jul. 30, 2014, 31 pages.
Non-Final Office Action mailed on Mar. 9, 2017, for U.S. Appl. No. 14/965,755, filed Dec. 10, 2015, 17 pages.
Non-Final Office Action mailed on Mar. 9, 2023 for U.S. Appl. No. 17/389,156, filed Jul. 29, 2021, 24 pages.
Non-Final Office Action mailed on May 13, 2022, for U.S. Appl. No. 15/913,709, filed Mar. 6, 2018, 20 pages.

(56) References Cited

OTHER PUBLICATIONS

Non-Final Office Action mailed on May 2, 2023, for U.S. Appl. No. 15/913,709, filed Mar. 6, 2018, 18 pages.
Non-Final Office Action mailed on May 24, 2023, for U.S. Appl. No. 18/086,543, filed Dec. 21, 2022, 19 pages.
Non-Final Office Action mailed on Nov. 1, 2017, for U.S. Appl. No. 15/687,145, filed Aug. 25, 2017, 19 pages.
Non-Final Office Action mailed on Nov. 26, 2021, for U.S. Appl. No. 16/051,398, filed Jul. 31, 2018, 15 pages.
Non-Final Office Action mailed on Nov. 29, 2021, for U.S. Appl. No. 17/389,153, filed Jul. 29, 2021, 14 pages.
Non-Final Office Action mailed on Nov. 4, 2021, for U.S. Appl. No. 16/169,939, filed Oct. 24, 2018, 20 pages.
Non-Final Office Action mailed on Oct. 16, 2020, for U.S. Appl. No. 16/051,398, filed Jul. 31, 2018, 13 pages.
Non-Final Office Action mailed on Sep. 15, 2023, for U.S. Appl. No. 16/051,398, filed Jul. 31, 2018, 12 pages.
Non-Final Office Action mailed on Sep. 16, 2020, for U.S. Appl. No. 15/913,709, filed Mar. 6, 2018, 15 pages.
Non-Final Office Action mailed on Sep. 3, 2020, for U.S. Appl. No. 16/169,939, filed Oct. 24, 2018, 19 pages.
Notice of Allowance (Corrected) mailed on Jan. 25, 2024, for U.S. Appl. No. 17/349,234, filed Jun. 16, 2021, 4 pages.
Notice of Allowance mailed on Aug. 24, 2018, for U.S. Appl. No. 15/687,145, filed Aug. 25, 2017, 7 pages.
Notice of Allowance mailed on Dec. 20, 2023, for U.S. Appl. No. 17/349,234, filed Jun. 16, 2021, 13 pages.
Notice of Allowance mailed on Feb. 13, 2018, for U.S. Appl. No. 14/843,926, filed Sep. 2, 2015, 8 pages.
Notice of Allowance mailed on Jul. 12, 2017, for U.S. Appl. No. 14/342,536, filed Jul. 30, 2014, 14 pages.
Notice of Allowance mailed on Jul. 6, 2017, for U.S. Appl. No. 14/965,755, filed Dec. 10, 2015, 12 pages.
Notice of Allowance mailed on Jun. 12, 2023, for U.S. Appl. No. 17/738,990, filed May 6, 2022, 7 pages.
Notice of Allowance mailed on Jun. 12, 2023, for U.S. Appl. No. 17/971,415, filed Oct. 21, 2022, 14 pages.
Notice of Allowance mailed on May 25, 2021, for U.S. Appl. No. 15/961,793, filed Apr. 24, 2018, 11 pages.
Notice of Allowance mailed on Sep. 12, 2022, for U.S. Appl. No. 17/389,153, filed Jul. 29, 2021, 8 pages.
Notice of Allowance mailed on Sep. 25, 2023, for U.S. Appl. No. 17/971,415, filed Oct. 21, 2022, 8 pages.
Notice of Allowance mailed on Sep. 26, 2023, for U.S. Appl. No. 17/738,990, filed May 6, 2022, 7 pages.
Office Action and Swedish Search Report mailed on Oct. 17, 2023, for SE Application No. 2251496-2, 8 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Singh, T.R.R. et al. (2010). "Microporation techniques for enhanced delivery of therapeutic agents," Recent Patents on Drug Delivery & Formulation 4:1-17.

Supplementary European Search Report mailed on Oct. 9, 2023, for EP Application No. 22808101.4, 4 pages.
Swedish Search Report mailed on Feb. 3, 2023 for SE Application No. 2350067-1, 7 pages.
Texas Instruments (Sep. 2007). Data sheet for a LMP2234 quad micropower, 1.6V, precision, operational amplifier with CMOS input, Sep. 2007, revised Mar. 2013. 31 total pages.
Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Written Opinion of the International Search Authority mailed on Sep. 10, 2020, for PCT Application No. PCT/US2020/037379, filed on Jun. 12, 2020, 4 pages.
Written Opinion of the International Searching Authority mailed on Aug. 29, 2022, for PCT Application No. PCT/US2022/028196, filed on May 6, 2022, 5 pages.
Written Opinion of the International Searching Authority mailed on Dec. 30, 2021, for PCT Application No. PCT/US2021/043786, filed on Jul. 29, 2021, 10 pages.
Written Opinion of the International Searching Authority mailed on Feb. 4, 2021, for PCT Application No. PCT/US2020/056517, filed on Oct. 20, 2020, 5 pages.
Written Opinion of the International Searching Authority mailed on Jun. 27, 2013, for PCT Application No. PCT/US2012/053544, filed on Aug. 31, 2012, 15 pages.
Written Opinion of the International Searching Authority mailed on Sep. 30, 2021, for PCT Application No. PCT/US2021/040385, filed on Jul. 2, 2021, 5 pages.
Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Extended European Search Report for European Application No. EP20898007.8 dated Nov. 29, 2023, 9 pages.
International Search Report and Written Opinion for PCT Application No. PCT/US2020/064700, mail date Mar. 9, 2021, 11 pages.
Battelino et al., "Continuous glucose monitoring and metrics for clinical trials: an international consensus statement" Lancet Diabetes Endocrinol (2023) 11:42-57.
Clutter et al., "Epinephrine plasma metabolic clearance rates and physiologic thresholds for metabolic and hemodynamic actions in man" J Clin Invest. (1980) 66(1):94-101.
Czupryniak et al., "Ambulatory Glucose Profile (AGP) Report in Daily Care of Patients with Diabetes: Practical Tips and Recommendations" Diabetes Ther (2022) 13:811-821.
Donnelly et al., "Microneedle Arrays Allow Lower Microbial Penetration Than Hypodermic Needles In Vitro" Pharmaceutical Research (2009) 26(11):2513-2522.
Fayfman et al., "Management of Hyperglycemic Crises: Diabetic ketoacidosis and hyperglycemic hyperosmolar state" Med Clin North Am. May 2017; 101(3):587-606.

(56) References Cited

OTHER PUBLICATIONS

Final Office Action for U.S. Appl. No. 17/073,331 mailed Dec. 17, 2024, 13 pages.
Gao et al., "Simultaneous detection of glucose, uric acid and cholesterol using flexible microneedle electrode array-based biosensor and multi-channel portable electrochemical analyzer" Sensors and Actuators B: Chemical (2019) 287:102-110.
Ghimire et al., "Ketoacidosis" StatPearls Publishing, Jan. 2024, NCBI Bookshelf, 8 pages.
Heinemann, "Interferences With CGM Systems: Practical Relevance?" Journal of Diabetes Science and Technology (2022) vol. 16(2) 271-274.
Henry et al., "Microfabricated microneedles: A novel approach to transdermal drug delivery" J. Pharmaceutical Sciences (1998) 87(8):922-925.
Mahs et al., "Effect of Acetaminophen on CGM Glucose in an Outpatient Setting" Diabetes Care (2015) 38:e158-e159.
Nguyen et al., "Human studies with microneedles for evaluation of their efficacy and safety" Expert Opinion on Drug Delivery (2018) 15:3, 235-245.
Non-Final Office Action for U.S. Appl. No. 17/389,156 mailed Jan. 22, 2025, 17 pages.
Non-Final Office Action for U.S. Appl. No. 18/630,936 mailed on Dec. 12, 2024, 18 pages.
Non-Final Office Action for U.S. Appl. No. 18/824,598 mailed Nov. 4, 2024, 14 pages.
Non-Final Office Action for U.S. Appl. No. 18/824,598 mailed on Dec. 23, 2024, 27 pages.
Non-Final Office Action for U.S. Appl. No. 18/926,029 mailed on Dec. 12, 2024, 10 pages.
Notice of Allowance for U.S. Appl. No. 17/389,156 mailed Dec. 27, 2024, 6 pages.
Notice of Allowance for U.S. Appl. No. 17/389,156 mailed Nov. 20, 2024, 5 pages.
Ohashi et al., "Analgesic Effect of Acetaminophen: A Review of Known and Novel Mechanisms of Action" Front Pharmacol. Nov. 30, 2020;11:580289, 6 pages.
Prausnitz, "Engineering Microneedle Patches for Vaccination and Drug Delivery to Skin" Annu. Rev. Chem. Biomol. Eng. (2017) 8:177-200.
Samant et al., "Mechanisms of sampling interstitial fluid from skin using a microneedle patch," Proc. Natl Acad. Sci. U.S.A. (2018) 115(8):4583-4588.
Vicente-Perez et al., "Repeat application of microneedles does not alter skin appearance or barrier function and causes No. measurable disturbance of serum biomarkers of infection, inflammation or immunity in mice in vivo" European Journal of Pharmaceutics and Biopharmaceutics (2017) 117:400-407.
Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development (2018) 7(1) 95-101.

\* cited by examiner

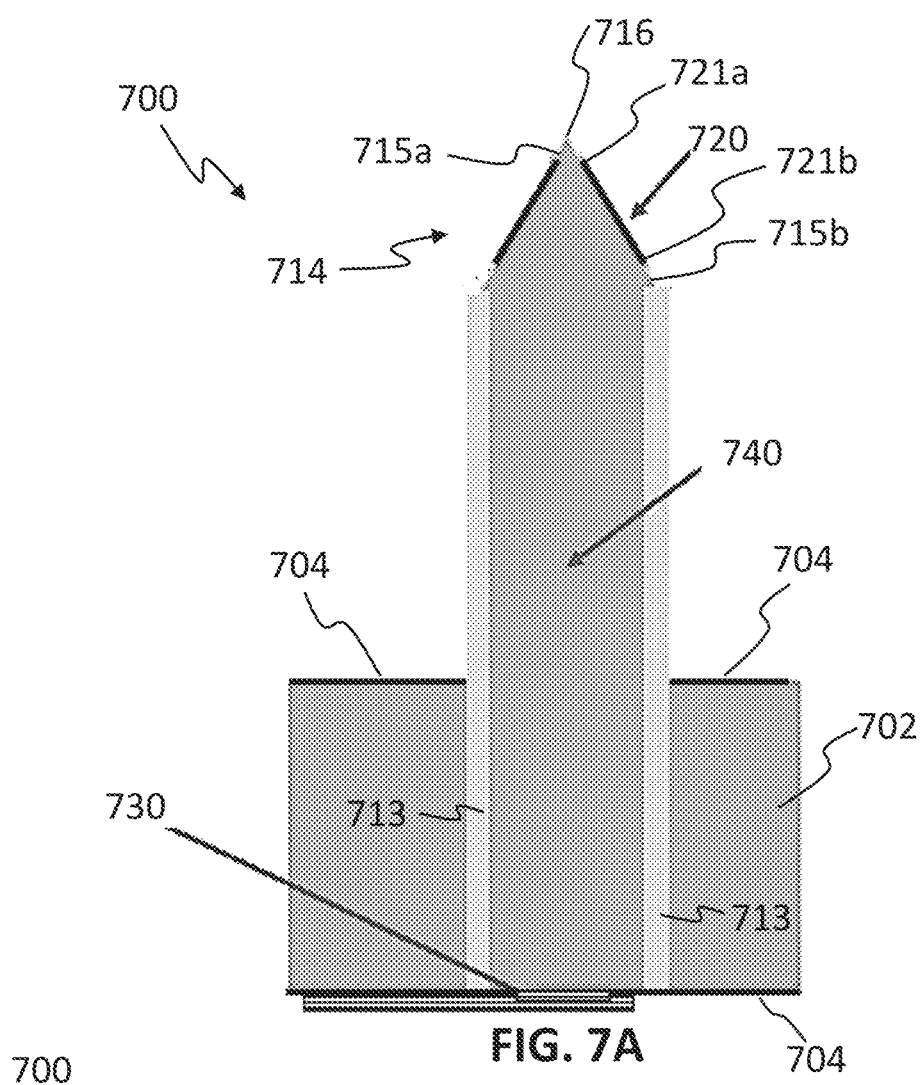
FIG. 7A
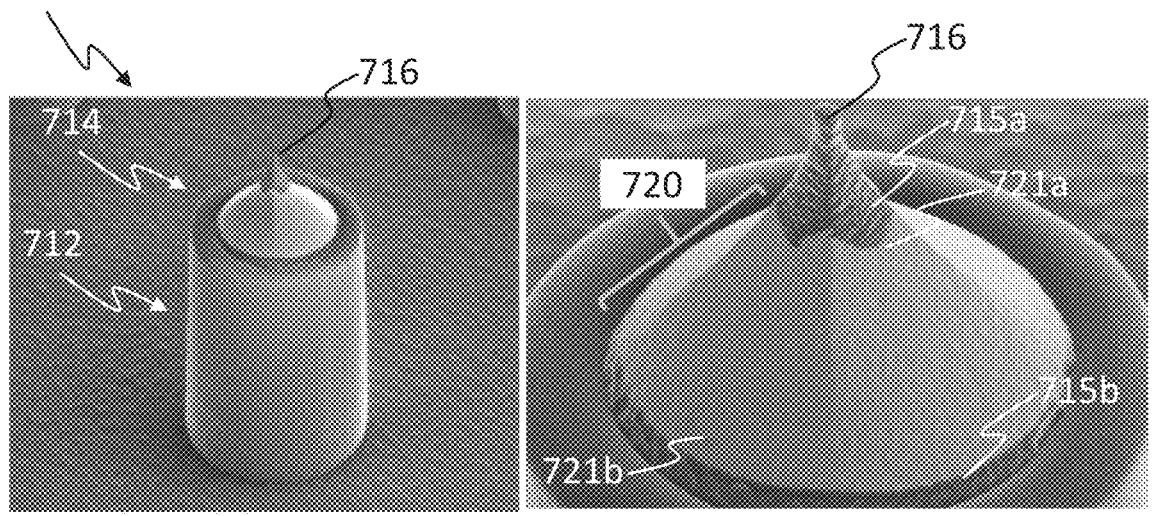
FIG. 7B
FIG. 7C

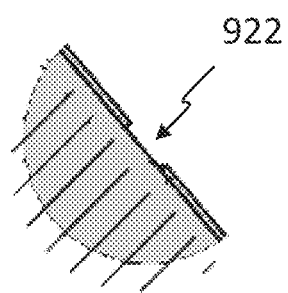
FIG. 9F
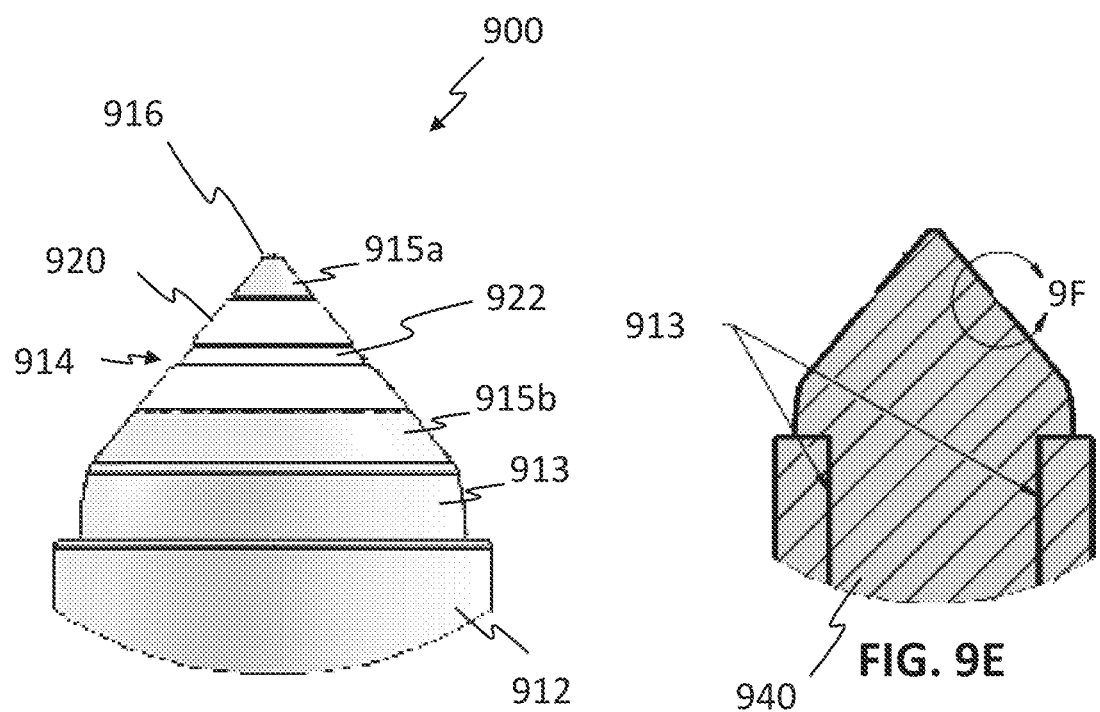
FIG. 9C
FIG. 9E
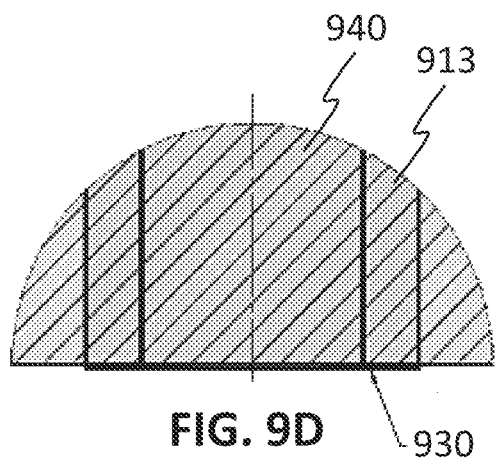
FIG. 9D

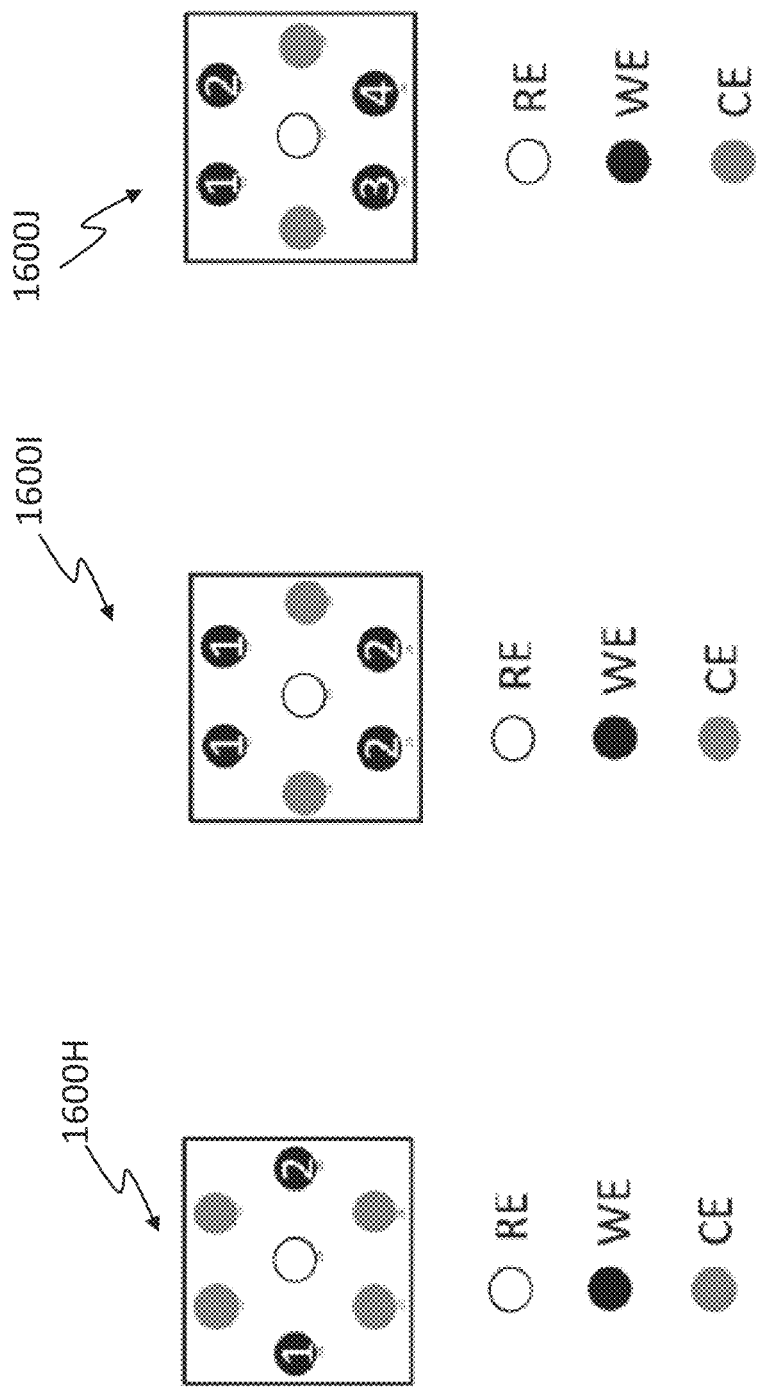

N = 48 for each group

METHOD FOR IMPROVED SENSOR SENSITIVITY OF A MICRONEEDLE-BASED CONTINUOUS ANALYTE MONITORING SYSTEM

CROSS-REFERENCE TO RELATED APPLICATIONS

This application claims the benefit of U.S. Provisional Patent Application No. 63/443,010, filed Feb. 2, 2023, U.S. Provisional Patent Application No. 63/443,024, filed Feb. 2, 2023, and U.S. Provisional Patent Application No. 63/613,566, filed Dec. 21, 2023, the content of each of which is herein incorporated by reference in their entirety.

REFERENCE TO AN ELECTRONIC SEQUENCE LISTING

The contents of the electronic sequence listing (BLNQ_044_02US_SeqList_ST26.xml; Size: 2,047 bytes; and Date of Creation: May 3, 2024) are herein incorporated by reference in its entirety.

TECHNICAL FIELD

This invention relates generally to the field of analyte monitoring, such as continuous glucose monitoring.

BACKGROUND

Diabetes is a chronic disease in which the body does not produce or properly utilize insulin, a hormone that regulates blood glucose. Insulin may be administered to a diabetic patient to help regulate blood glucose levels, though blood glucose levels must nevertheless be carefully monitored to help ensure that timing and dosage are appropriate. Without proper management of their condition, diabetic patients may suffer from a variety of complications resulting from hyperglycemia (high blood sugar levels) or hypoglycemia (low blood sugar levels).

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure glucose level in that blood sample. However, a patient using this process can typically only measure his or her glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion and signal latency (e.g., due to the time required for the glucose analyte to diffuse from capillary sources to the sensor). These weaknesses also lead to a number of drawbacks, such as pain experienced by the patient when electrochemical sensors are inserted, and limited accuracy in glucose measurements, particularly when blood glucose levels are changing rapidly. Accordingly, there is a need for a new and improved analyte monitoring system.

SUMMARY

According to a variation, the present disclosure relates to a system and method for improving stability of a microneedle-based continuous analyte monitoring system.

In variations, the present disclosure further relates to a device for use in sensing an analyte, comprising a microneedle, an electrode material on the microneedle, a biorecognition layer on the electrode material, the biorecognition layer comprising a polymer, a biorecognition element configured to react with the analyte, and an interferent blocking agent that fills voids within the polymer, and a diffusion-limiting layer on the biorecognition layer. In variations, the voids within the polymer traverse a thickness of the polymer. In variations, the interferent blocking agent is a non-conducting polymer, at least a portion of the interferent blocking agent is in contact with the electrode material, and/or the interferent blocking agent fills at least about 80% of the voids within the polymer to limit access by interferents to the electrode material, and/or the interferent blocking agent comprises one or more of resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol. In variations, the biorecognition element is within the polymer and/or the biorecognition element is glucose oxidase, glucose dehydrogenase, 3-hydroxybutyrate dehydrogenase, or lactate dehydrogenase, the polymer comprises one or more of aniline, acetylene, phenylene, phenylene vinylene, phenylene diamine, thiophene, 3,4-ethylenedioxythiophene, and aminophenylboronic acid. In variations, the diffusion-limiting layer is hydrophobic and/or the diffusion-limiting layer comprises one or more of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene. In variations, the analyte comprises one or more of glucose, ketone, and lactate. In variations, the electrode material comprises platinum, palladium, iridium, rhodium, gold, ruthenium, titanium, nickel, carbon, doped diamond, or combinations thereof. In variations, interference current at the electrode material of the device changes less than 70% over a one-week period, and/or interference current at the electrode material of the device changes less than 10% over a one-week period. In variations, at least a portion of the voids are exposed to a surface of the electrode material. In variations, the biorecognition element is physically entrapped within the polymer. In variations, the interferent blocking agent comprises phenol. In variations, the phenol is present within the biorecognition layer at a concentration of between about 0.1 mg/ml or 0.01% w/v and about 10 mg/ml or 1% w/v, and/or polymerized phenol is entrapped within the voids of the polymer.

In variations, the present disclosure further relates to a method for manufacturing a device for use in sensing an analyte, comprising depositing a biorecognition element and a polymer on an electrode material disposed on a microneedle, applying an interferent blocking agent to the polymer after deposition, thereby filling voids within the polymer with the interferent blocking agent, and depositing a diffusion-limiting layer on the polymer. In variations, the biorecognition element is configured to react with the analyte. In variations, applying comprises electropolymerizing the interferent blocking agent. In variations, the interferent blocking agent comprises phenol and is applied as a mixture having a concentration of between about 1 mM phenol and about 100 mM phenol.

In variations, the present disclosure further relates to a device for use in sensing an analyte, comprising a microneedle, an electrode material on the microneedle, a biorecognition layer on the electrode material, the biorecognition layer comprising a polymer, a biorecognition element configured to react with the analyte, and an interferent blocking agent that fills voids within the polymer, a diffusion-limiting layer, and an attachment enhancer configured to decrease analyte sensing variability, where the attachment enhancer is positioned between the biorecognition layer and the diffusion-limiting layer. In variations, the attachment enhancer comprises a plurality of molecules and a first end of each of the plurality of molecules is covalently bound to the biorecognition layer. In variations, the attachment enhancer comprises a plurality of molecules and a second end of each of the plurality of molecules is partially immobilized within the diffusion-limiting layer. In variations, the attachment enhancer covalently binds to the biorecognition element. In variations, the biorecognition element is glucose oxidase and the attachment enhancer covalently binds to the glucose oxidase. In variations, the polymer comprises one or more of aniline, acetylene, phenylene, phenylene vinylene, phenylene diamine, thiophene, 3,4-ethylenedioxythiophene, and aminophenylboronic acid. In variations, at least a portion of the interferent blocking agent is in contact with the electrode material. In variations, interference current at the electrode material of the device changes less than 10% over a one-week period. In variations, the second end comprises at least one hydroxyl group and/or the second end interacts with the diffusion-limiting layer via Van der Waals forces. In variations, each of the plurality of molecules is a cross-linking agent. In variations, the at least one hydroxyl group forms hydrogen bonds with the diffusion-limiting layer. In variations, the cross-linking agent comprises epoxide functional groups, the cross-linking agent comprises one selected from the group consisting of: 1,4-butanediol diglycidyl ether, 1,6-hexanediol diglycidyl ether, neopentyl glycol diglycidyl ether, poly(propylene glycol) diglycidyl ether, trimethylolethane diglycidyl ether, trimethylolethane triglycidyl ether, diglycidyl resorcinol ether, diglycidyl ether, 1,4-cyclohexane dimethanol diglycidyl ether, castor oil glycidyl ether, and bisphenol A diglycidyl ether, and/or the cross-linking agent comprises one selected from the group consisting of: glutaraldehyde, poly (dimethylsiloxane)-diglycidyl ether, tetracyclooxypropryl-4,4-diaminodiphenylmethane, polyethylene glycol diglycidyl ether, and 4-(2, 3-epoxypropoxy)-N,N-bis(2,3-epoxypropyl) aniline. In variations, the cross-linking agent comprises N (1, 2, 3, 4) epoxide functional groups connected to a linker. In variations, the linker is one selected from the group consisting of: aromatic, aliphatic, linear, and branched.

In variations, the present disclosure further relates to a method for manufacturing a device for use in sensing an analyte, comprising depositing a biorecognition element and a polymer on an electrode material disposed on a microneedle, applying an interferent blocking agent to the polymer, thereby filling voids within the polymer with the interferent blocking agent, exposing the polymer to an attachment enhancer, and after exposing the polymer to the attachment enhancer, depositing a diffusion-limiting layer on the biorecognition layer. In variations, the biorecognition element is configured to react with the analyte. In variations, the applying comprises electropolymerizing the interferent blocking agent. In variations, the interferent blocking agent comprises phenol and is applied as a mixture having a concentration of between about 1 mM phenol and about 100 mM phenol. In variations, exposing the polymer to the attachment enhancer comprises one or more of drop casting, spray coating, soaking, spin coating, and chemical vapor deposition and/or exposing the polymer to the attachment enhancer comprises soaking the polymer with a buffer solution including the attachment enhancer. In variations, the soaking is performed for a time period between about 5 minutes and about 3 days and/or the soaking is performed for a time period greater than about 16 hours.

In variations, the present disclosure further relates to a device for use in sensing an analyte, comprising a microneedle, an electrode material on the microneedle, and a biorecognition layer on the electrode material, the biorecognition layer comprising a polymer, a biorecognition element configured to react with the analyte, and an interferent blocking agent that fills voids within the polymer.

In some variations, the present disclosure further relates to a device for use in sensing an analyte, comprising a microneedle, an electrode material on the microneedle, a biorecognition layer on the electrode material, the biorecognition layer comprising phenylene diamine, a biorecognition element, and polyphenol, the polyphenol filling voids within the phenylene diamine, where the biorecognition element is configured to react with the analyte, and a polyurethane-based diffusion-limiting layer on the biorecognition layer.

In some variations, the present disclosure further relates to a method for manufacturing a device for use in sensing an analyte, comprising depositing a biorecognition element and a polymer on an electrode material disposed on a microneedle, where the biorecognition element is configured to react with the analyte, and applying an interferent blocking agent to the polymer after deposition, thereby filling voids within the polymer with the interferent blocking agent.

In some variations, the present disclosure further relates to a method for manufacturing a device for use in sensing an analyte, comprising depositing a biorecognition element and phenylene diamine on an electrode material disposed on a microneedle, where the biorecognition element is configured to react with the analyte, applying polyphenol to the phenylene diamine after deposition, thereby filling voids within the phenylene diamine with the polyphenol, and depositing a polyurethane-based diffusion-limiting layer on the phenylene diamine.

In some variations, the present disclosure further relates to a device for use in sensing an analyte, comprising a microneedle, an electrode material on the microneedle, a biorecognition layer on the electrode material, the biorecognition layer comprising phenylene diamine, a biorecognition element configured to react with the analyte, and polyphenol that fills voids within the phenylene diamine, a polyurethane-based diffusion-limiting layer, and an attachment enhancer configured to decrease analyte sensing variability, where the attachment enhancer comprises 1,4-butanediol diglycidyl ether and is positioned between the biorecognition layer and the polyurethane-based diffusion-limiting layer.

In some variations, the present disclosure further relates to a method for manufacturing a device for use in sensing an analyte, comprising depositing a biorecognition element and phenylene-diamine on an electrode material disposed on a microneedle, where the biorecognition element is configured to react with the analyte, applying polyphenol to the phenylene diamine, thereby filling voids within the phenylene diamine with the polyphenol, exposing the phenylene diamine to an attachment enhancer comprising 1,4-butanediol diglycidyl ether, and after exposing the phenylene diamine to the 1,4-butanediol diglycidyl ether, depositing a polyurethane-based diffusion-limiting layer on the biorecognition layer.

In some variations, the present disclosure further relates to an analyte monitoring device, comprising a plurality of microneedles arranged in an array, the plurality of microneedles comprising a plurality of working electrodes, a reference electrode, and a counter electrode, wherein the plurality of working electrodes are arranged between the reference electrode and the counter electrode.

In some variations, the present disclosure further relates to a microneedle array for use in sensing an analyte, comprising a plurality of sensing microneedles, each of the plurality of sensing microneedles comprising a working electrode comprising a biorecognition layer, the biorecognition layer comprising a biorecognition element configured to react with the analyte, a first microneedle comprising a counter electrode, and a second microneedle comprising a reference electrode, wherein the plurality of sensing microneedles are connected to the first microneedle such that current flows between the plurality of sensing microneedles and the first microneedle, the current resulting from a potential applied between the plurality of sensing microneedles and the second microneedle, and wherein the plurality of sensing microneedles are positioned between the first microneedle and the second microneedle.

BRIEF DESCRIPTION OF THE DRAWINGS

FIG. 7A depicts a cross-sectional side view of a columnar microneedle having a tapered distal end. FIGS. 7B and 7C are images depicting perspective and detailed views, respectively, of a variation of the microneedle shown in FIG. 7A.

FIGS. 9C-9F depict detailed partial views of an illustrative variation of a microneedle.

FIGS. 16A-16J depict illustrative schematics of different variations of microneedle array configurations.

DETAILED DESCRIPTION

Figure 1:
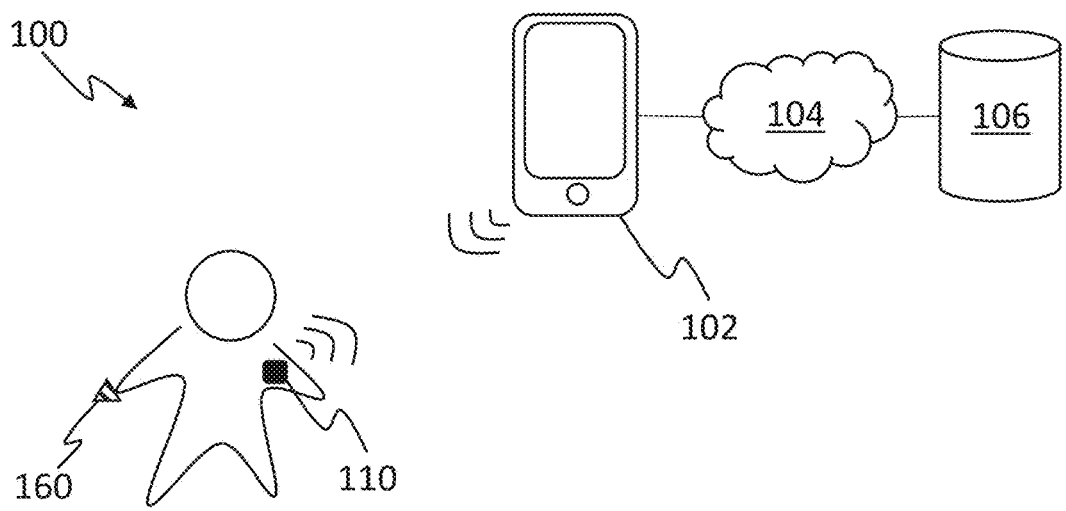
FIG. 1 depicts an illustrative schematic of an analyte monitoring system with a microneedle array.

The term "a" or "an" refers to one or more of that entity, i.e., can refer to plural referents. As such, the terms "a," "an," "one or more," and "at least one" are used interchangeably herein. In addition, reference to "an element" by the indefinite article "a" or "an" does not exclude the possibility that more than one of the elements is present, unless the context clearly requires that there is one and only one of the elements.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

An aptamer is a single-stranded oligonucleotide or a peptide that folds into a defined structure that selectively binds to a specific analyte (which may be referred to as target), which may be, by way of example, a protein, a peptide, a hormone, a nucleic acid, or a small molecule. Aptamers with affinity for a desired target may be conventionally selected from a large oligonucleotide library through a process called SELEX (Systematic Evolution of Ligands by Exponential Enrichment).

Through an iterative process, non-binding aptamers are discarded and aptamers binding to the proposed target are amplified by polymerase chain reaction (PCR). The iterative process may include counter-selection (using interferents and structurally similar molecules) to discard aptamers with insufficient selectivity toward analytes. Moreover, the conformational change of the aptamer effected by target binding and dissociation can be used to effect electrical, electrochemical, or chemical changes that can be harnessed to visualize the target binding/dissociation through an assay or sensor. If needed, the selected aptamers can be further modified (e.g., introduce truncations and mutations) to improve the aptamer conformational changes, thereby improving sensor signals. These properties make aptamers an attractive "biorecognition" element for use in detecting one or more desired analytes.

By way of example, in an aptamer-based sensor, the surface of a working electrode may be functionalized with an aptamer (analyte-binding aptamer) configured to selectively and reversibly bind a given analyte. Moreover, the aptamer is modified with the addition of a redox-active molecule. The aptamer may be configured so that, upon binding the analyte, the analyte-binding aptamer experiences a conformational change that moves the redox-active molecule closer, or further, from the electrode. The movement of the redox-active molecule may be detected as an analyte concentration-dependent electrochemical signal.

Non-limiting examples of various aspects and variations of the invention are described herein and illustrated in the accompanying drawings.

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure a glucose level in that blood sample. However, a patient using this process can typically only measure their glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion, which can cause patient pain, signal latency (e.g., due to the time required for the glucose analyte to diffuse from capillary sources to the sensor), signal noise, sensor damage resulting from insertion, and sensor fatigue (or sensor degradation) over its implanted life. Sensor damage and sensor fatigue, for instance, can result in increased sensor sensitivities and an increased likelihood of outlier measurements.

Causes of signal noise, sensor damage, and sensor fatigue in conventional CGM devices, which may include an electrode "stack" comprising one or more of a base layer, an electrode layer, a sensing layer, an insulating layer, a selective layer, a glucose and/or oxygen diffusion membrane, and a cover/protective layer, include interface deficiencies between sensing layers (such as enzyme containing layers) and other layers or coatings (such as a selective layer, an insulating layer, a protective layer, and the like) arranged thereon, or between sensing layers (such as enzyme containing layers) and an electrode layer, and chemistry voids within the sensing layer that expose the electrode layer to interferents.

For instance, interface deficiencies, which may include layer delamination, interface imperfections, interface irregularities between the outer membrane and the sensing layer, interface irregularities between the sensing layer and the electrode material, and the like, can directly contribute to variability in analyte sensor sensitivity and/or inconsistent sensitivity trends over time and generally reduce accuracy in analyte measurements.

Chemistry voids within the sensing layer undesirably expose the surface of the electrode layer to interferents that increase signal noise (also referred to herein as "interference current"). Such voids and exposure of the electrode surface to interferents can result in non-specific currents that overwhelm glucose catalytic currents, thereby reducing accuracy, sensitivity, and lifetime of the biosensor.

In an effort to remedy the above-described sensor interface deficiencies and interference current, the devices, systems, and methods described herein may utilize an electrode "stack" comprising one or more of an interferent blocking agent and an attachment enhancer (which may also be referred to herein as a "promoter"). In some variations, the interferent blocking agent may be configured to fill at least a portion of the chemistry voids within the sensing layer to decrease exposure of the electrode layer surface to interferents. Thus, inclusion of the interferent blocking agent within the sensing layer may reduce background interference, for example, over at least one week, thereby improving sensitivity. Additionally or alternatively, the attachment enhancer may be configured to bridge and adhere a sensing layer, an outer membrane, an electrode material, and/or any other layer within the electrode "stack". In this manner, inclusion of the attachment enhancer may reduce sensor sensitivity and variability in sensor sensitivity. It can be appreciated that, because the attachment enhancer and the interferent blocking agent are configured to provide different functionality to the electrode "stack", they may be used together (i.e., an electrode stack may include both an attachment enhancer and an interferent blocking agent) or separately (i.e., an electrode stack may include an attachment enhancer but not an interferent blocking agent, or an electrode stack may include an interferent blocking agent but not an attachment enhancer), and in combination with any other layer of an electrode "stack", as described herein.

As generally described herein, an analyte monitoring system may include an analyte monitoring device that is worn by a user and includes one or more sensors for monitoring at least one analyte of a user. The sensors may, for example, include one or more electrodes configured to perform electrochemical detection of at least one analyte. The analyte monitoring device may communicate sensor data to an external computing device for storage, display, and/or analysis of sensor data. For example, as shown in FIG. 1, an analyte monitoring system 100 may include an analyte monitoring device 110 that is worn by a user, and the analyte monitoring device 110 may be a continuous analyte monitoring device (e.g., continuous glucose monitoring device). The analyte monitoring device 110 may include, for example, a microneedle array comprising at least one electrochemical sensor for detecting and/or measuring one or more analytes in body fluid of a user. In some variations, the analyte monitoring device may be applied to the user using suitable applicator 160 or may be applied manually. The analyte monitoring device 110 may include one or more processors for performing analysis on sensor data, and/or a communication module (e.g., wireless communication module) configured to communicate sensor data to a mobile computing device 102 (e.g., smartphone) or other suitable computing device. In some variations, the mobile computing device 102 may include one or more processors executing a mobile application to handle sensor data (e.g., displaying data, analyzing data for trends, etc.) and/or provide suitable alerts or other notifications related to the sensor data and/or analysis thereof. It should be understood that while in some variations the mobile computing device 102 may perform sensor data analysis locally, other computing device(s) may alternatively or additionally remotely analyze sensor data and/or communicate information related to such analysis with the mobile computing device 102 (or other suitable user interface) for display to the user. Furthermore, in some variations the mobile computing device 102 may be configured to communicate sensor data and/or analysis of the sensor data over a network 104 to one or more storage devices 106 (e.g., server) for archiving data and/or other suitable information related to the user of the analyte monitoring device.

The analyte monitoring devices described herein have characteristics that improve a number of properties that are advantageous for a continuous analyte monitoring device such as a continuous glucose monitoring (CGM) device. For example, the analyte monitoring device described herein have improved sensitivity (amount of sensor signal produced per given concentration of target analyte), improved selectivity (rejection of endogenous and exogenous circulating compounds that can interfere with the detection of the target analyte), and improved stability to help minimize change in sensor response over time through storage and operation of the analyte monitoring device. Additionally, compared to conventional continuous analyte monitoring devices, the analyte monitoring devices described herein have a shorter warm-up time that enables the sensor(s) to quickly provide a stable sensor signal following implantation, as well as a short response time that enables the sensors(s) to quickly provide a stable sensor signal following a change in analyte concentration in the user. Furthermore, as described in further detail below, the analyte monitoring devices described herein may be applied to and function in a variety of wear sites and provide for pain-free sensor insertion for the user. Other properties such as biocompatibility, sterilizability, and mechanical integrity are also optimized in the analyte monitoring devices described herein.

Although the analyte monitoring systems described herein may be described with reference to monitoring of glucose (e.g., in users with Type 2 diabetes, Type 1 diabetes), it should be understood that such systems may additionally or alternatively be configured to sense and monitor other suitable analytes. As described in further detail below, suitable target analytes for detection may, for example, include glucose, ketones, lactate, and cortisol. One target analyte may be monitored, or multiple target analytes may be simultaneously monitored (e.g., in the same analyte monitoring device). For example, monitoring of other target analytes may enable the monitoring of other indications such as stress (e.g., through detection of rising cortisol and glucose) and ketoacidosis (e.g., through detection of rising ketones).

Various aspects of example variations of the analyte monitoring systems, and methods of use thereof, are described in further detail below.

Analyte Monitoring Device

Figure 2A:
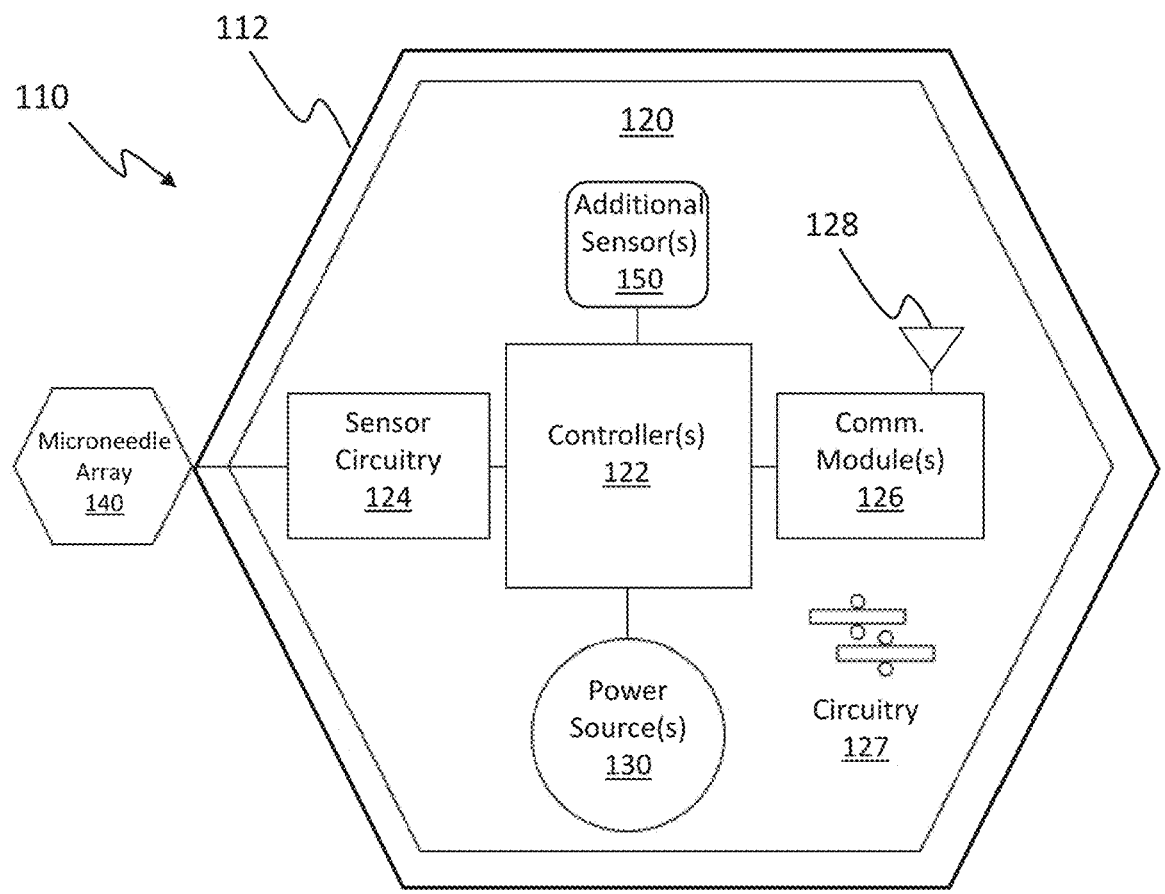
FIG. 2A depicts an illustrative schematic of an analyte monitoring device.

As shown in FIG. 2A, in some variations, an analyte monitoring device 110 may generally include a housing 112 and a microneedle array 140 extending outwardly from the housing. The housing 112, may, for example, be a wearable housing configured to be worn on the skin of a user such that the microneedle array 140 extends at least partially into the skin of the user. For example, the housing 112 may include an adhesive such that the analyte monitoring device 110 is a skin-adhered patch that is simple and straightforward for application to a user. The microneedle array 140 may be configured to puncture the skin of the user and include one or more electrochemical sensors (e.g., electrodes) configured for measuring one or more target analytes that are accessible after the microneedle array 140 punctures the skin of the user. In some variations, the analyte monitoring device 110 may be integrated or self-contained as a single unit, and the unit may be disposable (e.g., used for a period of time and replaced with another instance of the analyte monitoring device 110).

An electronics system 120 may be at least partially arranged in the housing 112 and include various electronic components, such as sensor circuitry 124 configured to perform signal processing (e.g., biasing and readout of electrochemical sensors, converting the analog signals from the electrochemical sensors to digital signals, etc.). The electronics system 120 may also include at least one microcontroller 122 for controlling the analyte monitoring device 110, at least one communication module 126, at least one power source 130, and/or other various suitable passive circuitry 127. The microcontroller 122 may, for example, be configured to interpret digital signals output from the sensor circuitry 124 (e.g., by executing a programmed routine in firmware), perform various suitable algorithms or mathematical transformations (e.g., calibration, etc.), and/or route processed data to and/or from the communication module 124. In some variations, the communication module 126 may include a suitable wireless transceiver (e.g., Bluetooth transceiver or the like) for communicating data with an external computing device 102 via one or more antennas 128. For example, the communication module 126 may be configured to provide unidirectional and/or bi-directional communication of data with an external computing device 102 that is paired with the analyte monitoring device 110. The power source 130 may provide power for the analyte monitoring device 110, such as for the electronics system. The power source 130 may include battery or other suitable source, and may, in some variations, be rechargeable and/or replaceable. Passive circuitry 127 may include various non-powered electrical circuitry (e.g., resistors, capacitors, inductors, etc.) providing interconnections between other electronic components, etc. The passive circuitry 127 may be configured to perform noise reduction, biasing and/or other purposes, for example. In some variations, the electronic components in the electronics system 120 may be arranged on one or more printed circuit boards (PCB), which may be rigid, semi-rigid, or flexible, for example. Additional details of the electronics system 120 are described further below.

In some variations, the analyte monitoring device 110 may further include one or more additional sensors 150 to provide additional information that may be relevant for user monitoring. For example, the analyte monitoring device 110 may further include at least one temperature sensor (e.g., thermistor) configured to measure skin temperature, thereby enabling temperature compensation for the sensor measurements obtained by the microneedle array electrochemical sensors.

Figure 2B:
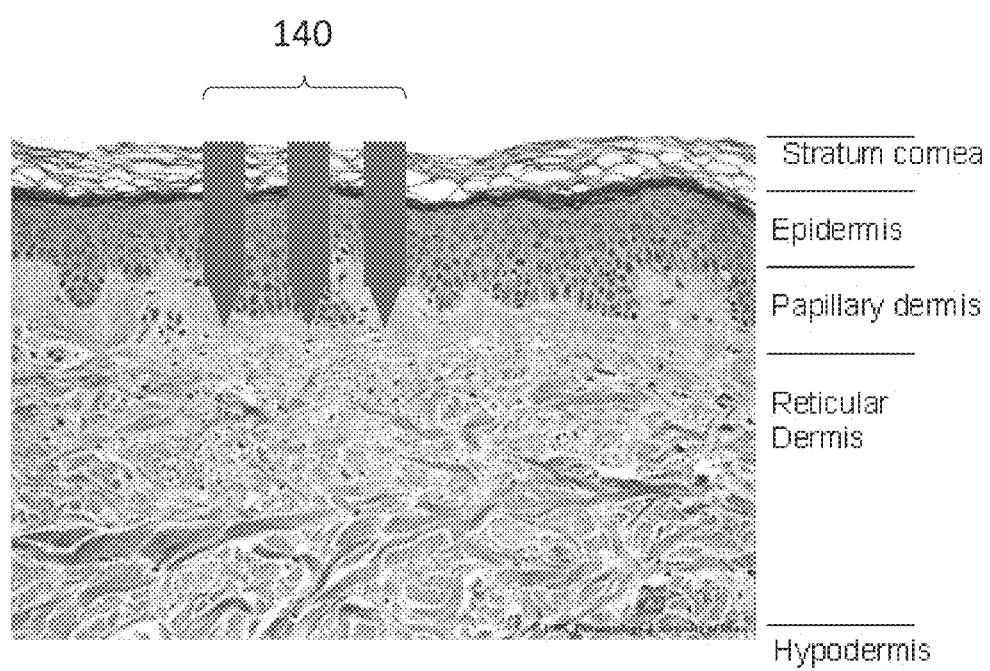
FIG. 2B depicts an illustrative schematic of microneedle insertion depth in an analyte monitoring device.

In some variations, the microneedle array 140 in the analyte monitoring device 110 may be configured to puncture skin of a user. As shown in FIG. 2B, when the device 110 is worn by the user, the microneedle array 140 may extend into the skin of the user such that electrodes on distal regions of the microneedles rest in the dermis. Specifically, in some variations, the microneedles may be designed to penetrate the skin and access the upper dermal region (e.g., papillary dermis and upper reticular dermis layers) of the skin, in order to enable the electrodes to access interstitial fluid that surrounds the cells in these layers. For example, in some variations, the microneedles may have a height generally ranging between at least 350 μm and about 515 μm. In some variations, one or more microneedles may extend from the housing such that a distal end of the electrode on the microneedle is located less than about 5 mm from a skin-interfacing surface of the housing, less than about 4 mm from the housing, less than about 3 mm from the housing, less than about 2 mm from the housing, or less than about 1 mm from the housing.

In contrast to traditional continuous analyte monitoring devices (e.g., CGM devices), which include sensors typically implanted between about 8 mm and about 10 mm beneath the skin surface in the subcutis or adipose layer of the skin, the analyte monitoring device 110 has a shallower microneedle insertion depth of about 0.25 mm (such that electrodes are implanted in the upper dermal region of the skin) that provides numerous benefits. These benefits include access to dermal interstitial fluid including one or more target analytes for detection, which is advantageous at least because at least some types of analyte measurements of dermal interstitial fluid have been found to closely correlate to those of blood. For example, it has been discovered that glucose measurements performed using electrochemical sensors accessing dermal interstitial fluid are advantageously highly linearly correlated with blood glucose measurements. Accordingly, glucose measurements based on dermal interstitial fluid are highly representative of blood glucose measurements.

Additionally, because of the shallower microneedle insertion depth of the analyte monitoring device 110, a reduced time delay in analyte detection is obtained compared to traditional continuous analyte monitoring devices. Such a shallower insertion depth positions the sensor surfaces in close proximity (e.g., within a few hundred micrometers or less) to the dense and well-perfused capillary bed of the reticular dermis, resulting in a negligible diffusional lag from the capillaries to the sensor surface. Diffusion time is related to diffusion distance according to $t=x^2/(2D)$ where t is the diffusion time, x is the diffusion distance, and D is the mass diffusivity of the analyte of interest. Therefore, positioning an analyte sensing element twice as far away from the source of an analyte in a capillary will result in a quadrupling of the diffusional delay time. Accordingly, conventional analyte sensors, which reside in the very poorly vascularized adipose tissue beneath the dermis, result in a significantly greater diffusion distance from the vasculature in the dermis and thus a substantial diffusional latency (e.g., typically 5-20 minutes). In contrast, the shallower microneedle insertion depth of the analyte monitoring device 110 benefits from low diffusional latency from capillaries to the sensor, thereby reducing time delay in analyte detection and providing more accurate results in real-time or near real-time. For example, in some variations, diffusional latency may be less than 10 minutes, less than 5 minutes, or less than 3 minutes.

Furthermore, when the microneedle array rests in the upper dermal region, the lower dermis beneath the microneedle array includes very high levels of vascularization and perfusion to support the dermal metabolism, which enables thermoregulation (via vasoconstriction and/or vasodilation) and provides a barrier function to help stabilize the sensing environment around the microneedles. Yet another advantage of the shallower insertion depth is that the upper dermal layers lack pain receptors, thus resulting in a reduced pain sensation when the microneedle array punctures the skin of the user, and providing for a more comfortable, minimally-invasive user experience.

Thus, the analyte monitoring devices and methods described herein enable improved continuous monitoring of one or more target analytes of a user. For example, as described above, the analyte monitoring device may be simple and straightforward to apply, which improves ease-of-use and user compliance. Additionally, analyte measurements of dermal interstitial fluid may provide for highly accurate analyte detection. Furthermore, compared to traditional continuous analyte monitoring devices, insertion of the microneedle array and its sensors may be less invasive and involve less pain for the user. Additional advantages of other aspects of the analyte monitoring devices and methods are further described below.

As described above, an analyte monitoring device may include a housing. The housing may at least partially surround or enclose other components of the analyte monitoring device (e.g., electronic components), such as for protection of such components. For example, the housing may be configured to help prevent dust and moisture from entering the analyte monitoring device. In some variations, an adhesive layer may attach the housing to a surface (e.g., skin) of a user, while permitting a microneedle array to extend outwardly from the housing and into the skin of the user. Furthermore, in some variations the housing may generally include rounded edges or corners and/or be low-profile so as to be atraumatic and reduce interference with clothing, etc. worn by the user.

FIG. 3A-FIG. 3D depict aspects of the analyte monitoring device 110. FIGS. 3A-3D depict an upper perspective view, a side view, a bottom view, and an exploded view, respectively, of the analyte monitoring device 110.

The analyte monitoring device 110 may include a housing which defines a cavity that at least partially surrounds or encloses other components (e.g., electronic components) of the analyte monitoring device 110, such as for protection of such components. For example, the housing may be configured to help prevent dust and moisture from entering the analyte monitoring device 110. In some variations, an adhesive layer may be provided at a distal end of the housing to attach the housing to a surface (e.g., skin) of a user. In some variations, after the house is attached to the surface, the microneedle array 140 may be deployed to extend outwardly from the housing and into the skin of the user. Furthermore, in some variations, the housing may generally include rounded edges or corners and/or be low-profile to reduce interference with clothing, etc. worn by the user.

For example, as shown in FIGS. 3A-3D, an example variation of the analyte monitoring device 110 may include a housing cover 320 and a base plate 330, configured to at least partially surround internal components of the analyte monitoring device 110. For example, the housing cover 320 and the base plate 330 may provide an enclosure for a sensor assembly 350 including the microneedle array 140 and electronic components. Once deployed, the microneedle array 140 extends outwardly from a portion of the base plate 330 in a skin-facing direction (e.g., an underside) of the analyte monitoring device 110.

The housing cover 320 and the base plate 330 may, for example, include one or more rigid or semi-rigid protective shell components that may couple together via suitable fasteners (e.g., mechanical fasteners), mechanically interlocking or mating features, and/or an engineering fit. The housing cover 320 and the base plate 330 may include radiused edges and corners and/or other atraumatic features. When coupled together, the housing cover 320 and the base plate 330 may form a cavity comprising an internal volume that houses internal components, such as the sensor assembly 350. For example, the internal components arranged in the internal volume may be arranged in a compact, low-profile stack-up as the sensor assembly 350.

The analyte monitoring device 110 may include one or more adhesive layers provided on a distal end of the housing to attach the analyte monitoring device 110 (e.g., the coupled together housing cover 320 and the base plate 330) to a surface (e.g., the skin) of a user. As shown in FIG. 3D, the one or more adhesive layers may include an inner adhesive layer 342 and an outer adhesive layer 344. The inner adhesive layer 342 may adhere to the base plate 330, and the outer adhesive layer 344 may adhere to the inner adhesive layer 342 and, on its outward facing side, provide an adhesive for adhering (e.g., temporarily) to the skin of the user. The inner adhesive layer 342 and the outer adhesive layer 344 together act as a double-sided adhesive for adhering the analyte monitoring device 110 to the skin of the user. The outer adhesive layer 344 may be protected by a release liner that the user removes to expose the adhesive prior to skin application. In some variations, a single adhesive layer is provided. In some variations, the outer adhesive layer 344, the inner adhesive layer 342, and/or the single adhesive layer may have a perimeter that extends farther than the perimeter or periphery of the housing cover 320 and the base plate 330. This may increase surface area for attachment and increase stability of retention or attachment to the skin of the user. The inner adhesive layer 342, the outer adhesive layer 344, and/or the single adhesive layer may each have an opening that permits passage of the outwardly extending microneedle array 140 when deployed, as further described below. The openings of the inner adhesive layer 342 and the outer adhesive layer 344 may generally align with one another but may, in some variations, differ in size such that one opening is smaller than the other opening. In some variations, the openings are substantially the same size.

The base plate 330 has a first surface (e.g., an outwardly exposed surface) opposite a second surface and serves as a support and/or connection structure and as a protective cover for the sensor assembly 350. The base plate 330 is sized and shaped to attach to the housing cover 320. The base plate 330 may be shaped to securely fit within the housing cover 320 such that outer edges of the base plate 330 align with corresponding edges of an opening of the housing cover 320. The alignment may be such that there is no gap between the outer edges of the base plate 330 and the corresponding edges of the opening of the housing cover 320.

A connection member 332 may be formed in a central or near central region of the first surface of the base plate 330. The connection member 332 is a protrusion (e.g., a projected hub) with sidewalls that extend from the first surface of the base plate 330 and with a first surface substantially parallel to the first surface of the base plate 330. Sidewalls extend from edges of the first surface of the connection member 332 to the first surface of the base plate 330. A remaining portion of the first surface of the base plate 330 surrounding the connection member 332 may be flat or substantially flat. One or more connector features 336 extend outwardly from the sidewalls of the connection member 332 to releasably engage with corresponding connectors of a microneedle enclosure that provides, for example, a sterile environment for the microneedle array 140. The first surface and the sidewalls of the connection member 332 define, in part, a chamber. The chamber may be further defined through a portion of the base plate 330 adjacent (e.g., below) the connection member 332. The chamber has an opening, and is accessible, on the second surface of the base plate 330. An aperture or distal opening 334 is formed through the first surface of the connection member 332. The distal opening 334 may be sized and shaped such that the microneedle array 140 fits securely within and extends through the distal opening 334 when in the deployed configuration. For example, sidewalls of the microneedle array 140 may align with corresponding sidewalls of the distal opening 334. In some variations, the distal opening 334 may be sized and shaped to correspond with an area surrounding the microneedle array 140. The openings in the inner adhesive layer 342 and the outer adhesive layer 344 (or the single adhesive layer) may be sized such that the connection member 332 extends through the openings without interference with the adhesive layers. For example, the diameter of the opening of the inner adhesive layer 342 and the diameter of the opening of the outer adhesive layer 344 is larger than that of the connection member 332. In some variations, the opening of the inner adhesive layer 342 and/or the opening of the outer adhesive layer 344 (or that of the single adhesive layer) is in proximity with the sidewalls of the connection member 332 with a clearance to accommodate the one or more connector features 336. In some variations, one or more slits or notches may be formed in the inner adhesive layer 342, the outer adhesive layer 344, and/or the single adhesive layer, extending from the opening to aid in placement of the respective adhesive layer.

Although the housing cover 320 and the base plate 330 depicted in FIGS. 3A-3D are substantially circular with the housing cover 320 having a dome shape, in other variations, the housing cover 320 and the base plate 330 may have any suitable shape. For example, in other variations the housing cover 320 and the base plate 330 may be generally prismatic and have an elliptical, triangular, rectangular, pentagonal, hexagonal, or other suitable shape. The outer adhesive layer 344 (or the single adhesive layer) may extend outwardly from the housing cover 320 and the base plate 330 to extend beyond the perimeter of the housing cover 320. The outer adhesive layer 344 (or the single adhesive layer) may be circular, as shown in FIGS. 3A-3D or may have an elliptical, triangular, rectangular, pentagonal, hexagonal, or other suitable shape and need not be the same shape as the housing cover 320 and/or the base plate 330.

FIGS. 4A-4E depict aspects of the sensor assembly 350 of the analyte monitoring device 110 in a perspective exploded view, a side exploded view, a lower perspective view, a side view, and an upper perspective view, respectively.

The sensor assembly 350 includes microneedle array components and electronic components to implement analyte detection and processing aspects of the microneedle array-based continuous analyte monitoring device 110 for the detection and measuring of an analyte. In some variations, the sensor assembly 350 is a compact, low-profile stack-up that is at least partially contained within the cavity comprising an internal volume defined by the housing cover 320 and the base plate 330.

In some variations, the sensor assembly 350 includes a microneedle array assembly 360 and an electronics assembly 370 that connect to one another to implement the microneedle array analyte detection and processing aspects further described herein. In some variations, the electronics assembly 370 includes a main printed circuit board (PCB) 450 on which electronic components are connected, and the microneedle array assembly 360 includes a secondary printed circuit board (PCB) 420 on which the microneedle array 140 is connected.

In some variations, the microneedle array assembly 360 includes, in addition to the secondary PCB 420 and the microneedle array 140, an epoxy skirt 410 and a secondary PCB connector 430. The microneedle array 140 is coupled to a top side (e.g., outer facing side) of the secondary PCB 420 so that the individual microneedles of the microneedle array 140 are exposed as described with reference to FIG. 3A-FIG. 3D. The secondary PCB connector 430 is coupled to a back side, opposite the top side, of the secondary PCB 420. The secondary PCB connector 430 may be an electromechanical connector and may communicatively couple to the primary PCB 450 through a primary PCB connector 470 on a top side (e.g., outer facing side) of the primary PCB 450 to allow for signal communication between the secondary PCB 420 and the primary PCB 450. For example, signals from the microneedle array 140 may be communicated to the primary PCB 450 through the secondary PCB 420, the secondary PCB connector 430, and the primary PCB connector 470.

The secondary PCB 420 may in part determine the distance to which the microneedle array 140 protrudes from the base plate 330 of the housing. Accordingly, the height of the secondary PCB 420 may be selected to help ensure that the microneedle array 140 is inserted properly into a user's skin. During microneedle insertion, the first surface (e.g., outer facing surface) of the connection member 332 of the base plate 330 may act as a stop for microneedle insertion. If the secondary PCB 420 has a reduced height and its top surface is flush or nearly flush with the first surface of the connection member 332, then the connection member 332 may prevent the microneedle array 140 from being fully inserted into the skin.

In some variations, other components (e.g., electronic components such as sensors or other components) may also be connected to the secondary PCB 420. For example, the secondary PCB 420 may be sized and shaped to accommodate electronic components on the top side or the back side of the secondary PCB 420.

Figure 3A:
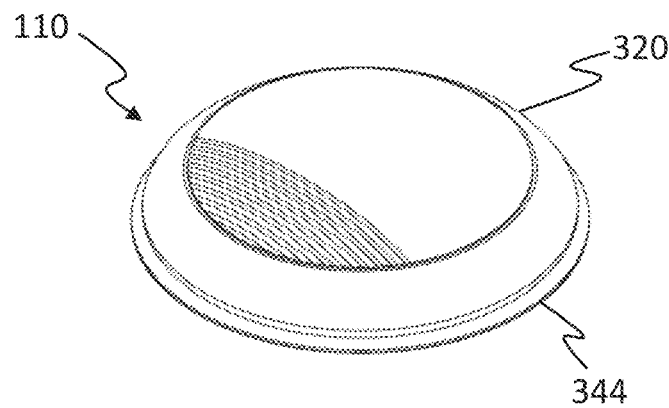
FIGS. 3A-3D depict an upper perspective view, a side view, a bottom view, and an exploded view, respectively, of an analyte monitoring device.
Figure 3B:
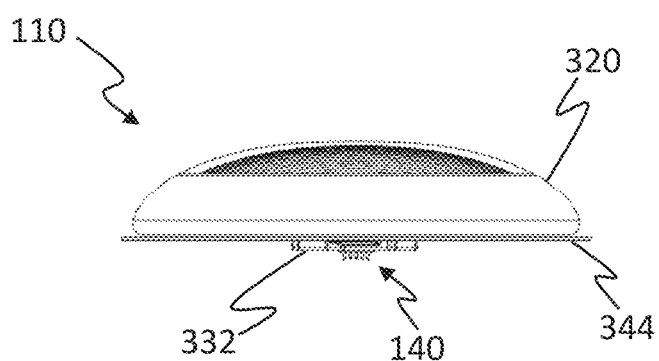
Figure 3C:
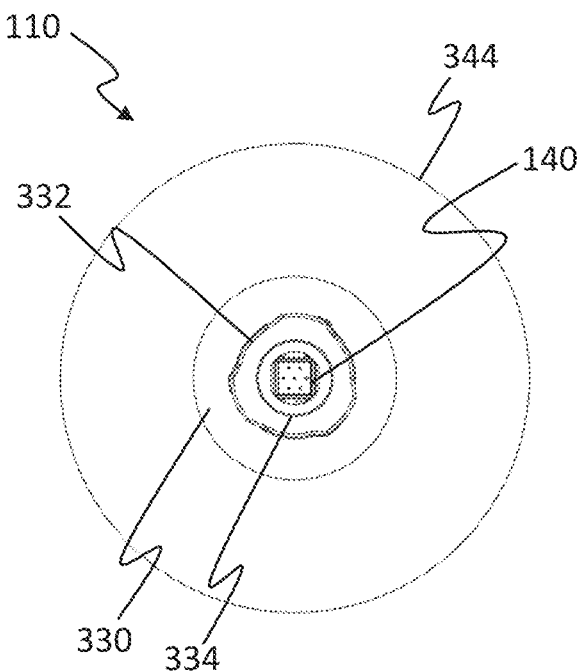
Figure 3D:
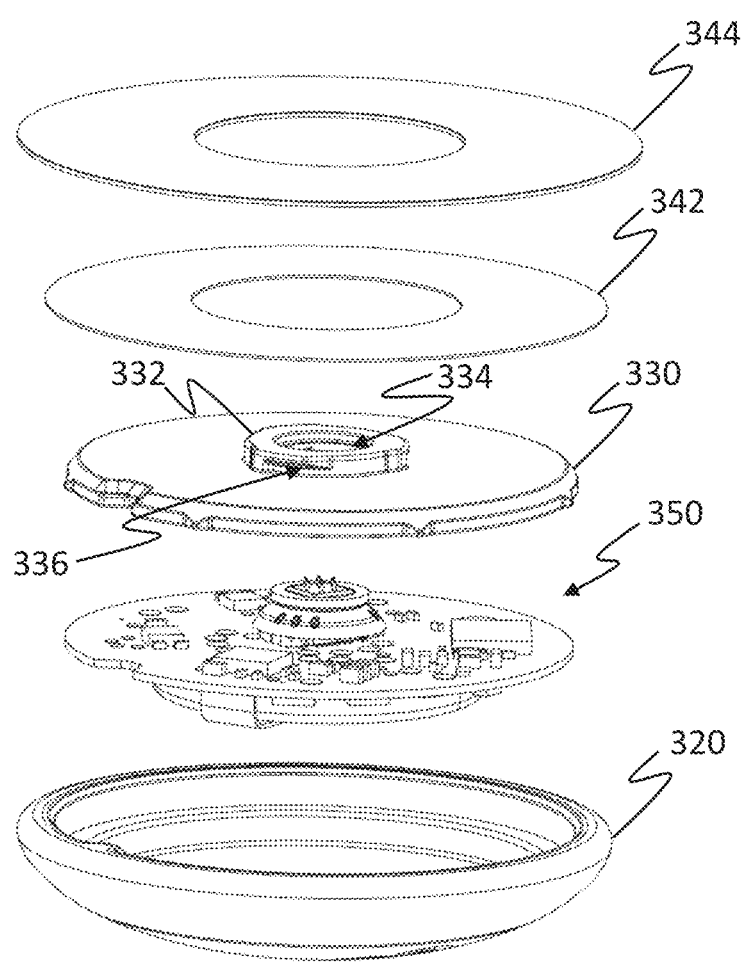

In some variations, the epoxy skirt 410 may be deposited along the edges (e.g., the outer perimeter) of the microneedle array 140 to provide a secure fit of the microneedle array 140 within the distal opening 334 formed in the connection member 332 of the base plate 330 and/or to relieve the sharp edges along the microneedle array 140, as shown in FIG. 3C and FIG. 3D. For example, the epoxy skirt 410 may occupy portions of the distal opening 334 not filled by the microneedle array 140 and/or portions of the chamber defined in the base plate 330 not filled by the secondary PCB 420. The epoxy skirt 410 may also provide a transition from the edges of the microneedle array 140 to the edge of the secondary PCB 420. In some variations, the epoxy skirt 410 may be replaced or supplemented by a gasket (e.g., a rubber gasket) or the like.

The electronics assembly 370, having the primary PCB 450, includes a battery 460 coupled to a back side of the primary PCB 450, opposite the top side on which the primary PCB connector 470 is coupled. In some variations, the battery 460 may be coupled on the top side of the primary PCB 450 and/or in other arrangements.

Figure 4A:
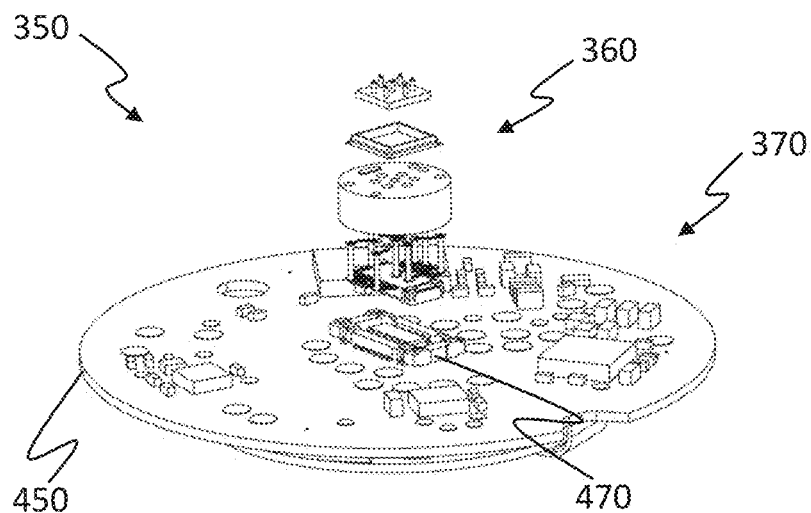
FIGS. 4A-4E depict a perspective exploded view, a side exploded view, a lower perspective view, a side view, and an upper perspective view, respectively, of a sensor assembly in an analyte monitoring device.
Figure 4B:
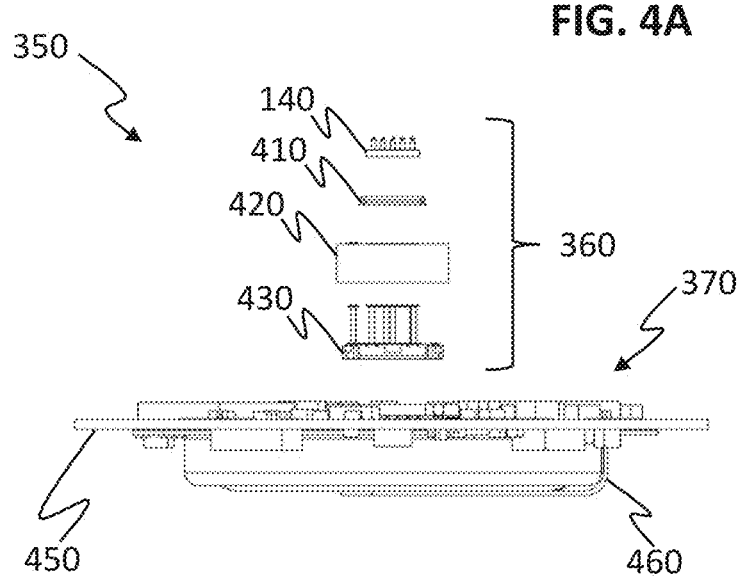
Figure 4C:
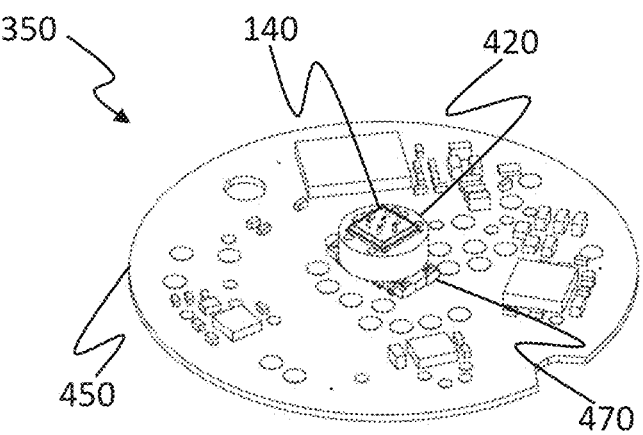
Figure 4D:
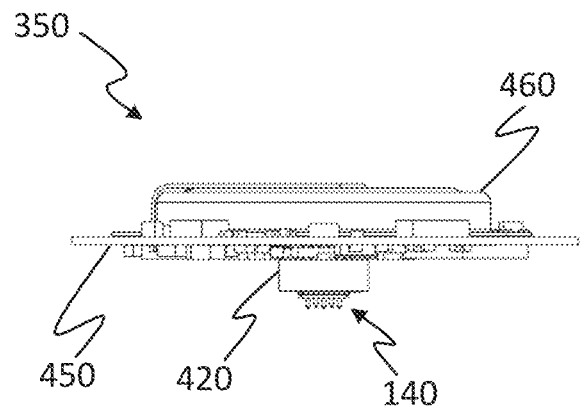
Figure 4E:
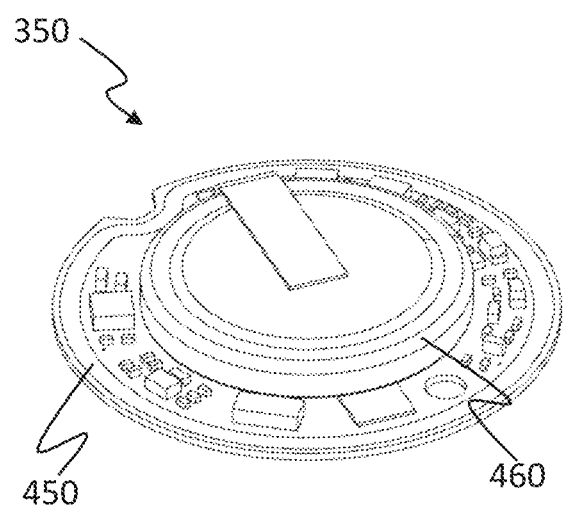
Figure 4F:
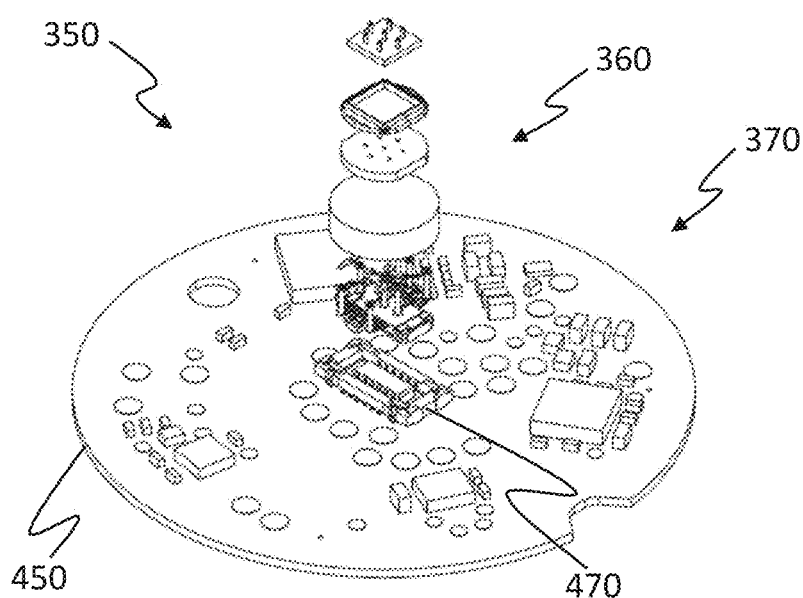
FIGS. 4F-4H depict a perspective exploded view, a side exploded view, and a side view, respectively, of a sensor assembly in an analyte monitoring device.
Figure 4G:
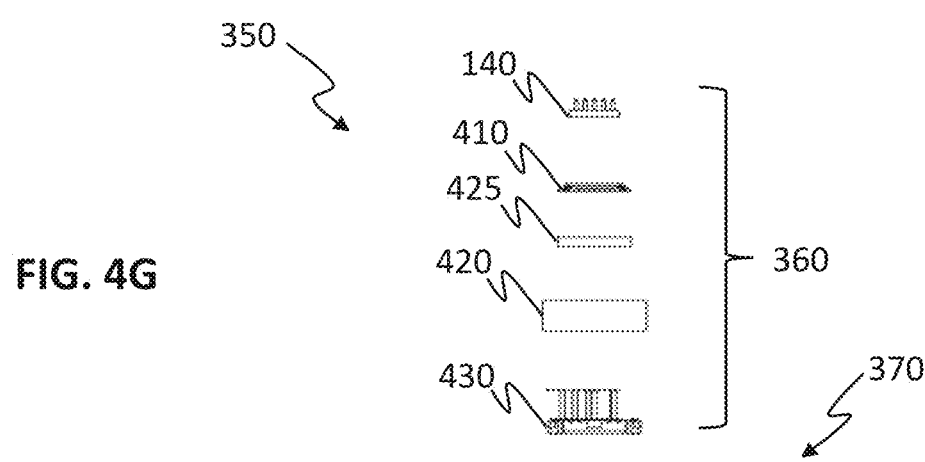
Figure 4H:
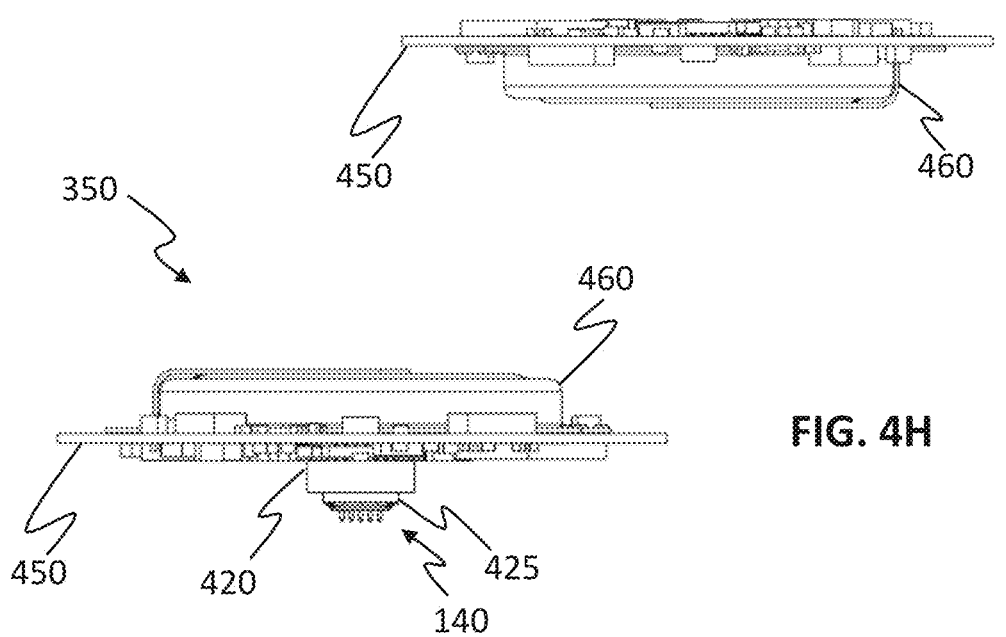

FIGS. 4F-4H depict aspects of an alternate variation of the sensor assembly 350 of the analyte monitoring device 110. A perspective exploded view, a side exploded view, and a side view of the sensor assembly 350 are provided, respectively, in FIGS. 4F-4H.

As shown, in the sensor assembly 350, an additional PCB component, an intermediate PCB 425, is incorporated. In some variations, the intermediate PCB 425 is part of the microneedle array assembly 360 and is positioned between and connected to the secondary PCB 420 and the microneedle array 140. The intermediate PCB 425 may be added to increase the height of the microneedle array assembly 360 such that the microneedle array 140 extends at a further distance from the base plate 330, which may aid in insertion of the microneedle array 140 into the skin of a user. The microneedle array 140 is coupled to a top side (e.g., outer facing side) of the intermediate PCB 425 so that the individual microneedles of the microneedle array 140 are exposed as described with reference to FIG. 3A-FIG. 3D. The secondary PCB 420 is coupled to a back side, opposite the top side, of the intermediate PCB 425, and the secondary PCB connector 430 is coupled to a back side, opposite the top side, of the secondary PCB 420. The epoxy skirt 410 (which may be replaced or supplemented by a gasket of the like) provides a transition from the edges of the microneedle array 140 to the edge of the intermediate PCB 425.

The intermediate PCB 425 with the secondary PCB 420, in part, determine the distance to which the microneedle array 140 protrudes through the distal opening 334 of the base plate 330. The incorporation of the intermediate PCB 425 provides an additional height to help ensure that the microneedle array 140 is properly inserted into a user's skin. In some variations, the top side (e.g., outer facing side) of the intermediate PCB 425 extends through and out of the distal opening 334 so that the first surface (e.g., top, exposed surface) of the connection member 332 surrounding the distal opening 334 does not prevent the microneedle array from being fully inserted into the skin. In some variations, the top side (e.g., outer facing side) of the intermediate PCB 425 does not extend out of the distal opening 334 but the increased height (by virtue of incorporating the intermediate PCB 425) ensures that the microneedle array 140 protrudes at a sufficient distance from the base plate 330 of the housing.

In some variations, a microneedle enclosure may be provided for releasable attachment to the analyte monitoring device 110. The microneedle enclosure may provide a protective environment or enclosure in which the microneedle array 140 may be safely contained, thereby ensuring the integrity of the microneedle array 140 during certain stages of manufacture and transport of the analyte monitoring device 110, prior to application of the analyte monitoring device 110. The microneedle enclosure is releasable or removable from the analyte monitoring device 110 to allow for the microneedle array 140 to be exposed and/or ready for insertion into the skin of the user, as further described herein.

In some variations, the microneedle enclosure, by providing an enclosed and sealed environment in which the microneedle array 140 may be contained, provides an environment in which the microneedle array 140 may be sterilized. For example, the microneedle enclosure with the microneedle array 140 may be subjected to a sterilization process, during which the sterilization penetrates the microneedle enclosure so that the microneedle array 140 is also sterilized. As the microneedle array 140 is contained in an enclosed environment, the microneedle array 140 remains sterilized until removed from the enclosed environment. In some variations, a removeable film is provided on the distal end of the housing, covering the distal opening 334 prior to application of the analyte monitoring device 110 on the skin surface of a subject. The removeable film may maintain a sterile environment and prevent intrusion of foreign objects or substances before application of the analyte monitoring device 110. A user may remove or peel off the film just prior to applying and/or adhering the analyte monitoring device 110 to the skin surface of a subject.

Microneedle Structure

Figure 5A:
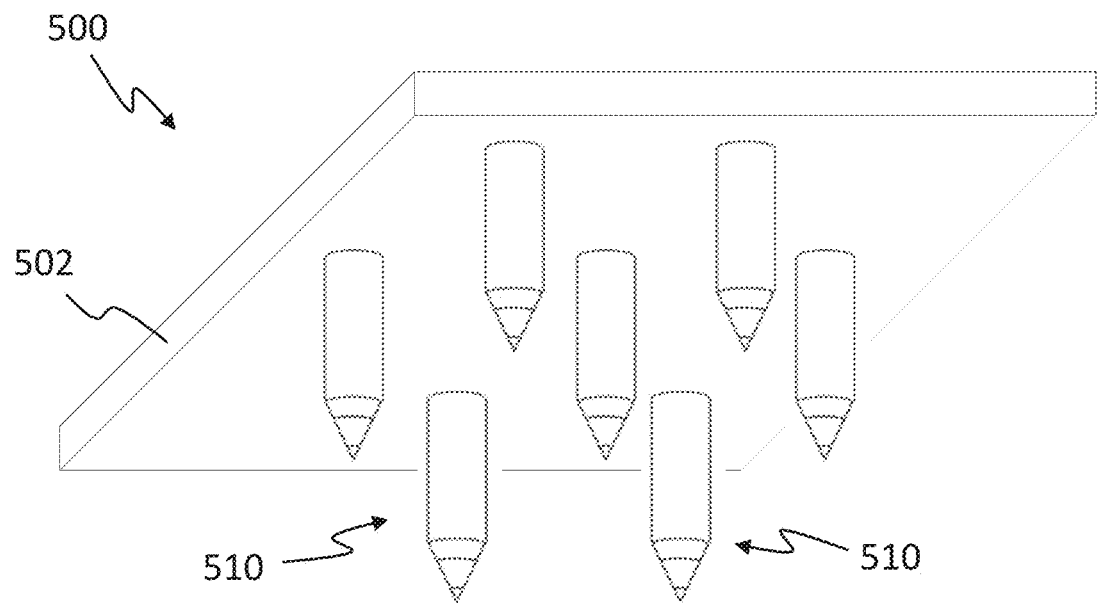
FIG. 5A depicts an illustrative schematic of a microneedle array.
Figure 5B:
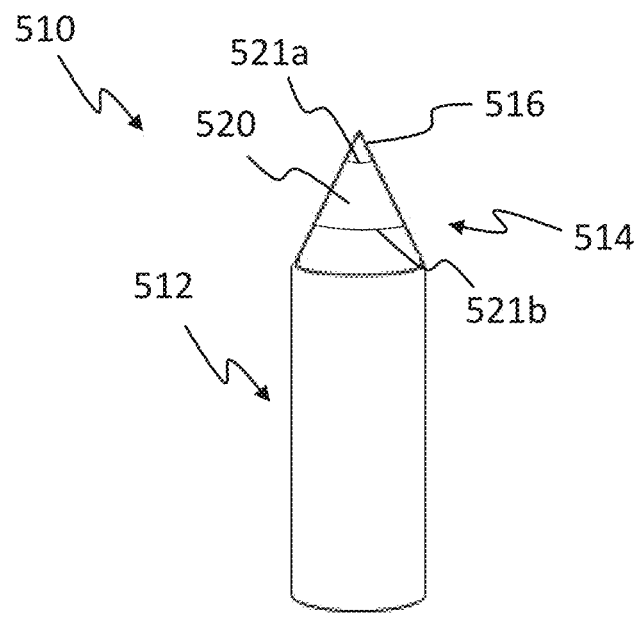
FIG. 5B depicts an illustrative schematic of a microneedle in the microneedle array depicted in FIG. 5A.

As shown in the schematic of FIG. 5A, in some variations, a microneedle array 510 for use in sensing one or more analytes may include one or more microneedles 510 projecting from a substrate surface 502. The substrate surface 502 may, for example, be generally planar and one or more microneedles 510 may project orthogonally from the planar surface. Generally, as shown in FIG. 5B, a microneedle 510 may include a body portion 512 (e.g., shaft) and a tapered distal portion 514 configured to puncture skin of a user. In some variations, the tapered distal portion 514 may terminate in an insulated distal apex 516. The microneedle 510 may further include an electrode 520 on a surface of the tapered distal portion. In some variations, electrode-based measurements may be performed at the interface of the electrode and interstitial fluid located within the body (e.g., on an outer surface of the overall microneedle). In some variations, the microneedle 510 may have a solid core (e.g., solid body portion), though in some variations the microneedle 510 may include one or more lumens, which may be used for drug delivery or sampling of the dermal interstitial fluid, for example. Other microneedle variations, such as those described below, may similarly either include a solid core or one or more lumens.

The microneedle array 500 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 500 may include a three electrode setup including a working (sensing) electrode having an electrochemical sensing coating (including a biorecognition element such as an enzyme) that enables detection of a target analyte, a reference electrode, and a counter electrode. In other words, the microneedle array 500 may include at least one microneedle 510 that includes a working electrode, at least one microneedle 510 including a reference electrode, and at least one microneedle 510 including a counter electrode. Additional details of these types of electrodes are described in further detail below.

Figure 6:
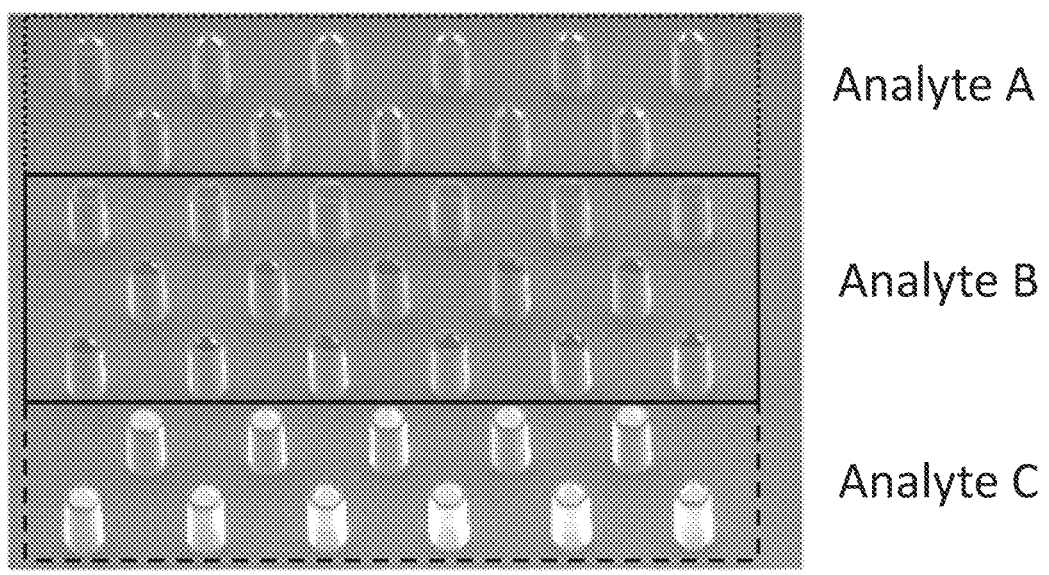
FIG. 6 depicts an illustrative schematic of a microneedle array used for sensing multiple analytes.

In some variations, the microneedle array 500 may include a plurality of microneedles that are insulated such that the electrode on each microneedle in the plurality of microneedles is individually addressable and electrically isolated from every other electrode on the microneedle array. The resulting individual addressability of the microneedle array 500 may enable greater control over each electrode's function, since each electrode may be separately probed. For example, the microneedle array 500 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 500 may additionally or alternatively be interrogated to simultaneously measure multiple analytes to provide a more comprehensive assessment of physiological status. For example, as shown in the schematic of FIG. 6, a microneedle array may include a portion of microneedles to detect a first Analyte A, a second portion of microneedles to detect a second Analyte B, and a third portion of microneedles to detect a third Analyte C. It should be understood that the microneedle array may be configured to detect any suitable number of analytes (e.g., 1, 2, 3, 4, 5 or more, etc.). Suitable target analytes for detection may, for example, include glucose, ketones, lactate, and cortisol. For example, in some variations, ketones may be detected in a manner similar to that described in U.S. patent application Ser. No. 16/701,784, which is incorporated herein in its entirety by this reference. Thus, individual electrical addressability of the microneedle array 500 provides greater control and flexibility over the sensing function of the analyte monitoring device.

In some variations of microneedles (e.g., microneedles with a working electrode), the electrode 520 may be located proximal to the insulated distal apex 516 of the microneedle. In other words, in some variations, the electrode 520 does not cover the apex of the microneedle. Rather, the electrode 520 may be offset from the apex or tip of the microneedle. The electrode 520 being proximal to or offset from the insulated distal apex 516 of the microneedle advantageously provides more accurate sensor measurements. For example, this arrangement prevents concentration of the electric field at the microneedle apex 516 during manufacturing, thereby avoiding non-uniform electro-deposition of sensing chemistry on the electrode surface 520 that would result in faulty sensing. In some variations, the electrode 520 may be configured to have an annular shape and may comprise a distal edge 521a and a proximal edge 521b.

As another example, placing the electrode 520 offset from the microneedle apex further improves sensing accuracy by reducing undesirable signal artefacts and/or erroneous sensor readings caused by stress upon microneedle insertion. The distal apex of the microneedle is the first region to penetrate into the skin, and thus experiences the most stress caused by the mechanical shear phenomena accompanying the tearing or cutting of the skin. If the electrode 520 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 520 sufficiently offset from the microneedle apex may improve sensing accuracy. For example, in some variations, the distal edge 521a of the electrode 520 may be located at least about 10 μm (e.g., between about 20 μm and about 30 μm) from the distal apex or tip of the microneedle, as measured along a longitudinal axis of the microneedle.

The body portion 512 of the microneedle 510 may further include an electrically conductive pathway extending between the electrode 520 and a backside electrode or other electrical contact (e.g., arranged on a backside of the substrate of the microneedle array). The backside electrode may be soldered to a circuit board, enabling electrical communication with the electrode 520 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 500 is built upon may be electrically conductive, and each microneedle 510 in the microneedle array 500 may be electrically isolated from adjacent microneedles 510 as described below. For example, in some variations, each microneedle 510 in the microneedle array 500 may be electrically isolated from adjacent microneedles 510 with an insulative barrier including electrically insulative material (e.g., dielectric material such as silicon dioxide) that surrounds the conductive pathway extending between the electrode 520 and backside electrical contact. For example, body portion 512 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, as described in further detail below with respective different variations of the microneedle, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays. For example, in some variations, the microneedle array may be formed at least in part using techniques described in U.S. patent application Ser. No. 15/913,709, which is incorporated herein in its entirety by this reference.

Described herein are multiple example variations of microneedle structure incorporating one or more of the above-described microneedle features for a microneedle array in an analyte monitoring device.

In some variations, a microneedle may have a generally columnar body portion and a tapered distal portion with an electrode. For example, FIGS. 7A-7C illustrate an example variation of a microneedle 700 extending from a substrate 702. FIG. 7A is a side cross-sectional view of a schematic of microneedle 700, while FIG. 7B is a perspective view of the microneedle 700 and FIG. 7C is a detailed perspective view of a distal portion of the microneedle 700. As shown in FIGS. 7B and 7C, the microneedle 700 may include a columnar body portion 712, a tapered distal portion 714 terminating in an insulated distal apex 716, and an annular electrode 720 that includes a conductive material (e.g., Pt, Ir, Au, Ti, Cr, Ni, combinations thereof, etc.), is arranged on the tapered distal portion 714, such as for example, on a segment thereof, and comprises a distal edge 721a and a proximal edge 721b. As shown in FIG. 7A, the annular electrode 720 may be proximal to (offset or spaced apart from) the distal apex 716. The electrode 720 may be electrically isolated from the distal apex 716 by a distal insulating surface 715a including an insulating material (e.g., $SiO_2$). For example, the distal edge 721a of the annular electrode 720 may be proximate to a proximal edge of the distal insulating surface 715a of the insulated distal apex 716. In some variations, the distal edge 721a of the annular electrode 720 may be proximal to (e.g., just proximal to, adjacent, abutting) a proximal edge of the distal apex 716 (a proximal edge of the distal insulating surface 715a), while in other variations, the distal edge 721a of the annular electrode 720 may be distal to (e.g., just distal to, adjacent) the proximal edge of the insulated distal apex 716 (proximal edge of the distal insulating surface 715a), but may remain proximal to the apex itself. Accordingly, in some variations, the electrode 720 may overlie a portion of the distal insulating surface 715a but may remain proximal to (and offset from) the insulated distal apex itself (see, e.g., FIG. 21C).

Also as shown in FIG. 7A, the proximal edge 721b of the electrode 720 may be distal to, and in some variations, offset or spaced apart from, the columnar body portion 712. In some variations, the proximal edge 721b of the electrode 720 may also be electrically isolated from the columnar body portion 712 by a second distal insulating surface 715b. For example, the proximal edge 721b of the annular electrode 720 may be proximate to a distal edge of the second distal insulating surface 715b. In some variations, the proximal edge 721b of the electrode 720 may be proximal to (e.g., just proximal to, adjacent, abutting) a distal edge the second distal insulating surface 715b, while in other variations, the proximal edge 721b of the electrode 720 may be distal to (e.g., just distal to, adjacent) the distal edge of the second distal insulating surface 715b but may remain proximal to the columnar body portion 712. Accordingly, in some variations, the electrode 720 may overlie a portion of the second distal insulating surface 715a but may remain proximal to (and offset from) the columnar body portion 712. As shown in FIG. 7A and in some other variations, the annular electrode 720 may be on only a segment of the surface of the tapered distal portion 714 and may or may not extend to the columnar boy portion 712.

The electrode 720 may be in electrical communication with a conductive core 740 (e.g., conductive pathway) passing along the body portion 712 to a backside electrical contact 730 (e.g., made of Ti/Au alloy or Ni/Au alloy) or other electrical pad in or on the substrate 702. For example, the body portion 712 may include a conductive core material (e.g., highly doped silicon). As shown in FIG. 7A, in some variations, an insulating moat 713 including an insulating material (e.g., polySi/SiO$_2$ or SiO$_2$) may be arranged around (e.g., around the perimeter) of the body portion 712 and extend at least partially through the substrate 702. Accordingly, the insulating moat 713 may, for example, help prevent electrical contact between the conductive core 740 and the surrounding substrate 702. The insulating moat 713 may further extend over the surface of the body portion 712. Upper and/or lower surfaces of the substrate 702 may also include a layer of substrate insulation 704 (e.g., SiO$_2$). Accordingly, the insulation provided by the insulating moat 713 and/or substrate insulation 704 may contribute at least in part to the electrical isolation of the microneedle 700 that enables individual addressability of the microneedle 700 within a microneedle array. Furthermore, in some variations the insulating moat 713 extending over the surface of the body portion 712 may function to increase the mechanical strength of the microneedle 700 structure.

The microneedle 700 may be formed at least in part by suitable MEMS fabrication techniques such as plasma etching, also called dry etching. For example, in some variations, the insulating moat 713 around the body portion 712 of the microneedle may be made by first forming a trench in a silicon substrate by deep reactive ion etching (DRIE) from the backside of the substrate, then filling that trench with a sandwich structure of SiO$_2$/polycrystalline silicon (poly-Si)/SiO$_2$ by low pressure chemical vapor deposition (LPCVD) or other suitable process. In other words, the insulating moat 713 may passivate the surface of the body portion 712 of the microneedle and continue as a buried feature in the substrate 702 near the proximal portion of the microneedle. By including largely compounds of silicon, the insulating moat 713 may provide good fill and adhesion to the adjoining silicon walls (e.g., of the conductive core 740, substrate 702, etc.). The sandwich structure of the insulating moat 713 may further help provide excellent matching of coefficient of thermal expansion (CTE) with the adjacent silicon, thereby advantageously reducing faults, cracks, and/or other thermally-induced weaknesses in the insulating structure 713.

The tapered distal portion may be fashioned out by an isotropic dry etch from the frontside of the substrate, and the body portion 712 of the microneedle 700 may be formed from DRIE. The frontside metal electrode 720 may be deposited and patterned on the distal portion by specialized lithography (e.g., electron-beam evaporation and/or lift-off) that permits metal deposition in the desired annular region for the electrode 720 without coating the distal apex 716. Furthermore, the backside electrical contact 730 of, for example, Ti/Au or Ni/Au may be deposited by suitable MEMS manufacturing techniques (e.g., sputtering).

Figure 8:
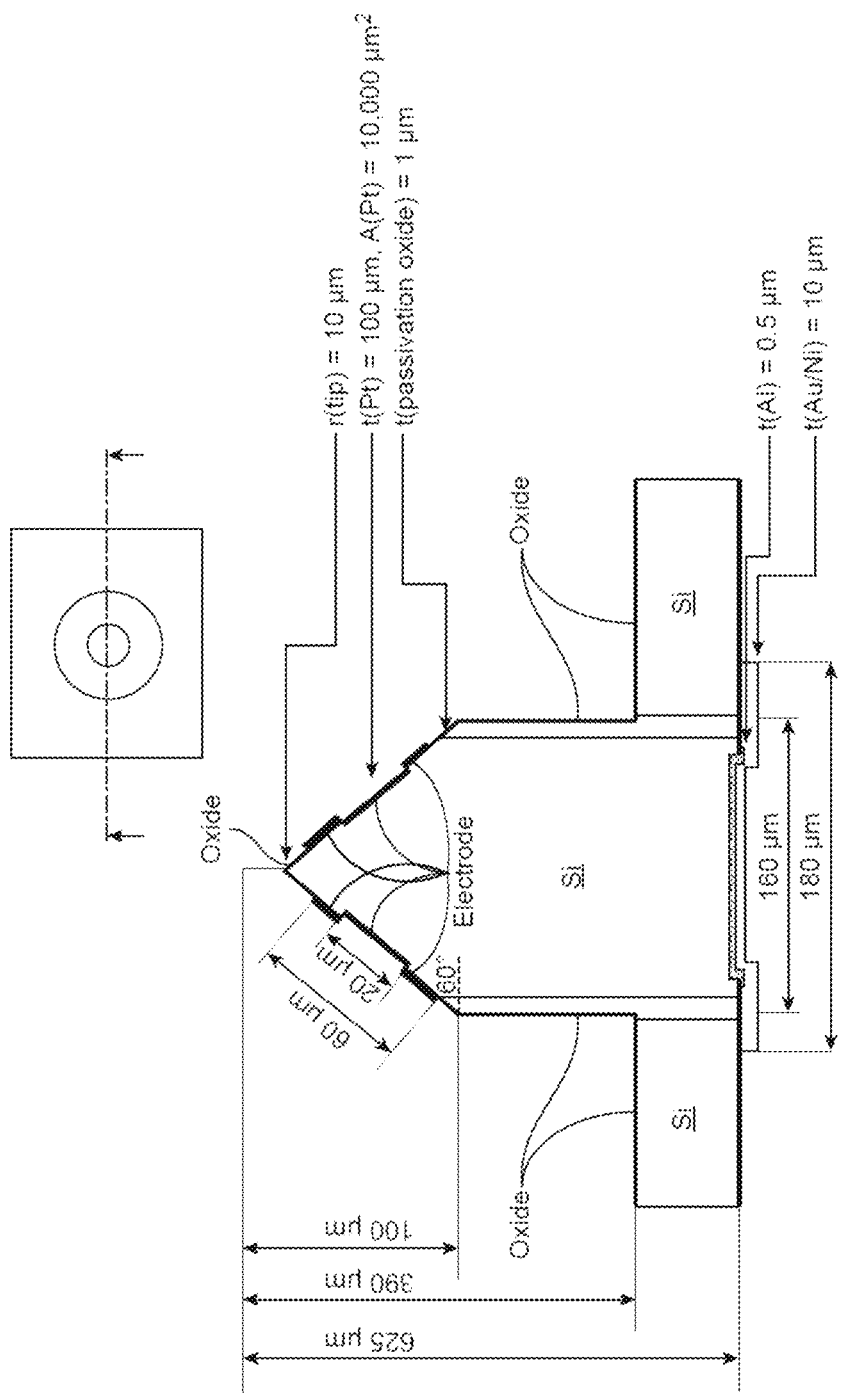
FIG. 8 depicts an illustrative schematic of a columnar microneedle having a tapered distal end.

The microneedle 700 may have any suitable dimensions. By way of illustration, the microneedle 700 may, in some variations, have a height of between about 300 µm and about 500 µm. In some variations, the tapered distal portion 714 may have a tip angle between about 60 degrees and about 80 degrees, and an apex diameter of between about 1 µm and about 15 µm. In some variations, the surface area of the annular electrode 720 may include between about 9,000 µm$^2$ and about 11,000 µm$^2$, or about 10,000 µm$^2$. FIG. 8 illustrates various dimensions of an example variation of a columnar microneedle with a tapered distal portion and annular electrode, similar to microneedle 700 described above. As with the microneedle 700 described above, the columnar microneedle of FIG. 8 comprises a columnar body portion, a tapered distal portion terminating in an insulated distal apex, a contact trench formed within the tapered distal portion, and an annular electrode (denoted by "Electrode" in FIG. 8) that is arranged on the tapered distal portion and overlays the contact trench. The annular electrode may comprise a conductive material (e.g., Pt, Ir, Au, Ti, Cr, Ni, combinations thereof, etc.). In some variations, the contact trench may have a width of about 1 µm, about 2 µm, about 3 µm, about 4 µm, about 5 µm, about 10 µm, about 15 µm, about 20 µm, about 25 µm, about 30 µm, about 35 µm, about 40 µm, about 45 µm, about 50 µm, or, as shown in FIG. 8, about 20 µm. The annular electrode may comprise a distal edge and a proximal edge, and in some variations, a distance between the distal edge and the proximal edge of the annular electrode may be about 20 µm, about 30 µm, about 40 µm about 50 µm, about 60 µm, about 70 µm, about 80 µm, about 90 µm, about 100 µm, or, as shown in FIG. 8, about 60 µm. In some variations, and as shown in FIG. 8 by the lines extending from "Electrode", the annular electrode may overlie the contact trench and, in some instances, a portion of the insulating surfaces (denoted by "Oxide" in FIG. 8) of the tapered distal portion.

Figure 9A:
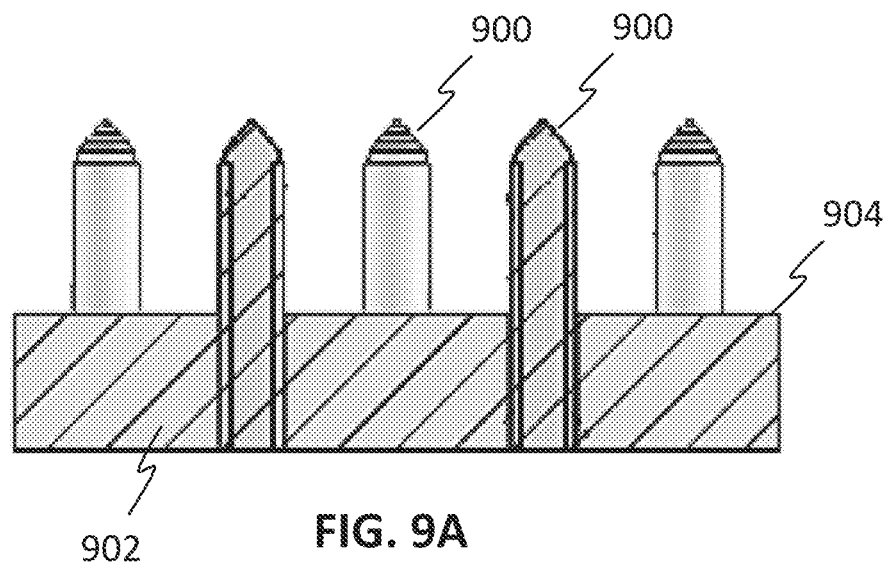
FIGS. 9A and 9B depict illustrative schematics of a microneedle array and a microneedle, respectively.
Figure 9B:
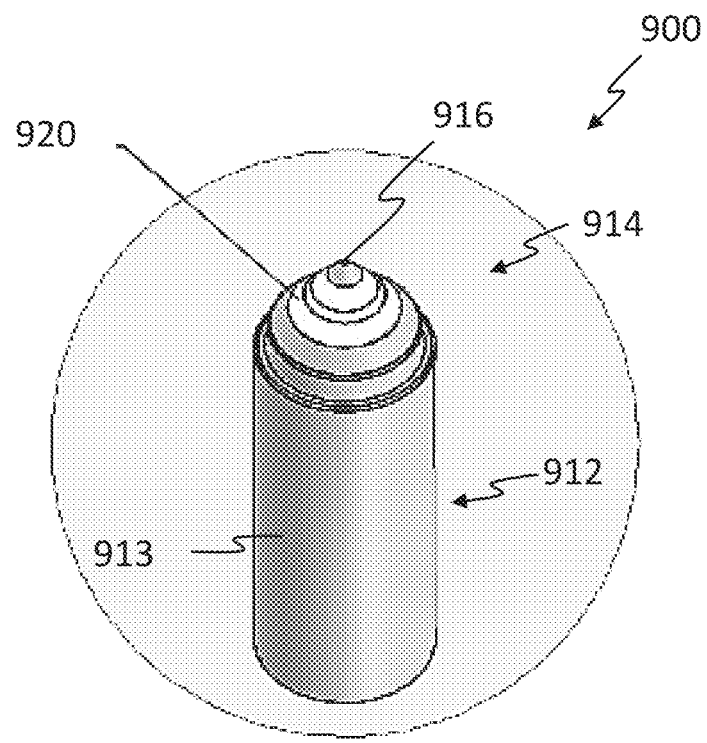

FIGS. 9A-9F illustrate another example variation of a microneedle 900 having a generally columnar body portion. The microneedle 900 may be similar to microneedle 700 as described above, except as described below. For example, like the microneedle 700, the microneedle 900 in FIG. 9A extends from a substrate 902. An upper surface of the substrate 902 may include a layer of substrate insulation 904. As shown in FIG. 9B, like the microneedle 700, the microneedle 900 may include a columnar body portion 912 and a tapered distal portion 914 terminating in an insulated distal apex 916. The microneedle 900 may further include an annular electrode 920 that includes a conductive material and is arranged on the tapered distal portion 914 at a location proximal to (or offset from or spaced apart from) the distal apex 916. The electrode 920 may be in electrical communication with a conductive core 940 passing along the body portion 912 to a backside electrical contact 930. Other elements of microneedle 900 have numbering similar to corresponding elements of microneedle 700.

However, compared to the microneedle 700, the microneedle 900 may have a sharper tip at the distal apex 916 and a modified insulating moat 913. For example, the distal apex 916 may have a sharper tip angle, such as between about 25 degrees and about 45 degrees, and an apex radius of less than about 100 nm, which provides a sharper microneedle profile that may penetrate skin with greater ease, lower velocity, less energy, and/or less trauma. Furthermore, in contrast to the insulating moat 713 (which extends through the substrate 702 and along the height of the microneedle body portion 712 as shown in FIG. 7A), in some variations, the modified insulating moat 913 may extend only through the substrate 902 such that the sandwich structure filling the trench (e.g., created by DRIE as described above) forms only the buried feature in the substrate. Although the sidewall of the microneedle 900 is shown in FIG. 9A as extending generally orthogonal to the substrate surface, it should be understood that, in variations where the modified insulating moat does not extend the entire height of the microneedle body portion 912, the sidewall of the microneedle 900 may be angled at non-orthogonal angles relative to the substrate (e.g., the sidewall may have a slight positive taper of between about 1 degree to about 10 degrees, or between about 5 degrees and about 10 degrees).

In some variations, the rest of the microneedle surface 900 (aside from the annular electrode 920) may include an insulating material extending from the substrate insulation 904. For example, a layer of an insulating material (e.g., $SiO_2$) may extend from a frontside surface of the substrate 902 to provide a body portion insulation and may further extend up over a proximal edge of the electrode 920, as shown in e.g., FIG. 9C. Another region of insulating material may similarly cover a distal edge of the electrode 920 and insulate the distal apex 916. Such region of insulating material and/or modified insulating moat 913 may help prevent electrical contact between the conductive core 940 and the surrounding substrate 902. Accordingly, like the microneedle 700, the microneedle 900 may maintain electrical isolation for individual addressability within a microneedle array. In some variations, the process to form microneedle 900 may result in higher yield and/or provide lower production cost compared to the process to form microneedle 700.

The microneedle 900 may have any suitable dimensions. By way of illustration, the microneedle 900 may, in some variations, include a height of between about 400 μm and about 600 μm, or about 500 μm. In some variations, the tapered distal portion 914 may have a tip angle of between about 25 degrees and about 45 degrees, with a tip radius of less than about 100 nm. Furthermore, the microneedle may have a shaft diameter of between about 160 μm and about 200 μm.

In some variations, the electrode 920 may be electrically isolated from the distal apex 916 by a distal insulating surface 915a including an insulating material (e.g., $SiO_2$). In some variations, the proximal edge of the electrode 920 may be electrically isolated from the columnar body portion 912 by a second distal insulating surface 915b. Other elements of microneedle 900 as shown in FIGS. 9A-9F have numbering similar to corresponding elements of microneedle 700.

As can most easily be seen in FIGS. 9B, 9C, and 9F, the tapered distal portion 914, and more specifically, the electrode 920 on the tapered distal portion 914 of the microneedle 900 may include a tip contact trench 922. This contact trench may be configured to establish ohmic contact between the electrode 920 and the underlying conductive core 940 of the microneedle. In some variations, the shape of the tip contact trench 922 may include an annular recess formed in the surface of the tapered distal portion 914. In some variations, the shape of the tip contact trench 922 may include an annular recess formed in the surface of the conductive core 940 (e.g., into the body portion of the microneedle, or otherwise in contact with a conductive pathway in the body portion). In some variations, the tip contact trench may be formed in the insulating material on the tapered distal portion 914 and may have a depth about equal to the thickness of the insulating material. In some instances, the depth of the contact trench may be greater than the thickness of the insulating material such that the contact trench extends beyond a surface of the conductive core 940 (i.e., into the conductive core 940). The electrode 920 may overlie the tip contact trench 922 such that ohmic contact is established between the electrode 920 and the conductive core 940. In some variations, the electrode 920 may extend beyond the tip contact trench 922 such that when the electrode 920 material is deposited onto the conductive core 940, the electrode 920 with the tip contact trench 922 may have a stepped profile when viewed from the side. The tip contact trench 922 may advantageously help provide a margin of error to ensure contact between the electrode 920 and the underlying conductive core 940. Any of the other microneedle variations described herein may also have a similar tip contact trench to help ensure contact between the electrode (which may be, for example, a working electrode, reference electrode, counter electrode, etc.) with a conductive pathway within the microneedle.

Figure 10A:
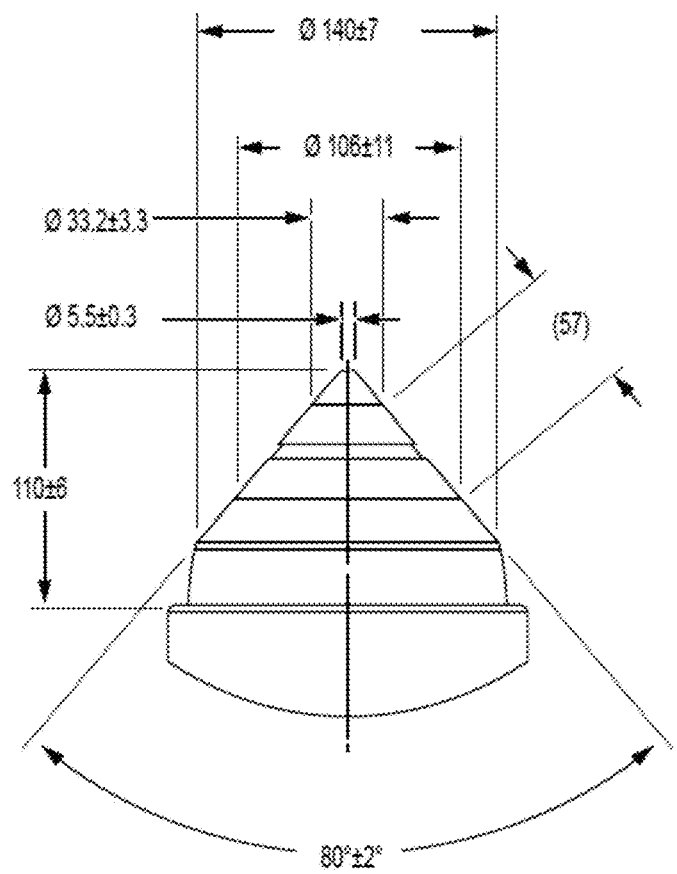
FIGS. 10A and 10B depict an illustrative variation of a microneedle.
Figure 10B:
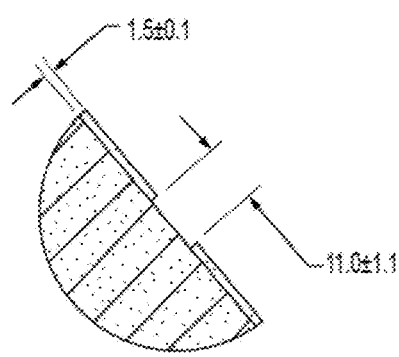

FIGS. 10A and 10B illustrate additional various dimensions of an example variation of a columnar microneedle with a tapered distal portion and annular electrode. For example, the variation of the microneedle shown in FIGS. 10A and 10B may have a tapered distal portion generally having a taper angle of about 80 degrees (or between about 78 degrees and about 82 degrees, or between about 75 degrees and about 85 degrees), and a cone diameter of about 140 μm (or between about 133 μm and about 147 μm, or between about 130 μm and about 150 μm). The cone of the tapered distal portion may be arranged on a cylinder such that the overall combined height of the cone and cylinder is about 110 μm (or between about 99 μm and about 116 μm, or between about 95 μm and about 120 μm). The annular electrode on the tapered distal portion may have an outer or base diameter of about 106 μm (or between about 95 μm and about 117 μm, or between about 90 μm and about 120 μm), and an inner diameter of about 33.2 μm (or between about 30 μm and about 36 μm, or between about 25 μm and about 40 μm). The length of the annular electrode, as measured along the slope of the tapered distal portion, may be about 57 μm (or between about 55 μm and about 65 μm), and the overall surface area of the electrode may be about 12,700 $\mu m^2$ (or between about 12,500 $\mu m^2$ and about 12,900 $\mu m^2$, or between about 12,000 $\mu m^2$ and about 13,000 $\mu m^2$). As shown in FIG. 10B, the electrode may furthermore have a tip contact trench extending around a central region of the cone of the tapered distal portion, where the contact may have a width of about 11 μm (or between about 5 μm and about 50 μm, between about 10 μm and about 12 μm, or between about 8 μm and about 14 μm) as measured along the slope of the tapered distal portion, and a trench depth of about 1.5 μm (or between about 0.1 μm and about 5 μm, or between about 0.5 μm and about 1.5 μm, or between about 1.4 μm and about 1.6 μm, or between about 1 μm and about 2 μm). The microneedle has an insulated distal apex having a diameter of about 5.5 μm (or between about 5.3 μm and about 5.8 μm, or between about 5 μm and about 6 μm).

Additional details of example variations of microneedle array configurations are described in further detail below.

Electrodes

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers, or other components, over the metallization layer that help facilitate the function of the particular electrode.

Generally, the working electrode is the electrode at which an oxidation reaction and/or a reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

As described herein, the working electrode is the electrode at which the oxidation reaction and/or the reduction reaction of interest occurs. In some variations, sensing may be performed at the interface of the working electrode and interstitial fluid located within the body (e.g., on an outer surface of the overall microneedle). In some variations, a working electrode may include an electrode material and a biorecognition layer, in which a biorecognition element (e.g., enzyme) is immobilized, on the working electrode to facilitate selective analyte quantification. In some variations, when the biorecognition layer includes an interferent blocking agent, as will be described in more detail herein, the biorecognition layer may also function to help prevent, limit, or otherwise inhibit endogenous and/or exogenous species from directly oxidizing (or reducing) at the electrode. In some variations, the working electrode may also include a diffusion-limiting layer that is a separate and distinct layer and similarly functions to minimize endogenous and/or exogenous species from directly oxidizing (or reducing) at the electrode. The separate and distinct diffusion-limiting layer may be referred to elsewhere herein as a glucose limiting layer or, more broadly, as an analyte limiting layer. In some variations, in addition to the biorecognition layer and/or the diffusion-limiting layer, an electrode protecting layer may be provided for additional protection of the electrode. In some variations, in which the biorecognition layer and the diffusion-limiting layer are separate and distinct layers, an attachment enhancer may be provided between and/or within the biorecognition layer and the diffusion-limiting layer to promote coupling between the layers and improve sensor stability and sensitivity. In some variations, to prevent, limit, or otherwise inhibit additional interferents such as foreign body response actors from reaching the electrode surface, an interferent blocking agent, separate from and/or in addition to the above-described diffusion-limiting layer, may be provided within the biorecognition layer such that voids within the biorecognition layer, which may traverse a full thickness of the biorecognition and/or may otherwise expose the metallization layer, are filled with the interferent blocking agent.

A redox current detected at the working electrode may be correlated to a detected concentration of an analyte of interest. This is because assuming a steady-state, diffusion-limited system, the redox current detected at the working electrode follows the Cottrell relation below:

$$i(t) = \frac{nFA\sqrt{D}\,C}{\sqrt{\pi t}}$$

where n is the stoichiometric number of electrons mitigating a redox reaction, F is Faraday's constant, A is electrode surface area, D is the diffusion coefficient of the analyte of interest, C is the concentration of the analyte of interest, and t is the duration of time that the system is biased with an electrical potential. Thus, the detected current at the working electrode scales linearly with the analyte concentration.

Moreover, because the detected current is a direct function of electrode surface area A, the surface area of the electrode may be increased to enhance the sensitivity (e.g., amperes per molar of analyte) of the sensor. For example, multiple singular working electrodes may be grouped into arrays of two or more constituents to increase total effective sensing surface area. Additionally, or alternatively, to obtain redundancy, multiple working electrodes may be operated as parallelized sensors to obtain a plurality of independent measures of the concentration of an analyte of interest. The working electrode can either be operated as the anode (such that an analyte is oxidized at its surface), or as the cathode (such that an analyte is reduced at its surface).

Generally, the counter electrode is the electrode that is sourcing or sinking electrons (via an electrical current) required to sustain the electrochemical reaction at the working electrode. The number of counter electrode constituents can be augmented in the form of a counter electrode array to enhance surface area such that the current-carrying capacity of the counter electrode does not limit the redox reaction of the working electrode. It thus may be desirable to have an excess of counter electrode area versus the working electrode area to circumvent the current-carrying capacity limitation. If the working electrode is operated as an anode, the counter electrode will serve as the cathode and vice versa. Similarly, if an oxidation reaction occurs at the working electrode, a reduction reaction occurs at the counter electrode and vice versa. Unlike the working or reference electrodes, the counter electrode is permitted to dynamically swing to electrical potentials required to sustain the redox reaction of interest on the working electrode.

Generally, the reference electrode functions to provide a reference potential for the system. That is, the electrical potential at which the working electrode is biased is referenced to the reference electrode. A fixed or at least controlled potential relationship may be established between the working and reference electrodes, and within practical limits no current is sourced from or sinked to the reference electrode.

Electrode Layers

As introduced above, the electrodes described herein may comprise one or more layers or components that facilitate the function of the electrode within the devices described here, such as, for example, in forming an electrochemical cell for the detection of an analyte of interest. Accordingly, the electrodes described herein may comprise one or more of, in any combination, an electrode material or metallization layer, an electrocatalytic layer, a redox-couple layer, a sensing layer, a biocompatibility layer, an attachment enhancer, an electrode protecting layer, an interferent blocking agent, and a diffusion-limiting layer. The sensing layer, which may be a biorecognition layer, may comprise a biorecognition element.

Unless described otherwise, the exemplary layers and components described above and in detail below may be present or omitted from the electrode(s) in any combination. Exemplary combinations will be described with reference to FIGS. 11A-12B.

a. Electrode Material or Metallization Layer

The electrode material or metallization layer may be the initial or base layer of the electrodes described herein and may provide electrical communication between any remaining layers of the electrode and the structure (e.g., microneedle) on which the electrode is positioned. When used in conjunction with a biorecognition element, the electrode material functions to encourage the electrocatalytic detection of an analyte or the product of the reaction of the analyte and the biorecognition element. The electrode material also provides ohmic contact and routes an electrical signal from the electrocatalytic reaction to processing circuitry. For example, in variations in which the electrode is positioned on a microneedle, and the microneedle comprises a conductive core or an otherwise conductive pathway, the electrode material may be in direct contact with the conductive core or component. The electrode material or metallization layer may comprise any suitable conductive or semiconductive material. For example, the electrode material or metallization layer may comprise platinum, palladium, iridium, rhodium, gold, ruthenium, titanium, nickel, carbon, doped diamond, or combinations thereof. In some variations, the electrode material may include a metal salt or metal oxide, which serves as a stable redox coupled with a well-known electrode potential. For example, the metal salt may include, for example, silver-silver chloride (Ag/AgCl) and the metal oxide may include iridium oxide (IrOx/$Ir_2O_3$/$IrO_2$). In other variations, noble and inert metal surfaces may function as quasi-reference electrodes and include platinum, palladium, iridium, rhodium, gold, ruthenium, titanium, nickel, carbon, doped diamond, or combinations thereof, and/or other suitable catalytic and inert material.

b. Redox-Couple Layer

In some variations, the electrodes described herein may comprise a redox-couple layer that may contain a surface-immobilized, solid-state redox couple with a stable thermodynamic potential. The redox-couple layer may allow an electrode to operate at a stable standard thermodynamic potential with respect to a standard hydrogen electrode (SHE). The high stability of the electrode potential may be attained by employing a redox system with constant (e.g., buffered or saturated) concentrations of each participant of the redox reaction. For example, the electrode may include saturated Ag/AgCl (E=+0.197V vs. SHE) or IrOx (E=+ 0.177 vs. SHE, pH=7.00) in the redox-couple layer. Other examples of redox-couple layers may include a suitable conducting polymer with a dopant molecule such as that described in U.S. Patent Pub. No. 2019/0309433, which is incorporated in its entirety herein by this reference. In some variations, the reference electrode may comprise a redox-couple layer, and the reference electrode may be used as a half-cell to construct a complete electrochemical cell.

c. Electrocatalytic Layer

In some variations, the electrodes described herein may comprise an electrocatalytic layer that may effectively increase the surface area of the metallization layer to increase sensitivity of the electrode. In this manner, inclusion of an electrocatalytic layer may augment the electrode surface area for enhanced sensitivity. In some instances, the electrode material of the electrode(s) may be coated with the electrocatalytic layer. In some variations, the electrocatalytic layer may be highly porous. In some variations, the electrocatalytic layer may be a platinum black layer and/or may comprise carbon nanotubes, carbon fibers, elemental platinum, graphene-based materials, metal nanoparticles, quantum dots iridium, metal-organic frameworks, and covalent organic frameworks, among others.

For a working electrode comprising a biorecognition layer, the electrocatalytic layer may, additionally or alternatively, enable the electrocatalytic oxidation or reduction of a product of a biorecognition reaction facilitated by the biorecognition layer. However, in some variations of the working electrode, the electrocatalytic layer may be omitted. In such instances, the electrode may enable the electrocatalytic oxidation or reduction of the product of the biorecognition reaction if the electrocatalytic layer is not present.

In some variations, the electrocatalytic layer can increase the surface area of the electrode up to 10 times the surface area of the electrode material alone. In some variations, the surface area of the electrode due to the electrocatalytic layer is about two times, about three times, about four times, about five times, about six times, about seven times, about eight times, about nine times, or about 10 times that of an electrode without an electrocatalytic layer.

d. Biocompatibility Layer

The electrodes described herein may, in some variations, further include a biocompatibility layer. The biocompatibility layer may be a hydrophilic layer that provides for a biocompatible interface to, for example, reduce the foreign body response. The hydrophilic layer may be added through, for example, plasma polymerization techniques or grafting techniques. In some variations, the hydrophilic layer may be omitted (e.g., if the diffusion-limiting layer expresses hydrophilic moieties to serve this purpose). In variations, the biocompatibility layer may comprise one or more materials selected from the group consisting of polyurethane, polyether, etc.

e. Biorecognition Layer

In some variations, the electrode(s) may comprise a biorecognition layer in which a biorecognition element is immobilized and stabilized to facilitate analyte quantification. For example, in some variations, the biorecognition layer may comprise a polymer and the biorecognition element may be immobilized therein. In variations, the biorecognition element may be physically entrapped, cross-linked, or otherwise attached to the polymer. For instance, though not bound to the polymer, the biorecognition element may be physically entrapped within the polymer during polymerization of the polymer. The biorecognition element facilitates selective analyte quantification for extended time periods (e.g. >7 days). In some variations, the biorecognition element may include an enzyme, such as an oxidase. As an exemplary variation for use in a glucose monitoring system, the biorecognition element may include glucose oxidase, which converts glucose, in the presence of oxygen, to an electroactive product (i.e., hydrogen peroxide) that can be detected at the electrode material surface. Specifically, the redox equation associated with this exemplary variation is Glucose+Oxygen→Hydrogen Peroxide+Gluconolactone (mediated by glucose oxidase); Hydrogen Peroxide→Water+Oxygen (mediated by applying an oxidizing potential at the working electrode).

However, in other variations, the biorecognition element may additionally or alternatively comprise another suitable enzyme, including oxidase and oxidoreductase enzymes, such as glucose dehydrogenase, 3-hydroxybutyrate dehydrogenase, lactate dehydrogenase, lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and/or xanthine oxidase.

In some variations, the biorecognition element may be cross-linked with an amine-condensing carbonyl chemical species that may help stabilize the biorecognition element within the biorecognition layer. As further described below, in some variations, the cross-linking of the biorecognition element may result in the microneedle array being compatible with ethylene oxide (EO) sterilization, which permits exposure of the entire analyte monitoring device (including sensing elements and electronics) to the same sterilization cycle, thereby simplifying the sterilization process and lowering manufacture costs. In some variations, the microneedle array may be compatible with other types of sterilization methods, such as but not limited to radiation sterilization.

For example, the biorecognition element may be cross-linked with glutaraldehyde, formaldehyde, glyoxal, malonaldehyde, succinaldehyde, and/or other suitable species. In some variations, the biorecognition element may be cross-linked with such an amine-condensing carbonyl chemical species to form cross-linked biorecognition element aggregates. Cross-linked biorecognition element aggregates that have at least a threshold molecular weight may then be embedded in a conducting polymer. By embedding only those aggregates that have a threshold molecular weight, any uncross-linked enzymes may be screened out and not incorporated into the biorecognition layer. Accordingly, only aggregates having a desired molecular weight may be selected for use in the conducting polymer, to help ensure that only sufficiently stabilized, cross-linked enzyme entities are included in the biorecognition layer, thereby contributing to a biorecognition layer that is overall better suited for EO sterilization without loss in sensing performance. In some variations, only cross-linked aggregates that have a molecular weight that is at least twice that of glucose oxidase may be embedded in the conducting polymer.

In some variations, the polymer of the biorecognition layer may be a conducting polymer. In these variations, the conducting polymer may be permselective to contribute to the biorecognition layer's robustness against circulating androgynous electroactive species (e.g., ascorbic acid, vitamin C, etc.), fluctuations of which may adversely affect the sensitivity of the sensor. Such a permselective conducting polymer in the biorecognition layer may further be more robust against pharmacological interferences (e.g., acetaminophen) in the interstitial fluid that may affect sensor accuracy. Conducting polymers may be made permselective by, for example, removing excess charge carriers by an oxidative electropolymerization process or by neutralizing these charge carriers with a counter-ion dopant, thereby transforming the conducting polymer into a non-conducting form. These oxidatively-polymerized conducting polymers exhibit permselectivity and are hence able to reject ions of similar charge polarity to the dopant ion (net positive or negative) or by via size exclusion due to the dense and compact form of the conducting polymers.

Furthermore, in some variations the conducting polymer of the biorecognition layer may exhibit self-sealing and/or self-healing properties. For example, the conducting polymer may undergo oxidative electropolymerization, during which the conducting polymer may lose its conductivity as the thickness of the deposited conducting polymer on the electrode increases, until the lack of sufficient conductivity causes the deposition of additional conducting polymer to diminish. In the event that the conducting polymer has succumbed to minor physical damage (e.g., during use), the polymeric backbone may re-assemble to neutralize free charge and thereby lower overall surface energy of the molecular structure, which may manifest as self-sealing and/or self-healing properties.

In some variations, the polymer may be a conducting polymer and may include one or more of aniline, pyrrole, acetylene, phenylene, phenylene vinylene, phenylene diamine, thiophene, 3,4-ethylenedioxythiophene, and aminophenylboronic acid.

In some variations, the biorecognition element in the biorecognition layer may be a molecule that selectively binds to a given analyte. In some variations, the biorecognition element in the biorecognition layer may be a molecule that selectively and reversibly binds to a given analyte. In some instances, the biorecognition element may be an oligonucleotide. In some variations, the oligonucleotide may be DNA or RNA. The oligonucleotide may be functionalized at the 3' end or the 5' end. One end may provide a chemical moiety ("immobilization moiety") for surface immobilization, such as an amine, aldehyde, carboxylic acid, thiol, disulfide, azide, n-hydroxysuccinimide (NHS), maleimide, vinyl, silane, chlorosilane, methoxysilane, ethoxysilane, or acetylene group. The immobilization moiety may be separated from the oligonucleotide sequence by a linker selected for its ability to create distance between the oligonucleotide sequence and the surface to which it is immobilized. The linker may also be chosen for its compatibility with other chemical layers on the electrode surface, for example, a hydrocarbon linker with equal or similar length to the hydrocarbon chain used in a self-assembled monolayer that is coating the remainder of the electrode surface. The opposite end of the oligonucleotide may be functionalized with one or more redox active molecules, by way of example methylene blue, ferrocene, pentamethyl ferrocene, C5-ferrocene, Nile blue, thionine, anthraquinone, hydroquinone, C5-anthraquinone, gallocyanine, indophenol, neutral red, dabcyl, $\pi$ extended tetrathiafulvalene (exTTF), or carboxy-X-rhodamine, that serve as a probe. These redox-active molecules may also be attached to the oligonucleotide through a custom linker. The backbone of the oligonucleotide may be modified to increase stability in physiological conditions. For example, an RNA sequence incorporating L-ribose or a DNA sequence incorporating L-deoxyribose, as opposed to their natural respective dextrorotary sugars, may be used to protect the oligonucleotide from degradation by enzymes in the body. In some variations, a backbone modification may include replacing ribose in RNA or deoxyribose in DNA with 2'-O-methyl ribose, also with the effect of protection from enzyme cleavage in physiological conditions.

In some variations, the oligonucleotide may comprise a region having a nucleotide sequence complementary to a given nucleic acid analyte, by way of example a viral or bacterial gene or regulatory region. In some variations, the oligonucleotide may be an aptamer.

In some instances, the biorecognition element may be a peptide. The peptide may be an antibody or a portion thereof, such as a nanobody (also known as an VHH antibody) that comprises an antigen binding fragment of heavy chain only antibodies, that selectively binds a given analyte.

In some instances, the molecule may be an aptamer (an "analyte-binding aptamer"). An aptamer is a peptide or single-stranded oligonucleotide that folds into a defined structure that selectively binds to a specific analyte (which may be referred to as target), which may be, by way of example, a protein, a peptide, a hormone, a nucleic acid, or a small molecule. Recognition and binding of an aptamer to its target involve three-dimensional, shape-dependent interactions as well as hydrophobic interactions, base-stacking, and intercalation, and are typically reversible through dissociation. Aptamers with affinity for a desired target are conventionally selected from a large oligonucleotide library through a process called SELEX (Systematic Evolution of Ligands by Exponential Enrichment). Through an iterative process, non-binding aptamers are discarded and aptamers binding to the proposed target are amplified by polymerase chain reaction (PCR). The iterative process may include counter-selection (using interferents and structurally similar molecules) to discard aptamers with insufficient selectivity toward analytes. Multiple rounds of SELEX may be performed with increasing stringency to enhance enrichment of the oligonucleotide pool, until one or more oligonucleotides having a desired degree of affinity and selectivity for the desired target are selected for use.

In some variations, the analyte-binding aptamer is an aptamer as described in U.S. Provisional Patent Application No. 63/478,482, filed Jan. 4, 2023, which is incorporated herein by reference in its entirety.

In some variations, the analyte-binding aptamer is a cortisol-binding aptamer defined by the following DNA sequence, 5'-GGACGACGCCAGAAGTTTACGAGGA-TATGGTAACATAGTCGT-3' (SEQ ID NO: 1), where G, A, C, and T represent the typical DNA nucleotides containing guanine, adenine, cytosine, and thymine, respectively.

In some variations, the analyte-binding aptamer may be selected not for maximal affinity for analyte, but for an intermediate degree of affinity such that the portion of a population of the selected aptamer having an analyte molecule bound to it is sensitive to a physiological concentration range of analyte within dermal interstitial fluid, which may be between about 1 pmol/L and about 10 mmol/L or between about 0.001 µmol/L and about 1 µmol/L. In some variations, selection criteria of the analyte-binding aptamer may include the analyte-binding aptamer having between about 10% and about 75% "on" gain from minimum to maximum analyte concentrations and/or having between about 10% to about 40% "off" gain from minimum to maximum analyte concentrations. A signal "on gain" may refer to a set of square wave voltammetry parameters (frequency, peak value, step height) selected towards maximizing a current signal obtained in the presence of a target analyte. A signal "off gain" may refer to a set of square wave voltammetry parameters selected towards minimizing the current signal obtained in the presence of a target analyte. Sensitivity of the aptamer to analyte in dermal interstitial fluid advantageously allows for avoiding interference or signal degradation over time from biofouling or irreversible changes to the aptamer structure due to folding or damage.

The analyte-sensing aptamer may be functionalized with a redox-active molecule, by way of example methylene blue, ferrocene, pentamethyl ferrocene, C5-ferrocene, Nile blue, thionine, anthraquinone, C5-anthraquinone, hydroquinone, gallocyanine, indophenol, neutral red, dabcyl, exTTF, or carboxy-X-rhodamine, Where the aptamer is an oligonucleotide, the redox-active molecule may be functionalized at the 3' end or 5' end of the aptamer. A specific and reversible binding of analyte to the analyte-binding aptamer and the resultant conformational change of the analyte-binding aptamer may leads to a change in the proximity, and thus electron transfer characteristics, between the redox-active molecule and the working electrode to which the aptamer is bound. that is corresponding to the analyte concentration. Due to the analyte-binding property of the aptamer, the change in the electron transfer characteristics of the electrode corresponds to analyte concentration, and the electron transfer characteristics may be interrogated by various electrochemical techniques such as voltammetry, potentiometry, chronoamperometry, and/or electrochemical impedance spectroscopy. Voltammetry techniques vary the potential as a function of time and the resulting current is plotted as a function of potential. For example, cyclic voltammetry (CV) sweeps the potential of the cell linearly across a voltage range, while a fast scan CV (FSCV) technique does this at a faster rate. Alternating current voltammetry (ACV) uses application of a sinusoidally oscillating voltage to an electrochemical cell. Square wave voltammetry (SWV) uses a square wave superimposed over a staircase function to provide a sweeping measurement that provides two sampling instances per potential. As a result of this sampling technique, the contribution to the total current that results from non-faradic currents is minimized in SWV. In potentiometry, an open circuit potential is measured between a reference electrode and a working electrode. In chronoamperometry, the potential is stepped at the beginning of a measurement and then remains constant throughout the duration of the measurement, and the current that results from this stimulus may be plotted as a function of time. In electrochemical impedance spectroscopy, the complex impedance of the electrode is determined at one or more frequencies. Contributions to impedance (or admittance) from resistive and reactive circuit elements may be dependent on the position of redox probes tethered to surface-bound aptamers and correlate with analyte concentration.

f. Diffusion-Limiting Layer

In some variations, the electrodes described herein may comprise a diffusion-limiting layer that may function to limit the flux of the analyte of interest in order to reduce the sensitivity of the sensor to endogenous oxygen fluctuations. For example, the diffusion-limiting layer may attenuate the concentration of the analyte of interest so that it becomes the limiting reactant to an aerobic enzyme. In some variations, the diffusion-limiting layer may be a glucose limiting layer. In variations, the diffusion-limiting layer may comprise one or more materials selected from the group consisting of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene.

g. Attachment Enhancer

In some variations, the electrodes described herein may comprise an attachment enhancer within and between layers of the respective electrodes. In some variations, the attachment enhancer may comprise a plurality of molecules, which may be reactive molecules (e.g., cross-linker). The reactive molecule may interact with and/or bind to moieties within and between layers of the respective electrodes. In some variations, the reactive molecule may be at least monofunctional, bifunctional (i.e., homobifunctional or heterobifunctional), and/or trifunctional. The reactive molecule may be amine-reactive. The reactive molecule may have at least one functional group selected from the group including alkanes, alkenes, alkynes, aromatic rings, alcohols, ethers (including epoxides), amines, thiols, alkyl halides, aldehydes, ketones, carboxylic acids, esters, amides, acid halides, anhydrides, nitriles, thioethers, nitro, imine, and azide. In some variations, the reactive molecule may comprise N (1, 2, 3, 4) epoxide functional groups connected to a linker. Such linker may be an aromatic or an aliphatic, linear or branched, of different lengths, and/or may comprise various arrangements of repeating units of oxygen, nitrogen, carbon, and/or sulfur. In some variations, the reactive molecule may be at least one selected from the group including carboxyls, sulfhydrls, carbonyls, carbodiimides, N-hydroxysuccinimide (NHS) esters, imidoesters, epoxides, maleimides, haloacetyls, pyridyldisulfides, hydrazides, alkoxyamines, diazirines, and aryl azides, In some variations, the reactive molecule may be one or more of 1,6-hexanediol diglycidyl ether, neopentyl glycol diglycidyl ether, poly(propylene glycol) diglycidyl ether, trimethylolethane diglycidyl ether, trimethylolpropane triglycidyl ether, diglycidyl resorcinol ether, diglycidyl ether, diethylene glycol diglycidyl ether, 1,4-cyclohexane dimethanol diglycidyl ether, castor oil glycidyl ether, bisphenol A diglycidyl ether, and 1,4-butanediol diglycidyl ether.

In some variations in which the electrodes is a working electrode comprising a biorecognition layer and a diffusion-limiting layer, the attachment enhancer may be between and/or within the biorecognition layer and the diffusion-limiting layer. The attachment enhancer may improve the stability of the sensor by interacting with and/or binding to moieties in each of the biorecognition layer and the diffusion-limiting layer.

The attachment enhancer may improve stability of the sensor by interacting with and/or binding to moieties in each of the biorecognition layer, the diffusion-limiting layer, and/or the electrode material. Presence or absence of the attachment enhancer may be based on, independently or together, relative affinities, material properties, and/or structural properties of other layers, such as, for example, the biorecognition layer and the diffusion-limiting layer. For instance, a relative affinity between the diffusion-limiting layer and the biorecognition layer may determine whether the attachment enhancer is needed. When the relative affinity is low, the attachment enhancer may be helpful to ensure adhesion between the layers and prevent delamination upon insertion. Similarly, a thickness of the diffusion-limiting layer may determine whether the attachment enhancer is helpful. When the thickness of the diffusion-limiting layer increases such that there is an elevated risk for sensor damage (e.g., delamination) upon insertion, the attachment enhancer may be included. Conversely, when the thickness of the diffusion-limiting layer is decreased such that there is minimal risk of sensor damage upon insertion, the attachment enhancer may be excluded.

The attachment enhancer may interact with the biorecognition layer and the diffusion-limiting layer in a variety of ways. For instance, a first end of the attachment enhancer may covalently bind to moieties within the biorecognition layer. Such moieties may include a biorecognition element (e.g., an enzyme) and/or a functional group of the polymer matrix of the biorecognition layer. A second end of the attachment enhancer may be interwoven with moieties of the diffusion-limiting layer via one or more hydrophilic-hydrophilic interactions, hydrogen bonding, and Van der Waals forces, among others.

In some variations, the reactive molecule of the attachment enhancer may be a bifunctional molecule comprising e.g., amine-reactive functional groups, appreciating that enzymes are proteins and thus have free amines. For example, the attachment enhancer may be an epoxide-bearing bifunctional molecule such as 1,4-butanediol diglycidyl ether (BDDGE). BDDGE is a homobifunctional molecule comprising epoxide functional groups connected by a linker (similar to the linkers described above). Though described below with reference to the working electrode of FIGS. 12A and 12B, it can be appreciated that the attachment enhancer is generally applicable to electrode(s) having the structures and functional groups described herein.

h. Interferent Blocking Agent

The electrodes described herein comprising an electrode material and a biorecognition layer (i.e., the working electrodes), may further include an interferent blocking agent. The interferent blocking agent may be within at least a portion of a plurality of voids of the biorecognition layer. Electropolymerization of the biorecognition layer may result in the formation of an electropolymerized network having voids. The voids may include defects, openings, and the like that are within the biorecognition layer. The voids may independently be any shape and/or size, may be interconnected or isolated, and/or may be distributed uniformly or nonuniformly throughout the biorecognition layer. The voids may traverse a thickness of the biorecognition layer and/or may be exposed to a surface of the electrode material, thus exposing the electrode surface to potential interferents. As discussed above, access by interferents to the electrode material via the voids may result in increased interference current and a deterioration of an analyte signal. Accordingly, in order to limit access by interferents to the surface of the electrode material via the voids, one or more of the voids within the biorecognition layer may be at least partially occupied by, or filled with, the interferent blocking agent. In this manner, the interferent blocking agent may be directly in contact with the electrode material via voids within the biorecognition layer.

In some variations, the interferent blocking agent many occupy at least a portion of the voids of the biorecognition layer. For example, the interferent blocking agent may fill at least about 10%, at least about 20%, at least about 30%, at least about 40%, at least about 50%, at least about 60%, at least about 70%, at least about 80%, at least about 90%, or at least about 95% of the collective volume of the voids ("collective void volume"). In another example, the interferent blocking agent may fill between about 10% and about 95%, between about 20% and about 90%, between about 30% and about 80%, between about 40% and about 70%, or between about 50% and about 60% of the collective void volume. In some variations, the interferent blocking agent may occupy at least a portion of each of the filled voids. For example, of the voids of the biorecognition layer that are filled, the interferent blocking agent may occupy at least a portion of each of the filled voids.

In some variations, the interferent blocking agent may be within the biorecognition layer at a variety of concentrations. For example, the interferent blocking agent may comprise between about 1% weight by volume (w/v) and about 90% w/v, between about 2% w/v and about 80% w/v, between about 3% w/v and about 70% w/v, between about 4% w/v and about 60% w/v, between about 5% w/v and about 50% w/v, between about 10% w/v and about 40% w/v, or between about 20% w/v and about 30% w/v of the interferent blocking agent in the biorecognition layer. In another example, the interferent blocking agent may comprise at least about 1% w/v, at least about 2% w/v, at least 3% w/v, at least about 4% w/v, at least about 5% w/v, at least about 6% w/v, at least about 7% w/v, at least about 8% w/v, at least about 9% w/v, at least about 10% w/v, at least about 12% w/v, at least about 14% w/v, at least about 16% w/v, at least about 18% w/v, at least about 20% w/v, at least about 25%, at least about 30% w/v, at least about 40% w/v, at least about 50% w/v, at least about 70% w/v, and/or at least about 90% w/v of the interferent blocking agent in the biorecognition layer.

In some variations, there may be a gradient of interferent blocking agent within the biorecognition layer. For instance, the interferent blocking agent may be preferentially disposed towards the electrode surface, decreasing in concentration within the biorecognition layer as it moves away from the electrode surface. Similar gradients, which may be linear, non-linear, or a combination thereof, may be present across the surface of the electrode material.

Exemplary interferent blocking agents may include monomers that, when polymerized, are substantially free of defects. In some variations, the interferent blocking agent may comprise one or more of resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol. The polymerized monomers, or polymers, may be conducting polymers and/or non-conducting polymers. Non-conducting polymers may include those polymers that lack long chain conjugation or a reversible redox site.

In some variations, the interferent blocking agent may be a material configured to be one or more of continuous (e.g., free of defects), insulating, and self-limiting. In variations, the interferent blocking agent strongly adsorbs onto electrode surfaces. The adsorbed interferent blocking agent can be grown under electrochemical control from aqueous buffered solution at physiological pH. For instance, the interferent blocking agent can be formed by electropolymerization. In variations, the interferent blocking agent may be a conducting polymer or a non-conducting polymer. Additionally, the interferent blocking agent may demonstrate, via size-based exclusion or other mechanism, good permselectivity against common interferents including acetaminophen and ascorbate. By being continuous, the interferent blocking agent can be used for corrosion protection. As an example, the interferent blocking agent may comprise phenol. Polyphenol, which comprises polymerized phenol monomer, is generally continuous, insulating, and self-limiting with strong adsorption onto platinum surfaces.

In some variations, inclusion of the interferent blocking agent within the biorecognition layer reduces interference current measured at the electrode material. For example, inclusion of the interferent blocking agent can maintain interference current at the electrode material over a one-week period within about 5%, within about 10%, within about 20%, within about 30%, within about 40%, within about 50%, within about 60%, within about 70%, within about 80%, and/or within about 90% of its day one value. In another example, inclusion of the interferent blocking agent can maintain interference current at the electrode material over a one-week period within a range of between about 0% and about 60%, between about 1% and about 50%, between about 2% and about 40%, between about 3% and about 30%, between about 4% and about 20%, between about 5% and about 10%, between about 6% and about 9%, or between about 7% and about 8% of its day one value.

In some variations, inclusion of the interferent blocking agent within the biorecognition layer improves sensor sensitivity variability by decreasing median sensitivity to an interferent (e.g., acetaminophen) by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% when compared to a biorecognition layer without the interferent blocking agent.

i. Electrode Protecting Layer

The electrodes described herein may, in some variations, further include an electrode protecting layer. The electrode protecting layer may be a polymer-based layer that protects the electrode material. For example, the electrode protecting layer may be a permselective layer or a blocking layer. The electrode protecting layer may prevent fouling and/or interactions between the electrode material and electroactive species. The electrode protecting layer may include hydrophilic materials or charged materials. In variations, the electrode protecting layer may comprise one or more materials selected from the group consisting of polyurethane, polyether, etc.

i. Working Electrode Exemplary Embodiments

As described above, the working electrode comprises a biorecognition element which interacts with an analyte of interest as party of detection and quantification of the analyte. In some variations, the detection of the analyte may be performed at the interface of the working electrode and interstitial fluid located within the body (e.g., on an outer surface of the overall microneedle). Generally, a working electrode may include an electrode material and a biorecognition layer in which a biorecognition element (e.g., an aptamer, an enzyme) is immobilized on the working electrode to facilitate selective analyte quantification. The biorecognition layer may also function as an interferent-blocking layer and may help prevent, limit, or otherwise inhibit endogenous and/or exogenous species from directly oxidizing (or reducing) at the electrode. In some variations, the working electrode may also include a diffusion-limiting layer, an electrocatalytic layer, an electrode protecting layer, a biocompatibility layer, an attachment enhancer, and/or an interferent blocking agent in any combination and/or arrangement thereof.

Referring now to FIGS. 11A and 11D-11N, exemplary variations of a working electrode will be described in the context of exemplary electrode layering, or electrode "stack", configurations.

Figure 11A:
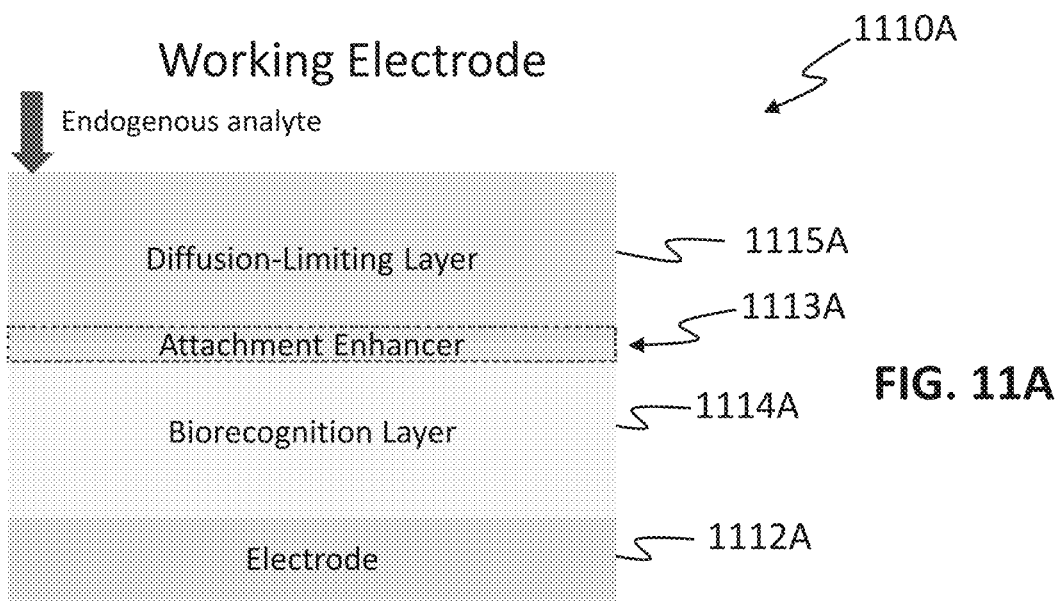
FIGS. 11A-11C depict illustrative schematics of layered structures of a working electrode, a counter electrode, and a reference electrode, respectively.

FIG. 11A depicts a schematic of an exemplary set of layers for a working electrode 1110A comprising an attachment enhancer. For example, in some variations, the working electrode 1110A may include an electrode material 1112A, a sensing layer comprising a biorecognition layer 1114A including a biorecognition element, and an attachment enhancer 1113A. The biorecognition layer 1114A may be arranged over (or disposed on) the electrode material 1112A (or an electrocatalytic layer, if present). The working electrode 1110A may further include a diffusion-limiting layer 1115A arranged over (or disposed on) the biorecognition layer 1114A. The diffusion-limiting layer 1115A may function to, as described above, limit the flux of the analyte of interest in order to reduce the sensitivity of the sensor to endogenous oxygen fluctuations. The attachment enhancer 1113A may be disposed between and within the biorecognition layer 1114A and the diffusion-limiting layer 1115A to promote adhesion therebetween.

Figure 11B:
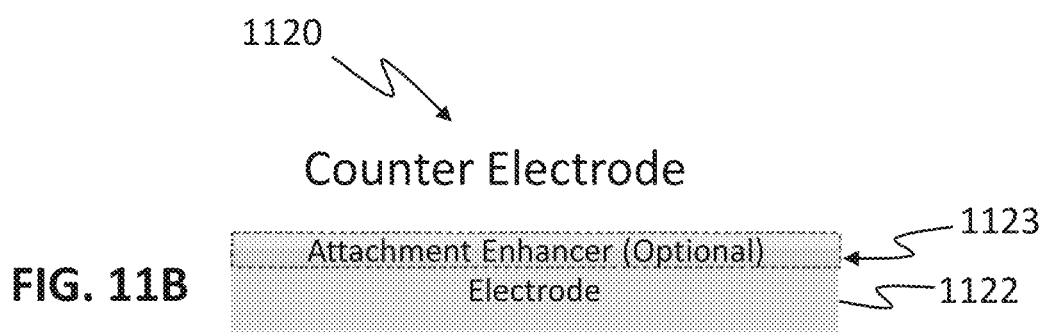
Figure 11C:
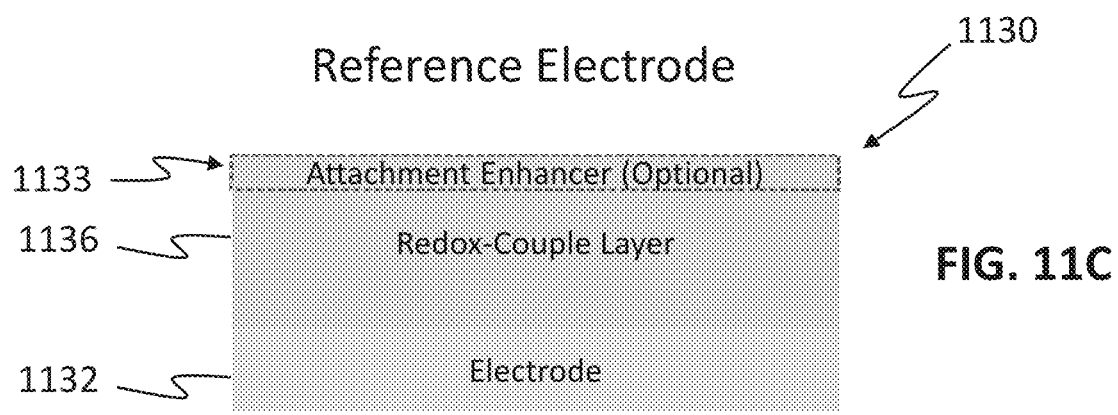
Figure 11D:
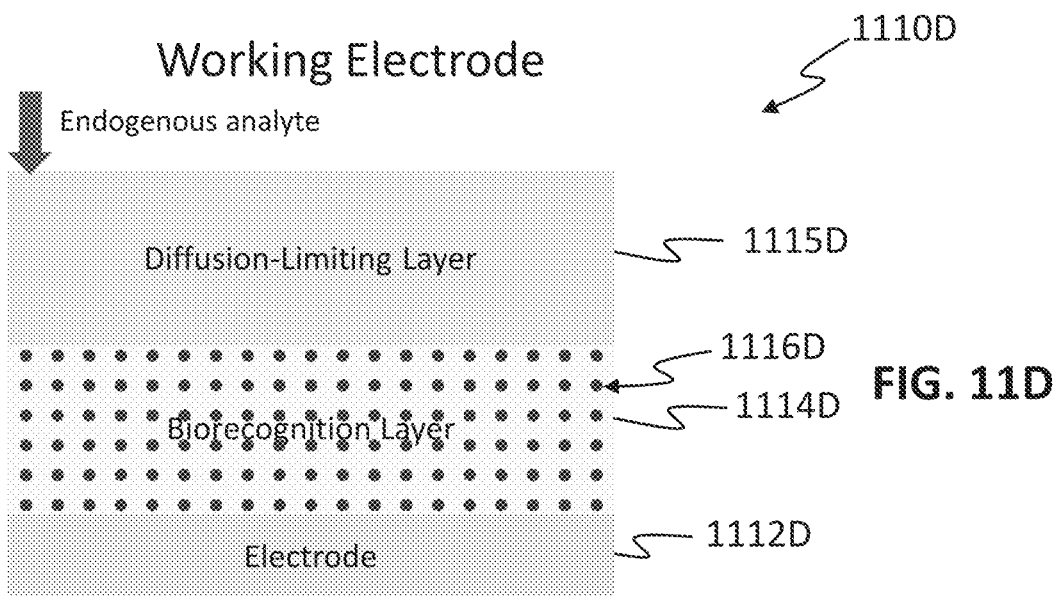
FIGS. 11D-11N depict illustrative schematics of layered structures of a working electrode.

FIG. 11D depicts a schematic of an exemplary set of layers for a working electrode 1110D comprising an interferent blocking agent. For example, in some variations, the working electrode 1110D may include an electrode material 1112D, a sensing layer comprising a biorecognition layer 1114D including a biorecognition element, and an interferent blocking agent 1116D. The biorecognition layer 1114D may be arranged over (or disposed on) the electrode material 1112D (or an electrocatalytic layer, if present). The working electrode 1110D may further include a diffusion-limiting layer 1115D arranged over (or disposed on) the biorecognition layer 1114D. The diffusion-limiting layer 1115D may function to, as described above, limit the flux of the analyte of interest in order to reduce the sensitivity of the sensor to endogenous oxygen fluctuations. The interferent blocking agent 1116D may fill voids within the biorecognition layer 1114D to prevent, limit, or otherwise inhibit exposure of the surface of the electrode material 1112D to foreign bodies and the like.

Figure 11E:
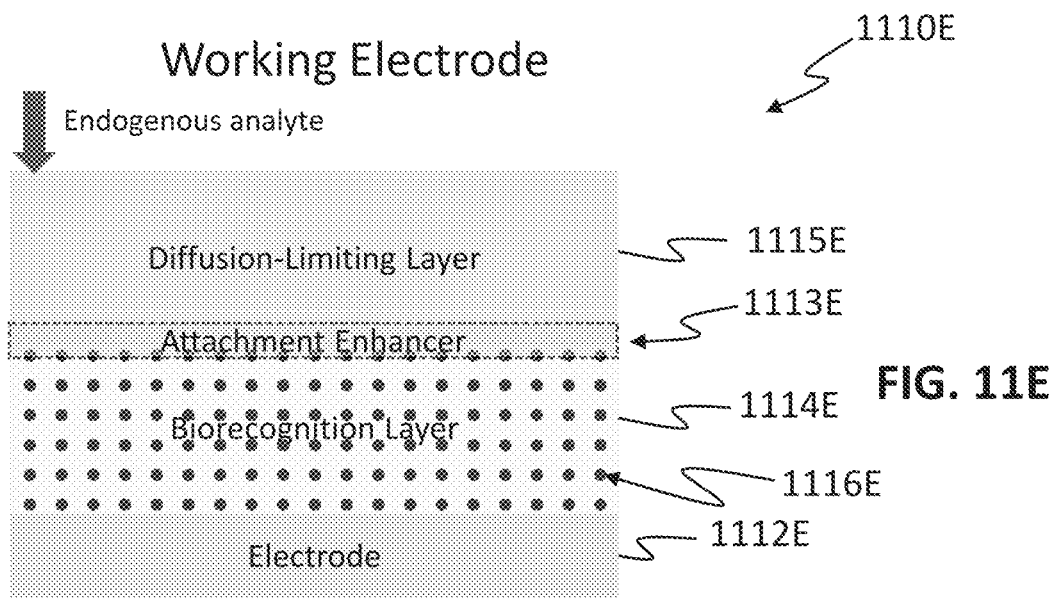

FIG. 11E depicts a schematic of an exemplary set of layers for a working electrode 1110E comprising an attachment enhancer and an interferent blocking agent. As shown, the working electrode 1110E comprises an electrode material 1112E, a sensing layer comprising a biorecognition layer 1114E including a biorecognition element, an interferent blocking agent 1116E, an attachment enhancer 1113E, and a diffusion-limiting layer 1115E. The attachment enhancer 1113E may be disposed between and within the biorecognition layer 1114E and the diffusion-limiting layer 1115E to promote adhesion therebetween. The attachment enhancer 1113E may be disposed between and/or within a portion of the biorecognition layer 1114E and the diffusion-limiting layer 1115E. The interferent blocking agent 1116E may fill voids within the biorecognition layer 1114E to prevent, limit, or otherwise inhibit exposure of the surface of the electrode material 1112E to endogenous oxygen fluctuations and/or other solutes, proteins, molecules, foreign bodies, and the like.

Figure 12A:
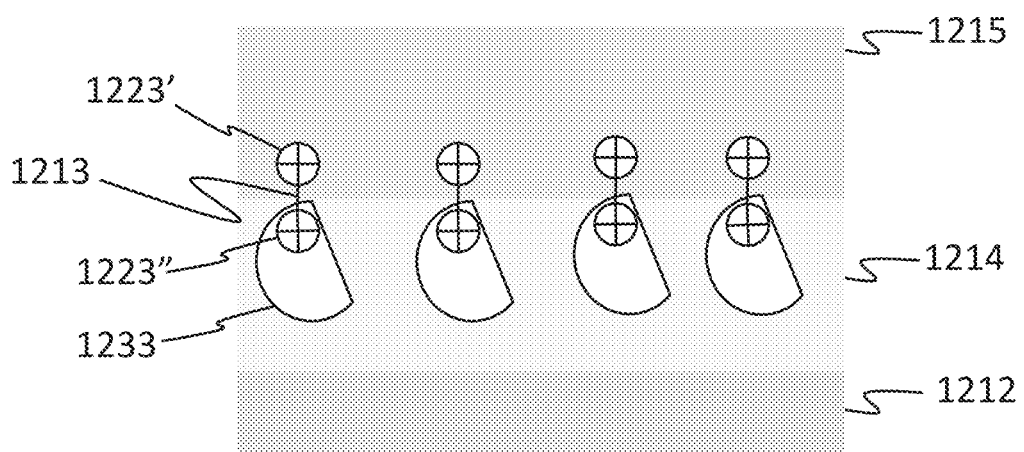
FIGS. 12A and 12B depict illustrative schematics of an attachment enhancer interacting with components and layers of an electrode.

FIG. 12A includes an exemplary variation of a working electrode in which an attachment enhancer interacts with each of a biorecognition layer and a diffusion-limiting layer. To this end, the working electrode comprises at least an electrode material 1212, a biorecognition layer 1214, and a diffusion-limiting layer 1215. Further, the working electrode may comprise an attachment enhancer comprising a linker 1213 separating a first reactive group 1223' at a first end of the attachment enhancer from a second reactive group 1223" at a second end of the attachment enhancer. In some variations, the first reactive group 1223' interacts with the diffusion-limiting layer 1215, and the second reactive group 1223" interacts across the layer interface with a biorecognition element (e.g. enzyme 1233) within the biorecognition layer 1233. In some variations, the attachment enhancer may be a bifunctional ether (e.g., BDDGE) and the linker 1213 separates, a first epoxide group as the first reactive group 1223' at the first end, and a second epoxide group as the second reactive group 1223" at the second end. To this end, at least one hydroxyl group of the first epoxide group may interact with the diffusion-limiting layer 1215 via one or more of hydrogen bonding and Van der Waals forces, thereby partially immobilizing the attachment enhancer, and the second epoxide group may interact with the biorecognition element (e.g., enzyme 1233, which may be glucose oxidase) and/or a functional group of the polymer matrix of the biorecognition layer by covalent bonding (e.g., via free amines). In some variations, the attachment enhancer may also interact only within the biorecognition layer 1214 or only within the diffusion-limiting layer 1215. For instance, when the biorecognition layer 1214 comprises a polymer matrix such as phenylenediamine, free amines of the phenylenediamine may interact with both ends of the attachment enhancer 1213 (when the attachment enhancer is an amine-reactive bifunctional molecule).

Figure 12B:
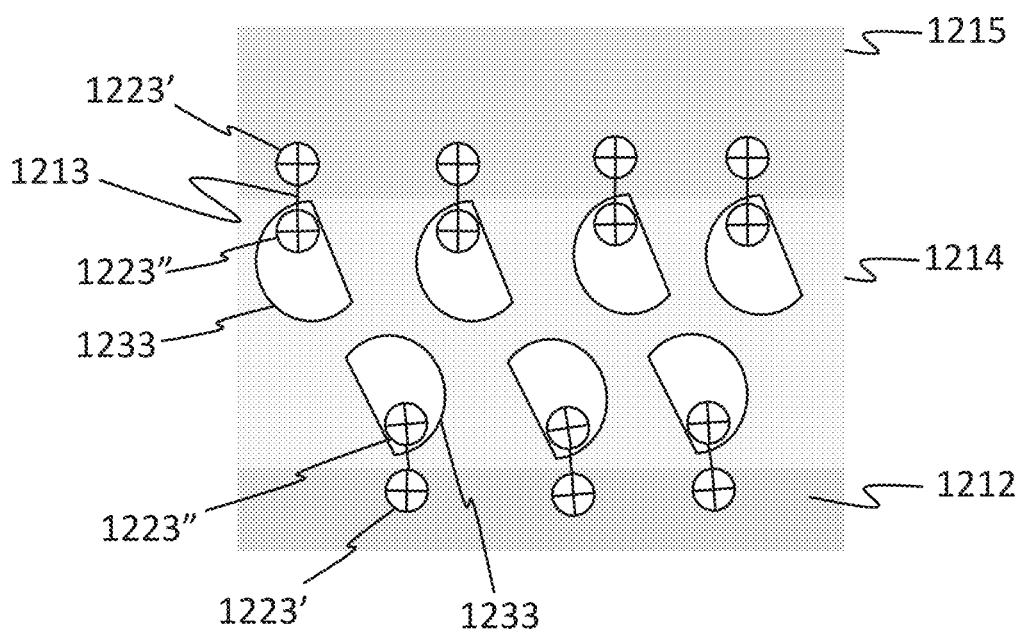

Turning to FIG. 12B, the working electrode may comprise at least an electrode material 1212, a biorecognition layer 1214, and a diffusion-limiting layer 1215. Further, the working electrode may comprise, an attachment enhancer comprising a linker 1213 separating a first reactive group 1223' from a second reactive group 1223". Unlike the attachment enhancer of FIG. 12A, the attachment enhancer of FIG. 12B may interact with any of the layers of the working electrode. In one instance, the first reactive group 1223' may interact with the diffusion-limiting layer 1215, and the second reactive group 1223" may interact across the layer interface with a biorecognition element (e.g. enzyme 1233) within the biorecognition layer 1233. To this end, when the first reactive group 1223' is a first epoxide group, at least one hydroxyl group of the first epoxide group may interact with the diffusion-limiting layer 1215 via one or more of hydrogen bonding and Van der Waals forces, thereby partially immobilizing the attachment enhancer. Further, when the second reactive group 1223" is a second epoxide group, the second epoxide group may interact with the biorecognition element (e.g., enzyme 1233, which may be glucose oxidase) and/or a functional group of the polymer matrix of the biorecognition layer by covalent bonding. In another instance, which may occur concurrently in the presence of a plurality of attachment enhancer molecules, the first reactive group 1223' may interact with moieties of the electrode material 1212, and the second reactive group 1223" may interact across the layer interface with a biorecognition element (e.g., enzyme 1233) and/or a functional group of the polymer matrix within the biorecognition layer 1233. To this end, when the first reactive group 1223' is a first epoxide group, at least one hydroxyl group of the first epoxide group may interact with the moieties of the electrode material 1212 via adhesion, and, when the second reactive group 1223" is a second epoxide group, the second epoxide group may interact with the biorecognition element (e.g., enzyme 1233, which may be glucose oxidase) and/or the functional group of the polymer matrix of the biorecognition layer by covalent bonding.

Figure 11F:
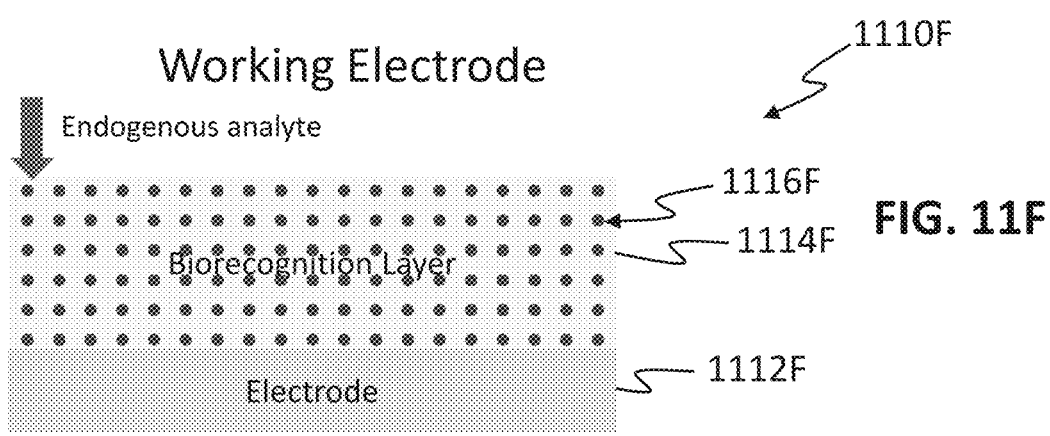

FIG. 11F depicts a schematic of a working electrode 1110 comprising an interferent blocking agent without an attachment enhancer or a separate diffusion-limiting layer. Instead of a separate diffusion-limiting layer, as in FIGS. 11A, 11D, and 11E, the working electrode 1110 of FIG. 11F comprises an electrode material 1112, a sensing layer comprising a biorecognition layer 1114 including a biorecognition element, and an interferent blocking agent 1116. The interferent blocking agent 1116 may be within the voids of the biorecognition layer 1114 and may function to limit flux of the analyte of interest and/or other interferents within the tissue to a surface of the electrode material 1112 in order to reduce the sensitivity of the sensor to endogenous oxygen fluctuations and/or other solutes, proteins, molecules, foreign bodies, and the like. For example, the interferent blocking agent 1116 may attenuate the concentration of the analyte of interest so that it becomes the limiting reactant to an aerobic enzyme.

Figure 11G:
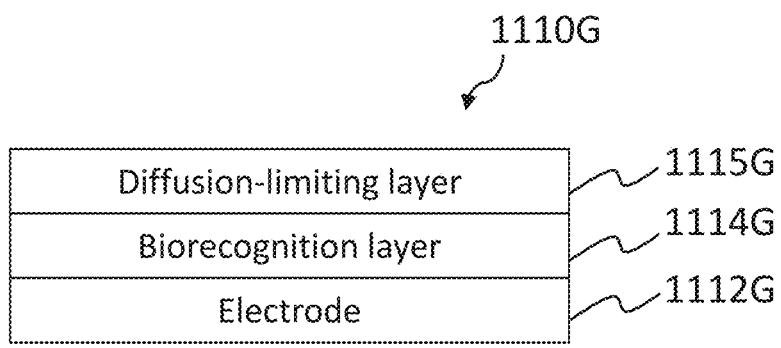

FIG. 11G depicts a schematic of an exemplary set of layers for a working electrode 1110G. For example, as described above, in some variations the working electrode 1110G may include an electrode material 1112G and a biorecognition layer 1114G including a biorecognition element. The biorecognition layer 1114G may be arranged over the electrode material 1112G and functions to immobilize and stabilize the biorecognition element which facilitates selective analyte quantification for extended time periods. In some variations, the working electrode 1110G further includes a diffusion-limiting layer 1115G arranged over the biorecognition layer 1114G.

Figure 11H:
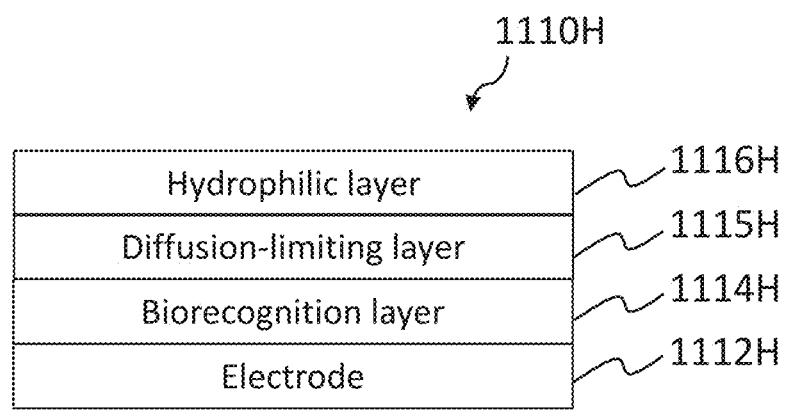

FIG. 11H depicts an additional configuration of a working electrode 1110H. In this variation, the working electrode 1110H may further include a hydrophilic layer 1116H as an outermost layer over the diffusion-limiting layer 1115H.

Figure 11I:
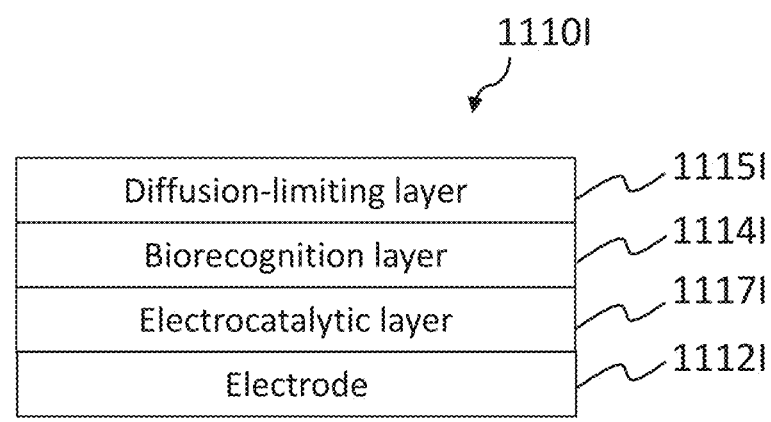

FIG. 11I depicts an additional configuration of a working electrode 1110I. In this variation, the electrode material 1112I may be coated with an electrocatalytic layer 1117I. The configuration of the working electrode 1110I further includes a biorecognition layer 1114I and a diffusion-limiting layer 1115I as the outermost layer.

Figure 11J:
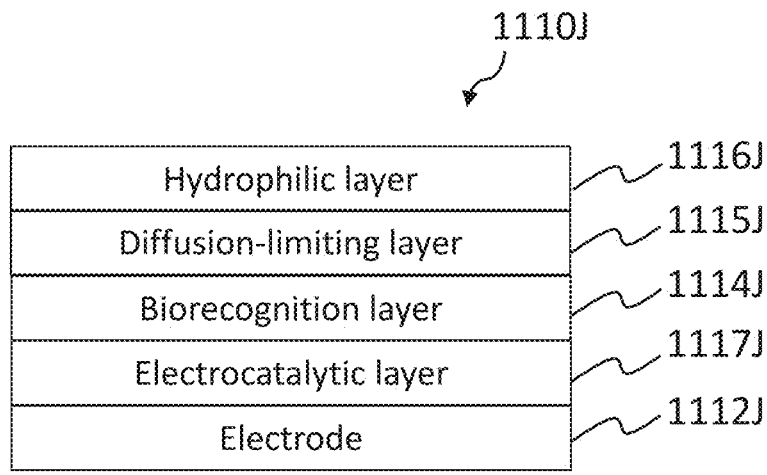

FIG. 11J depicts an additional configuration of a working electrode 1110J. In this variation, the electrode material 1112J may be coated with an electrocatalytic layer 1117J. A biorecognition layer 1114J is arranged over the electrocatalytic layer 1117J, a diffusion-limiting layer 1115J is arranged over the biorecognition layer 1114J, and a hydrophilic layer 1116J is the outermost layer of the working electrode 1110J.

Figure 11K:
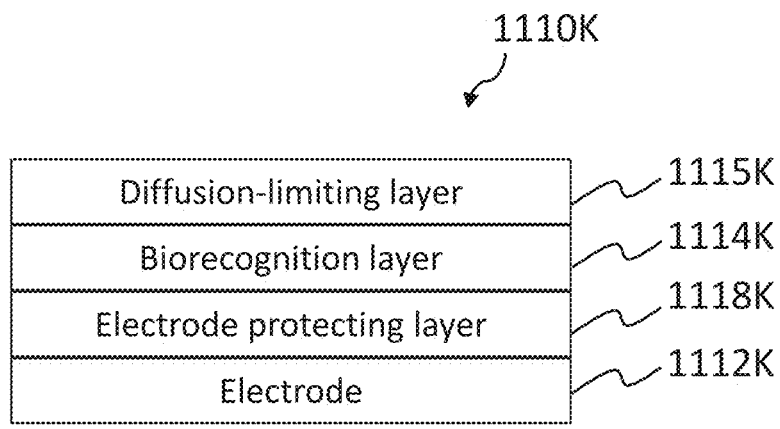

FIG. 11K depicts an additional configuration of a working electrode 1110K. In this variation, an electrode protecting layer 1118K is arranged over the electrode material 1112K. The biorecognition layer 1114K is arranged over the electrode protecting layer 1118K. The diffusion-limiting layer 1115K, arranged over the biorecognition layer 1114K, may function to limit the flux of the analyte of interest to reduce the sensitivity of the sensor to endogenous oxygen fluctuations.

Figure 11L:
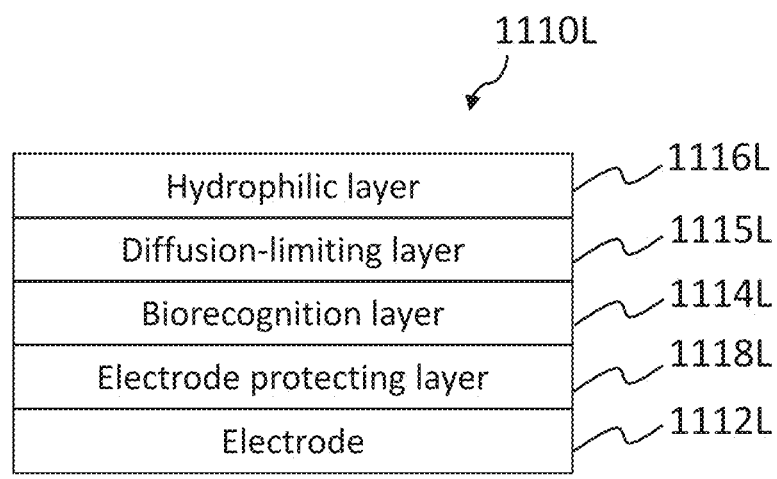

FIG. 11L depicts an additional configuration of a working electrode 1110L in which a hydrophilic layer 1116L is arranged as an outermost layer over the diffusion-limiting layer 1115L, the biorecognition layer 1114L, the electrode protecting layer 1118L, and the electrode material 1112L. As shown, a hydrophilic layer 1116L is arranged over the diffusion-limiting layer 1115L. An electrode protecting layer 1118L is arranged over the electrode material 1112L. The biorecognition layer 1114L is arranged over the electrode protecting layer 1118L. The diffusion-limiting layer 1115L is arranged over the biorecognition layer 1114L.

Figure 11M:
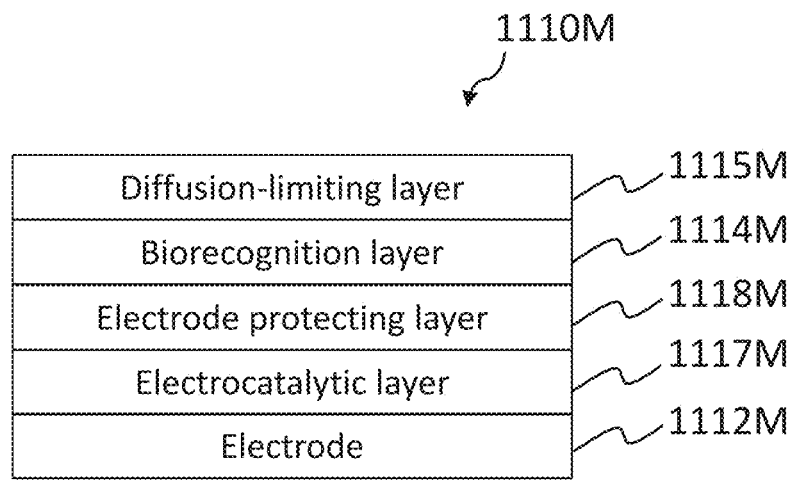
Figure 11N:
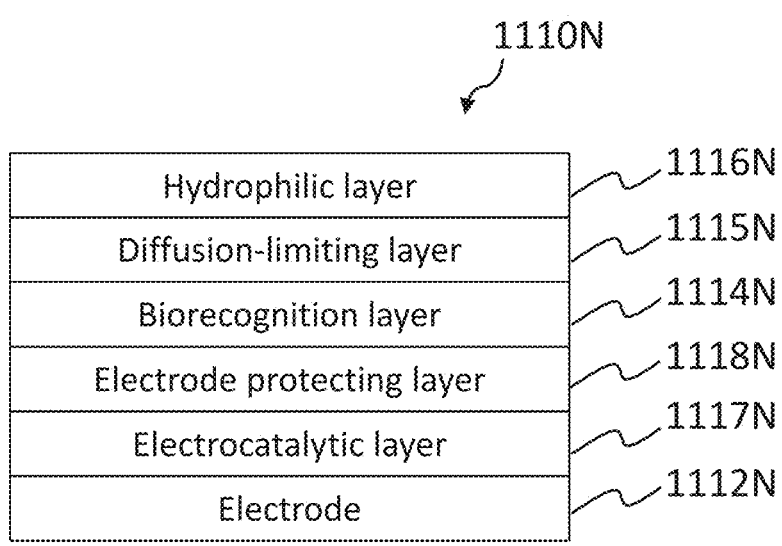

An electrocatalytic layer 1117M, 1117N and an electrode protecting layer 1118M, 1118N may be incorporated in a structure of a working electrode 1110M, 1110N, as shown in FIG. 11M and FIG. 11N. In each configuration of the working electrode 1110M, 1110N, an electrocatalytic layer 1117M, 1117N is arranged over the electrode material 1112M, 1112N and the electrode protecting layer 1118M, 1118N is arranged over the electrocatalytic layer 1117M, 1117N. A biorecognition layer 1114M, 1114N is arranged over the electrode protecting layer 1118M, 1118N with a diffusion-limiting layer 1114M, 1114N arranged over the biorecognition layer 1114M, 1114N. A hydrophilic layer 1116N may be provided as an outermost layer, as shown in FIG. 11N.

ii. Counter Electrode Exemplary Embodiments

As described above, the counter electrode is the electrode that is sourcing or sinking electrons (via an electrical current) required to sustain the electrochemical reaction at the working electrode. FIG. 11B depicts an exemplary variation of a counter electrode 1120. As shown there, the counter electrode 1120 may include an electrode material 1122, similar to electrode material 1112A, 1112D, 1112E, 1112F, each of which may include any of the properties and/or characteristics described in section Electrode Layers (a) above on the electrode material. For example, like the electrode material 1112A, 1112D, 1112E, 1112F, the electrode material 1122 in the counter electrode 1120 may include a noble metal such as gold, platinum, palladium, iridium, carbon, doped diamond, and/or other suitable catalytic and inert material. In some variations, the electrode material 1122 in the counter electrode 1120 may be platinum. In some variations, and as shown in FIG. 11B, the counter electrode 1120 may be bare (i.e., have no additional layers over the electrode material 1122). In other variations, the counter electrode 1120 may include an attachment enhancer 1123 within and on the electrode material 1122 of the counter electrode 1120. The attachment enhancer 1123 may bind by e.g., adhesion to moieties within the electrode material 1122. In some variations, the counter electrode may also include a diffusion-limiting layer, an electrocatalytic layer, an electrode protecting layer, a biocompatibility layer, and/or an interferent blocking agent in any combination and/or arrangement thereof.

As described above, the counter electrode is the electrode that sources or sinks electrons (via an electrical current) required to sustain the electrochemical reaction at the working electrode. The number of counter electrodes can be augmented in the form of a counter electrode array to enhance surface area such that the current-carrying capacity of the counter electrode does not limit the redox reaction of the working electrode. It thus may be desirable to have an excess of counter electrode area versus the working electrode area to circumvent the current-carrying capacity limitation. If the working electrode is operated as an anode, the counter electrode will serve as the cathode and vice versa. Similarly, if an oxidation reaction occurs at the working electrode, a reduction reaction occurs at the counter electrode and vice versa. Unlike the working or reference electrodes, the counter electrode is permitted to dynamically swing to electrical potentials required to sustain the redox reaction of interest on the working electrode.

Figure 11O:
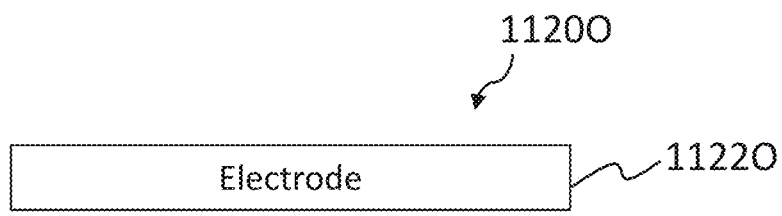
FIGS. 11O-11V depict illustrative schematics of layered structures of a counter electrode.

As shown in FIG. 11O, a counter electrode 11200 may include an electrode material 11220.

In some variations, the counter electrode 11200 may have no additional layers over the electrode material 11220. In some variations, however, additional layers may be incorporated.

Figure 11P:
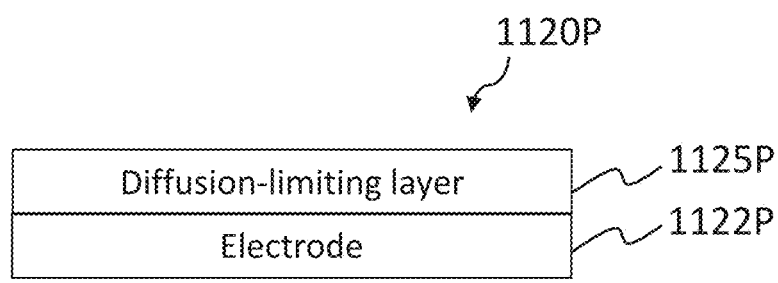

FIG. 11P depicts an additional configuration of a counter electrode 1120P. In this variation, the counter electrode 1120P may include a diffusion-limiting layer 1125P arranged over the electrode material 1122P.

Figure 11Q:
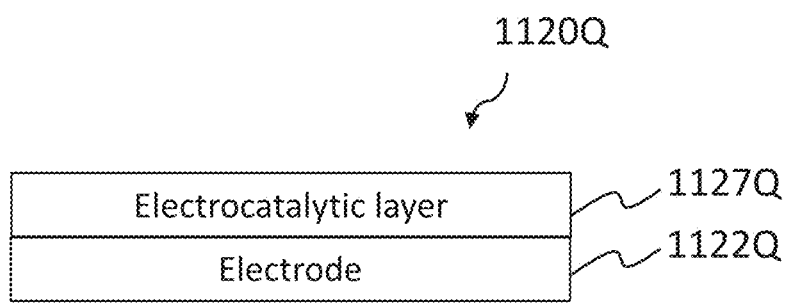

FIG. 11Q depicts an additional configuration of a counter electrode 1120Q. In this variation, an electrocatalytic layer 1127Q is arranged over the electrode material 1122Q.

Figure 11R:
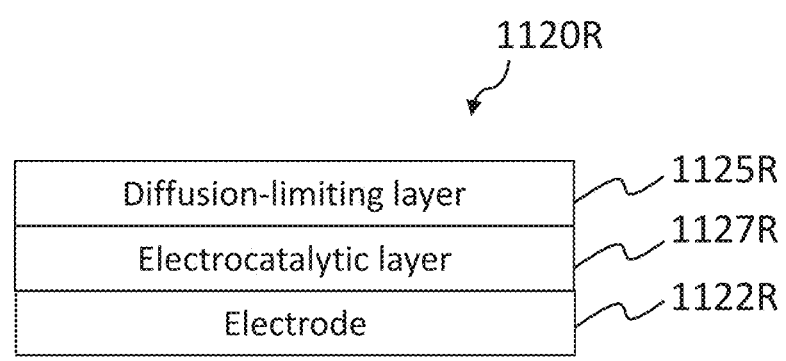

FIG. 11R depicts an additional configuration of a counter electrode 1120R. In this variation, an electrocatalytic layer 1127R is arranged over the electrode material 1122R, and a diffusion-limiting layer 1125R is arranged over the electrocatalytic layer 1127R.

Figure 11S:
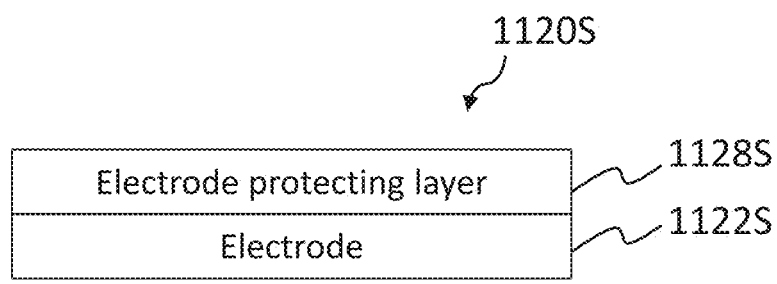
Figure 11T:
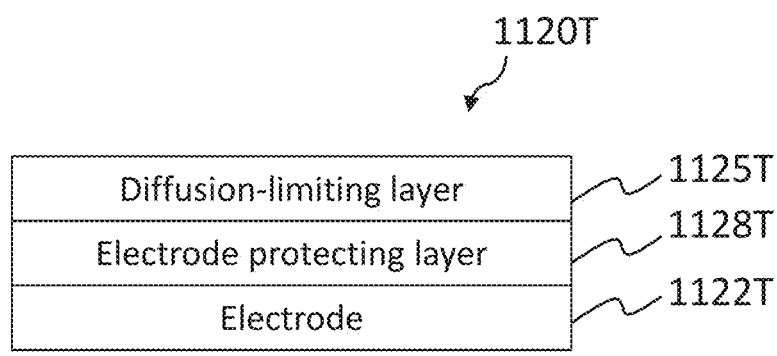

FIG. 11S depicts an additional configuration of a counter electrode 1120S. In this variation, an electrode protecting layer 1128S is arranged over the electrode material 1122S. In another variation of a counter electrode 1120S, as shown in FIG. 11T, the electrode protecting layer 1128T is arranged over the electrode material 1122T, and the diffusion-limiting layer 1125T is arranged over the electrode protecting layer 1128T.

Figure 11U:
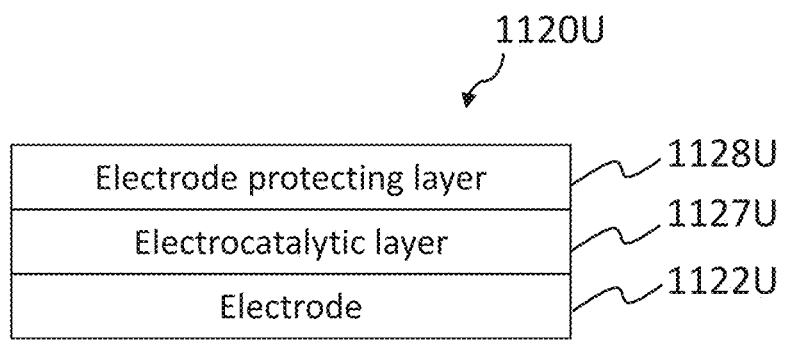

FIG. 11U depicts an additional configuration of a counter electrode 1120U. In this variation, the electrocatalytic layer 1127U is arranged over the electrode material 1122U. The electrode protecting layer 1128U is arranged over the electrocatalytic layer 1127U.

Figure 11V:
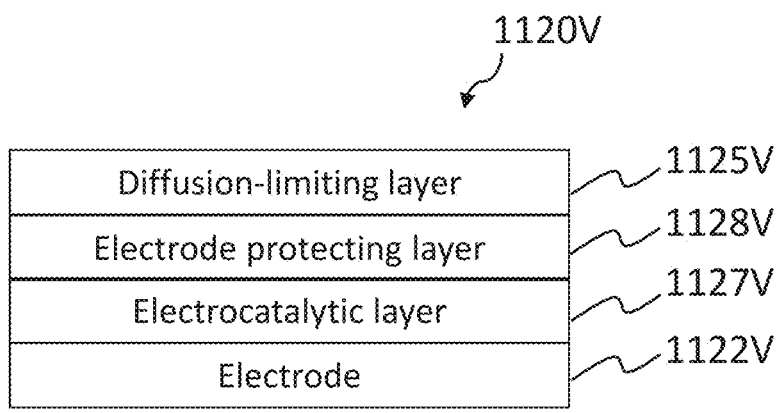

FIG. 11V depicts a counter electrode 1120V that includes the diffusion-limiting layer 1125V. In particular, the electrocatalytic layer 1127V is arranged over the electrode material 1122V. The electrode protecting layer 1128V is arranged over the electrocatalytic layer 1127V. The diffusion-limiting layer 1125V is arranged over the electrode protecting layer 1128V. In some variations, a hydrophilic layer may be arranged over the diffusion-limiting layer 1125V.

iii. Reference Electrode Exemplary Embodiments

As described above, the reference electrode functions to provide a reference potential for the system. FIG. 11C depicts an exemplary configuration for a reference electrode as described herein. As shown there, a reference electrode 1130 may include an electrode material 1132, similar to electrode material 1112A, 1112D, 1112E, 1112F, and 1122, which may include any of the properties and/or characteristics described in section Electrode Layers (a) above on the electrode material. In some variations the reference electrode 1130 may be textured or otherwise roughened in such a way to enhance adhesion with any subsequent layers. Such subsequent layers on the electrode material 1132 may include an electrocatalytic layer, which may be a platinum black layer. However, in some variations, the electrocatalytic layer may be omitted. In some variations, the reference electrode may also include a diffusion-limiting layer, an electrode protecting layer, a biocompatibility layer, and/or an interferent blocking agent in any combination and/or arrangement thereof.

The reference electrode 1130 may, in some variations, further include a redox-couple layer 1136, as described above in more detail in section Electrode Layers (b).

In some variations, the reference electrode 1130 may include an attachment enhancer 1133 similar to the attachment enhancer described in section Electrode Layers (g). In some variations, the attachment enhancer 1123 may optionally be applied to the reference electrode 1130 to improve stability of the sensor by interacting with and/or binding to moieties in each of the redox couple layer 1136 and/or the electrode material 1132.

In some variations, and in view of the exemplary arrangement of FIG. 11C, at least one end of the attachment enhancer 1133 may interact with moieties within the redox couple layer 1136. Such interaction may be by covalent bonding and/or adhesion.

Figure 11W:
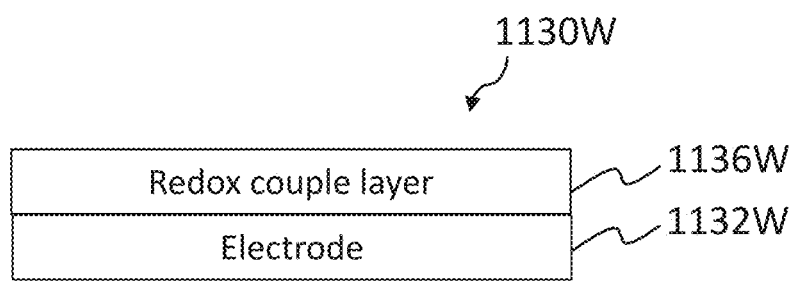
FIGS. 11W-11Z depict illustrative schematics of layered structures of a reference electrode.

As shown in FIG. 11W, a reference electrode 1130W may include an electrode material 1132W, similar to electrode material 1112W.

Figure 11X:
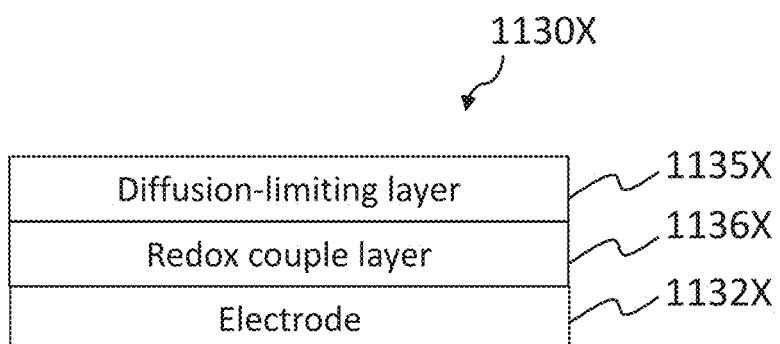

Additionally, or alternatively, in some variations as shown in FIG. 11X, the reference electrode 1130X may include a diffusion-limiting layer 1135X (e.g., arranged over the electrode and/or the redox-couple layer).

Figure 11Y:
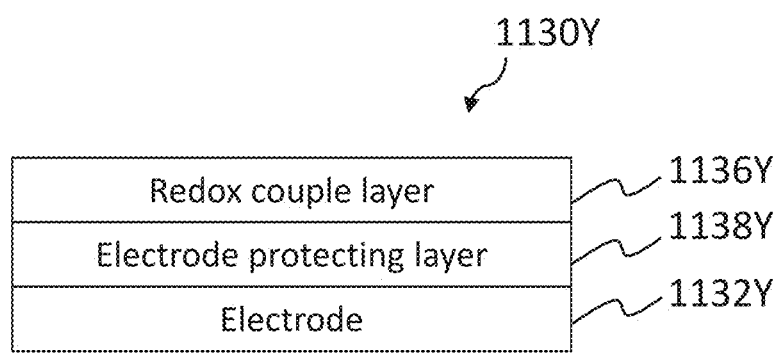

FIG. 11Y depicts an additional configuration of a reference electrode 1130Y. In this variation, an electrode protecting layer 1138Y is arranged over the electrode material 1132Y, and the redox couple layer 1136Y is arranged over the electrode protecting layer 1138Y.

Figure 11Z:
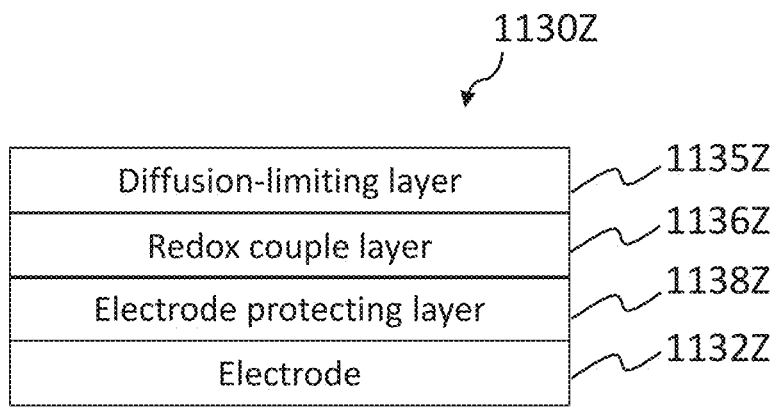

FIG. 11Z depicts an additional configuration of a reference electrode 1130Z in which the electrode protecting layer 1138Z is arranged over the electrode material 1132Z. The redox couple layer 1136Z is arranged over the electrode protecting layer 1138Z, and the diffusion-limiting layer 1135Z is arranged over the redox couple layer 1136Z.

Electrode Formation

Various layers of the working electrode, counter electrode, and reference electrode may be applied to the microneedle array and/or functionalized using suitable processes such as those described below.

Initially, in a pre-processing step for the microneedle array, the microneedle array may be plasma cleaned in an inert gas (e.g., RF-generated inert gas such as argon) plasma environment to render the surface of the material, including the electrode material (e.g., electrode material 1112, 1122, and 1132 as described above), to be more hydrophilic and chemically reactive. This pre-processing functions to not only physically remove organic debris and contaminants, but also to clean and prepare the electrode surface to enhance adhesion of subsequently deposited films on its surface.

iv. Working Electrode-Formation

Various layers of the working electrode may be applied to the microneedle array and/or functionalized using suitable processes such as those described below with reference to FIGS. 13A and 13D-13F.

As will be described with reference to the method 1300A provided in FIG. 13A, an attachment enhancer may be applied to the working electrode as, for instance, a solution, as a vapor, and/or as a gas, and in a variety of ways.

As will now be described with reference to the method 1300D of FIG. 13D, the method 1300E of FIG. 13E, and the method 1300F of FIG. 13F, the interferent blocking agent may be applied to the working electrode as, for instance, a solution, as a vapor, and/or as a gas, and in a variety of ways, including soaking and electropolymerization, among others. As stated above, the interferent blocking agent may be a material configured to be one or more of continuous (e.g., free of defects), insulating, and self-limiting. In variations, the interferent blocking agent strongly adsorbs onto electrode surfaces. The interferent blocking agent may demonstrate, via size-based exclusion or other mechanism, good permselectivity against common interferents including acetaminophen and ascorbate. By being continuous, the interferent blocking agent can be used for corrosion protection. In some variations, inclusion of the interferent blocking agent within the biorecognition layer reduces interference current, or interference current, measured at the electrode material.

Regardless of which exemplary working electrode is described, anodization and activation are performed after pre-processing, as described above.

Specifically, to configure the working electrode after the pre-processing step, the electrode material may undergo an anodization treatment using an amperometry approach in which the electrode constituent(s) assigned for the working electrode function is (are) subject to a fixed high anodic potential (e.g., between +1.0-+1.3 V vs. Ag/AgCl reference electrode) for a suitable amount of time (e.g., between about 30 sec and about 10 min) in a moderate-strength acid solution (e.g., 0.1-3M $H_2SO_4$). In this process, a thin, yet stable native oxide layer may be generated on the electrode surface. Owing to the low pH arising at the electrode surface, any trace contaminants may be removed as well.

In an alternative variation using a coulometry approach, anodization can proceed until a specified amount of charge has passed (measured in Coulombs). The anodic potential may be applied as described above; however, the duration of this might vary until the specified amount of charge has passed.

Following the anodization process, the working electrode constituents may be subjected to a cyclically-scanned potential waveform in an activation process using cyclic voltammetry. In the activation process, which may occur in a moderate-strength acid solution (e.g. 0.1-3M $H_2SO_4$), the potential applied may time-varying in a suitable function (e.g., sawtooth function). For example, the voltage may be linearly scanned between a cathodic value (e.g., between −0.3-−0.2 V vs. Ag/AgCl reference electrode) and an anodic value (e.g., between +1.0-+1.3 V vs. Ag/AgCl reference electrode) in an alternating function (e.g., 15-50 linear sweep segments). The scan rate of this waveform can take on a value between 1-1000 mV/sec. It should be noted that a current peak arising during the anodic sweep (sweep to positive extreme) corresponds to the oxidation of a chemical species, while the current peak arising during the ensuing cathodic sweep (sweep to negative extreme) corresponds to the reduction of said chemical species.

With reference to each of FIGS. 13A and 13D-13F, and after completion of pre-processing, anodization, and activation of the electrode material, which may each be performed as described above, the working electrode constituents may be functionalized with the biorecognition layer at step 1310 of the methods 1300A, 1300D, 1300E, and 1300F. A voltage may be linearly scanned between a cathodic value (e.g., between −0.5 V to 0.0 V vs. Ag/AgCl reference electrode) and an anodic value (e.g., between 0.5 V+1.5 V vs Ag/AgCl reference electrode) in an alternating function (e.g., 10 linear sweep segments). In an example variation, the scan rate of this waveform can take on a value between about 1 mV/sec and about 1,000 mV/sec in an aqueous solution comprised of a monomeric precursor to the entrapment conducting polymer and a cross-linked biorecognition element (e.g., enzyme, such as glucose oxidase). In this process, a thin film (e.g., between about 10 nm and about 1000 nm) of biorecognition layer comprising a polymer with a dispersed cross-linked biorecognition element may be generated (e.g., electrodeposited or electropolymerized) on the working electrode surface. In some variations, the polymer may be a conducting polymer.

In some variations, the working electrode surface may be electrochemically roughened in order to enhance adhesion of the biorecognition layer to the electrode material surface. The roughening process may involve a cathodization treatment (e.g., cathodic deposition, a subset of amperometry) wherein the electrode is subject to a fixed cathodic potential (e.g., between −0.4-+0.2 V vs. Ag/AgCl reference electrode) for a certain amount of time (e.g., 5 sec-10 min) in an acid solution containing the desired metal cation dissolved therein (e.g., 0.01-100 mM $H_2PtCl_6$). Alternatively, the electrode is subject to a fixed cathodic potential (e.g., between about −0.4 to about +0.2 V vs. Ag/AgCl reference electrode) until a certain amount of charge has passed (e.g., 0.1 mC-100 mC) in an acid solution containing the desired metal cation dissolved therein (e.g., 0.01-100 mM $H_2PtCl_6$). In this process, a thin, yet highly porous layer of the metal may be generated on the electrode surface, thereby augmenting the electrode surface area dramatically.

Figure 13A:
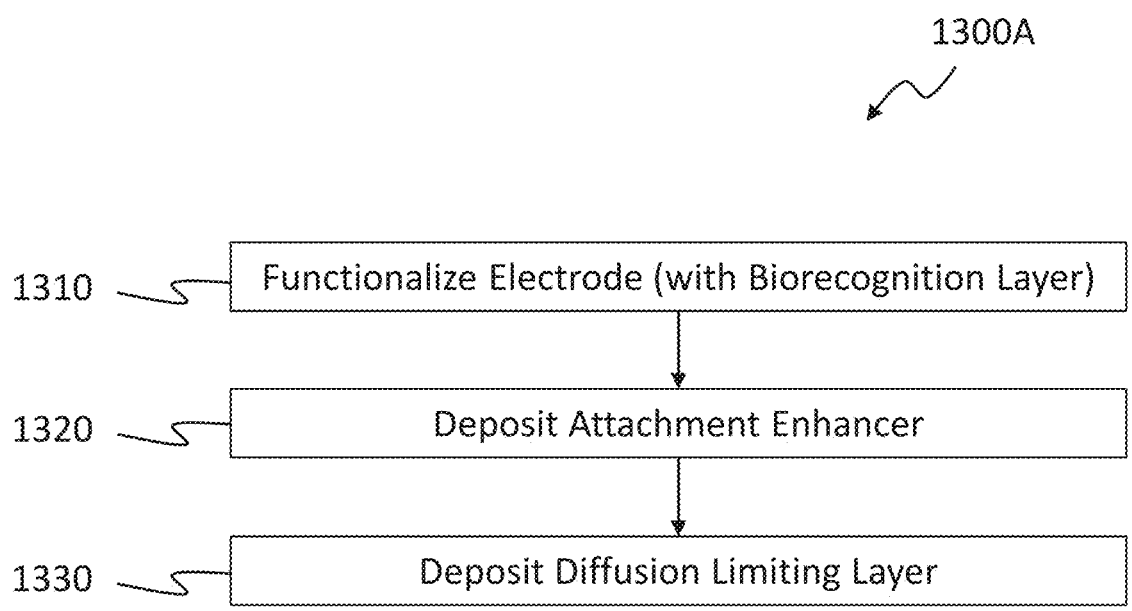
FIG. 13A is an illustrative flowchart of a method for improving attachment within and/or between layered structures of a working electrode.
Figure 13B:
FIG. 13B is an illustrative flowchart of a method for improving attachment within and between layered structures of a counter electrode.
Figure 13C:
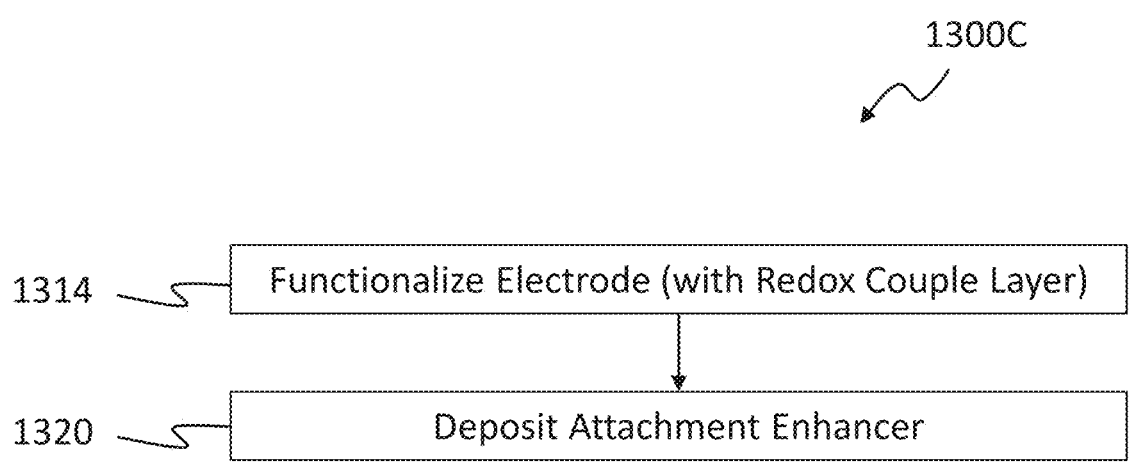
FIG. 13C is an illustrative flowchart of a method for improving attachment within and between layered structures of a reference electrode.
Figure 13D:
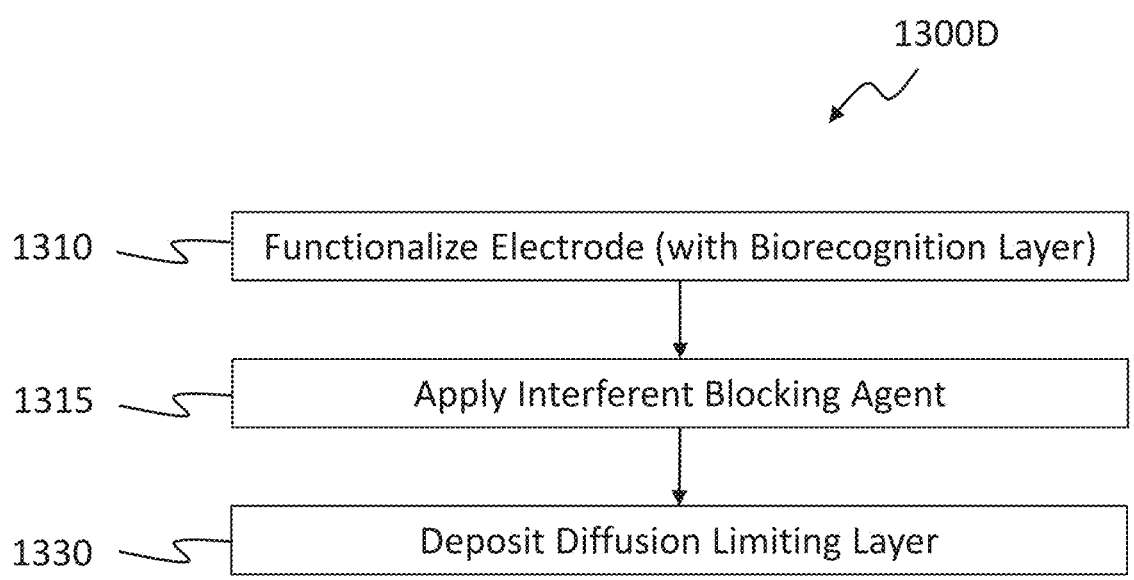
FIG. 13D is an illustrative flowchart of a method for forming layered structures of a working electrode.
Figure 13E:
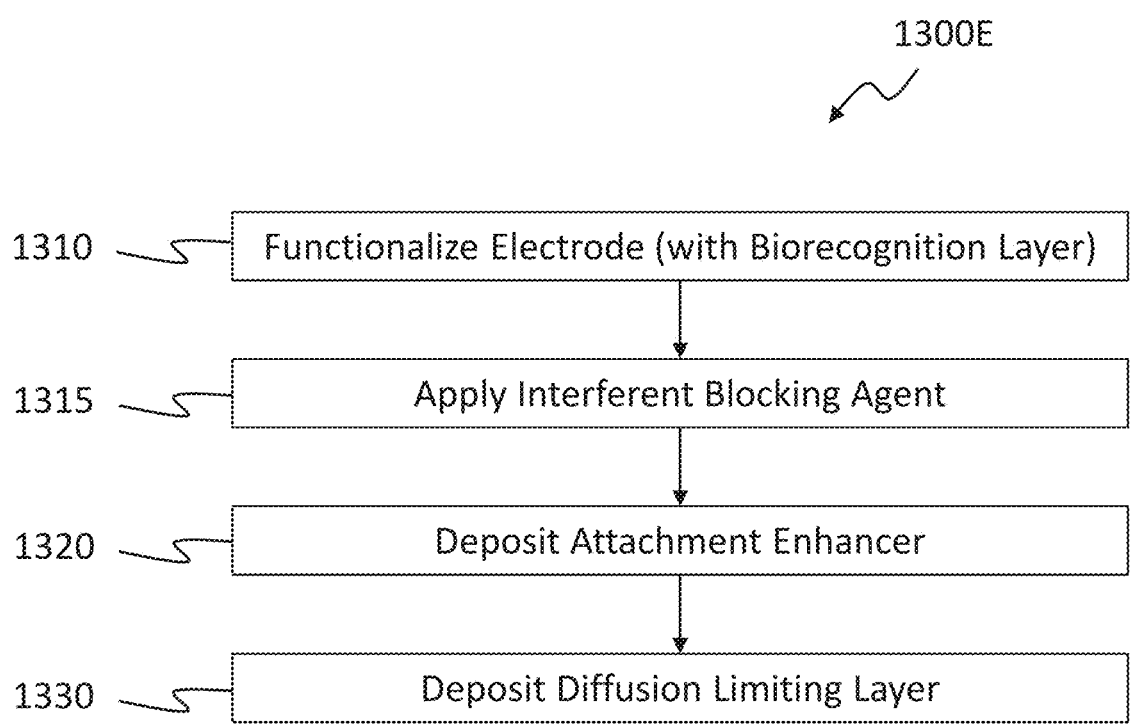
FIG. 13E is an illustrative flowchart of a method for improving attachment within and/or between layered structures of a working electrode and for reducing interference current.

With particular reference first to FIG. 13A and FIG. 13E, following deposition of the biorecognition layer at step 1310, an attachment enhancer may be deposited (i.e., applied) on the biorecognition layer at step 1320 of method 1300A, 1300E. The attachment enhancer may be deposited according to any suitable method, including but not limited to drop casting, spray coating, soaking, spin coating, and chemical deposition. For instance, the attachment enhancer may be deposited on the biorecognition layer by soaking the functionalized and activated electrode material in a solution comprising the attachment enhancer. In some variations, the soaking may be performed for a duration of between 0 hours and 2 weeks, between 1 day and 13 days, between 2 days and 12 days, between 3 days and 11 days, between 4 days and 10 days, between 5 days and 9 days, and/or between 6 days and 8 days. In some variations, the soaking may be performed for a duration of between about 0.1 hours and about 24 hours, between about 0.2 hours and about 23 hours, between about 0.3 hours and about 22 hours, between about 0.4 hours and about 21 hours, between about 0.5 hours and about 20 hours, between about 0.6 hours and about 19 hours, between about 0.7 hours about 18 hours, between about 0.8 hours and about 17 hours, between about 0.9 hours and about 16 hours, between about 1 hour and about 15 hours, between about 2 hours and about 14 hours, between about 3 hours and about 13 hours, between about 4 hours and about 12 hours, between about 5 hours and about 11 hours, between about 6 hours and about 10 hours, and/or between about 7 hours and about 9 hours. In some variations, the soaking may be performed for a duration of between about 1 minute and about 30 minutes, between about 2 minutes and about 25 minutes, between about 3 minutes and about 20 minutes, between about 4 minutes and about 15 minutes, between about 5 minutes and about 10 minutes, and/or between about 7 minutes and about 8 minutes. In some variations, the solution may have a pH of between about 4 and about 14, between about 5 and about 13, between about 6 and about 12, between about 7 and about 11, and/or between about 8 and about 10. In some variations, the solution may have a pH of between about 7 and about 10, between about 7.5 and about 9.5, and between about 8 and/or about 9. In some variations, a concentration of the attachment enhancer in the solution may be between about 0.05% and about 30% w/v or w/w. In some variations, a concentration of the attachment enhancer in the solution may be between about 0.1% and about 20%, between about 0.5% and about 15%, between about 1% and about 10%, between about 2% and about 9%, between about 3% and about 8%, between about 4% and about 7%, and/or between about 5% and about 6%.

Figure 13F:
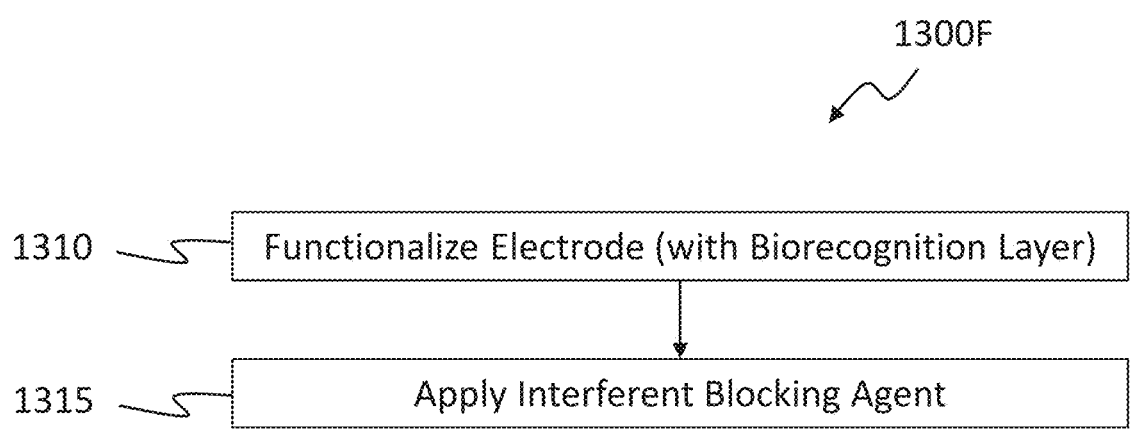
FIG. 13F is an illustrative flowchart of a method for reducing interference current of a working electrode.

With particular reference now to FIG. 13D, FIG. 13E, and FIG. 13F, following deposition of the biorecognition layer at step 1310, an interferent blocking agent may be deposited (i.e., applied) on the biorecognition layer at step 1315 of the methods 1300D, 1300E, 1300F of FIGS. 13D, 13E, and 13F. The interferent blocking agent may be deposited according to any suitable method, including but not limited to drop casting, spray coating, soaking, spin coating, and chemical deposition. For instance, the interferent blocking agent may be applied to the biorecognition layer by soaking the functionalized and activated electrode material in a solution comprising the interferent blocking agent. In some variations, the soaking may be performed for a duration of between 0 hours and 2 weeks, between 1 day and 13 days, between 2 days and 12 days, between 3 days and 11 days, between 4 days and 10 days, between 5 days and 9 days, and/or between 6 days and 8 days. In some variations, the soaking may be performed for a duration of between about 0.1 hours and about 24 hours, between about 0.2 hours and about 23 hours, between about 0.3 hours and about 22 hours, between about 0.4 hours and about 21 hours, between about 0.5 hours and about 20 hours, between about 0.6 hours and about 19 hours, between about 0.7 hours about 18 hours, between about 0.8 hours and about 17 hours, between about 0.9 hours and about 16 hours, between about 1 hour and about 15 hours, between about 2 hours and about 14 hours, between about 3 hours and about 13 hours, between about 4 hours and about 12 hours, between about 5 hours and about 11 hours, between about 6 hours and about 10 hours, and/or between about 7 hours and about 9 hours. In some variations, the soaking may be performed for a duration of between about 1 minute and about 30 minutes, between about 2 minutes and about 25 minutes, between about 3 minutes and about 20 minutes, between about 4 minutes and about 15 minutes, between about 5 minutes and about 10 minutes, and/or between about 7 minutes and about 8 minutes. In some variations, the solution may have a pH of between about 4 and about 14, between about 5 and about 13, between about 6 and about 12, between about 7 and about 11, and/or between about 8 and about 10. In some variations, the solution may have a pH of between about 7 and about 10, between about 7.5 and about 9.5, and between about 8 and/or about 9. In some variations, a concentration of the interferent blocking agent in the solution may be between about 0.05% and about 30% w/v or w/w. In some variations, a concentration of the interferent blocking agent in the solution may be between about 0.1% and about 20%, between about 0.5% and about 15%, between about 1% and about 10%, between about 2% and about 9%, between about 3% and about 8%, between about 4% and about 7%, and/or between about 5% and about 6%. In some variations, a concentration of the interferent block agent in the solution may be between about 0.1 mM and about 1 M, between about 1 mM and about 100 mM, between about 5 mM and about 20 mM, and/or between about 7.5 mM and about 10 mM.

In the variation shown in FIG. 13F, following deposition of the interferent blocking agent at step 1315 of the method 1300F, the working electrode is ready for use.

In other variations, as shown in FIGS. 13A, 13D, and 13E, following deposition of one or more of the attachment enhancer at step 1320 of the method 1300A of FIG. 13A and the method 1300E of FIG. 13E, and of the interferent blocking agent at step 1315 of the method 1300D of FIG. 13D and the method 1300E of FIG. 13E, the working electrode constituents may be functionalized with a diffusion-limiting layer. One or more of the following methods may be employed to apply the diffusion-limiting layer, which may be a thin film of thickness between about 100 nm to about 10,000 nm.

In some variations, a diffusion-limiting layer may be applied by a spray coating method in which an aerosolized polymer formulation (dispersed in water or a solvent) is applied to the microneedle array device with a specified spray pattern and duration in a controlled-environment setting. This creates a thin film with the desired thickness and porosity required to restrict the diffusion of an analyte of interest to the biorecognition layer.

In some variations, the diffusion-limiting layer may be applied by a plasma-induced polymerization method in which a plasma source generates a gas discharge that provides energy to activate a cross-linking reaction within a gaseous, aerosolized, or liquid monomeric precursor (e.g., vinylpyridine). This converts the monomeric precursor to a polymeric coating that may be deposited on the microneedle array to a specified thickness, thereby creating a thin film with the desired thickness and porosity required to restrict the diffusion of an analyte of interest to the biorecognition layer.

Furthermore, in some variations, a diffusion-limiting layer may be applied by electrophoretic or dielectrophoretic deposition, such as example techniques described in U.S. Pat. No. 10,092,207, which is incorporated herein in its entirety by this reference.

V. Counter Electrode-Formation

Various layers of the counter electrode may be applied to the microneedle array and/or functionalized, etc. using suitable processes such as those described below.

In some variations, the counter electrode material may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the counter electrode may alternatively use a coulometry approach as described above.

In some variations, following the anodization process, the counter electrode constituents may be subjected to a cyclically-scanned potential waveform in an activation process using cyclic voltammetry. In some variations, the activation process may be similar to that described above for the working electrode.

Furthermore, in some variations, the counter electrode surface may be electrochemically roughened in order to enhance the current-sinking or current-sourcing capacity of this electrode contingent. The electrochemical roughening process may be similar to that described above for the working electrode.

In some variations, the attachment enhancer may be applied to the counter electrode as, for instance, a solution, as a vapor, and/or as a gas, and by a number of means, as will now be described with reference to method 1300B of FIG. 13B.

With reference again to FIG. 13B, and after completion of pre-processing, anodization, activation, and/or roughening of the electrode material, which may each be performed as described above, an attachment enhancer may be deposited (i.e., applied) on the electrode material at step 1320 of the method 1300B of FIG. 13B. The attachment enhancer may be deposited according to any suitable method, including but not limited to drop casting, spray coating, soaking, spin coating, and chemical deposition. For instance, the attachment enhancer may be deposited on the electrode material by soaking the functionalized and activated electrode material in a solution comprising the attachment enhancer. In some variations, the soaking may be performed for a duration of between 0 hours and 2 weeks, between 1 day and 13 days, between 2 days and 12 days, between 3 days and 11 days, between 4 days and 10 days, between 5 days and 9 days, and/or between 6 days and 8 days. In some variations, the soaking may be performed for a duration of between about 0.1 hours and about 24 hours, between about 0.2 hours and about 23 hours, between about 0.3 hours and about 22 hours, between about 0.4 hours and about 21 hours, between about 0.5 hours and about 20 hours, between about 0.6 hours and about 19 hours, between about 0.7 hours about 18 hours, between about 0.8 hours and about 17 hours, between about 0.9 hours and about 16 hours, between about 1 hour and about 15 hours, between about 2 hours and about 14 hours, between about 3 hours and about 13 hours, between about 4 hours and about 12 hours, between about 5 hours and about 11 hours, between about 6 hours and about 10 hours, and/or between about 7 hours and about 9 hours. In some variations, the soaking may be performed for a duration of between about 1 minute and about 30 minutes, between about 2 minutes and about 25 minutes, between about 3 minutes and about 20 minutes, between about 4 minutes and about 15 minutes, between about 5 minutes and about 10 minutes, and/or between about 7 minutes and about 8 minutes. In some variations, the solution may have a pH of between about 4 and about 14, between about 5 and about 13, between about 6 and about 12, between about 7 and about 11, and/or between about 8 and about 10. In some variations, the solution may have a pH of between about 7 and about 10, between about 7.5 and about 9.5, and between about 8 and/or about 9. In some variations, a concentration of the attachment enhancer 1123 in the solution may be between about 0.05% and about 30% w/v or w/w. In some variations, a concentration of the attachment enhancer 1123 in the solution may be between about 0.1% and about 20%, between about 0.5% and about 15%, between about 1% and about 10%, between about 2% and about 9%, between about 3% and about 8%, between about 4% and about 7%, and/or between about 5% and about 6%.

In some variations, the counter electrode may have few or no additional layers over the electrode material. However, in some variations the counter electrode may benefit from increased surface area to increase the amount of current it can support. For example, the counter electrode material may be textured or otherwise roughened in such a way to augment the surface area of the electrode material for enhanced current sourcing or sinking ability. In some variations, the counter electrode may include an electrocatalytic layer. The electrocatalytic layer may include a platinum black layer, which may augment electrode surface as described above with respect to the electrocatalytic layer described in section Electrode Layers (c). However, in some variations of the counter electrode, the electrocatalytic layer of platinum black may be omitted (e.g., as shown in FIG. 11B).

vi. Reference Electrode-Formation

Various layers of the reference electrode may be applied to the microneedle array and/or functionalized, etc. using suitable processes such as those described below.

Like the working and counter electrodes as described above, the reference electrode may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the reference electrode may alternatively use a coulometry approach as described above.

Following the anodization process, the reference electrode constituents may be subjected to a cyclically-scanned potential waveform in an activation process using cyclic voltammetry. In some variations, the activation process may be similar to that described above for the working electrode.

Furthermore, in some variations the reference electrode surface may be electrochemically roughened in order to enhance adhesion of the surface-immobilized redox couple. The electrochemical roughening process may be similar to that described above for the working electrode.

In some variations, the attachment enhancer 1133 may be applied to the reference electrode 1130 as, for instance, a solution, as a vapor, and/or as a gas, and by a number of means, as will now be described with reference to method 1300C of FIG. 13C.

With reference again to FIG. 13C, and after completion of pre-processing, anodization, and activation of the electrode material 1132, which may each be performed as described above, the reference electrode constituents may be functionalized with the redox couple layer 1136 at step 1314 of method 1300C. To this end, a fixed anodic potential (e.g., between +0.4-+1.0 V vs. Ag/AgCl reference electrode) may be applied for a certain suitable duration (e.g., between about 10 sec and about 10 min) in an aqueous solution. Alternatively, the reference electrode is subject to a fixed anodic potential (e.g., between about +0.4 to about +1.0 V vs. Ag/AgCl reference electrode) until a certain amount of charge has passed (e.g., 0.01 mC-10 mC) in an aqueous solution. In some variations, the aqueous solution may include a monomeric precursor to a conducting polymer and a charged dopant counter ion or material (e.g., poly(styrene sulfonate)) carrying an opposing charge. In this process, a thin film (e.g., between about 10 nm and about 10,000 nm) of a conducting polymer with a dispersed counter ion or material may be generated on a surface of the reference electrode material 1132. This creates a surface-immobilized, solid-state redox couple with a stable thermodynamic potential. In some variations, the conducting polymer may include one or more of aniline, pyrrole, acetylene, phenylene, phenylene vinylene, phenylene diamine, thiophene, 3,4-ethylenedioxythiophene, and aminophenylboronic acid.

In some alternative variations, a native iridium oxide film (e.g., $IrO_2$ or $Ir_2O_3$ or $IrO_4$) may be electrochemically grown on an iridium electrode surface in an oxidative process. This also creates a stable redox couple, as discussed above.

Following deposition of the redox-couple layer at step 1314, an attachment enhancer may be deposited (i.e. applied) on the redox couple layer. The attachment enhancer may be deposited according to any suitable method, including but not limited to drop casting, spray coating, soaking, spin coating, and chemical deposition. For instance, the attachment enhancer may be deposited on the redox couple layer by soaking the functionalized and activated electrode material in a solution comprising the attachment enhancer. In some variations, the soaking may be performed for a duration of between 0 hours and 2 weeks, between 1 day and 13 days, between 2 days and 12 days, between 3 days and 11 days, between 4 days and 10 days, between 5 days and 9 days, and/or between 6 days and 8 days. In some variations, the soaking may be performed for a duration of between about 0.1 hours and about 24 hours, between about 0.2 hours and about 23 hours, between about 0.3 hours and about 22 hours, between about 0.4 hours and about 21 hours, between about 0.5 hours and about 20 hours, between about 0.6 hours and about 19 hours, between about 0.7 hours about 18 hours, between about 0.8 hours and about 11 hours, between about 0.9 hours and about 16 hours, between about 1 hour and about 15 hours, between about 2 hours and about 14 hours, between about 3 hours and about 13 hours, between about 4 hours and about 12 hours, between about 5 hours and about 11 hours, between about 6 hours and about 10 hours, and/or between about 7 hours and about 9 hours. In some variations, the soaking may be performed for a duration of between about 1 minute and about 30 minutes, between about 2 minutes and about 25 minutes, between about 3 minutes and about 20 minutes, between about 4 minutes and about 15 minutes, between about 5 minutes and about 10 minutes, and/or between about 7 minutes and about 8 minutes. In some variations, the solution may have a pH of between about 4 and about 14, between about 5 and about 13, between about 6 and about 12, between about 7 and about 11, and/or between about 8 and about 10. In some variations, the solution may have a pH of between about 7 and about 10, between about 7.5 and about 9.5, and between about 8 and/or about 9. In some variations, a concentration of the attachment enhancer in the solution may be between about 0.05% and about 30% w/v or w/w. In some variations, a concentration of the attachment enhancer in the solution may be between about 0.1% and about 20%, between about 0.5% and about 15%, between about 1% and about 10%, between about 2% and about 9%, between about 3% and about 8%, between about 4% and about 7%, and/or between about 5% and about 6%.

Additionally, or alternatively, in some variations, the reference electrode may include a diffusion-limiting layer (e.g., arranged over or disposed on the electrode and/or the redox-couple layer). The diffusion-limiting layer may, for example, be similar to the diffusion-limiting layer described above in section Electrode Layers (f). In some variations in which the diffusion-limiting layer is included, the reference electrode may further include a hydrophilic layer that provides for a biocompatible interface to, for example, reduce the foreign body response. The hydrophilic layer may be arranged over (or disposed on) the diffusion-limiting layer.

In some variations, the reference electrode may include an electrode protecting layer, such as that described with reference to the working electrode and/or the counter electrode. The electrode protecting layer may be arranged over (or disposed on) the electrode material or, in variations with the electrocatalytic layer, the electrode protecting layer, if provided, is arranged over the electrocatalytic layer.

Other features and techniques for forming the reference electrode may be similar to that described in, for example, U.S. Patent Pub. No. 2019/0309433, which was incorporated above by reference.

Microneedle Array Configurations

The microneedle arrays described herein may have a high degree of configurability concerning where the working electrode(s), counter electrode(s), and reference electrode(s) are located within the microneedle array. This configurability may be facilitated by the electronics system.

Figure 14:
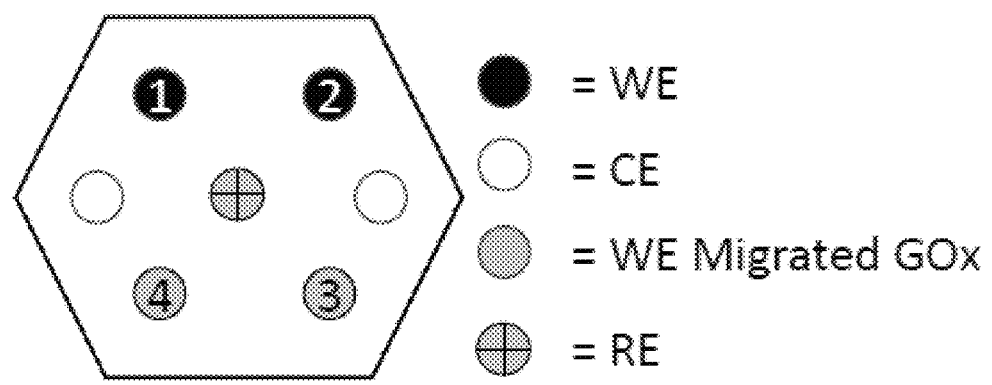
FIG. 14 depicts an illustrative schematic of an arrangement of electrodes in a microneedle array.
Figure 15:
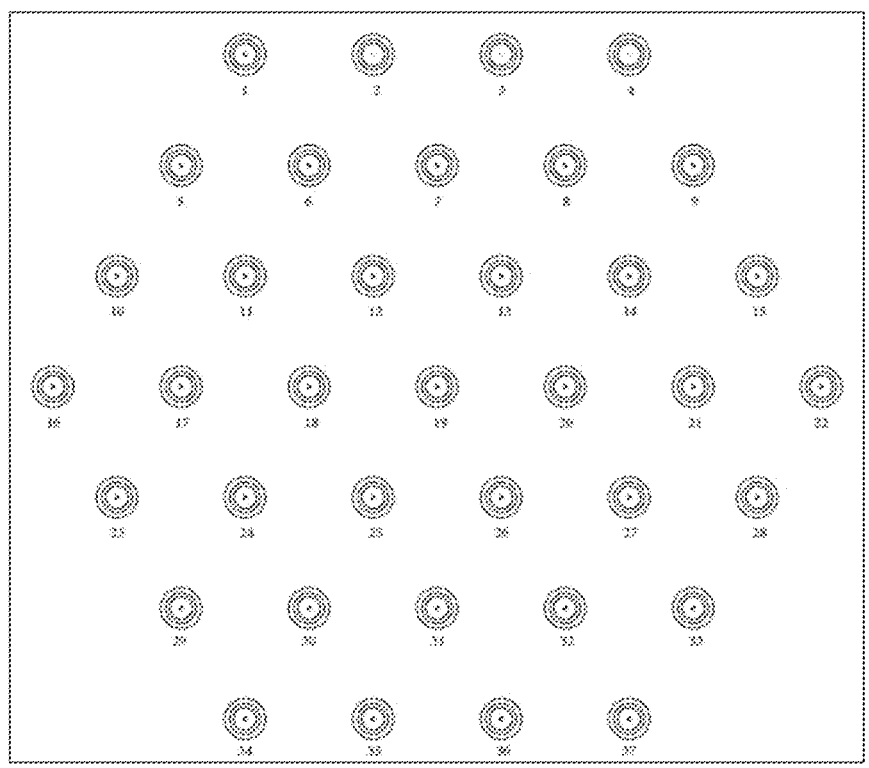
FIG. 15 depicts an illustrative schematic of a microneedle array configuration.

In some variations, for more consistent penetration, microneedles may be spaced equidistant from one another (e.g., same pitch in all directions). To that end, in some variations, the microneedles in a microneedle array may be arranged in a hexagonal configuration as shown in FIGS. 14, 15, 16A-16J, 17A-17F and 20A. For instance, as shown in FIG. 14, an example variation of a microneedle array with 7 microneedles is depicted. The microneedle arrangement contains four microneedles assigned as two independent groupings (½ and ¾) of two working electrodes (WE) each, a counter electrode (CE) contingent comprised of 2 microneedles, and a single reference electrode (RE). There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance. Alternatively, the microneedles in a microneedle array may arranged in a rectangular array (e.g., square array), or in another suitable symmetrical manner. Alternatively, the microneedles in a microneedle array may arranged in a rectangular array (e.g., square array), or in another suitable symmetrical manner.

Figure 16A:
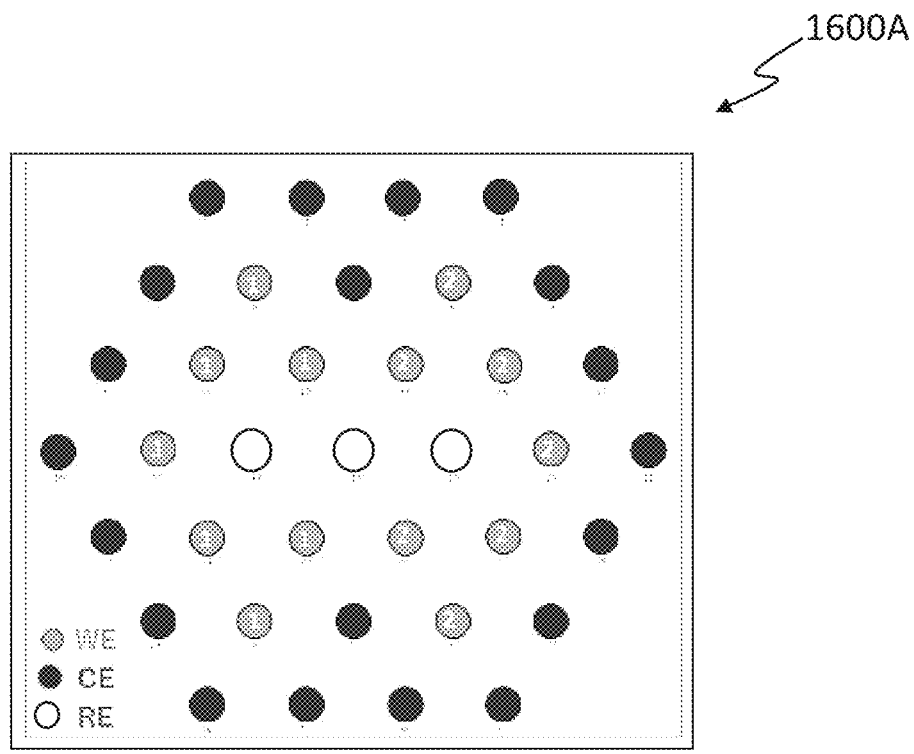

In some variations, a microneedle array may include electrodes distributed in two or more groups in a symmetrical or non-symmetrical manner in the microneedle array, with each group featuring the same or differing number of electrode constituents depending on requirements for signal sensitivity and/or redundancy. For example, electrodes of the same type (e.g., working electrodes) may be distributed in a bilaterally or radially symmetrical manner in the microneedle array. For example, FIG. 16A depicts a variation of a microneedle array 1600A including two symmetrical groups of seven working electrodes (WE), with the two working electrode groups labeled "1" and "2". In this variation, the two working electrode groups are distributed in a bilaterally symmetrical manner within the microneedle array. The working electrodes are generally arranged between a central region of three reference electrodes (RE) and an outer perimeter region of twenty counter electrodes (CE). In some variations, each of the two working electrode groups may include seven working electrodes that are electrically connected amongst themselves (e.g., to enhance sensor signal). Alternatively, only a portion of one or both of the working electrode groups may include multiple electrodes that are electrically connected amongst themselves. As yet another alternative, the working electrode groups may include working electrodes that are standalone and not electrically connected to other working electrodes. Furthermore, in some variations the working electrode groups may be distributed in the microneedle array in a non-symmetrical or random configuration.

Figure 16B:
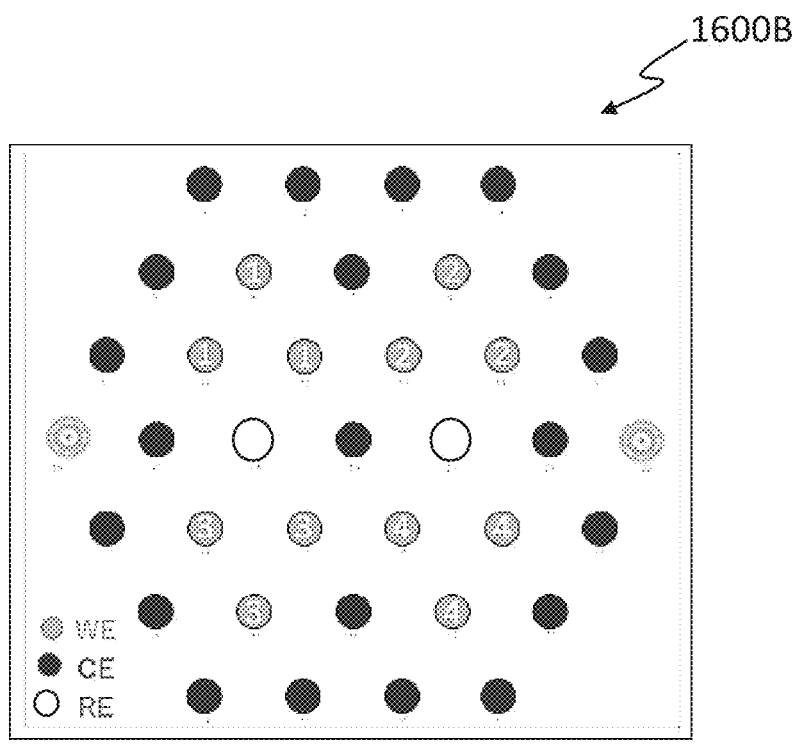

As another example, FIG. 16B depicts a variation of a microneedle array 1600B including four symmetrical groups of three working electrodes (WE), with the four working electrode groups labeled "1", "2", "3", and "4." In this variation, the four working electrode groups are distributed in a radially symmetrical manner in the microneedle array. Each working electrode group is adjacent to one of two reference electrode (RE) constituents in the microneedle array and arranged in a symmetrical manner. The microneedle array also includes counter electrodes (CE) arranged around the perimeter of the microneedle array, except for two electrodes on vertices of the hexagon that are inactive or may be used for other features or modes of operation.

Figures 16C, 16D, 16E:
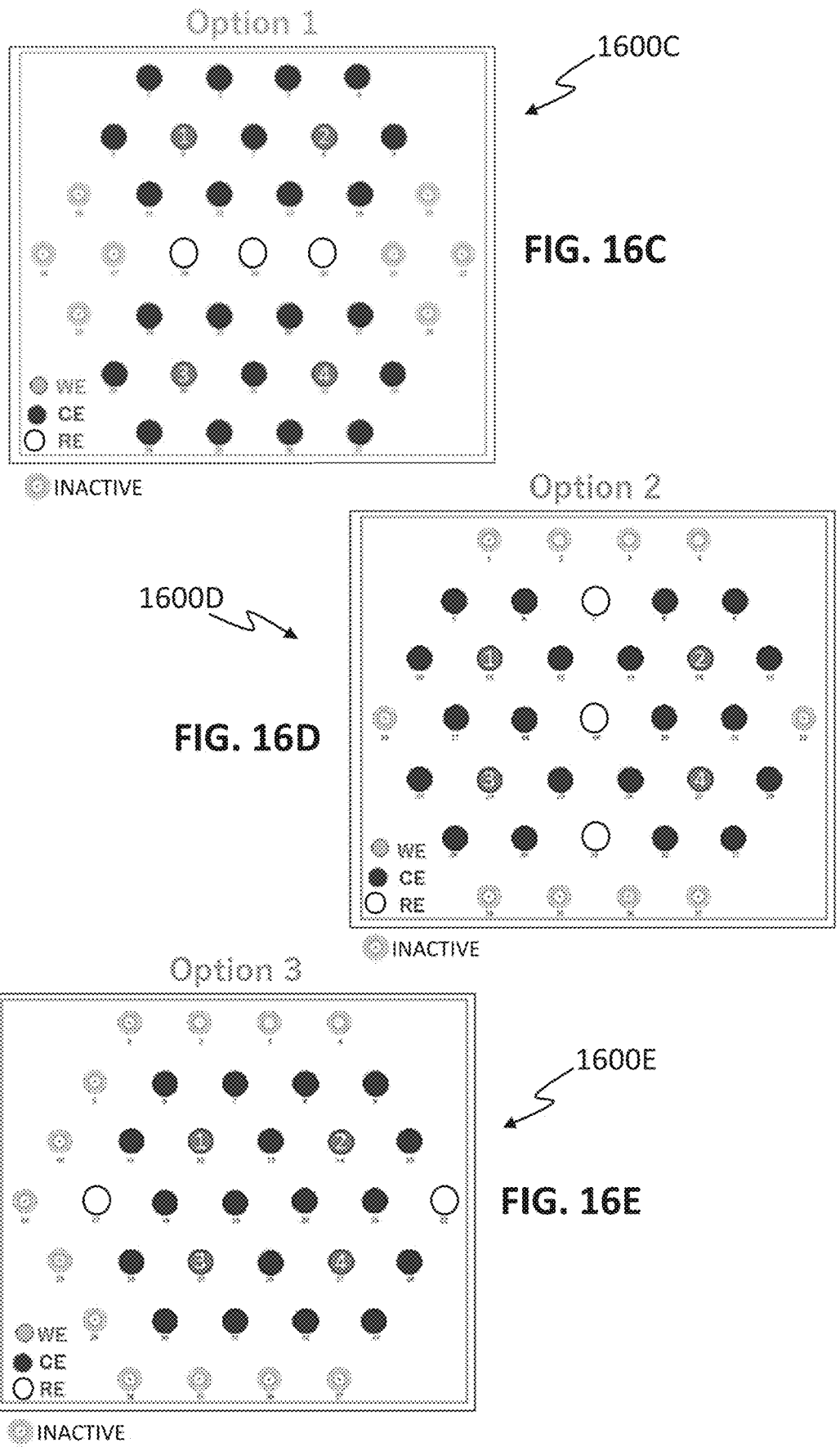

In some variations, only a portion of microneedle array may include active electrodes. For example, FIG. 16C depicts a variation of a microneedle array 1600C with 37 microneedles and a reduced number of active electrodes, including four working electrodes (labeled "1", "2", "3", and "4") in a bilaterally symmetrical arrangement, twenty-two counter electrodes, and three reference electrodes. The remaining eight electrodes in the microneedle array are inactive.

As another example, FIG. 16D depicts a variation of a microneedle array 1600D with 37 microneedles and a reduced number of active electrodes, including four working electrodes (labeled "1", "2", "3", and "4") in a bilaterally symmetrical arrangement, twenty counter electrodes, and three reference electrodes, where the remaining ten electrodes in the microneedle array are inactive.

As another example, FIG. 16E depicts a variation of a microneedle array 1600E with 37 microneedles and a reduced number of active electrodes, including four working electrodes (labeled "1", "2", "3", and "4"), eighteen counter electrodes, and two reference electrodes. The remaining thirteen electrodes in the microneedle array are inactive. The inactive electrodes are along a partial perimeter of the overall microneedle array, thereby reducing the effective size and shape of the active microneedle arrangement to a smaller hexagonal array. Within the active microneedle arrangement, the four working electrodes are generally in a radially symmetrical arrangement, and each of the working electrodes is surrounded by a group of counter electrodes.

Figure 16F:
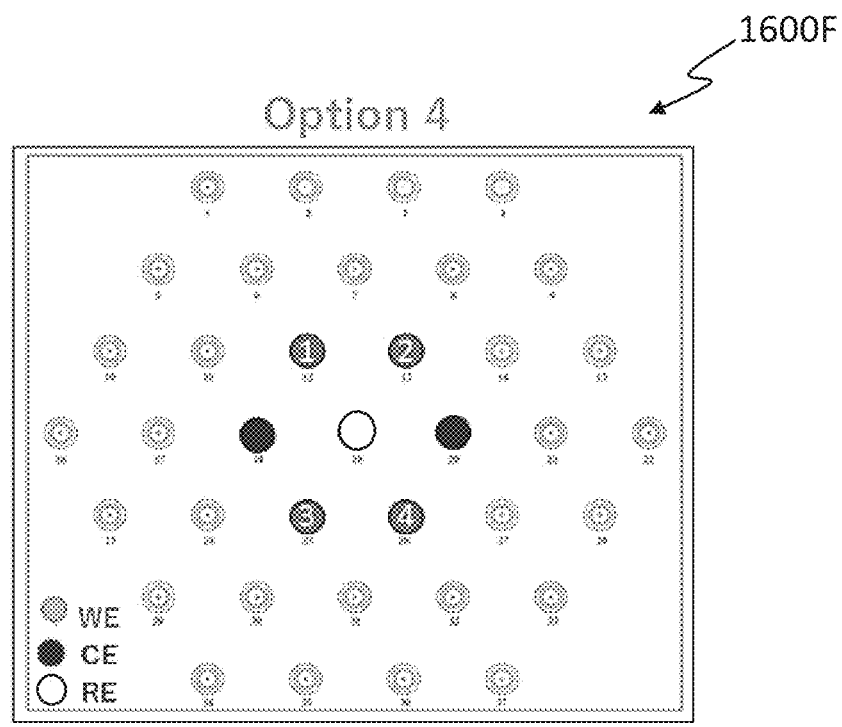

FIG. 16F depicts another example variation of a microneedle array 1600F with 37 microneedles and a reduced number of active electrodes, including four working electrodes (labeled "1", "2", "3", and "4"), two counter electrodes, and one reference electrode. The remaining thirty electrodes in the microneedle array are inactive. The inactive electrodes are arranged in two layers around the perimeter of the overall microneedle array, thereby reducing the effective size and shape of the active microneedle arrangement to a smaller hexagonal array centered around the reference electrode. Within the active microneedle arrangement, the four working electrodes are in a bilaterally symmetrical arrangement and the counter electrodes are equidistant from the central reference electrode.

Figure 16G:
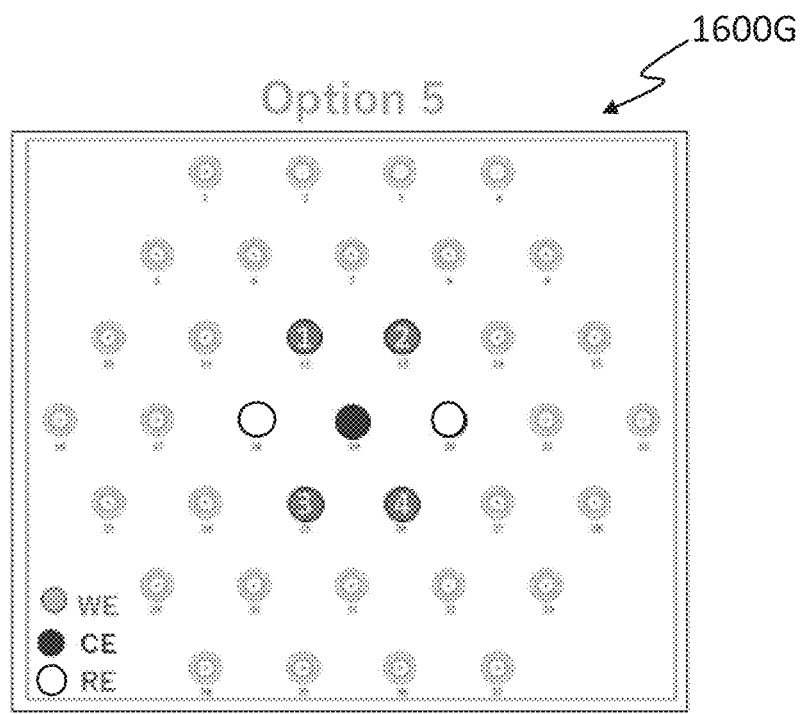

FIG. 16G depicts another example variation of a microneedle array 1600G with 37 microneedles and a reduced number of active electrodes. The active electrodes in microneedle array 1600G are arranged in a similar manner as that in microneedle array 1600F shown in FIG. 16F, except that the microneedle array 1600G includes one counter electrode and two reference electrodes, and the smaller hexagonal array of active microneedles is centered around the counter electrode. Within the active microneedle arrangement, the four working electrodes are in a bilaterally symmetrical arrangement and the reference electrodes are equidistant from the central counter electrode.

FIG. 16H depicts another example variation of a microneedle array 1600H with seven microneedles. The microneedle arrangement contains two microneedles assigned as independent working electrodes (1 and 2), a counter electrode contingent comprised of 4 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 16I depicts another example variation of a microneedle array 1600I with seven microneedles. The microneedle arrangement contains four microneedles assigned as two independent groupings (1 and 2) of two working electrodes each, a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 16J depicts another example variation of a microneedle array 1600J with seven microneedles. The microneedle arrangement contains four microneedles assigned as independent working electrodes (1, 2, 3, and 4), a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

While FIGS. 16A-16J illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

Considerations of how to configure the microneedles include factors such as desired insertion force for penetrating skin with the microneedle array, optimization of electrode signal levels and other performance aspects, manufacturing costs and complexity, etc.

Multiple microneedles (e.g., any of the microneedle variations described herein, each of which may have a working electrode, a counter electrode, or a reference electrode) may be arranged in a microneedle array. For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 µm). Accordingly, in some variations the microneedles in a microneedle array may have a pitch of at least 200 µm, at least 300 µm, at least 400 µm, at least 500 µm, at least 600 µm, at least 700 µm, or at least 750 µm. For example, the pitch may be between about 200 µm and about 800 µm, between about 300 µm and about 700 µm, or between about 400 µm and about 600 µm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles, as shown in FIG. 17E and FIG. 17F, or a microneedle array including seven microneedles, as shown in FIGS. 17A-17D. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, as described in further detail below, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

Figure 17A:
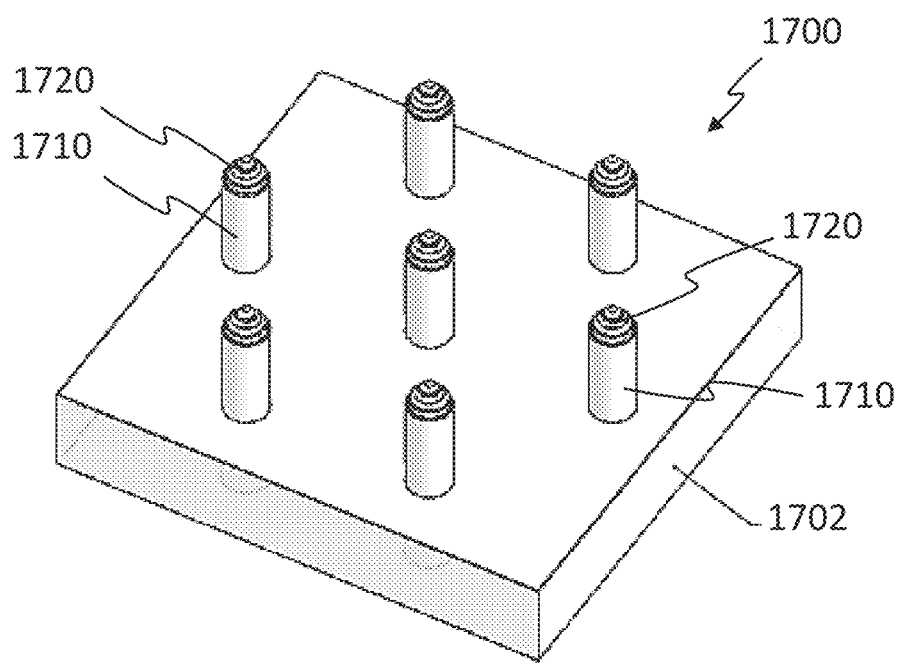
FIGS. 17A and 17B depict illustrative schematics of a microneedle array configuration.
Figure 17B:
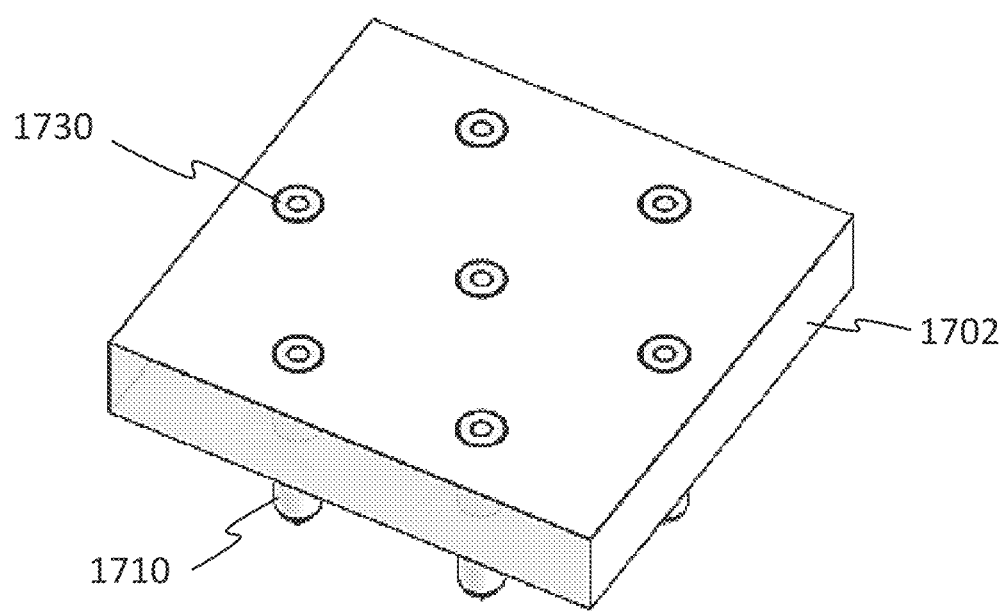
Figure 17C:
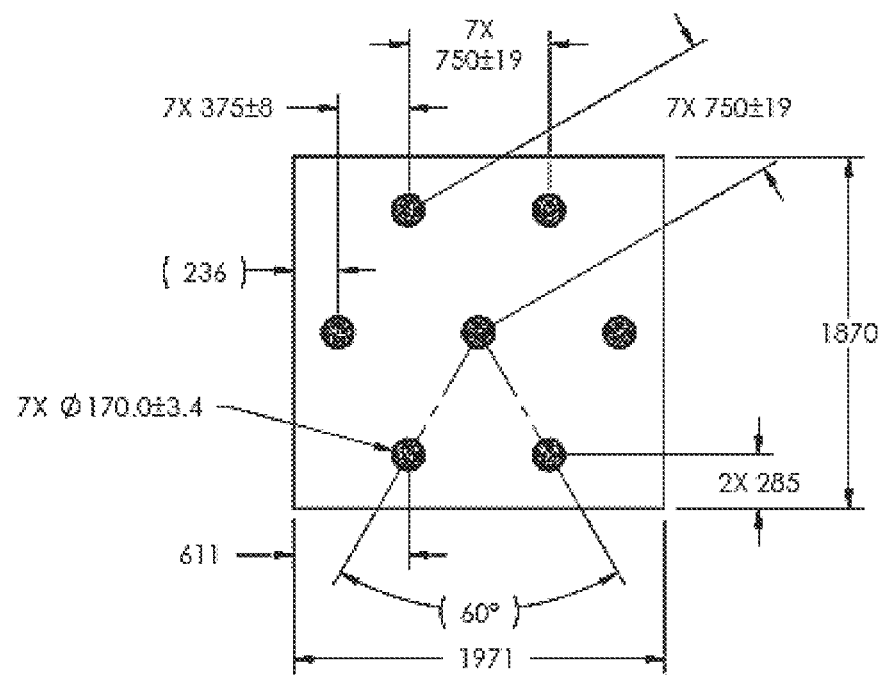
FIGS. 17C and 17D depict illustrative schematics of a microneedle array configuration.
Figure 17D:
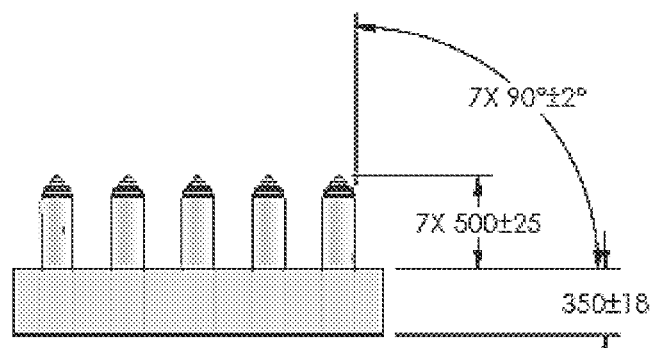
Figure 17E:
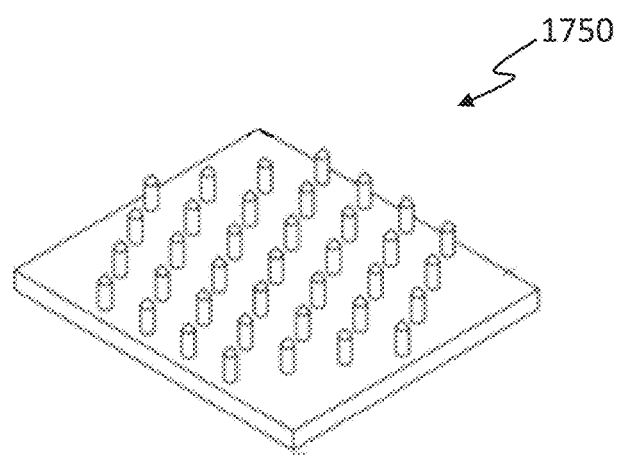
FIG. 17E and FIG. 17F depict illustrative schematics of a microneedle array configuration.
Figure 17F:
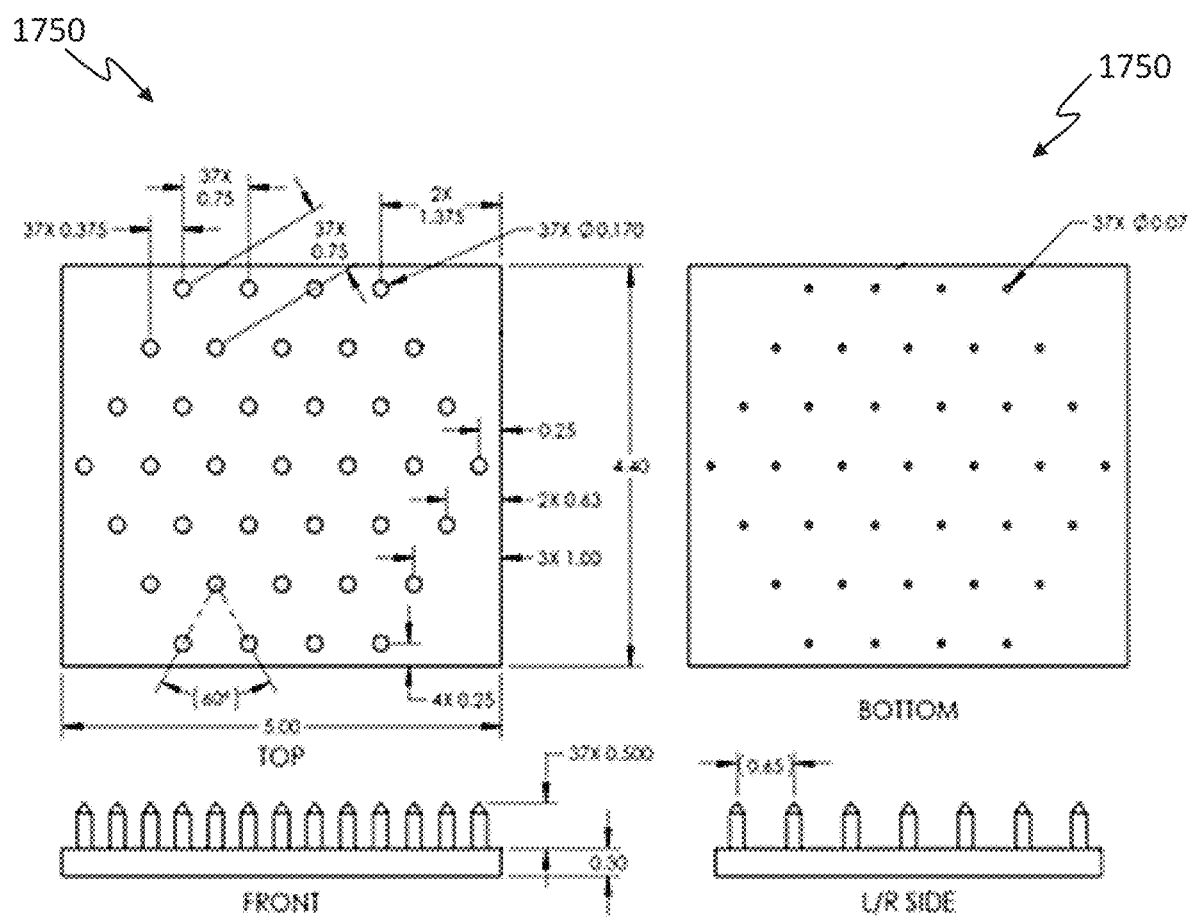

FIGS. 17A and 17B depict perspective views of an illustrative schematic of seven microneedles 1710 arranged in an example variation of a microneedle array 1700. The seven microneedles 1710 are arranged in a hexagonal array on a substrate 1702. As shown in FIG. 17A, the electrodes 1720 are arranged on distal portions of the microneedles 1710 extending from a first surface of the substrate 1702. As shown in FIG. 17B, proximal portions of the microneedles 1710 are conductively connected to respective backside electrical contacts 1730 on a second surface of the substrate 1702 opposite the first surface of the substrate 1702. FIGS. 17C and 17D depict plan and side views of an illustrative schematic of a microneedle array similar to microneedle array 1700. As shown in FIGS. 17C and 17D, the seven microneedles are arranged in a hexagonal array with an inter-needle center-to-center pitch of about 750 μm between the center of each microneedle and the center of its immediate neighbor in any direction. In other variations the inter-needle center-to-center pitch may be, for example, between about 700 μm and about 800 μm, or between about 725 μm and about 775 μm. The microneedles may have an approximate outer shaft diameter of about 170 μm (or between about 150 μm and about 190 μm, or between about 125 μm and about 200 μm) and a height of about 500 μm (or between about 475 μm and about 525 μm, or between about 450 μm and about 550 μm).

FIG. 17E and FIG. 17F depict an illustrative schematic of 37 microneedles arranged in an exemplary variation of a microneedle array. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction. FIG. 17E depicts an illustrative schematic of an example variation of a die 1750 including the microneedle arrangement. Exemplary dimensions of the die 1200 (e.g., about 4.4 mm by about 5.0 mm) and the microneedle array 1750 are shown in FIG. 17F.

Due to the structure of the microneedle array with separate and spaced apart microneedles, each configured to function as a specific electrode type, additional considerations of how to configure (e.g., arrange) the electrode types among the microneedle array may be beneficial. For example, user tissue located between the microneedles due to the spaced apart configuration of the electrodes may affect the operation of the electrochemical cell.

In the electrochemical cell including the working electrode, the counter electrode, and the reference electrode, the working electrode requires a constant bias (also referred to as a reference potential and/or a reference bias). The reference electrode is used as a bias set point for the negative terminal of the working electrode. The counter electrode attempts to maintain the constant bias by adjusting the voltage of the counter electrode through feedback received from the reference electrode. However, due to the microneedle array configuration with spaced apart electrodes (e.g., the tissue between the electrodes has an associated resistance), tissue resistance is inserted into the system and impacts operation of the electrochemical cell. The tissue resistance in conjunction with the current that flows between the working electrode and the counter electrode may induce a voltage drop between the working electrode and the reference electrode, which leads to bias degradation at the working electrode. Moreover, the bias degradation varies with normal working electrode operation (e.g., concentration of analyte under measurement is represented by a range of current values) and with tissue resistance, which is not a controlled variable and may vary across insertion sites.

In microneedle array configurations with more than one working electrode, the problem can be confounded. Since variability exists not only within the tissue resistance but also between the resistance of the working electrodes, the working electrode bias degradation is not consistent among the working electrodes. This inconsistency may lead to different tracking performance levels among the working electrodes in a multiple working electrode configuration.

In an ideal environment, a constant voltage drop across each of the working electrodes is required. In the electrochemical cell with a working electrode, a counter electrode, and a reference electrode, a constant voltage drop is attempted to be maintained through the counter electrode based on feedback from the reference electrode and through adjustments of the counter electrode voltage. The ability of the counter electrode to maintain the constant voltage drop is dependent on construction of the electrodes and deployment characteristics (e.g., insertion characteristics of the microneedles). The adjustments made by the counter electrode take into account changes in impedance and current of the working electrode as well as process-induced impedance variations among the working electrodes. However, the counter electrode voltage adjustment capability is limited in practical implementations, and the electrochemical cell is only effective across a specific current range of the working electrode.

Thus, there is a need for improved stabilization of the working electrode bias as well as improved bias match in systems with multiple working electrodes.

Aspects of the present disclosure are directed to configuring the microneedle array by taking into consideration tissue (e.g., body) resistance. In an effort to remedy the above-described deficiencies, the present disclosure provides a microneedle array with a zero-current environment within a voltage guard in which only residual reference electrode current flows. As current flows between the working electrode and the current electrode in the microneedle array configuration, the zero-current environment makes the working electrode bias impervious to effects of tissue resistance and reference electrode resistance.

Figure 18A:
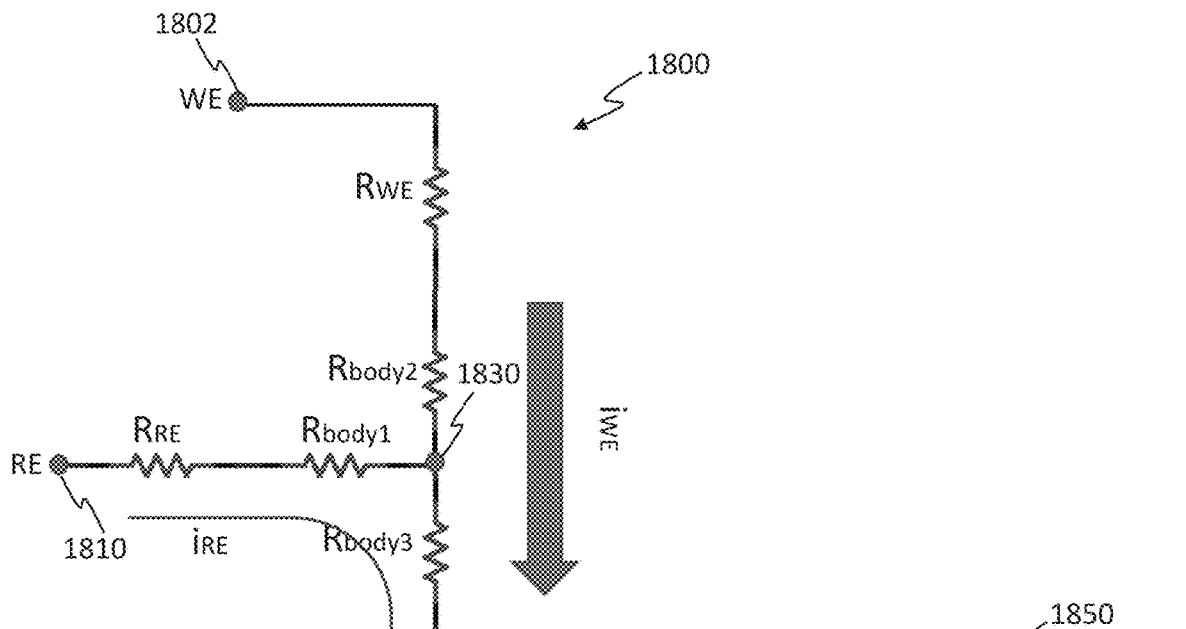
FIGS. 18A and 18B depict schematics of a microneedle array sensor model.

FIG. 18A is a simplified microneedle array sensor model 1800 that reflects aspects related to spacing between the electrodes. In addition to naturally-occurring and intrinsic resistance from each electrode (e.g., $R_{WE}$ from a working electrode 1802, RRE from a reference electrode 1810, and RCE from a counter electrode 1820), tissue resistance is present between each electrode 1802, 1810, 1820 and a body interface 1830. For example, $R_{body1}$ is the tissue resistance between the reference electrode 1810 and the body interface 1830, $R_{body2}$ is the tissue resistance between the working electrode 1802 and the body interface 1830, and $R_{body3}$ is the tissue resistance between the counter electrode 1820 and the body interface 1830. Tissue resistance between the working electrode 1802 and the reference electrode 1810 induces a voltage drop proportional to the current flow between them, resulting in working electrode bias degradation that is dependent on the tissue resistance. Since the tissue resistance is an uncontrolled variable, the working electrode bias degradation varies across application sites and may lead to loss of analyte tracking ability. In addition, a high tissue resistance value of $R_{body3}$ may cause the counter electrode 1820 to appear to have exceeded its current-carrying capacity. This causes the voltage at the counter electrode 1820 to rail.

Figure 18B:
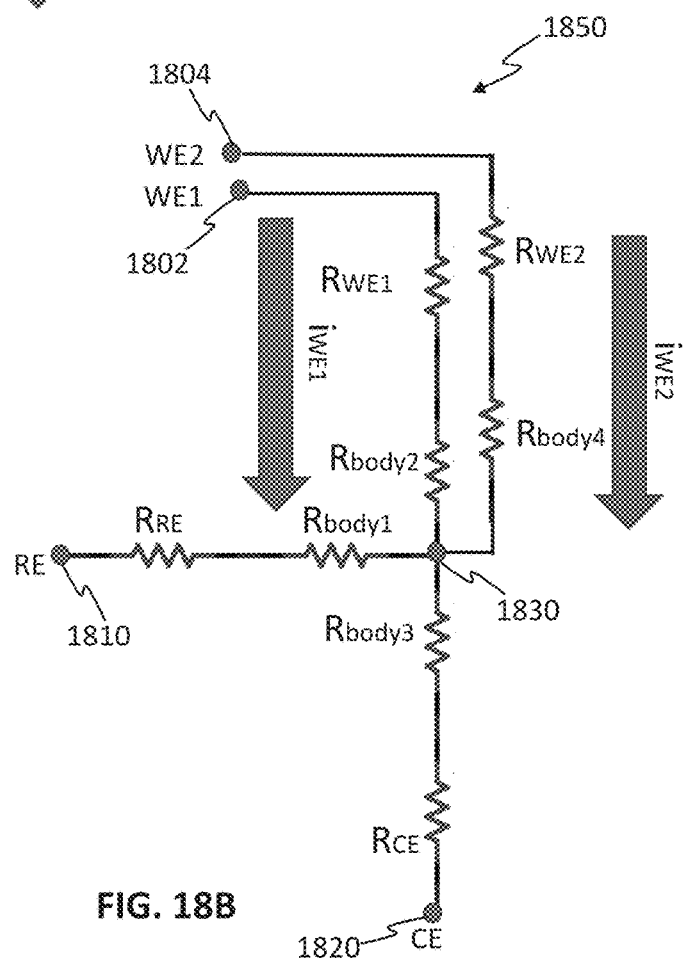

FIG. 18B is a simplified microneedle array sensor model 1850 that reflects aspects related to spacing between the electrodes with two working electrodes, working electrode 1802 and working electrode 1804. In multiple channel configurations in which two or more working electrodes are incorporated, such as that shown in FIG. 18B, the working electrode bias degradation is inconsistent and may lead to channel-to-channel performance differences on the same microneedle array. Variability between the resistance of the working electrodes ($R_{WE1}$ and $R_{WE2}$) and between the tissue resistance values may lead to variability in analyte tracking performance among the working electrodes 1802 and 1804. Moreover, the variability is also dependent on deployment of the microneedle array (e.g., insertion of the microneedles) and thus changes among each use.

Figure 19A:
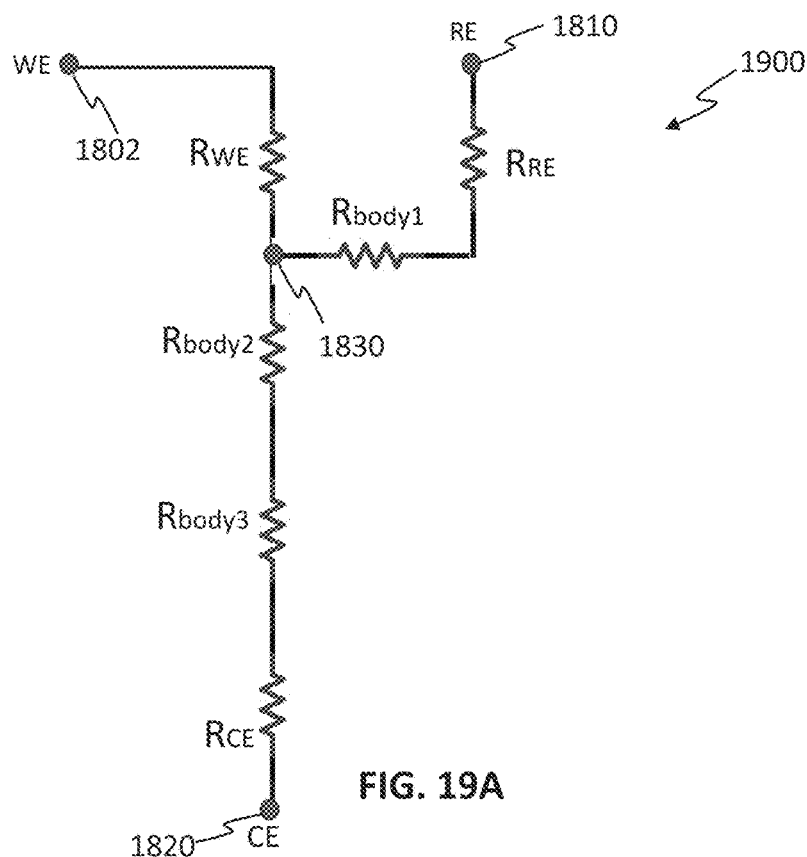
FIGS. 19A and 19B depict schematics of a microneedle array sensor model with a stabilized working electrode configuration.

FIG. 19A is a microneedle array sensor model 1900 depicting aspects related to stabilizing the working electrode bias for use in tissue resistance environments. As shown, the reference electrode 1910 is moved to a position in which errors induced by $R_{body2}$ are outside of the voltage guard of the reference electrode 1910.

To stabilize the working electrode bias in a microneedle array configuration, the present disclosure provides a zero-current environment within a voltage guard in which only reference electrode resistance flows. As current flows between the working electrode and the current electrode in the microneedle array configuration, the zero-current environment makes the working electrode bias impervious to effects of tissue resistance and reference electrode resistance.

To implement aspects of the sensor model 1910 of FIG. 19A in a microneedle array configuration, the effects of the geometric distribution of tissue resistance may be offset by taking into account the non-uniform current flow across the microneedle array.

Figure 19B:
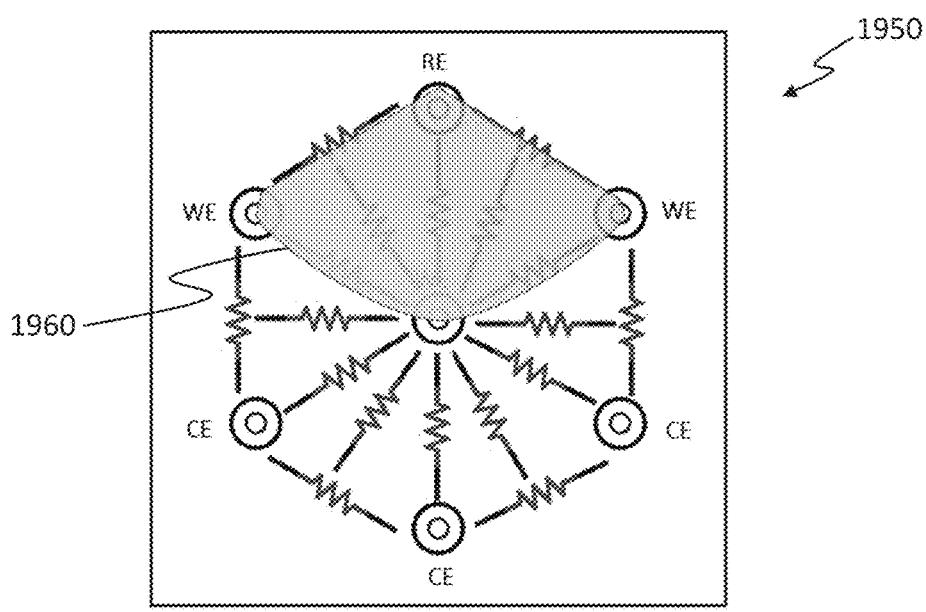

FIG. 19B provides a representation of a microneedle array configuration 1950 in which the reference electrode 1810 is positioned in a zero-current (e.g., constant potential) zone 1960. As current flows between the working electrodes and the counter electrodes, the working electrode bias effects due to voltage drops from tissue resistance are minimized. The zero-current and constant potential zone 1960 in which the reference electrode is contained provides for the reference electrode voltage to be diffused evenly to the working electrodes, thus providing improved stabilization of the working electrode bias and matching the bias of each working electrode provided in the microneedle array configuration.

In some variations, the number of working electrodes required is at least the minimum number necessary to isolate the reference electrode from the current flowing between the working electrodes and the counter electrodes. As the number of microneedles may be fixed due to substrate and/or manufacturing constraints or requirements, the electrodes may be configured accordingly to form the zero-current zone. In particular, with a fixed number of microneedles (and hence electrodes), the electrodes may be allocated among the microneedle array to satisfy the requirement to isolate the reference electrode from the current flowing between the working electrodes and the counter electrodes.

In some variations in which a plurality of counter electrodes are included in the microneedle array configuration, the counter electrodes may be electrically connected in parallel. In this arrangement, the current from a first working electrodes flows primarily to the counter electrode proximally closest to the first working electrode. For example, a majority portion of current from a first working electrode flows to a first counter electrode where the first counter electrode is positioned most proximal to the first working electrode in relation to the other counter electrodes.

FIGS. 20A-20F depict illustrative schematics of different variations of microneedle array configurations. As further described herein, each electrode may be arranged on a surface of a tapered distal portion of a respective microneedle of the plurality of microneedles that form the microneedle array.

Figure 20A:
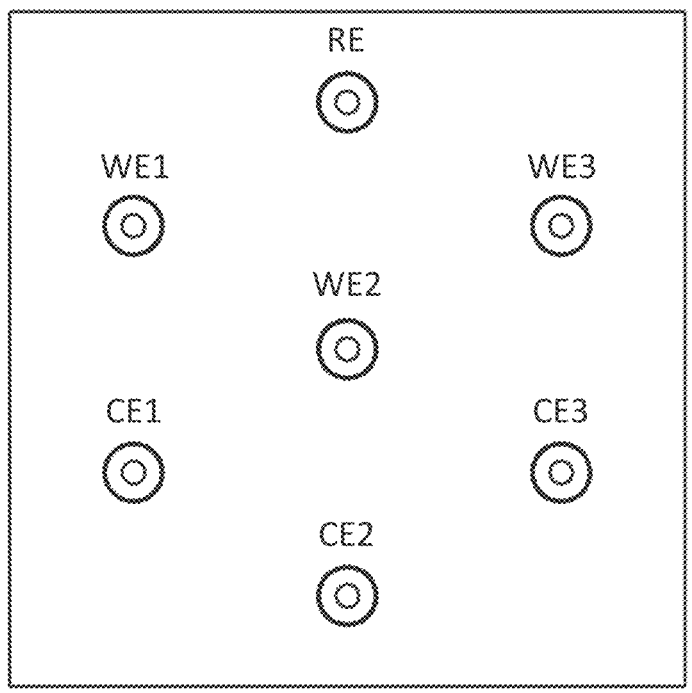
FIGS. 20A-20F depict illustrative schematics of different variations of microneedle array configurations.

FIG. 20A depicts a microneedle array 2000 with seven microneedles arranged in a hexagonal configuration. The microneedle array 2000 includes three working electrodes (WE1, WE2, and WE3), three counter electrodes (CE1, CE2, and CE3), and one reference electrode (RE). The three working electrodes form a barrier around the one reference electrode to provide stabilization of the working electrode bias according to aspects described herein. The barrier between the one reference electrode and the counter electrodes formed by the working electrodes prevents the current that flows from the working electrodes to the counter electrodes from flowing through the one reference electrode.

In the configuration of the microneedle array 2000, one working electrode (WE2) on a respective microneedle is arranged (e.g., positioned) in a central region of the semiconductor substrate on the central microneedle. The microneedles on which the counter electrodes are formed are at edges of the microneedle array 2000, proximal (e.g., adjacent) to a first edge of the semiconductor substrate. The microneedle on which the reference electrode is formed is also at an edge of the microneedle array, proximal (e.g., adjacent) to a second edge of the semiconductor substrate opposite the first edge. In the variation shown in FIG. 20A, the microneedles are spaced equidistant from one another (e.g., same pitch in all directions), and the working electrodes are uniformly distributed from the reference electrode. The distances between the microneedles of WE1 and CE1, WE2 and CE2, and WE3 and CE3 are equal, thus a majority portion of current from WE1 flows to CE1, and a majority portion of current from WE3 flows to CE3. In the configuration of the microneedle array 2000 of FIG. 20A, each microneedle is the same distance from the central microneedle on which WE2 is positioned.

Figure 20B:
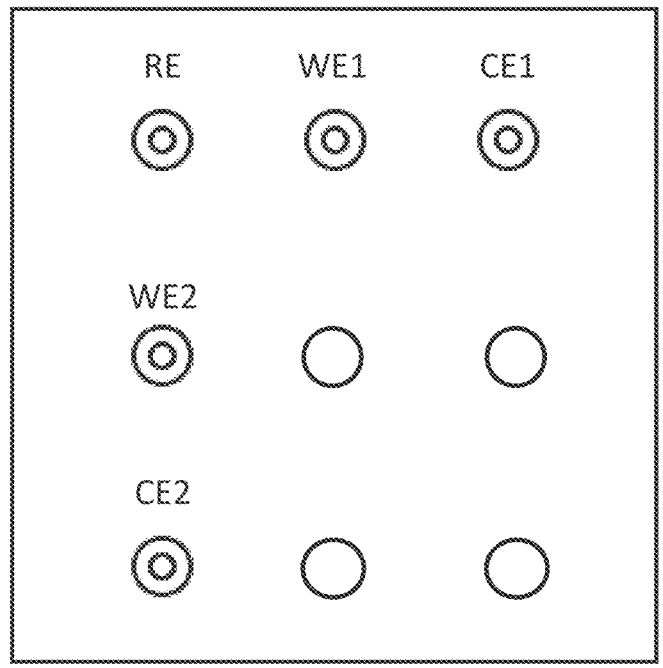

In some variations, only a portion of a microneedle array may include active electrodes. For example, one or more of the microneedles of a microneedle array may not include electrodes or may include electrodes that are inactive. In such arrangements, the electrodes may be allocated among the microneedle array without factoring in the inactive electrodes. For example, FIG. 20B depicts a microneedle array 2010 with nine microneedles arranged in a rectangular configuration. The microneedle array 2010 includes two working electrodes (WE1 and WE2), two counter electrodes (CE1 and CE2), and one reference electrode (RE). The remaining four microneedles do not include active electrodes (e.g., an electrode material and/or layers thereon are not provided). The two working electrodes form a barrier around the one reference electrode to provide stabilization of the working electrode bias according to aspects described herein. The distances between the microneedles of WE1 and CE1 and the microneedles of WE2 and CE2 are equal, and thus a majority portion of current from WE1 flows to CE1, and a majority portion of current from WE3 flows to CE3.

Figure 20C:
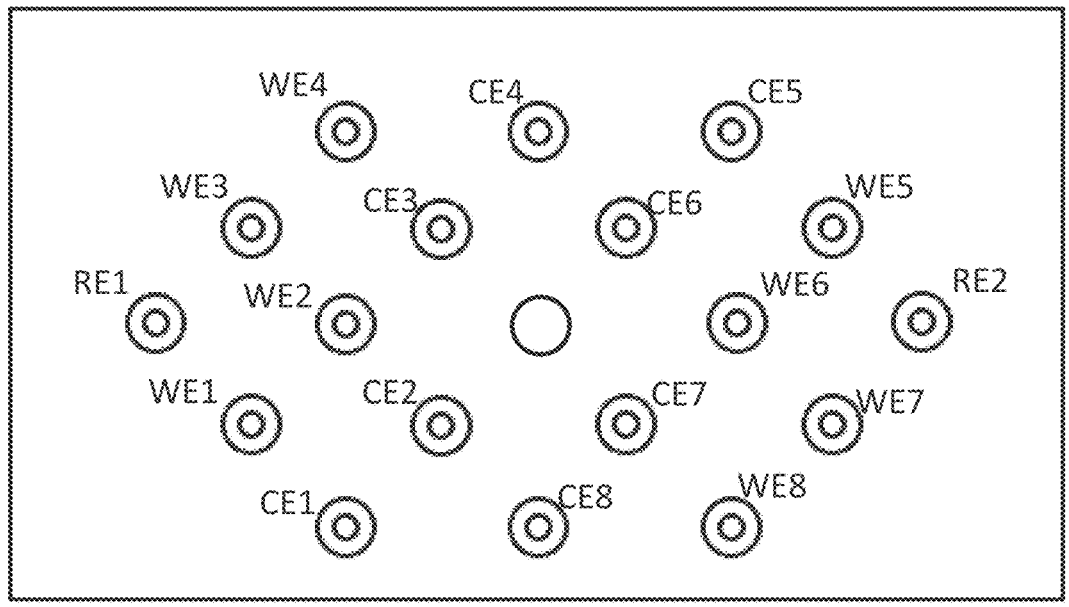

FIG. 20C depicts a microneedle array 2020 with 19 microneedles arranged in a hexagonal configuration. The configuration shown in FIG. 20C includes two reference electrodes (RE1 and RE2) on respective outer edges of the microneedle array 2020, each surrounded by a plurality of working electrodes (WE1, WE2, WE3, and WE4 surrounding RE1, and WE5, WE6, WE7, and WE8 surrounding RE2) that form a barrier between the respective reference electrode (RE1 and RE2) and respective counter electrodes (CE1, CE2, CE3, and CE4, and CE5, CE6, CE7, and CE8). In some variations, and as shown in FIG. 20C, the centrally located microneedle does not include an active electrode. In the variation shown in FIG. 20C, the microneedles are spaced equidistant from one another (e.g., same pitch in all directions).

In some variations utilizing the microneedle array with 19 microneedles in a hexagonal configuration, the centrally located microneedle may be configured as an additional counter electrode. In some variations, one or more of the other counter electrodes may be configured as working electrodes (e.g., the number of counter electrodes does not need to equal the number of working electrodes).

Figure 20D:
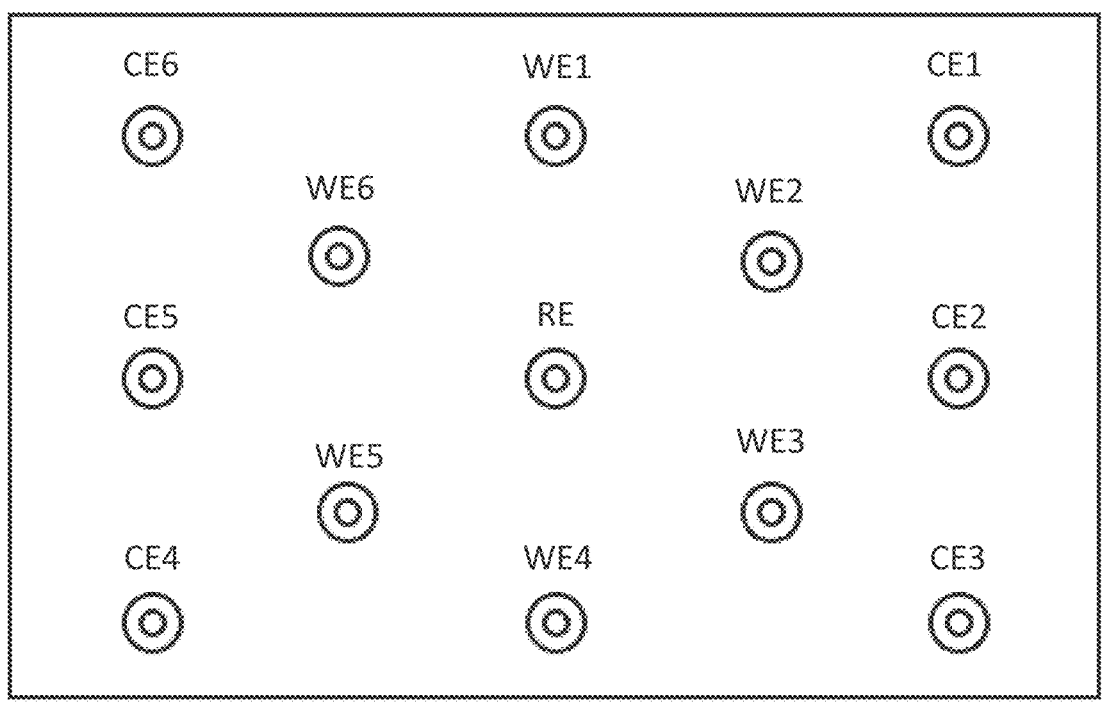

FIG. 20D depicts a microneedle array 2030 with a centrally-positioned reference electrode (RE) surrounded by six working electrodes (WE1, WE2, WE3, WE4, WE5, and WE6). The counter electrodes (CE1, CE2, CE3, CE4, CE5, and CE6) are arranged outside of the barrier created by the working electrodes. In some variations, and as shown in the example configuration of FIG. 20D, two groupings of counter electrodes (CE1, CE2, and CE3 as one group, and CE4, CE5, and CE6 as a second group) may be provided. In some variations, the number of working electrodes and/or the number of counter electrodes may vary. For example, the groupings of counter electrodes may include one or more counter electrodes. In variations in which the number of counter electrodes are reduced, additional working electrodes may be provided or some of the microneedles may not include active electrodes.

Figure 20E:
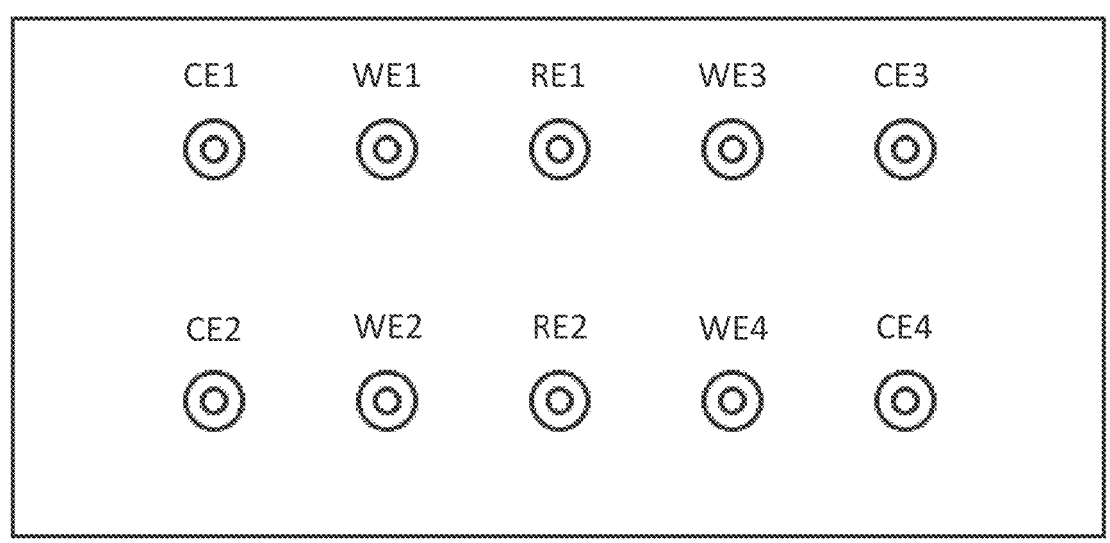

FIG. 20E depicts a microneedle array 2040 with two centrally positioned reference electrodes (RE1 and RE2) surrounded by a plurality (e.g., six) of working electrodes. The counter electrodes (CE1, CE2, CE3, and CE4) are positioned outside of the barriers created by the working electrodes. In some variations, fewer counter electrodes may be provided. In some variations, additional working electrodes may be provided. Thus, the number of working electrodes and/or the number of counter electrodes may vary from the example shown in FIG. 20E. Alternatively, one of the reference electrodes may be replaced by a working electrode.

Figure 20F:
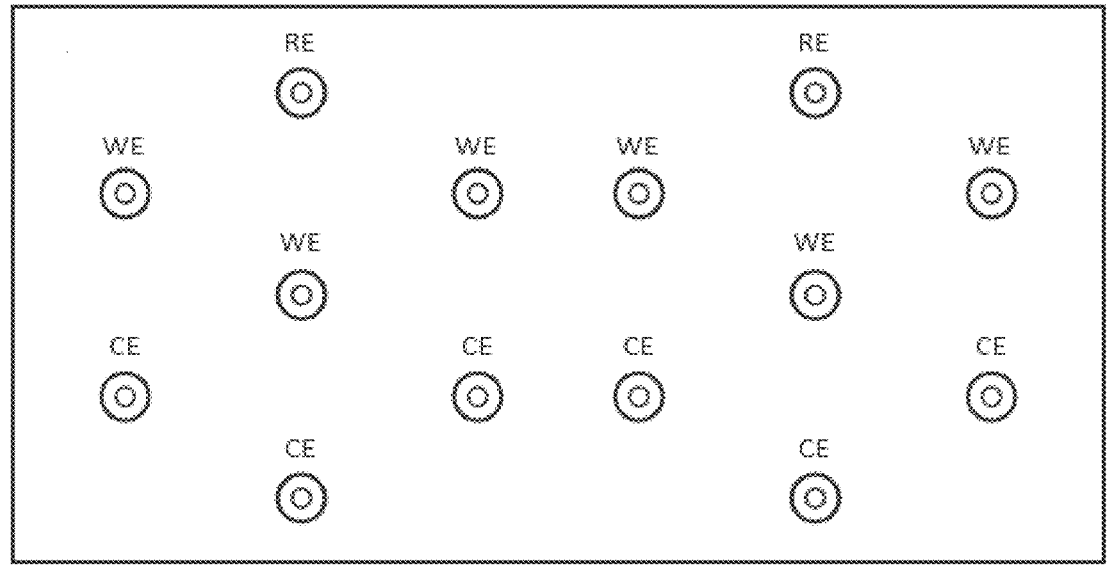

FIG. 20F depicts a microneedle array 2050 with two hexagonal arrangements of microneedles. Each hexagonal arrangement includes the configuration 2000 shown in FIG. 20A. While the two hexagonal arrangements are placed side by side in the variation shown in FIG. 20F, they may be placed in different configurations with respect to each other. Additional arrangements (hexagonal or otherwise) of microneedles may also be incorporated.

While FIGS. 20A-20F depict specific microneedle and electrode configurations, the present disclosure is not limited to the specific arrangements shown. For example, the numbers of working electrodes, counter electrodes, and reference electrodes may vary from the examples shown. Additionally or alternatively, the arrangement of the electrodes may vary. For example, the microneedles may be fabricated in a variety of manners such that the disclosure is not limited to hexagonal and rectangular configurations.

As seen in FIGS. 20A-20F, the one or more reference electrodes (which may be only one reference electrode) are removed from the current path between the one or more working electrodes and the one or more counter electrodes. Generally, the one or more working electrodes create a barrier between the one or more reference electrodes and the one or more counter electrodes. The reference electrode (or reference electrodes) is surrounded by the working electrodes, which are surrounded by the counter electrodes, and the working electrodes form a barrier around the reference electrode. This is in contrast to earlier and conventional implementations in which the focus of microneedle array configuration was to arrange the working electrodes at the periphery of the microneedle array. Placement of the working electrodes at the periphery was thought to increase accuracy of analyte measurements. This arrangement, however, failed to take into account the tissue resistance and associated bias stabilization issues of the working electrodes that are the focus of the current subject matter.

In some variations, a microneedle array consistent with implementations of the current subject matter may be configured to sense multiple analytes. For example, referring to FIG. 18B, distinct working electrode potentials $V_{WE1}$ and $V_{WE2}$ may create different working electrode biases needed for sensing different analytes against a common reference electrode. In some variations, two distinct electrochemical cells may be provided on a single substrate, such as in the configurations of FIG. 20C, FIG. 20E, and FIG. 20F.

Use of Analyte Monitoring System

Described below is an overview of various aspects of a method of use and operation of the analyte monitoring system, including the analyte monitoring device and peripheral devices, etc.

As described above, the analyte monitoring device is applied to the skin of a user such that the microneedle array in the device penetrates the skin and the microneedle array's electrodes are positioned in the upper dermis for access to dermal interstitial fluid. For example, in some variations, the microneedle array may be geometrically configured to penetrate the outer layer of the skin, the stratum corneum, bore through the epidermis, and come to rest within the papillary or upper reticular dermis. The sensing region, confined to the electrode at the distal extent of each microneedle constituent of the array (as described above) may be configured to rest and remain seated in the papillary or upper reticular dermis following application in order to ensure adequate exposure to circulating dermal interstitial fluid (ISF) without the risk of bleeding or undue influence with nerve endings.

In some variations, the analyte monitoring device may include a wearable housing or patch with an adhesive layer configured to adhere to the skin and fix the microneedle array in position. While the analyte monitoring device may be applied manually (e.g., removing a protective film on the adhesive layer, and manually pressing the patch onto the skin on a desired wear site), in some variations the analyte monitoring device may be applied to the skin using a suitable applicator.

The analyte monitoring device may be applied in any suitable location, though in some variations it may be desirable to avoid anatomical areas of thick or calloused skin (e.g., palmar and plantar regions), or areas undergoing significant flexion (e.g., olecranon or patella). Suitable wear sites may include, for example, on the arm (e.g., upper arm, lower arm), shoulder (e.g., over the deltoid), back of hands, neck, face, scalp, torso (e.g., on the back such as in the thoracic region, lumbar region, sacral region, etc. or on the chest or abdomen), buttocks, legs (e.g., upper legs, lower legs, etc.), and/or top of feet, etc.

As described above, in some variations the analyte monitoring device may be configured to automatically activate upon insertion, and/or confirm correct insertion into skin. Details of these features are described in further detail above. In some variations, methods for performing such activation and/or confirmation may be similar to that described in U.S. patent application Ser. No. 16/051,398, which was incorporated by reference above.

Once the analyte monitoring device is inserted and warm-up and any calibration has completed, the analyte monitoring device may be ready for providing sensor measurements of a target analyte. The target analyte (and any requisite co-factor(s)) diffuses from the biological milieu, through the biocompatible and diffusion-limiting layers on the working electrode, and to the biorecognition layer including the biorecognition element. In the presence of a co-factor (if present), the biorecognition element may convert the target analyte to an electroactive product.

A bias potential may be applied between the working and reference electrodes of the analyte monitoring device, and an electrical current may flow from the counter electrode to maintain the fixed potential relationship between the working and reference electrodes. This causes the oxidation or reduction of the electroactive product, causing a current to flow between the working electrodes and counter electrodes. The current value is proportional to the rate of the redox reaction at the working electrode and, specifically, to the concentration of the analyte of interest according to the Cottrell relation as described in further detail above.

The electrical current may be converted to a voltage signal by a transimpedance amplifier and quantized to a digital bitstream by means of an analog-to-digital converter (ADC). Alternatively, the electrical current may be directly quantized to a digital bitstream by means of a current-mode ADC. The digital representation of the electrical current may be processed in the embedded microcontroller(s) in the analyte monitoring device and relayed to the wireless communication module for broadcast or transmission (e.g., to one or more peripheral devices). In some variations, the microcontroller may perform additional algorithmic treatment to the data to improve the signal fidelity, accuracy, and/or calibration, etc.

In some variations, the digital representation of the electrical current, or sensor signal, may be correlated to an analyte measurement (e.g., glucose measurement) by the analyte monitoring device. For example, the microcontroller may execute a programmed routine in firmware to interpret the digital signal and perform any relevant algorithms and/or other analysis. Keeping the analysis on-board the analyte monitoring device may, for example, enable the analyte monitoring device to broadcast analyte measurement(s) to multiple devices in parallel, while ensuring that each connected device has the same information. Thus, generally, the user's target analyte (e.g., glucose) values may be estimated and stored in the analyte monitoring device and communicated to one or more peripheral devices.

Data exchange can be initiated by either the mobile application or by the analyte monitoring device. For example, the analyte monitoring device may notify the mobile application of new analyte data as it becomes available. The frequency of updates may vary, for example, between about 5 seconds and about 5 minutes, and may depend on the type of data. Additionally, or alternatively, the mobile application may request data from the analyte monitoring device (e.g., if the mobile application identifies gaps in the data it has collected, such as due to disconnections).

If the mobile application is not connected to the analyte monitoring device, the mobile application may not receive data from the sensor electronics. However, the electronics in the analyte monitoring device may store each actual and/or estimated analyte data point. When the mobile application is reconnected to the analyte monitoring device, it may request data that it has missed during the period of disconnection and the electronics on the analyte monitoring device may transmit that set of data as well (e.g., backfill).

Generally, the mobile application may be configured to provide display of real-time or near real-time analyte measurement data, such as on the display of the mobile computing device executing the mobile application. In some variations, the mobile application may communicate through a user interface regarding analysis of the analyte measurement, such as alerts, alarms, insights on trends, etc. such as to notify the user of analyte measurements requiring attention or follow-up action (e.g., high analyte values, low analyte values, high rates of change, analyte values outside of a pre-set range, etc.). In some variations, the mobile application may additionally or alternatively facilitate communication of the measurement data to the cloud for storage and/or archive for later retrieval.

EXAMPLES

Example 1. Attachment Enhancer Layer

As described in detail herein, inclusion of an attachment enhancer within the electrodes may improve sensing at, e.g., the working electrode. Exemplary data obtained for a working electrode formed according to method 1300A of FIG. 13A will now be described with reference to FIGS. 21A-25.

Figure 21A:
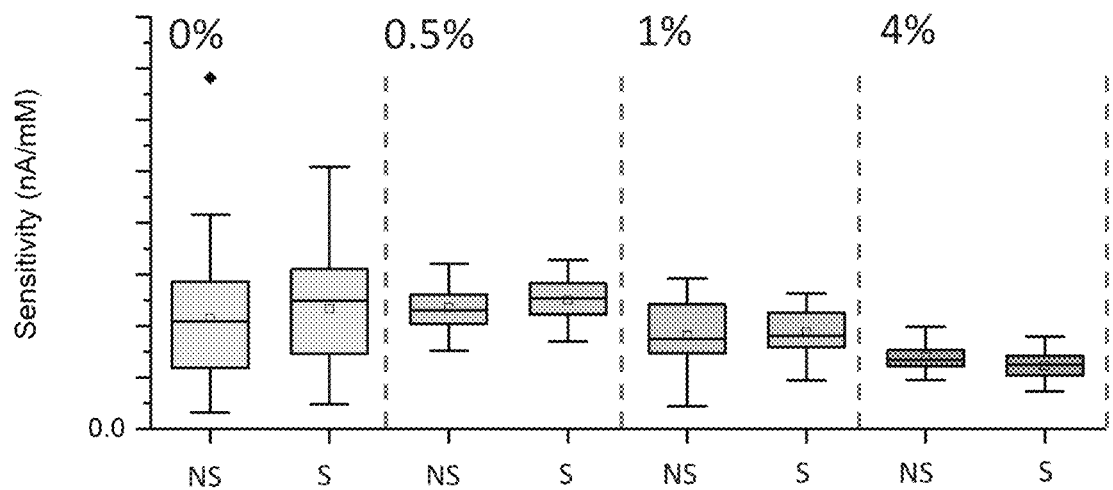
FIGS. 21A-21J depict exemplary data demonstrating the impact of attachment enhancer concentration on sensor sensitivity.

FIG. 21A graphically depicts, for a working electrode, the impact of increasing concentration of attachment enhancer on sensor sensitivity and with sterilization (S) or without sterilization (NS). Sensor sensitivity is on the y-axis. 48 samples were evaluated for each group. Sterilization may be performed as described elsewhere herein. Notably, as the attachment enhancer concentration increases from 0% to 0.5% to 1% to 4%, a decreasing sensor sensitivity and decreasing variability in sensor sensitivity are observed. In other words, these data suggest sensor sensitivity can be tailored by adjusting attachment enhancer concentration. Moreover, FIG. 21A depicts that sterilization does not significantly impact the sensitivity of the working electrode at any concentration of the attachment enhancer.

Figure 21B:
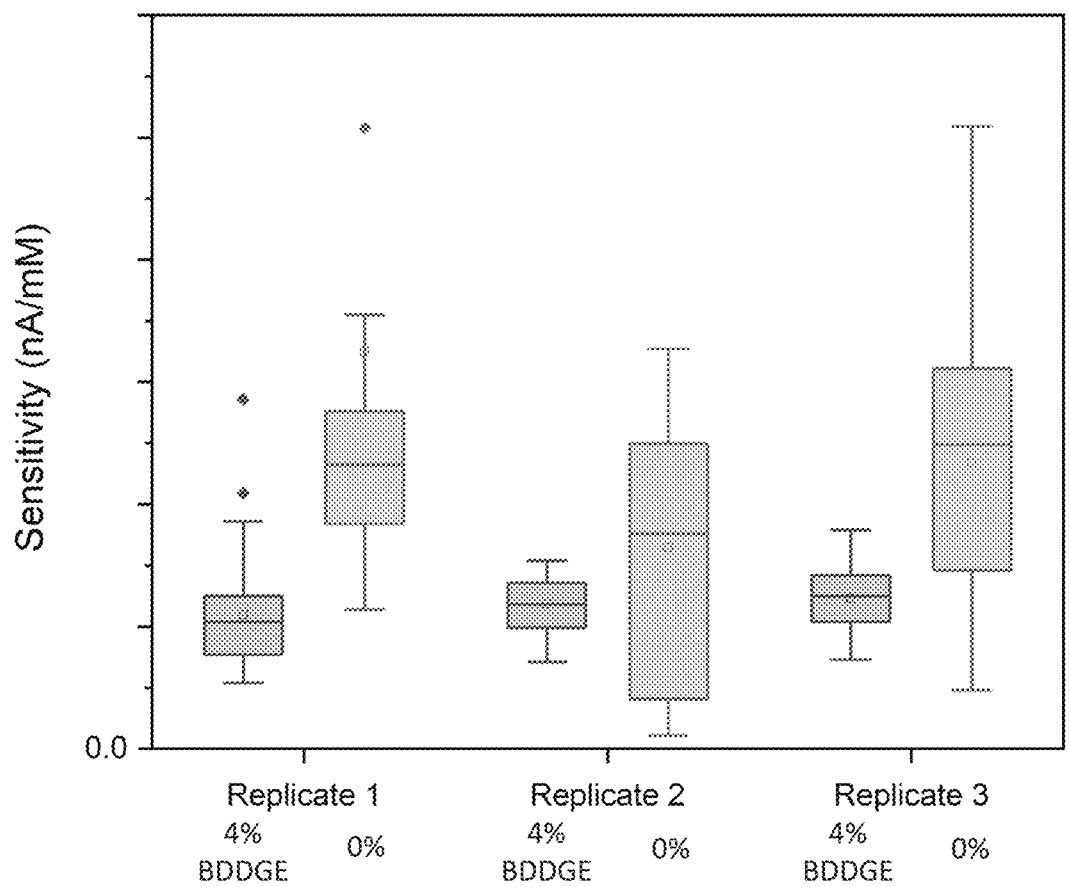

FIG. 21B graphically depicts, for a working electrode treated by soaking with BDDGE at a 4% concentration in solution, the reproducibility of treatment with an attachment enhancer. Sensor sensitivity is on the y-axis. As in FIG. 21A, the three replicates (Replicate 1, Replicate 2, Replicate 3) of FIG. 21B demonstrate the significant reduction in sensor sensitivity and reduction in variability of sensor sensitivity realized with modification by the attachment enhancer (e.g., BDDGE).

Figure 21C:
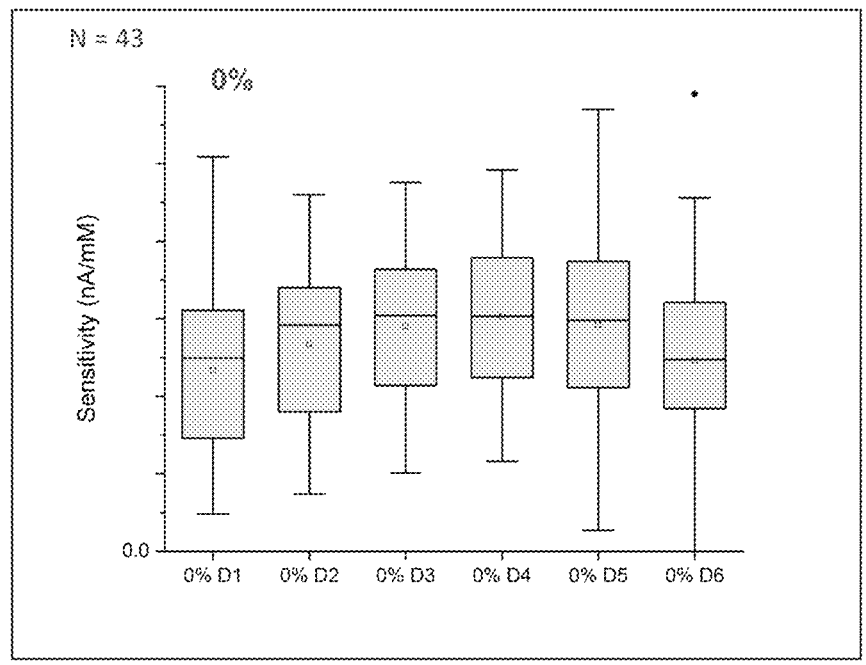
Figure 21D:
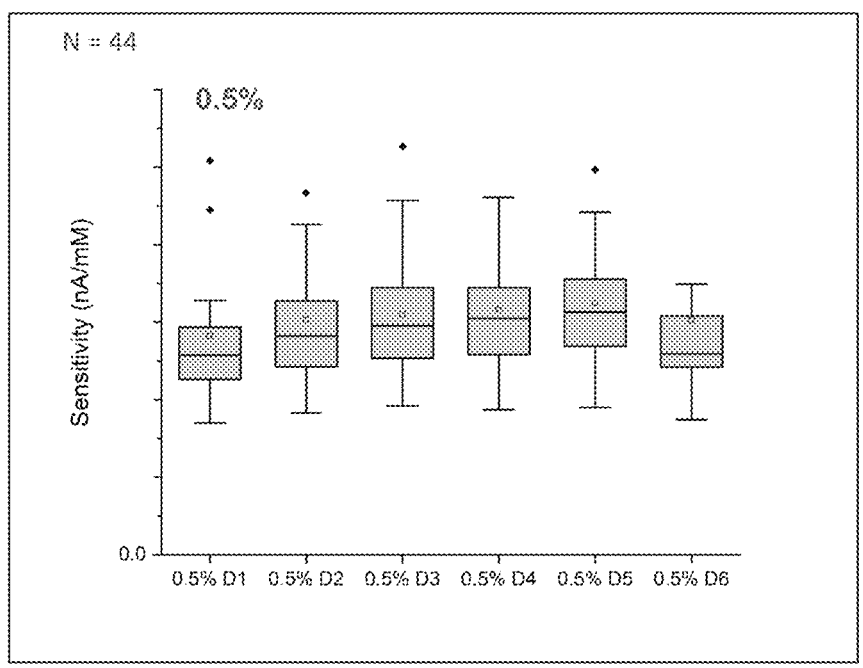
Figure 21E:
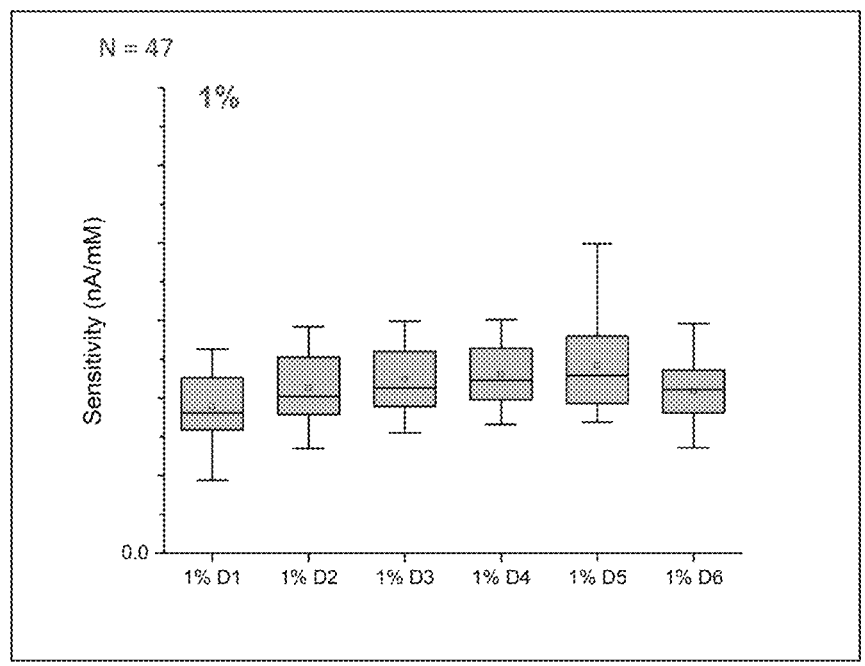
Figure 21F:
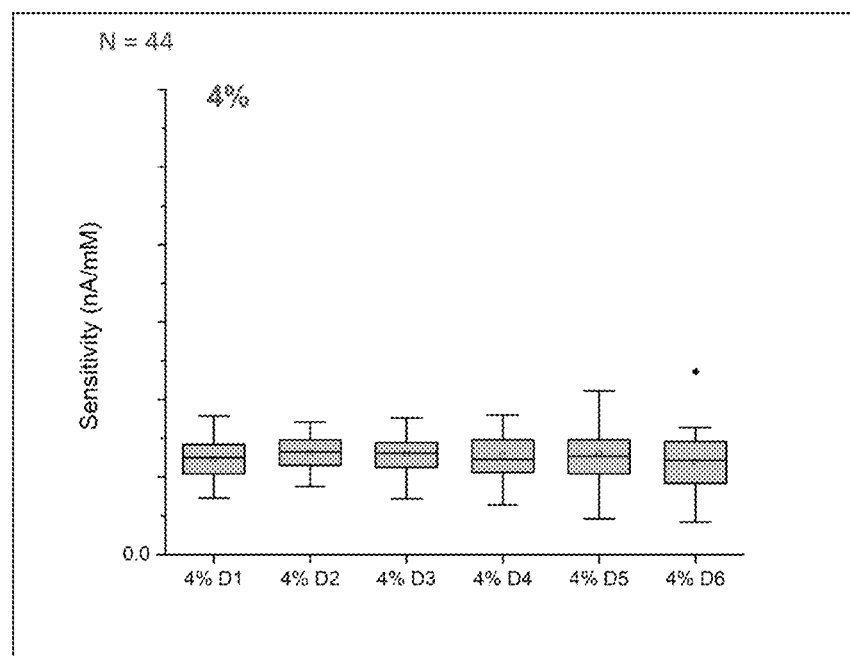

Similarly, FIGS. 21C-21F graphically depict the longevity of the attachment enhancer treatment. For each of FIGS. 21C-21F, sensor sensitivity is on the y-axis and days after treatment are shown on the x-axis. In FIG. 21C, 43 samples were evaluated. In FIG. 21D, 44 samples were evaluated. In FIG. 21E, 47 samples were evaluated. In FIG. 21F, 44 samples were evaluated. For each group, calibration with glucose standards were performed on each day with 0 mM, 2 mM, 10 mM, and 22 mM glucose. At night, each sensor was soaked in 2 mM glucose. Consistent with the results of FIG. 21A, it can be appreciated from FIGS. 21C-21F that the average sensor sensitivity, as shown on the y-axis, is reduced with increasing concentration of attachment enhancer while the vertical height of each box (of the box and whisker plots) is reduced with increasing concentration of attachment enhancer. This confirms that increasing concentration of the attachment enhancer reduces sensor sensitivity and reduces variability of sensor sensitivity.

Figure 21G:
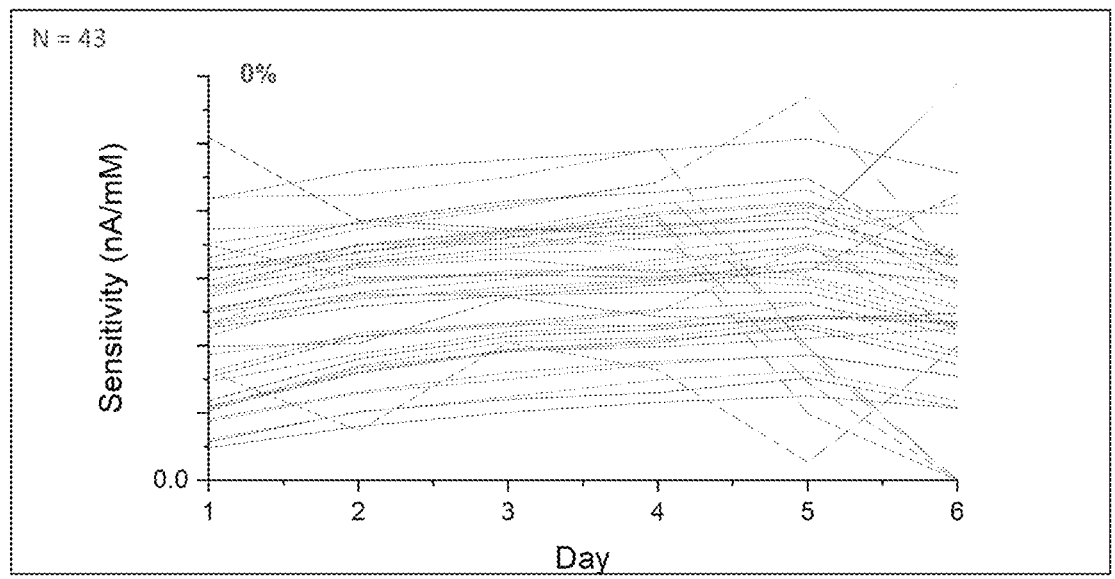
Figure 21H:
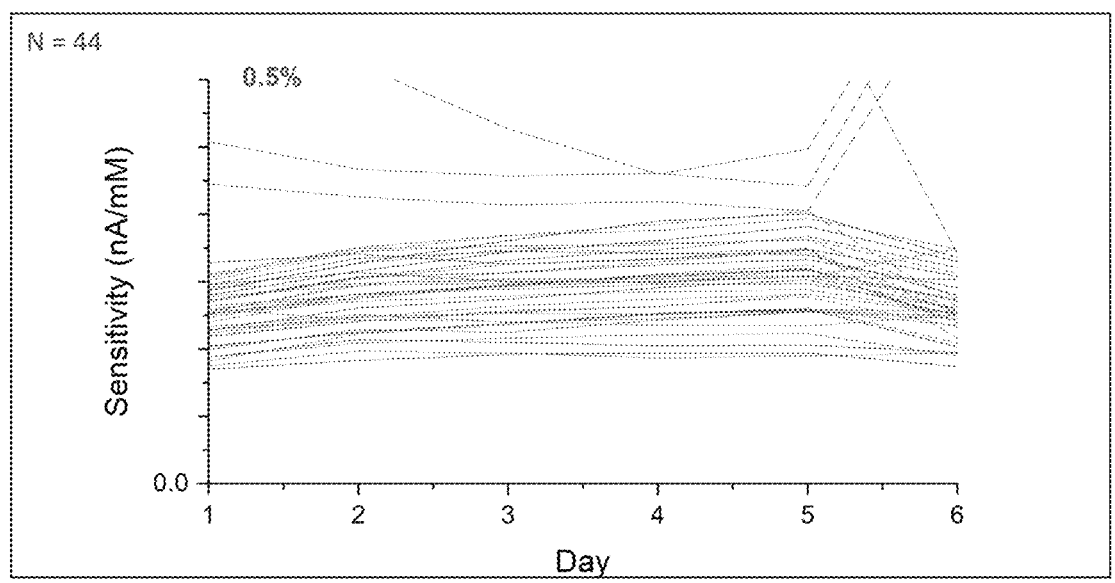
Figure 21I:
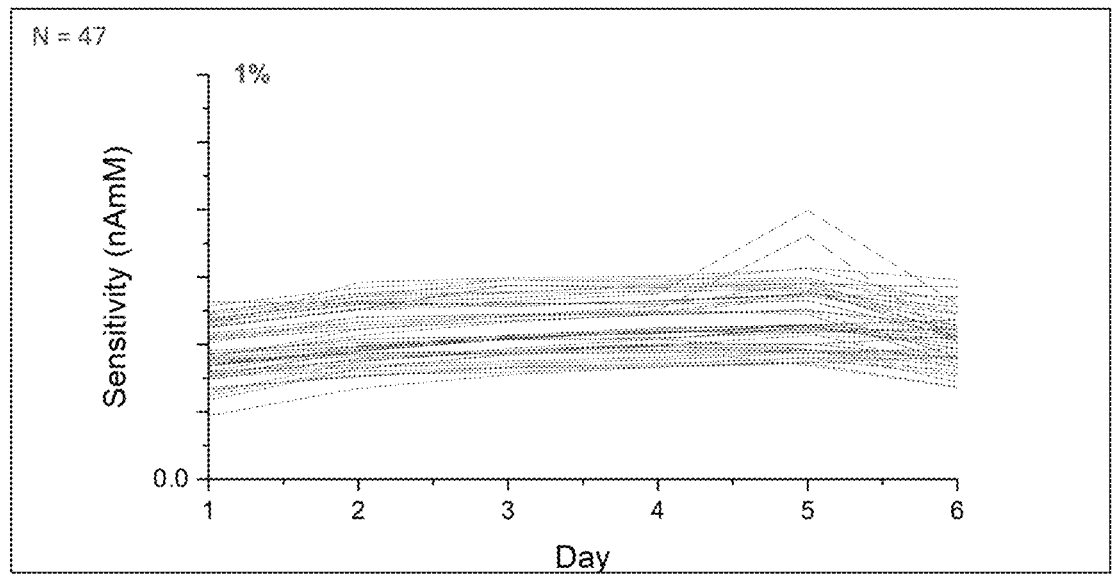
Figure 21J:
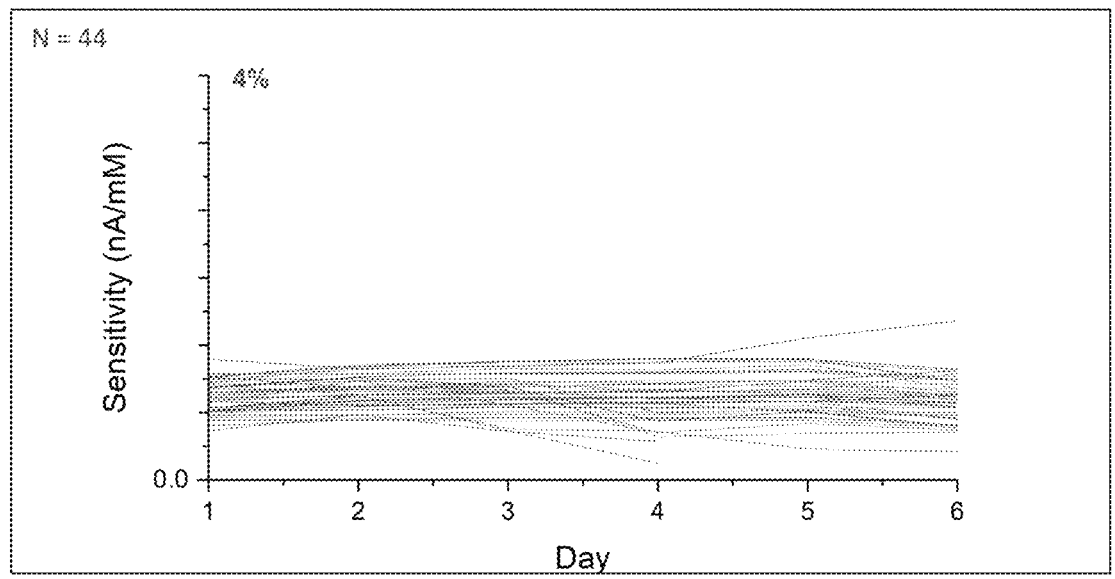

FIGS. 21G-21J convey similar information, graphically depicting sensor drift over time. For each of FIGS. 21G-21J, sensor sensitivity is on the y-axis and days after treatment are shown on the x-axis. Each trace in FIGS. 21G-21J represents a measurement of a particular sample. In FIG. 21G, 43 samples were evaluated. In FIG. 21H, 44 samples were evaluated. In FIG. 21I, 47 samples were evaluated. In FIG. 21J, 44 samples were evaluated. For each group, calibration with glucose standards were performed on each day with 0 mM, 2 mM, 10 mM, and 22 mM glucose. At night, each sensor was soaked in 2 mM glucose. As can be observed, sensor variability improved with increasing concentration of the attachment enhancer, and this improvement was maintained over the 6 days of the study.

Figure 22A:
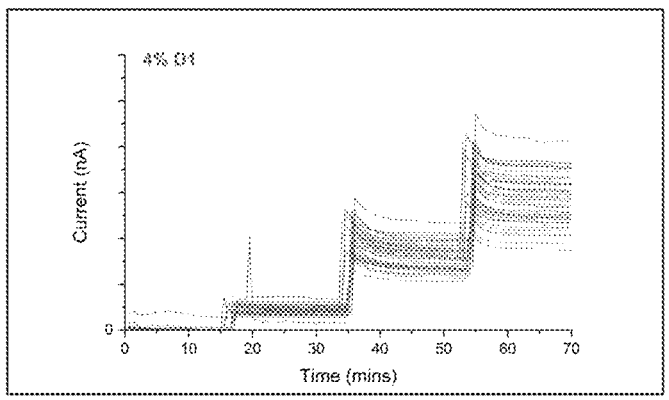
FIGS. 22A-22D depict exemplary data demonstrating the impact of attachment enhancer concentration on sensor stability under current.
Figure 22B:
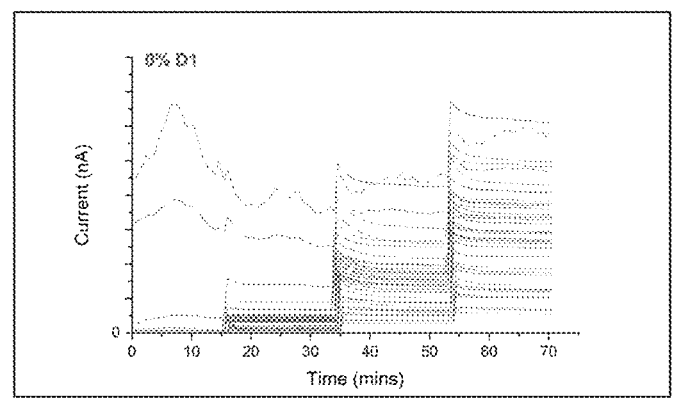
Figure 22C:
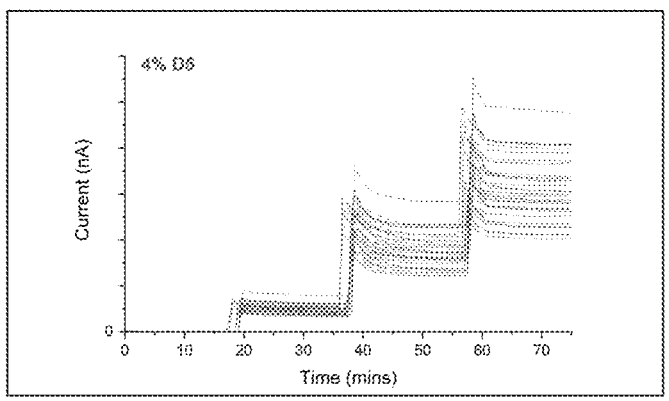
Figure 22D:
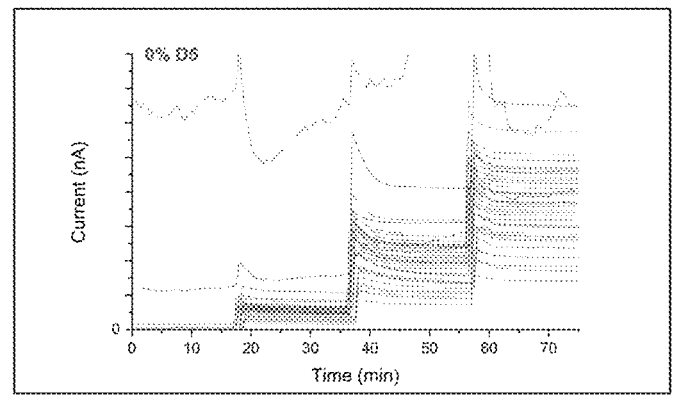

FIGS. 22A-22D graphically depict longevity of sensor response (in nanoamperes) to periodically increased glucose exposure. In FIG. 22A and FIG. 22C, the sensor was treated with an BDDGE at a 4% concentration. In FIG. 22B and FIG. 22D, the sensor was not treated with an attachment enhancer. For each of FIGS. 22A-22D, current generated by the sensor is on the y-axis and time of glucose introduction, where spikes reflect increased glucose introduction, is shown on the x-axis. Each trace in FIGS. 22A-22D represents a sensor measurement of a particular sample. As can be observed, sensor sensitivity decreased with increasing concentration of the attachment enhancer, and this improvement was maintained over the 6 days of the study. Moreover, sensor variability is also improved in the sensors treated with an attachment enhancer, as shown by the lack of errant traces in FIG. 22A and FIG. 22C with increasing glucose concentration.

Figure 23:
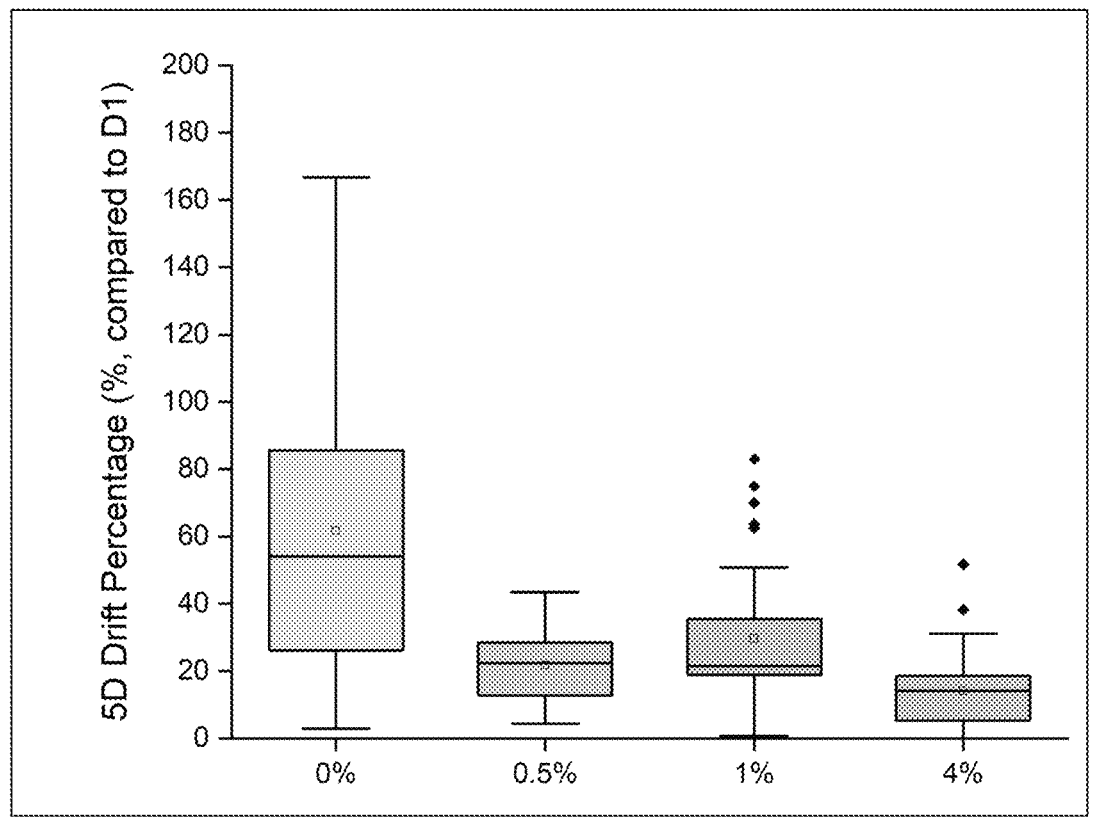
FIG. 23 depicts exemplary data demonstrating the impact of attachment enhancer concentration on sensor stability after five (5) days.

FIG. 23 graphically depicts sensor drift at day 5 as normalized to day 1. The y-axis indicates the percentage difference between day 5 sensor sensitivity and day 1 sensor sensitivity, and the x-axis indicates concentration of attachment enhancer applied to the sensor. Specifically, the y-axis reflects numerical values in percentage drift calculated as the difference between day 1 sensitivity and day 5 sensitivity normalized by the day 1 sensitivity. As can be observed, sensor drift was significantly improved with application of attachment enhancer at any concentration.

Figures 24A, 24B:
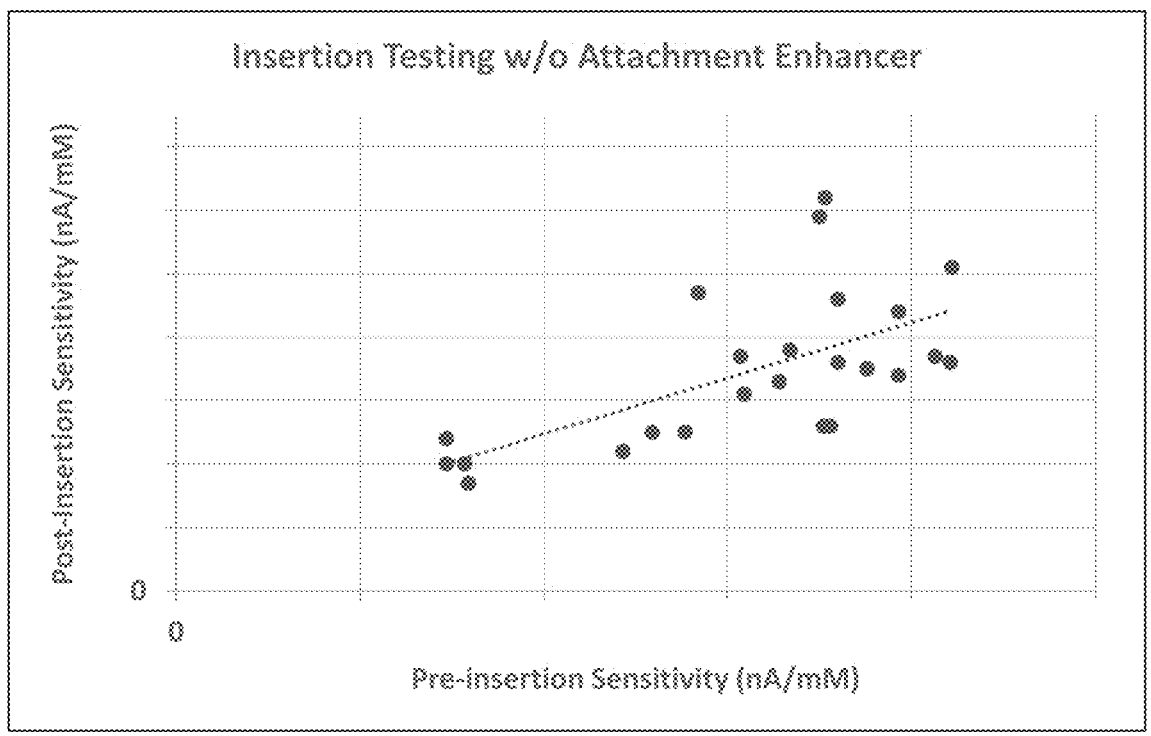
FIGS. 24A and 24B depict exemplary data demonstrating the increase in sensor stability realized by using an attachment enhancer.

FIG. 24A and FIG. 24B graphically depict sensor performance before and after insertion and with and without application of an attachment enhancer. With pre-insertion sensitivity on the x-axis and post-insertion sensitivity on the y-axis, it can be appreciated that application of the attachment enhancer improves stability of the sensor. The spray of FIG. 24A indicates the insertion damaged the untreated sensor, resulting in unpredictable sensitivities. The treated sensor of FIG. 24B, however, appears to be minimally affected by insertion.

Figure 25:
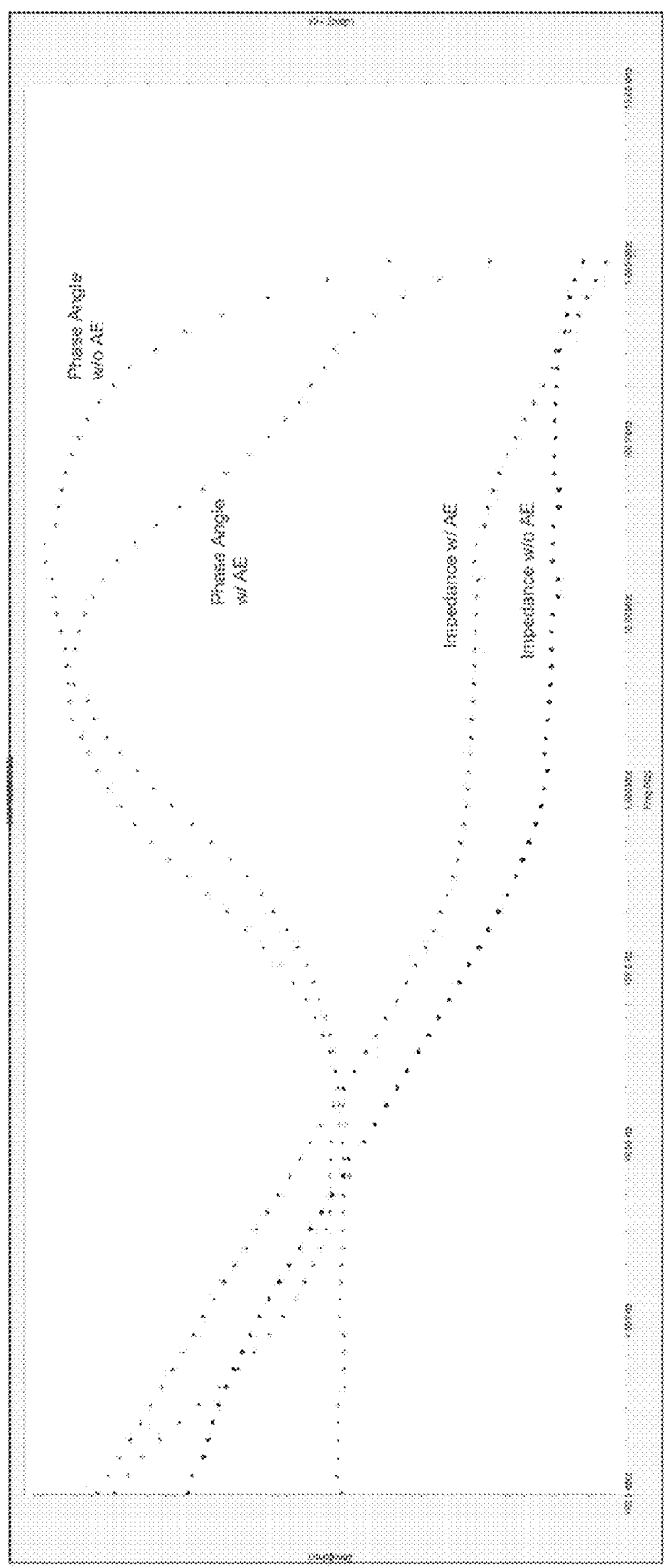
FIG. 25 depicts exemplary data demonstrating the impact of using an attachment enhancer on the phase angle and impedance of a sensor.

FIG. 25 graphically depicts the impact of an attachment enhancer on the impedance and phase angle of a sensor under applied frequencies. Impedance and phase angle are on the left y-axis and the right y-axis, respectively, and frequency is on the x-axis. Phase angle for treated samples (w/AE) can be observed to decrease significantly with increasing frequency as compared to controls (w/o AE).

Specifically, FIG. 25 is a Bode plot. Certain frequencies or frequency bands translate to the biorecognition layer properties. As evidenced by the impedance difference between these two groups, the impedance is greater when the attachment enhancer is included, showing that the biorecognition layer comprises a greater degree of cross-linking density and resulting in improved stability.

Example 2. Interferent Blocking Agent

As stated at the outset, inclusion of the interferent blocking agent within the electrodes described herein improves sensing at the working electrode by reducing interference current caused by interferent exposure to the electrode surface. Exemplary data obtained for a working electrode formed according to the method 1300E of FIG. 13E will now be described with reference to FIGS. 26A-29. It should be appreciated, however, that similar results would be expected with a working electrode formed according to method 1300D of FIG. 13D, which similarly features the interferent blocking agent but does not include an attachment enhancer.

Figure 26A:
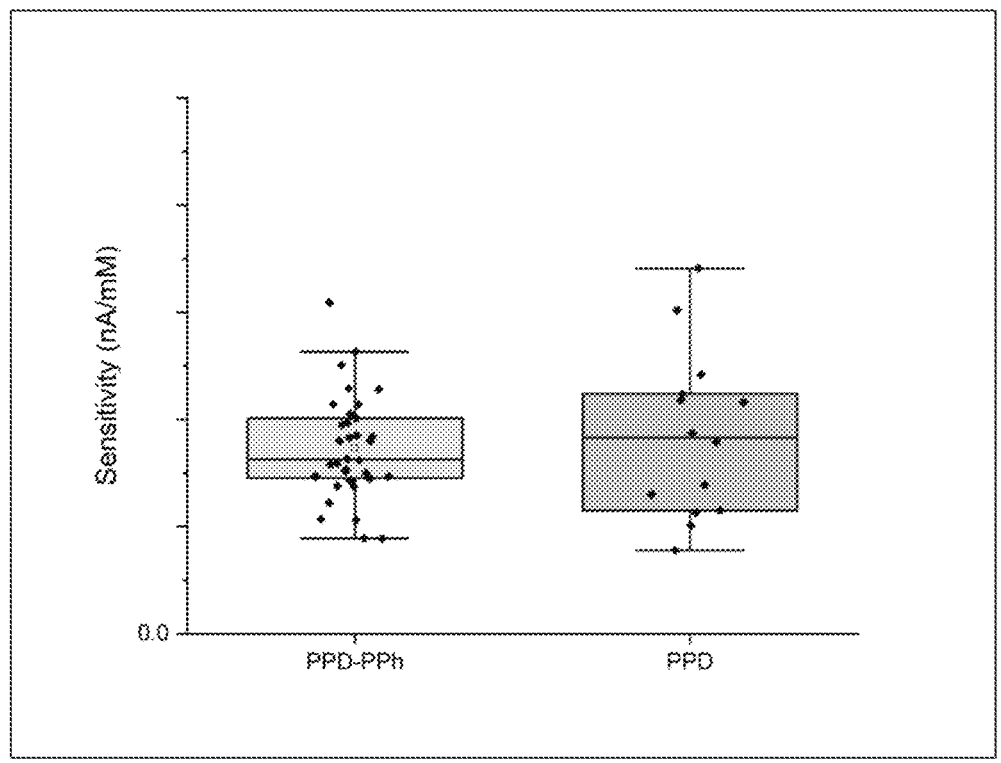
FIG. 26A depicts data demonstrating the impact of an exemplary interferent blocking agent on sensor sensitivity.
Figure 26B:
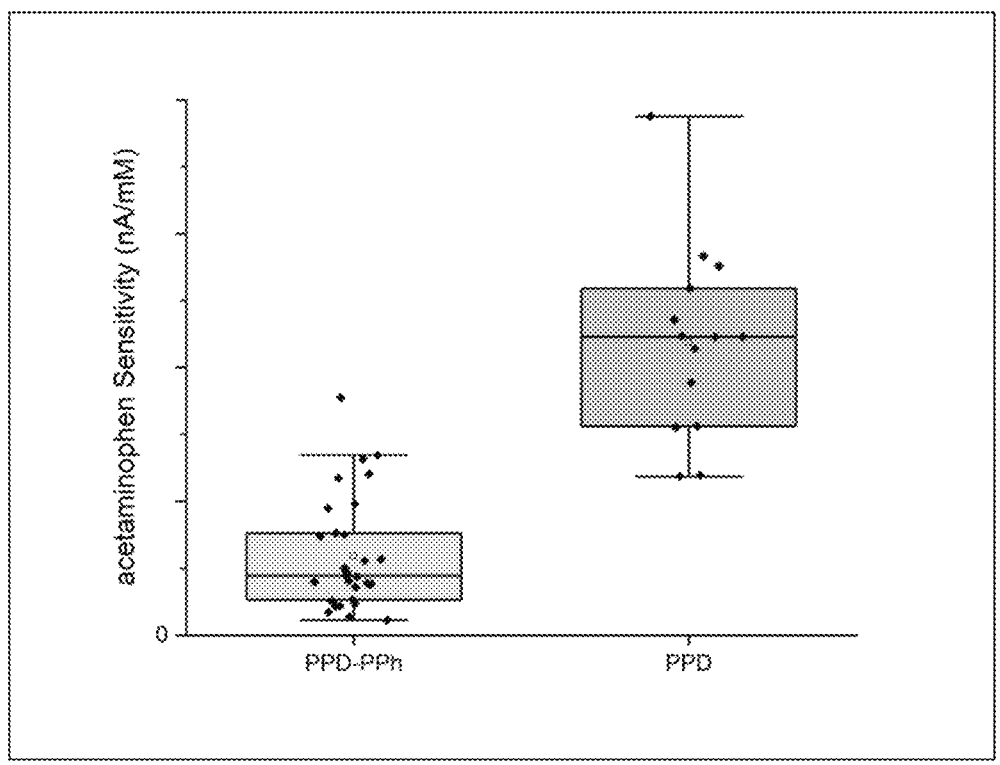
FIG. 26B depicts data demonstrating the impact of an exemplary interferent blocking agent on sensor sensitivity to acetaminophen as an interferent analog.

FIG. 26A and FIG. 26B graphically depict, for a working electrode according to FIG. 11E, the impact of inclusion of an interferent blocking agent on sensitivity of the working electrode. The working electrode of FIG. 26A and FIG. 26B includes a biorecognition layer comprising phenylene diamine (PPD) and, optionally, an interferent blocking agent comprising polyphenol (PPh). Thirty-two working electrodes were functionalized and randomly assigned into two groups: (a) control group (1× sample size) and (b) experimental group (3× sample size). Interference sensitivity was measured at 0.1 mM, 0.2 mM, and 0.5 mM acetaminophen in PBS without glucose. Results indicated, as shown in FIG. 26A, that the inclusion of the interferent blocking agent improved sensor sensitivity variability and decreased median sensitivity to acetaminophen by about 75% when compared to PPH without the interferent blocking agent (as shown in FIG. 26B).

Figure 27:
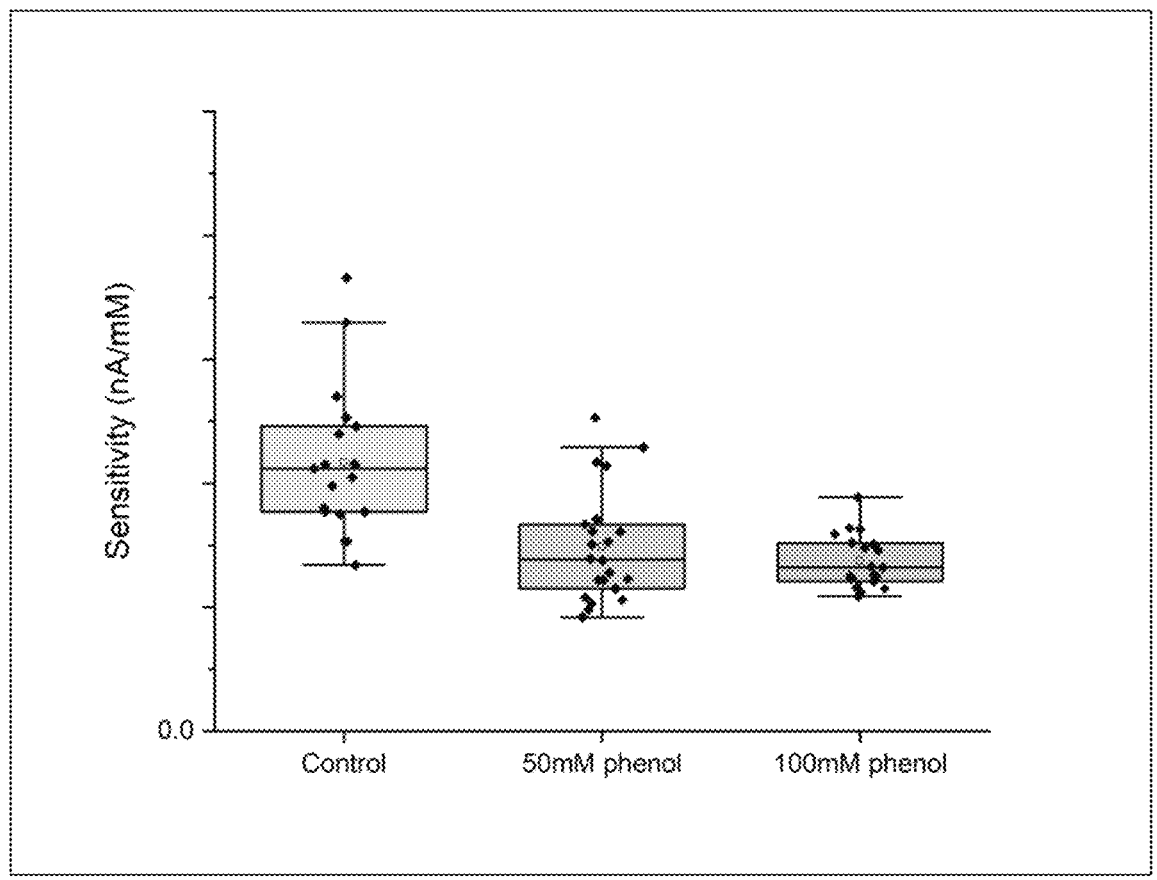
FIG. 27 depicts data demonstrating the impact of concentration of an exemplary interferent blocking agent on sensor sensitivity.

FIG. 27 graphically depicts, for a working electrode according to FIG. 11E, the impact of increasing a concentration of an interferent blocking agent on sensor sensitivity. The working electrode of FIG. 27 includes a biorecognition layer comprising PPD and, optionally, an interferent blocking agent comprising phenol. Three experimental groups (0 mM, 50 mM, and 100 mM phenol monomer solution in pH 7.5 PBS) were evaluated over a 5-day period to determine the impact of phenol on long term sensor sensitivity. As shown, as the interferent blocking agent concentration increases from 0 mM to 50 mM to 100 mM, decreasing sensor sensitivity and decreasing variability in sensor sensitivity was observed.

Figure 28A:
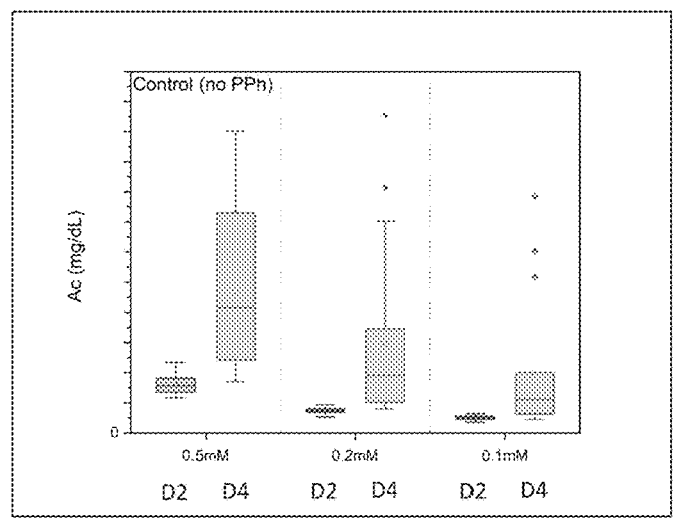
FIGS. 28A-28C depict longitudinal data demonstrating the impact of concentration of an exemplary interferent blocking agent on sensor sensitivity to acetaminophen as an interferent analog.
Figure 28B:
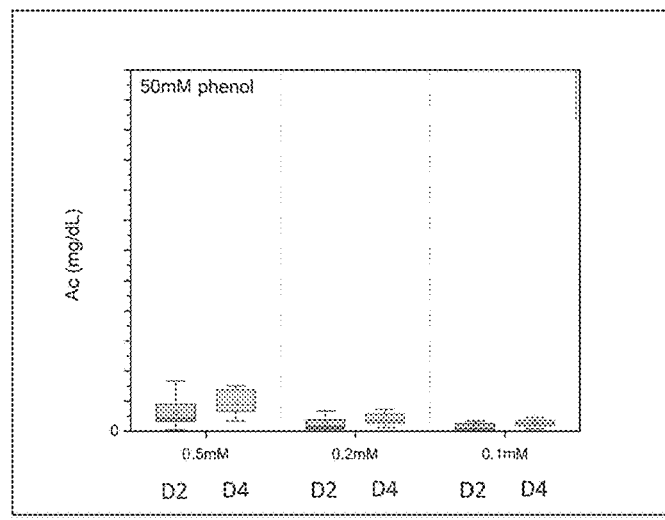
Figure 28C:
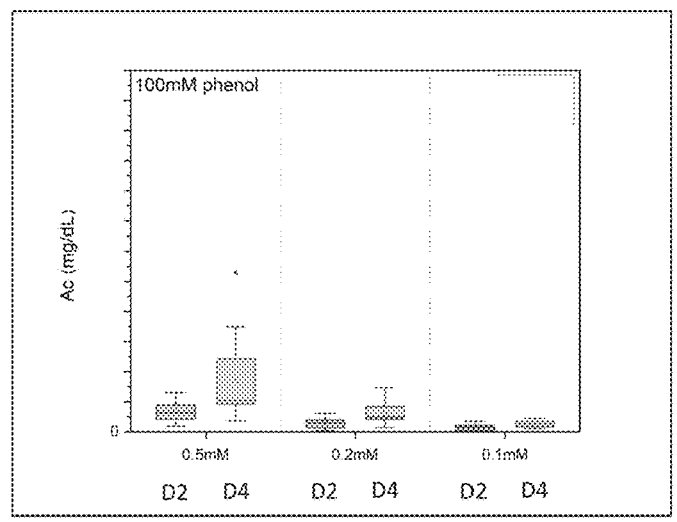

FIGS. 28A-28C graphically depict, for a working electrode according to FIG. 11E, the impact across time (e.g., day 2 and day 4 are shown on the x-axis) of increasing acetaminophen concentration and increasing interferent blocking agent concentration on sensor sensitivity. The working electrode of FIGS. 28A-28C includes a biorecognition layer comprising PPD and, optionally, an interferent blocking agent comprising PPh. Namely, without the interferent blocking agent, sensor sensitivity and variability increased with increasing acetaminophen concentration. In the presence of increasing concentrations of the interferent blocking agent, however, sensor sensitivity and variability were comparatively reduced in the presence of increasing acetaminophen concentrations.

Figure 29:
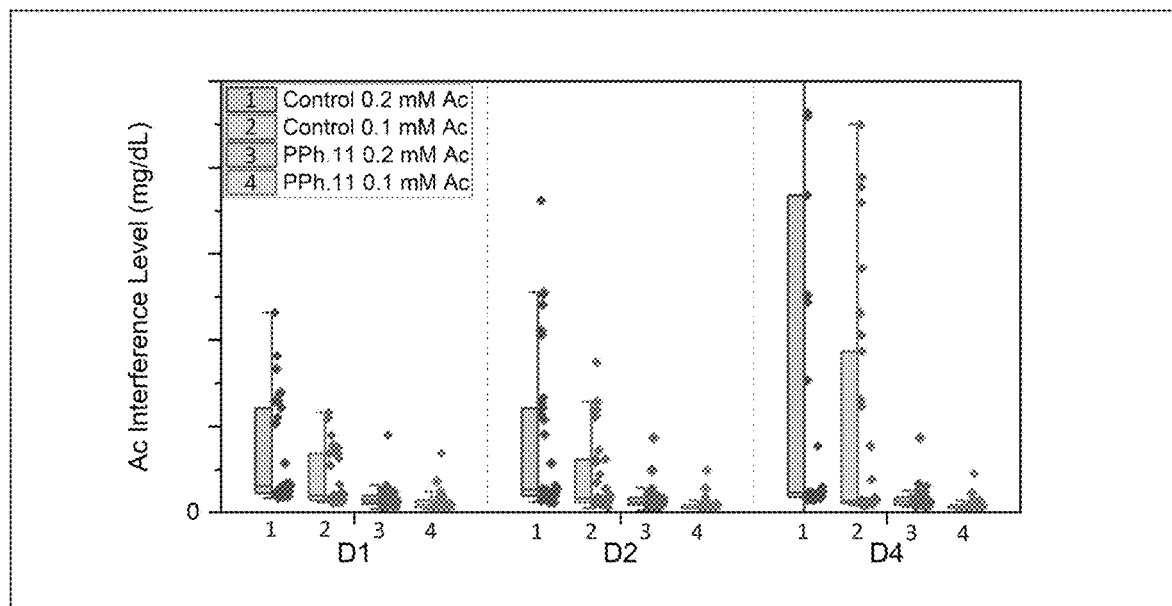
FIG. 29 depicts longitudinal data demonstrating the impact of concentration of an exemplary interferent blocking agent on sensor sensitivity to different concentrations of acetaminophen as an interferent analog.

FIG. 29 graphically depicts, for a working electrode according to FIG. 11D, the impact of the presence and increasing concentration of acetaminophen on sensor sensitivity. The working electrode of FIG. 11D includes a biorecognition layer comprising PPD and, optionally, an interferent blocking agent comprising PPh. As shown, the interferent blocking agent significantly reduces sensor sensitivity at any concentration of acetaminophen.

The results of FIG. 29 are corroborated in Table 1, which provides a tabular representation of the impact of the presence of, and the increasing concentration of, phenol within the working electrode described herein on reducing the presence of acetaminophen (Ac) within the working electrode over time.

The foregoing description, for purposes of explanation, used specific nomenclature to provide a thorough understanding of the invention. However, it will be apparent to one skilled in the art that specific details are not required in order to practice the invention. Thus, the foregoing descriptions of specific variations of the invention are presented for purposes of illustration and description. They are not intended to be exhaustive or to limit the invention to the precise forms disclosed; obviously, many modifications and variations are possible in view of the above teachings. The variations were chosen and described in order to explain the principles of the invention and its practical applications, they thereby enable others skilled in the art to utilize the invention and various variations with various modifications as are suited to the particular use contemplated. It is intended that the following claims and their equivalents define the scope of the invention.

NUMBERED EMBODIMENTS OF THE INVENTION

Notwithstanding the appended claims, the disclosure sets forth the following numbered embodiments:

(1) A device for use in sensing an analyte, comprising a microneedle, an electrode material on the microneedle, a biorecognition layer on the electrode material, the biorecognition layer comprising a polymer, a biorecognition element configured to react with the analyte, and an interferent blocking agent that fills voids within the polymer, and a diffusion-limiting layer on the biorecognition layer.

(2) The device of (1), wherein the voids within the polymer traverse a thickness of the polymer.

(3) The device of (1) or (2), wherein at least a portion of the voids are exposed to a surface of the electrode material.

(4) The device of any one of (1) to (3), wherein at least a portion of the interferent blocking agent is in contact with the electrode material.

(5) The device of any one of (1) to (4), wherein the interferent blocking agent fills at least about 80% of the voids within the polymer to limit access by interferents to the electrode material.

(6) The device of any one of (1) to (5), wherein the biorecognition element is within the polymer.

(7) The device of (6), wherein the biorecognition element is physically entrapped within the polymer.

(8) The device of any one of (1) to (7), wherein the biorecognition element is glucose oxidase, glucose dehydrogenase, 3-hydroxybutyrate dehydrogenase, or lactate dehydrogenase.

(9) The device of any one of (1) to (8), wherein the polymer comprises one or more of aniline, acetylene, phenylene, phenylene vinylene, phenylene diamine, thiophene, 3,4-ethylenedioxythiophene, and aminophenylboronic acid.

TABLE 1

|  | Control | | | 50 mM Phenol | | | 100 mM Phenol | | |
| --- | --- | --- | --- | --- | --- | --- | --- | --- | --- |
| mM Ac | 0.5 | 0.2 | 0.1 | 0.5 | 0.2 | 0.1 | 0.5 | 0.2 | 0.1 |
| Day-2 Median ([Ac](mg/dL)]) | 50-100 | 30-50 | 20-35 | 15-50 | 5-25 | 2-10 | 25-50 | 10-25 | 2-10 |
| Day-4 Median ([Ac](mg/dL)]) | 100-350 | 60-175 | 35-100 | 30-75 | 15-30 | 5-15 | 45-125 | 20-50 | 5-15 |

(10) The device of any one of (1) to (9), wherein the diffusion-limiting layer is hydrophobic.

(11) The device of any one of (1) to (10), wherein the diffusion-limiting layer comprises one or more of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene.

(12) The device of any one of (1) to (11), wherein the analyte comprises one or more of glucose, ketone, and lactate.

(13) The device of any one of (1) to (12), wherein the interferent blocking agent is a non-conducting polymer.

(14) The device of any one of (1) to (13), wherein the interferent blocking agent comprises one or more of resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol.

(15) The device of (14), wherein the interferent blocking agent comprises phenol.

(16) The device of (15), wherein the phenol is present within the biorecognition layer at a concentration of between about 0.1 mg/ml or 0.01% w/v and about 10 mg/ml or 1% w/v.

(17) The device of (15) or (16), wherein polymerized phenol is entrapped within the voids of the polymer.

(18) The device of any one of (1) to (17), wherein the electrode material comprises platinum, palladium, iridium, rhodium, gold, ruthenium, titanium, nickel, carbon, doped diamond, or combinations thereof.

(19) The device of any one of (1) to (18), wherein interference current at the electrode material of the device changes less than 70% over a one-week period.

(20) The device of any one of (1) to (19), wherein interference current at the electrode material of the device changes less than 10% over a one-week period.

(21) A method for manufacturing a device for use in sensing an analyte, comprising depositing a biorecognition element and a polymer on an electrode material disposed on a microneedle, wherein the biorecognition element is configured to react with the analyte, applying an interferent blocking agent to the polymer after deposition, thereby filling voids within the polymer with the interferent blocking agent, and depositing a diffusion-limiting layer on the polymer.

(22) The method of (21), wherein the voids within the polymer traverse a thickness of the polymer.

(23) The method of (22), wherein at least a portion of the voids are exposed to a surface of the electrode material.

(24) The method of any one of (21) to (23), wherein the interferent blocking agent fills at least about 80% of the voids within the polymer, to limit access by interferents to the electrode material.

(25) The method of any one of (21) to (24), wherein the biorecognition element is glucose oxidase, glucose dehydrogenase, 3-hydroxybutyrate dehydrogenase, or lactate dehydrogenase.

(26) The method of any one of (21) to (25), wherein the polymer comprises one or more of aniline, acetylene, phenylene, phenylene vinylene, phenylene diamine, thiophene, 3,4-ethylenedioxythiophene, and aminophenylboronic acid.

(27) The method of any one of (21) to (26), wherein the diffusion-limiting layer comprises one or more of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene.

(28) The method of any one of (21) to (27), wherein the applying comprises electropolymerizing the interferent blocking agent.

(29) The method of any one of (21) to (28), wherein the interferent blocking agent comprises one or more of resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol.

(30) The method of any one of (21) to (29), wherein the interferent blocking agent comprises phenol.

(31) The method of (30), wherein the phenol is applied as a mixture having a concentration of between about 0.01 mM phenol and about 100 mM phenol.

(32) The method of any one of (21) to (31), wherein at least a portion of the interferent blocking agent is in contact with the electrode material.

(33) The method of any one of (21) to (32), wherein interference current at the electrode material of the device changes less than 10% over a one-week period.

(34) A device for use in sensing an analyte, comprising a microneedle, an electrode material on the microneedle, a biorecognition layer on the electrode material, the biorecognition layer comprising a polymer, a biorecognition element configured to react with the analyte, and an interferent blocking agent that fills voids within the polymer, a diffusion-limiting layer, and an attachment enhancer configured to decrease analyte sensing variability, wherein the attachment enhancer is positioned between the biorecognition layer and the diffusion-limiting layer.

(35) The device of (34), wherein the voids within the polymer traverse a thickness of the polymer.

(36) The device of (35), wherein at least a portion of the voids are exposed to a surface of the electrode material.

(37) The device of any one of (34) to (36), wherein the interferent blocking agent fills at least about 80% of the voids within the polymer to limit access by interferents to the electrode material.

(38) The device of any one of (34) to (37), wherein the biorecognition element is within the polymer.

(39) The device of (38), wherein the biorecognition element is physically entrapped within the polymer.

(40) The device of any one of (34) to (39), wherein the biorecognition element is glucose oxidase, glucose dehydrogenase, 3-hydroxybutyrate dehydrogenase, or lactate dehydrogenase.

(41) The device of any one of (34) to (40), wherein the polymer comprises one or more of aniline, acetylene, phenylene, phenylene vinylene, phenylene diamine, thiophene, 3,4-ethylenedioxythiophene, and aminophenylboronic acid.

(42) The device of any one of (34) to (41), wherein the diffusion-limiting layer is hydrophobic.

(43) The device of any one of (34) to (42), wherein the diffusion-limiting layer comprises one or more of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene.

(44) The device of any one of (34) to (43), wherein the analyte comprises one or more of glucose, ketone, and lactate.
(45) The device of any one of (34) to (44), wherein the interferent blocking agent is a non-conducting polymer.
(46) The device of any one of (34) to (45), wherein the interferent blocking agent comprises at least one agent selected from the group consisting of: resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol.
(47) The device of any one of (34) to (46), wherein the interferent blocking agent comprises phenol.
(48) The device of (47), wherein the phenol is present within the biorecognition layer at a concentration of between about 0.1 mg/ml or 0.01% w/v and about 10 mg/ml or 1% w/v.
(49) The device of (47), wherein polymerized phenol is entrapped within the voids of the polymer.
(50) The device of any one of (34) to (49), wherein the electrode material comprises platinum, palladium, iridium, rhodium, gold, ruthenium, titanium, nickel, carbon, doped diamond, or combinations thereof.
(51) The device of any one of (34) to (50), wherein the attachment enhancer comprises a plurality of molecules, and wherein a first end of each of the plurality of molecules is covalently bound to the biorecognition layer.
(52) The device of any one of (34) to (51), wherein the attachment enhancer comprises a plurality of molecules, and wherein a second end of each of the plurality of molecules is partially immobilized within the diffusion-limiting layer.
(53) The device of (52), wherein the second end comprises at least one hydroxyl group.
(54) The device of (53), wherein the at least one hydroxyl group forms hydrogen bonds with the diffusion-limiting layer.
(55) The device of (52), wherein the second end interacts with the diffusion-limiting layer via Van der Waals forces.
(56) The device of (51) or (52), wherein each of the plurality of molecules is a cross-linking agent.
(57) The device of (56), wherein the cross-linking agent comprises epoxide functional groups.
(58) The device of (57), wherein the cross-linking agent comprises N (1, 2, 3, 4) epoxide functional groups connected to a linker.
(59) The device of (58), wherein the linker is one selected from the group consisting of: aromatic, aliphatic, linear, and branched.
(60) The device of (56), wherein the cross-linking agent comprises one selected from the group consisting of: 1,4-butanediol diglycidyl ether, 1,6-hexanediol diglycidyl ether, neopentyl glycol diglycidyl ether, poly (propylene glycol) diglycidyl ether, trimethylolethane diglycidyl ether, trimethylolethane triglycidyl ether, diglycidyl resorcinol ether, diglycidyl ether, 1,4-cyclohexane dimethanol diglycidyl ether, castor oil glycidyl ether, and bisphenol A diglycidyl ether.
(61) The microneedle of (56), wherein the cross-linking agent comprises one selected from the group consisting of: glutaraldehyde, poly (dimethylsiloxane)-diglycidyl ether, tetracyclooxypropryl-4,4-diaminodiphenylmethane, polyethylene glycol diglycidyl ether, and 4-(2,3-epoxypropoxy)-N,N-bis(2,3-epoxypropyl) aniline.
(62) The device of any one of (34) to (61), wherein the attachment enhancer covalently binds to the biorecognition element.
(63) The device of any one of (34) to (62), wherein the biorecognition element is glucose oxidase and the attachment enhancer covalently binds to the glucose oxidase.
(64) The device of any one of (34) to (63), wherein the polymer comprises one or more of aniline, acetylene, phenylene, phenylene vinylene, phenylene diamine, thiophene, 3,4-ethylenedioxythiophene, and aminophenylboronic acid.
(65) The device of any one of (34) to (64), wherein at least a portion of the interferent blocking agent is in contact with the electrode material.
(66) The device of any one of (34) to (65), wherein interference current at the electrode material of the device changes less than 10% over a one-week period.
(67) A method for manufacturing a device for use in sensing an analyte, comprising depositing a biorecognition element and a polymer on an electrode material disposed on a microneedle, wherein the biorecognition element is configured to react with the analyte, applying an interferent blocking agent to the polymer, thereby filling voids within the polymer with the interferent blocking agent, exposing the polymer to an attachment enhancer, and after exposing the polymer to the attachment enhancer, depositing a diffusion-limiting layer on the biorecognition layer.
(68) The method of (67), wherein the voids within the polymer traverse a thickness of the polymer.
(69) The method of (68), wherein at least a portion of the voids are exposed to a surface of the electrode material.
(70) The method of any one of (67) to (69), wherein the interferent blocking agent occupies at least about 80% of the voids within the polymer to limit access by interferents to the electrode material.
(71) The method of any one of (67) to (70), wherein the biorecognition element is glucose oxidase, glucose dehydrogenase, 3-hydroxybutyrate dehydrogenase, or lactate dehydrogenase.
(72) The method of any one of (67) to (71), wherein the polymer comprises one or more of aniline, acetylene, phenylene, phenylene vinylene, phenylene diamine, thiophene, 3,4-ethylenedioxythiophene, and aminophenylboronic acid.
(73) The method of any one of (67) to (72), wherein the diffusion-limiting layer is hydrophobic.
(74) The method of any one of (67) to (73), wherein the diffusion-limiting layer one or more of polydimethylsiloxane, polyurethane, polyvinyl chloride, polyvinylpyrrolidone, polycarbonate, polyethylene, polyethylene terephthalate, polyester, high density polyethylene, low density polyethylene, and polytetrafluoroethylene.
(75) The method of any one of (67) to (74), wherein the applying comprises electropolymerizing the interferent blocking agent.
(76) The method of any one of (67) to (75), wherein the interferent blocking agent comprises one or more of resorcinol, hydroquinone quinol, 2-amino-4,6-dinitro phenol picramic acid, 3,5-dihydroxy toluene orcinol, 2,4,6-trinitro resorcinol styphnic acid, 2-hydroxy phenol catechol, 9-phenanthrol, pyrogallol, α-napthol, anisole, phenetole, picric acid, and phenol.

(77) The method of any one of (67) to (76), wherein the interferent blocking agent comprises phenol.
(78) The method of (77), wherein the phenol is applied as a mixture having a concentration of between about 0.01 mM phenol and about 100 mM phenol.
(79) The method of any one of (67) to (78), wherein the electrode material comprises platinum, palladium, iridium, rhodium, gold, ruthenium, titanium, nickel, carbon, doped diamond, or combinations thereof.
(80) The method of any one of (67) to (79), wherein the attachment enhancer comprises a plurality of molecules, and wherein, during the exposing, a first end of each of the plurality of molecules covalently binds to the biorecognition layer.
(81) The method of any one of (67) to (80), wherein the attachment enhancer comprises a plurality of molecules, and wherein, during the exposing, a second end of each of the plurality of molecules is partially immobilized within the diffusion-limiting layer.
(82) The method of (81), wherein the second end comprises at least one hydroxyl group.
(83) The method of (82), wherein the at least one hydroxyl group forms hydrogen bonds with the diffusion-limiting layer.
(84) The method of (81), wherein the second end interacts with the diffusion-limiting layer via Van der Waals forces.
(85) The method of (80) or (81), wherein each of the plurality of molecules is a cross-linking agent.
(86) The method of (85), wherein the cross-linking agent comprises epoxide functional groups.
(87) The method of (85) or (86), wherein the cross-linking agent comprises N (1, 2, 3, 4) epoxide functional groups connected to a linker.
(88) The method of any one of (85) to (87), wherein the linker is one selected from the group consisting of: aromatic, aliphatic, linear, and branched.
(89) The method of any one of (85) to (88), wherein the cross-linking agent comprises one selected from the group consisting of: 1,4-butanediol diglycidyl ether, 1,6-hexanediol diglycidyl ether, neopentyl glycol diglycidyl ether, poly(propylene glycol) diglycidyl ether, trimethylolethane diglycidyl ether, trimethylolethane triglycidyl ether, diglycidyl resorcinol ether, diglycidyl ether, 1,4-cyclohexane dimethanol diglycidyl ether, castor oil glycidyl ether, and bisphenol A diglycidyl ether.
(90) The method of any one of (85) to (89), wherein the cross-linking agent comprises one selected from the group consisting of: glutaraldehyde, poly (dimethylsiloxane)-diglycidyl ether, tetracyclooxypropryl-4,4-diaminodiphenylmethane, polyethylene glycol diglycidyl ether, and 4-(2,3-epoxypropoxy)-N,N-bis(2,3-epoxypropyl) aniline.
(91) The method of any one of (67) to (90), wherein the attachment enhancer covalently binds to the biorecognition element.
(92) The method any one of (67) to (91), wherein the biorecognition element is glucose oxidase and the attachment enhancer covalently binds to the glucose oxidase.
(93) The method of any one of (67) to (92), wherein exposing the polymer to the attachment enhancer comprises one or more of drop casting, spray coating, soaking, spin coating, and chemical vapor deposition.
(94) The method of any one of (67) to (93), wherein exposing the polymer to the attachment enhancer comprises soaking the polymer with a buffer solution including the attachment enhancer.
(95) The method of (94), wherein the buffer solution has a pH between about 7 and about 10.
(96) The method of (94) or (95), wherein the soaking is performed for a time period between about 5 minutes and about 3 days.
(97) The method of any one of (94) to (96), wherein the soaking is performed for a time period greater than about 16 hours.
(98) The method of any one of (94) to (97), wherein the attachment enhancer comprises a cross-linking agent and a concentration of the cross-linking agent within the buffer solution is between about 0.1% to about 20% w/w or w/v.
(99) A device for use in sensing an analyte, comprising a microneedle, an electrode material on the microneedle, and a biorecognition layer on the electrode material, the biorecognition layer comprising a polymer, a biorecognition element configured to react with the analyte, and an interferent blocking agent that fills voids within the polymer.
(100) A device for use in sensing an analyte, comprising a microneedle, an electrode material on the microneedle, a biorecognition layer on the electrode material, the biorecognition layer comprising phenylene diamine, a biorecognition element, and polyphenol, the polyphenol filling voids within the phenylene diamine, wherein the biorecognition element is configured to react with the analyte, and a polyurethane-based diffusion-limiting layer on the biorecognition layer.
(101) A method for manufacturing a device for use in sensing an analyte, comprising depositing a biorecognition element and a polymer on an electrode material disposed on a microneedle, wherein the biorecognition element is configured to react with the analyte, and applying an interferent blocking agent to the polymer after deposition, thereby filling voids within the polymer with the interferent blocking agent.
(102) A method for manufacturing a device for use in sensing an analyte, comprising depositing a biorecognition element and phenylene diamine on an electrode material disposed on a microneedle, wherein the biorecognition element is configured to react with the analyte, applying polyphenol to the phenylene diamine after deposition, thereby filling voids within the phenylene diamine with the polyphenol, and depositing a polyurethane-based diffusion-limiting layer on the phenylene diamine.
(103) A device for use in sensing an analyte, comprising a microneedle, an electrode material on the microneedle, a biorecognition layer on the electrode material, the biorecognition layer comprising phenylene diamine, a biorecognition element configured to react with the analyte, and polyphenol that fills voids within the phenylene diamine, a polyurethane-based diffusion-limiting layer, and an attachment enhancer configured to decrease analyte sensing variability, wherein the attachment enhancer comprises 1,4-butanediol diglycidyl ether and is positioned between the biorecognition layer and the polyurethane-based diffusion-limiting layer.
(104) A method for manufacturing a device for use in sensing an analyte, comprising depositing a biorecognition element and phenylene-diamine on an electrode material disposed on a microneedle, wherein the biorecognition element is configured to react with the analyte, applying polyphenol to the phenylene diamine, thereby filling voids within the phenylene diamine with the polyphenol, exposing the phenylene diamine to an attachment enhancer comprising 1,4-butanediol diglycidyl ether, and after exposing the phenylene diamine to the 1,4-butanediol diglycidyl ether, depositing a polyurethane-based diffusion-limiting layer on the biorecognition layer.

(105) An analyte monitoring device, comprising a plurality of microneedles arranged in an array, the plurality of microneedles comprising a plurality of working electrodes, a reference electrode, and a counter electrode, wherein the plurality of working electrodes are arranged between the reference electrode and the counter electrode.

(106) The analyte monitoring device of (105), wherein the plurality of working electrodes are uniformly distributed from the reference electrode.

(107) The analyte monitoring device of either (105) or (106), wherein the plurality of working electrodes are connected to the counter electrode such that current flows from each of the plurality of working electrodes to the counter electrode.

(108) The analyte monitoring device of (107), wherein the current results from a potential applied between the plurality of working electrodes and the reference electrode.

(109) The analyte monitoring device of any one of (105) to (108), wherein the plurality of microneedles comprises a plurality of counter electrodes, and wherein the plurality of working electrodes are arranged between the reference electrode and the plurality of counter electrodes.

(110) The analyte monitoring device of (109), wherein the plurality of counter electrodes are electrically connected in parallel, and wherein each of the plurality of working electrodes is connected to the plurality of counter electrodes.

(111) The analyte monitoring device of (110), wherein the plurality of counter electrodes are connected in parallel to one another.

(112) The analyte monitoring device of (110), wherein a majority portion of current from a first working electrode of the plurality of working electrodes flows to a first counter electrode of the plurality of counter electrodes, and wherein the first counter electrode is positioned most proximal to the first working electrode in relation to the other counter electrodes.

(113) The analyte monitoring device of (112), wherein the current results from a potential applied between the first working electrode and the reference electrode.

(114) The analyte monitoring device of (109), wherein a number of the plurality of working electrodes is equal to a number of the plurality of counter electrodes.

(115) The analyte monitoring device of (109), wherein the plurality of working electrodes comprise three working electrodes, and wherein the plurality of counter electrodes comprises three counter electrodes.

(116) The analyte monitoring device of (115), wherein the three working electrodes form a barrier around the reference electrode.

(117) The analyte monitoring device of (116), wherein the barrier prevents current that flows from the plurality of working electrodes to the plurality of counter electrodes from flowing through the reference electrode.

(118) The analyte monitoring device of any one of (105) to (118), wherein a number of the plurality of working electrodes comprises at least a minimum number to isolate the reference electrode from current flowing between the plurality of working electrodes and the counter electrode.

(119) The analyte monitoring device of any one of (105) to (119), wherein each of the plurality of working electrodes is arranged on a surface of a tapered distal portion of a respective microneedle of the plurality of microneedles.

(120) The analyte monitoring device of (119), wherein each of the plurality of working electrodes comprises a biorecognition layer, the biorecognition layer comprising a biorecognition element configured to react with an analyte.

(121) The analyte monitoring device of any one of (105) to (120), further comprising a semiconductor substrate, wherein the plurality of microneedles extend from the semiconductor substrate.

(122) The analyte monitoring device of (121), wherein each working electrode of the plurality of working electrodes is arranged on a respective microneedle of the plurality of microneedles, and
wherein a first microneedle comprising a first working electrode is arranged in a central region of the semiconductor substrate.

(123) The analyte monitoring device of (122), wherein the counter electrode is arranged on a second microneedle of the plurality of microneedles, the second microneedle proximal to a first edge of the semiconductor substrate.

(124) The analyte monitoring device of (123), wherein the reference electrode is arranged on a third microneedle of the plurality of microneedles, the third microneedle proximal to a second edge of the semiconductor substrate, the second edge opposite the first edge.

(125) The analyte monitoring device of (124), wherein the plurality of microneedles comprises a plurality of counter electrodes, each counter electrode arranged on a respective microneedle of the plurality of microneedles, each proximal to the first edge of the semiconductor substrate.

(126) The analyte monitoring device of (121), wherein the reference electrode is arranged on a central microneedle of the plurality of microneedles, the central microneedle positioned in a central region of the semiconductor substrate, and wherein the plurality of working electrodes surround the reference electrode.

(127) The analyte monitoring device of (126), wherein the counter electrode is arranged on a respective microneedle of the plurality of microneedles, the respective microneedle proximal to a first edge of the semiconductor substrate/

(128) The analyte monitoring device of (127), wherein the plurality of microneedles comprises a plurality of counter electrodes proximal to an outer edge of the semiconductor substrate.

(129) A microneedle array for use in sensing an analyte, comprising a plurality of sensing microneedles, each of the plurality of sensing microneedles comprising a working electrode comprising a biorecognition layer, the biorecognition layer comprising a biorecognition element configured to react with the analyte, a first microneedle comprising a counter electrode, and a second microneedle comprising a reference electrode, wherein the plurality of sensing microneedles are connected to the first microneedle such that current flows between the plurality of sensing microneedles and the first microneedle, the current resulting from a potential applied between the plurality of sensing microneedles and the second microneedle, and wherein the plurality of sensing microneedles are positioned between the first microneedle and the second microneedle.

The invention claimed is:

1. A device for use in sensing an analyte, comprising:
a microneedle;
an electrode material on the microneedle;
a biorecognition layer on the electrode material, the biorecognition layer comprising a polymer, a biorecognition element configured to react with the analyte, and an interferent blocking agent that fills voids within the polymer, at least a portion of the interferent blocking agent being in contact with the electrode material; and
a diffusion-limiting layer on the biorecognition layer,
wherein the interferent blocking agent comprises polymerized phenol and the polymerized phenol is present within the biorecognition layer at a concentration of between about 0.1 mg/ml or 0.01% w/v and about 10 mg/ml or 1% w/v.

2. The device of claim 1, wherein the interferent blocking agent is non-conducting.

3. The device of claim 1, wherein the interferent blocking agent further comprises one or more of a polymerized form of resorcinol, hydroquinone, catechol, 9-phenanthrol, pyrogallol, or α-napthol.

4. The device of claim 1, wherein the polymerized phenol is entrapped within the voids of the polymer.

5. The device of claim 1, wherein interference current at the electrode material of the device changes less than 70% over a one-week period.

6. The device of claim 1, wherein the biorecognition element is physically entrapped within the polymer.

7. The device of claim 1, wherein the polymer of the biorecognition layer comprises one or more of aniline, phenylene, phenylene vinylene, phenylene diamine, thiophene, 3,4-ethylenedioxythiophene, or aminophenylboronic acid.

8. A device for use in sensing an analyte, comprising:
a microneedle;
an electrode material on the microneedle;
a biorecognition layer on the electrode material, the biorecognition layer comprising a polymer, a biorecognition element configured to react with the analyte, and an interferent blocking agent that fills voids within the polymer, the voids traversing a thickness of the polymer; and
a diffusion-limiting layer on the biorecognition layer,
wherein the interferent blocking agent comprises polymerized phenol and the polymerized phenol is present within the biorecognition layer at a concentration of between about 0.1 mg/ml or 0.01% w/v and about 10 mg/ml or 1% w/v.

9. The device of claim 8, wherein the interferent blocking agent comprises one or more of a polymerized form of resorcinol, hydroquinone, catechol, 9-phenanthrol, pyrogallol, or α-napthol.

10. The device of claim 8, wherein the polymerized phenol is entrapped within the voids of the polymer.

11. The device of claim 8, wherein interference current at the electrode material of the device changes less than 10% over a one-week period.

12. The device of claim 8, wherein at least a portion of the voids are exposed to a surface of the electrode material.

13. The device of claim 8, wherein the interferent blocking agent fills at least about 80% of the voids within the polymer to limit access by interferents to the electrode material.

14. The device of claim 8, wherein the polymer of the biorecognition layer comprises one or more of aniline, phenylene, phenylene vinylene, phenylene diamine, thiophene, 3,4-ethylenedioxythiophene, or aminophenylboronic acid.

15. The device of claim 8, wherein the diffusion-limiting layer comprises one or more of polydimethylsiloxane, polyurethane, polyvinyl chloride, polyvinylpyrrolidone, polycarbonate, polyethylene, polyethylene terephthalate, polyester, high density polyethylene, low density polyethylene, or polytetrafluoroethylene.

* * * * *

SEQUENCE LISTING

```
Sequence total quantity: 1
SEQ ID NO: 1            moltype = DNA  length = 42
FEATURE                 Location/Qualifiers
source                  1..42
                        mol_type = other DNA
                        organism = synthetic construct
SEQUENCE: 1
ggacgacgcc agaagtttac gaggatatgg taacatagtc gt                           42
```